(12) United States Patent
Crawford et al.

(10) Patent No.: US 7,959,929 B2
(45) Date of Patent: Jun. 14, 2011

(54) MATERIALS AND METHODS FOR RESPIRATORY DISEASE CONTROL IN CANINES

(75) Inventors: Patti C. Crawford, Gainesville, FL (US); Paul J. Gibbs, Gainesville, FL (US); Edward J. Dubovi, Ithaca, NY (US); Ruben Omar Donis, Atlanta, GA (US); Jacqueline Katz, Atlanta, GA (US); Alexander I. Klimov, Atlanta, GA (US); Nallakannu P. Lakshmanan, Millsboro, DE (US); Melissa Anne Lum, Millsboro, DE (US); Daniel Ghislena Emiel Goovaerts, The Netherlands (BE); Mark William Mellencamp, Desoto, KS (US); Nancy J. Cox, Atlanta, GA (US); William L. Castleman, Gainesville, FL (US)

(73) Assignees: University of Florida Research Foundation, Inc., Gainesville, FL (US); Cornell Research Foundation, Inc., Ithaca, NY (US); The United States of America as represented by the Secretary of the Department of Health and Human Services, Washington, DC (US); Centers for Disease Control and Prevention, Atlanta, GA (US); Intervet International B.V. (NL)

( * ) Notice: Subject to any disclaimer, the term of this patent is extended or adjusted under 35 U.S.C. 154(b) by 900 days.

(21) Appl. No.: 11/584,818

(22) Filed: Oct. 19, 2006

(65) Prior Publication Data

US 2008/0075736 A1    Mar. 27, 2008

Related U.S. Application Data

(63) Continuation-in-part of application No. 11/409,416, filed on Apr. 21, 2006, now abandoned.

(60) Provisional application No. 60/673,443, filed on Apr. 21, 2005, provisional application No. 60/728,449, filed on Oct. 19, 2005, provisional application No. 60/754,881, filed on Dec. 29, 2005, provisional application No. 60/759,162, filed on Jan. 14, 2006, provisional application No. 60/761,451, filed on Jan. 23, 2006, provisional application No. 60/779,080, filed on Mar. 3, 2006.

(51) Int. Cl.
| | |
|---|---|
| A61K 49/00 | (2006.01) |
| A61K 39/00 | (2006.01) |
| A61K 39/12 | (2006.01) |
| A61K 39/145 | (2006.01) |
| A61K 45/00 | (2006.01) |
| C12Q 1/70 | (2006.01) |
| C12N 7/00 | (2006.01) |
| C12N 7/04 | (2006.01) |
| C07K 14/00 | (2006.01) |
| C07K 16/00 | (2006.01) |
| A61K 39/285 | (2006.01) |

(52) U.S. Cl. ............... 424/206.1; 424/9.1; 424/184.1; 424/185.1; 424/186.1; 424/204.1; 424/205.1; 424/209.1; 424/281.1; 435/5; 435/235.1; 435/236; 530/350; 530/396

(58) Field of Classification Search ................... None
See application file for complete search history.

(56) References Cited

U.S. PATENT DOCUMENTS

| | | |
|---|---|---|
| 3,541,206 A | 11/1970 | Hall |
| 3,655,871 A | 4/1972 | Werner |
| 3,869,546 A | 3/1975 | Lund |
| 4,009,258 A | 2/1977 | Kilbourne |
| 4,024,235 A | 5/1977 | Weetall et al. |
| 4,206,287 A | 6/1980 | Hannoun et al. |
| 4,500,513 A | 2/1985 | Brown et al. |
| 4,631,191 A | 12/1986 | Dale et al. |
| 4,683,137 A | 7/1987 | Coggins et al. |
| 4,683,195 A | 7/1987 | Mullis et al. |
| 4,683,202 A | 7/1987 | Mullis |
| 4,689,224 A | 8/1987 | Bull et al. |
| 4,800,159 A | 1/1989 | Mullis et al. |
| RE33,164 E | 2/1990 | Brown et al. |
| 4,911,910 A | 3/1990 | Mifflin |
| 4,965,188 A | 10/1990 | Mullis et al. |
| 5,034,322 A | 7/1991 | Rogers et al. |
| 5,106,739 A | 4/1992 | Comai et al. |
| 5,674,499 A | 10/1997 | Willemse et al. |

(Continued)

FOREIGN PATENT DOCUMENTS

GB    1067463    5/1967

(Continued)

OTHER PUBLICATIONS

Mochalova et al., Receptor-binding properties of modern human influenza viruses primarily isolated in Vero and MDCK cells and chicken embryonated eggs, 2003, Virology, vol. 313, pp. 473-480.*
Wood et al., Studies with Inactivated Equine Influenza Vaccine: 1. Serological Responses of Ponies to Graded Doses of Vaccine, 1983, The Journal of Hygiene, vol. 90, No. 3, pp. 371-384.*
University of Florida News, UF Researchers: Equine Influenza Virus Likely Involved in Recent Respiratory Disease Outbreak in Racing Greyhounds, 2004, accessed online at <http://news.ufl.edu/2004/04/22/racedogflu/> on Nov. 4, 2009.*

(Continued)

Primary Examiner — Zachariah Lucas
Assistant Examiner — Benjamin P Blumel
(74) Attorney, Agent, or Firm — Saliwanchik, Lloyd & Eisenschenk

(57) ABSTRACT

The subject invention pertains to isolated influenza virus that is capable of infecting canids and causing respiratory disease in the canid. The subject invention also pertains to compositions and methods for inducing an immune response against an influenza virus of the present invention. The subject invention also pertains to compositions and methods for identifying a virus of the invention and diagnosing infection of an animal with a virus of the invention.

96 Claims, 9 Drawing Sheets

(4 of 9 Drawing Sheet(s) Filed in Color)

U.S. PATENT DOCUMENTS

| | | | |
|---|---|---|---|
| 5,783,195 A | 7/1998 | Cochran et al. | |
| 5,994,056 A | 11/1999 | Higuchi | |
| 6,033,886 A | 3/2000 | Conzelmann | |
| 6,045,790 A | 4/2000 | Campbell | |
| 6,177,082 B1 | 1/2001 | Dowling et al. | |
| 6,207,166 B1 | 3/2001 | Audonnet et al. | |
| 6,344,354 B1 | 2/2002 | Webster et al. | |
| 6,348,450 B1 | 2/2002 | Tang et al. | |
| 6,398,774 B1 | 6/2002 | Penner et al. | |
| 6,436,408 B1 | 8/2002 | Dowling et al. | |
| 6,455,760 B1 | 9/2002 | Zhao et al. | |
| 6,482,414 B1 | 11/2002 | Dowling et al. | |
| 6,558,674 B1 | 5/2003 | Audonnet et al. | |
| 6,579,528 B1* | 6/2003 | Dowling et al. | 424/209.1 |
| 6,696,623 B1 | 2/2004 | Doerner et al. | |
| 6,713,068 B1 | 3/2004 | Audonnet et al. | |
| 6,727,078 B2 | 4/2004 | Montelaro et al. | |
| 6,814,934 B1 | 11/2004 | Higuchi | |
| 7,029,903 B2 | 4/2006 | Dowling et al. | |
| 7,033,748 B2 | 4/2006 | Hillman | |
| 7,037,707 B2 | 5/2006 | Webster et al. | |
| 7,041,300 B1 | 5/2006 | Sanchez et al. | |
| 7,074,414 B2 | 7/2006 | Dowling et al. | |
| 7,163,926 B1 | 1/2007 | Audonnet et al. | |
| 7,244,435 B2 | 7/2007 | Lai | |
| 7,468,187 B2 | 12/2008 | Yoon et al. | |
| 7,572,620 B2 | 8/2009 | Olsen et al. | |
| 7,682,619 B2 | 3/2010 | Dubovi | |
| 2002/0025325 A1 | 2/2002 | Chu et al. | |
| 2003/0045492 A1 | 3/2003 | Tang et al. | |
| 2003/0084486 A1 | 5/2003 | Bruce et al. | |
| 2003/0177536 A1 | 9/2003 | Grundler et al. | |
| 2003/0180322 A1 | 9/2003 | Dowling et al. | |
| 2004/0019934 A1 | 1/2004 | Ekramoddoullah et al. | |
| 2004/0029251 A1* | 2/2004 | Hoffman et al. | 435/239 |
| 2004/0067506 A1 | 4/2004 | Scheres et al. | |
| 2004/0078841 A1 | 4/2004 | Atkinson et al. | |
| 2004/0123349 A1 | 6/2004 | Xie et al. | |
| 2004/0142450 A1 | 7/2004 | Seo et al. | |
| 2004/0180058 A1 | 9/2004 | Shneider et al. | |
| 2005/0013826 A1 | 1/2005 | Shneider et al. | |
| 2005/0054846 A1 | 3/2005 | Webster et al. | |
| 2006/0057163 A1 | 3/2006 | Audonnet et al. | |
| 2006/0153871 A1 | 7/2006 | Olsen et al. | |
| 2006/0286591 A1 | 12/2006 | Duke et al. | |
| 2007/0009548 A1 | 1/2007 | Sterner et al. | |
| 2007/0031512 A1 | 2/2007 | Hughes | |
| 2007/0031941 A1 | 2/2007 | Duke et al. | |
| 2007/0048819 A1 | 3/2007 | Minke et al. | |
| 2007/0048821 A1 | 3/2007 | Minke et al. | |
| 2007/0065452 A1 | 3/2007 | Schiltz et al. | |
| 2007/0082012 A1 | 4/2007 | Shields et al. | |
| 2007/0092537 A1 | 4/2007 | Chiang et al. | |
| 2007/0098742 A1 | 5/2007 | Yoon et al. | |
| 2007/0253981 A1 | 11/2007 | Dubovi | |

FOREIGN PATENT DOCUMENTS

| | | |
|---|---|---|
| GB | 1183506 | 3/1970 |
| GB | 1212886 | 11/1970 |
| GB | 1450557 | 9/1976 |
| WO | WO8701942 | 4/1987 |
| WO | WO9417826 | 8/1994 |
| WO | WO9507994 | 3/1995 |
| WO | WO9617072 | 6/1996 |
| WO | WO9734008 | 9/1997 |
| WO | WO9803198 | 1/1998 |
| WO | WO9908713 | 2/1999 |
| WO | WO9951269 | 10/1999 |
| WO | WO 00/09702 | 2/2000 |
| WO | WO0103736 | 1/2001 |
| WO | WO0111081 | 2/2001 |
| WO | WO0160849 | 8/2001 |
| WO | WO0162902 | 8/2001 |
| WO | WO0197792 | 12/2001 |
| WO | WO0197804 | 12/2001 |
| WO | WO0202139 | 1/2002 |
| WO | WO02089586 | 11/2002 |
| WO | WO 2003/086454 | 10/2003 |
| WO | WO2004/057021 | 7/2004 |
| WO | WO2004058188 | 7/2004 |
| WO | WO2005014778 | 2/2005 |
| WO | WO2005024039 | 3/2005 |
| WO | WO2005120564 | 12/2005 |
| WO | WO2006/073436 | 7/2006 |
| WO | WO2006088481 | 8/2006 |
| WO | WO2006108846 | 10/2006 |
| WO | WO2006/116082 | 11/2006 |
| WO | WO2006128294 | 12/2006 |
| WO | WO2007/002008 | 1/2007 |
| WO | WO2007002007 | 1/2007 |
| WO | WO2007/019250 | 2/2007 |
| WO | WO 2007/024947 | 3/2007 |
| WO | WO2007027321 | 3/2007 |
| WO | WO 2007/042884 | 4/2007 |
| WO | WO 2007/047728 | 4/2007 |
| WO | WO 2007/048086 A2 | 4/2007 |
| WO | WO2007/061969 | 5/2007 |
| WO | WO2007124327 | 11/2007 |
| WO | WO 2008/076371 | 6/2008 |

OTHER PUBLICATIONS

Genbank Accession # AAX23575, hemagglutinin precursor [Influenza A virus (A/equine/Kentucky/5/2002(H3N8))], Mar. 12, 2005.*

Accession No. AY855338, "Influenza A virus (A/equine/Kentucky/5/02(H3N8)) PB2 polymerase 2 gene, complete cds" Mar. 12, 2005.

De Wit et al., "Efficient generation and growth of influenza virus A/PR/8/34 from eight cDNA fragments", *Virus Research*, 2004, pp. 155-161, vol. 103.

Massin, P. et al., "Cloning of the Chicken RNA Polymerase I Promoter and Use for Reverse Genetics of Influenza A Viruses in Avian Cells", *Journal of Virology*, Nov. 2005, p. 13811-13816.

CDC Media Relations—Telebriefing Transcript—Sep. 26, 2005, http://www.cdc.gov/od/oc/media/transcripts/t050926.htm.

Payungporn, S. et al. "Influenza A Virus (H3N8) in Dogs with Respiratory Disease, Florida" *Emerging Infectious Diseases*, Jun. 2008, pp. 902-908, vol. 14, No. 6.

Castleman, W., et al. "Pathologic findings in dogs infected with newly emerged canine H3N8 influenza virus." *FASEB Journal*, Mar. 6, 2006, pp. A214, vol. 20, No. 4. Abstract Only.

Hanshaw, D., et al. "Canine H3N8 influenza virus infection in mice." *FASEB Journal*, Apr. 28, 2007, pp. A406, vol. 21, No. 5. Abstract Only.

Daly, J.M., "Equine influenza in dogs: Too late to bolt the stable door?" *The Veterinary Journal*, 2006, pp. 7-8, vol. 171.

Karaca, K., et al. "Immunogenicity of Fowlpox Virus Expressing the Avian Influenza Virus H5 Gene (TROVAC AIV-H5) in Cats." *Clinical and Diagnostic Laboratory Immunology*, Nov. 2005, pp. 1340-1342, vol. 12, No. 11.

Hampton, T., "Equine Influenza Jumps to Canines." *JAMA*, Oct. 26, 2005 pp. 2015, vol. 294, No. 16.
Clark, A., "Canine Influenza Virus Surfaces." *JAVMA*, Nov. 1, 2005, pp. 1377-1378, vol. 227, No. 9.
Von Grotthuss, M., et al. "Influenza Mutation from Equine to Canine." *Science*, Mar. 3, 2006, pp. 124, vol. 311.
Ramanujan, K., "Contagious equine flu virus infecting dogs across U.S. is isolated by Cornell researchers." *Posted by Cornell University News Service*, Sep. 27, 2005 http://www.news.cornell.edu/stories/Sept05?Dog_Flu.kr.html.
Troyer, H.L., "Canine Influenza Virus ('Dog Flu'): A Summary of Clinical Cases at the Oradell Animal Hospitald, Paramus, New Jersey" Oct. 2005.
"Canine Influenza Backgrounder." *AVMA*, Oct. 24, 2005 http://www.avma.org/public_ health/influenza/canine_bgnd.asp.
"European advice on H5N1 avian influenza in cats." *The Veterinary Record, News & Reports*, Mar. 11, 2006, p. 314.
Lewis, D.B., "Avian Flu to Human Influenza." *Annu. Rev. Med.* 2006, pp. 139-154, vol. 57.
Butler, D., "Thai dogs carry bird-flu virus, but will they spread it?" *Nature*, Feb. 16, 2006, pp. 773, vol. 439.

"Canine Influenza Virus Detected in Dogs in New York State" *Cornell University Animal Health Diagnostic Center*, Sep. 29, 2005, http://diaglab.vet.cornell.edu/pdf/CIV-NYS.pdf.

"Appropriate Samples for Detecting the Presence of Canine Influenza Virus" *Cornell University Animal Health Diagnostic Center*, Mar. 27, 2006, http://diaglab.vet.cornell.edu/pdf/CIV-Samp.pdf.

Gibbs, E.P.J., "Emerging zoonotic epidemics in the interconnected global community." *The Veterinary Record*, Nov. 26, 2005, pp. 673-679, vol. 157.

Jeremijenko, A., et al., "From the front lines." *Nature*, Apr. 6, 2006, pp. 726-727, vol. 440.

Kuiken, T., et al. "Feline friend or potential foe?" *Nature*, Apr. 6, 2006, pp. 741-742, vol. 440.

Songserm, T., et al. "Avian Influenza H5N1 in Naturally Infected Domestic Cat." *Emerging Infectious Diseases*, Apr. 2006, pp. 681-683, vol. 12, No. 4.

"Animal alerts, a scary flu; a move to change laws to save pets." *Belvoir Media Group, LLC*, Nov. 22, 2005, http://www.whole-dog-journal.com/issues/8_11/features/15765-1.html.

Crawford, P. C. et al. "Supporting Online Material for Transmission of Equine Influenza Virus to Dogs" *Science*, Sep. 29, 2005, pp. S1-S19, http://www.sciencemag.org/cgi/content/full/1117950/DC1.

Greyhound Daily News, Jan. 28, 1999. National Greyhound Association (NGA), Abilene, Kansas. http://www.NGAgreyhounds.com.

CDC Media Relations "Media Briefing on Canine Influenza" *CDC Media Relations—Telebriefing Transcript*, Sep. 26, 2005, pp. 1-13, www.cdc.gov/od/oc/media/transcripts/t050926.htm.

Altschul, S. F. et al. "Basic Local Alignment Search Tool", *J. Mol. Biol.*, 1990, pp. 403-410, vol. 215.

Altschul, S. F. et al. "Gapped BLAST and PSI-BLAST: A New Generation of Protein Database Search Programs", *Nucl. Acids Res.*, 1997, pp. 3389-3402, vol. 25. No. 17.

Byars, N. E. et al. "Adjuvant Formulation for Use in Vaccines to Elicit Both Cell-Mediated and Humoral Immunity", *Vaccine*, 1987, pp. 223-228, vol. 5.

Crawford, P. C. et al. "Transmission of Equine Influenza Virus to Dogs", *Science*, 2005, pp. 482-485, vol. 310.

Dacso, C. C. et al. "Sporadic occurrence of Zoonotic Swine Influenza Virus Infections", *J. Clin. Microbiol.*, 1984, pp. 833-835, vol. 20, No. 4.

De Boer, H. A. et al. "The Tac Promoter: A Functional Hybrid Derived from the *trp* and *lac* Promoters", *Proc. Natl. Acad. Sci. USA*, 1983, pp. 21-25, vol. 80, No. 1.

Fouchier et al. "Detection of Influenza A Viruses from Different Species by PCR Amplification of Conserved Sequences in the Matrix Gene" *Journal of Clinical Microbiology*, 2000, pp. 4096-4101, vol. 38, No. 11.

Good, X. et al. "Reduced Ethylene Synthesis by Transgenic Tomatoes Expressing S-Adenosylmethionine Hydrolase", *Plant Molec. Biol.*, 1994, pp. 781-790, vol. 26.

Guan, Y. et al. "H5N1 Influenza: A Protean Pandemic Threat", *Proc. Natl Acad. Sci. USA*, 2004, pp. 8156-8161, vol. 101, No. 21.

Guo, Y et al. "Characterization of a New Avian-Like Influenza A Virus from Horses in China", *Virology*, 1992, pp. 245-255, vol. 188, No. 1. Abstract Only.

Houser, R. E. et al. "Evidence of Prior Infection with Influenza A/Texas/77 ($H_3N_2$) Virus in Dogs with Clinical Parainfluenza", *Can. J. Comp. Med.*, Oct. 1980, pp. 396-402, vol. 44.

Karasin, A. I. et al. "Isolation and Characterization of H4N6 Avian Influenza Viruses from Pigs with Pneumonia in Canada", *J. Virol.*, 2000, pp. 9322-9327, vol. 74, No. 19.

Karlin, S. et al. "Methods for Assessing the Statistical Significance of Molecular Sequence Features by Using General Scoring Schemes", *Proc. Natl. Acad. Sci. USA*, 1990, pp. 2264-2268, vol. 87.

Karlin, S. et al. "Applications and Statistics for Multiple High-Scoring Segments in Molecular Sequences", *Proc. Natl. Acad. Sci. USA*, 1993, pp. 5873-5877, vol. 90.

Kawaoka, Y. et al "Avian-to-Human Transmission of the PB1 Gene of Influenza A Viruses in the 1957 and 1968 Pandemics", *J. Virol.*, 1989, pp. 4603-4608, vol. 63, No. 11.

Keawcharoen, J. et al. "Avian Influenza H5N1 in Tigers and Leopards", *Emerg. Infect. Dis.*, 2004, pp. 2189-2191, vol. 10, No. 12.

Kilbourne, E. D. et al. "Demonstration of Antibodies to Both Hemagglutinin and Neuraminidase Antigens of H3N2 Influenza A Virus in Domestic Dogs", *Intervirology*, 1975, pp. 315-318, vol. 6.

Kimura, K. et al. "Fatal Case of Swine Influenza Virus in an Immunocompetent Host", *Mayo Clin. Proc.*, 1998, pp. 243-245, vol. 73.

Klimov, A. I. et al. "Sequence Changes in the Live Attenuated, Cold-Adapted Variants of Influenza A/Leningrad/134/57 (H2N2) Virus", *Virology*, 1992, pp. 795-797, vol. 186, No. 2. Abstract Only.

Klimov, A. et al. "Subtype H7 Influenza Viruses: Comparative Antigenic and Molecular Analysis of the Ha-, M-, and NS-genes", *Arch Virol.*, 1992, pp. 143-161, vol. 122.

Kovacova, A. et al. "Sequence Similarities and Evolutionary Relationships of Influenza Virus A Hemagglutinins", *Virus Genes*, 2002, pp. 57-63, vol. 24, No. 1.

Kuiken, T. et al. "Avian H5N1 Influenza in Cats", *Science*, 2004, pp. 241, vol. 306.

Lee, L. G. et al. "Allelic Discrimination by Nick-Translation PCR with Fluorogenic Probes", *Nucleic Acids Res.*, 1993, pp. 3761-3766, vol. 21, No. 16. Abstract Only.

Lipatov, A. S. et al "Influenza: Emergence and Control", *J. Virol.*, 2004, pp. 8951-8959, vol. 78, No. 17.

Livak, K. J. et al. "Oligonucleotides with Fluorescent Dyes at Opposite Ends Provide a Quenched Probe System Useful for Detecting PCR Product and Nucleic Acid Hybridization", *PCR Methods Appl.*, 1995, pp. 357-362, vol. 4, No. 6. Abstract Only.

Matrosovich, M. et al. "Early Alterations of the Receptor-Binding Properties of H1, H2, and H3 Avian Influenza Virus Hemagglutinins After Their Introduction into Mammals", *J. Virol.*, 2000, pp. 8502-8512, vol. 74, No. 18.

Maertzdorf et al. "Real-Time Reverse Transcriptase PCR Asay for Detection of Human Metapneumoviruses from All Known Genetic Lineages", *Clin. Microbiol.*, 2004, pp. 981-986, vol. 42, No. 3.

Merrifield, R. B. et al. "Solid Phase Peptide Synthesis. I. The Synthesis of a Tetrapeptide", *J. Amer. Chem. Soc.*, 1963, pp. 2149-2154, vol. 85.

Nikitin, T. et al. "Epidemiological Studies of A/Hong Kong/68 Virus Infection in Dogs", *Bull. World Health Organ.*, 1972, pp. 471-479, vol. 47.

Nobusawa, E. et al. "Comparison of Complete Amino Acid Sequences and Receptor-Binding Properties Among 13 Serotypes of Hemagglutinins of Influenza A Viruses", *Virology*, 1991, pp. 475-485, vol. 182, No. 2.

Patriarca, P. A. et al. "Lack of Significant Person-to-Person Spread of Swine Influenza-like Virus Following Fatal Infection in an Immunocompromised Child", *Am. J. Epidemiol.*, 1984, pp. 152-158, vol. 119, No. 2.

Peiris, M. et al. "Human Infection with Influenza H9N2", *Lancet*, 1999, pp. 916-917, vol. 354.

Peiris, J. S. et al. "Re-Emergence of Fatal Human Influenza A Subtype H5N1 Disease", *Lancet*, 2004, pp. 617-619, vol. 363.

Posnett, D. N. et al. "A Novel Method for Producing Anti-Peptide Antibodies", *J. Biol. Chem.*, 1988, pp. 1719-1725, vol. 263, No. 4.

Putnam, B. "Two Illnesses Seen in Death of Dogs", *St. Petersburg Times*, Feb. 10, 1999.

Reid, A. H. et al. "Evidence of an Absence: The Genetic Origins of the 1918 Pandemic Influenza Virus", *Nat. Rev. Microbiol.*, 2004, pp. 909-914, vol. 2.

Rowe, T. et al. "Detection of Antibody to Avian Influenza A (H5N1) Virus in Human Serum by Using a Combination of Serologic Assays", *J. Clin. Microbiol.*, 1999, pp. 937-943, vol. 37, No. 4.

Saiki, R. "Enzymatic Amplification of Beta-Globin Genomic Sequences and Restriction Site Analysis for Diagnosis of Sickle Cell Anemia", *Science*, 1985, pp. 1350-1354, vol. 230.

Subbarao, K. et al. "Characterization of an Avian Influenza A (H5N1) Virus Isolated from a Child with a Fatal Respiratory Illness", *Science*, 1998, pp. 393-396, vol. 279.

Suzuki, Y. et al. "Sialic Acid Species as a Determinant of the Host Range of Influenza A Viruses", *J. Virol.*, 2000, pp. 11825-11831, vol. 74, No. 24.

Tam, J. P. et al. "Synthetic Peptide Vaccine Design: Synthesis and Properties of a High Density Multiple Antigenic Peptide System", *PNAS USA*, 1988, pp. 5409-5413, vol. 85, No. 15.

Top, F. H. et al. "Swine Influenza A at Fort Dix, New Jersey (Jan.-Feb. 1976). IV. Summary and Speculation", *J. Infect. Dis.*, 1977, pp. S376-S380, vol. 136, Supp.

Vines, A. et al. "The Role of Influenza A Virus Hemagglutinin Residues 226 and 228 in Receptor Specificity and Host Range Restriction", *J. Virol.*, 1998, pp. 7626-7631, vol. 72, No. 9.

Wagner, R. et al. "N-Glycans Attached to the Stem Domain of Haemagglutinin Efficiently Regulate Influenza A Virus Replication", *J. Gen. Virol.*, 2002, pp. 601-609, vol. 83.

Webby, R. et al. "Molecular Constraints to Interspecies Transmission of Viral Pathogens", *Nat. Med.*, 2004, pp. S77-S81, vol. 10, No. 12.

Webster, R. G. "Influenza: An Emerging Disease", *Emerg. Infect. Dis.*, 1998, pp. 436-441, vol. 4, No. 3.

Webster, R. G. et al. "Evolution and Ecology of Influenza A Viruses", *Microbiol. Rev.*, 1992, pp. 152-179, vol. 56, No. 1.

Weis, W. et al. "Structure of the Influenza Virus Haemagglutinin Complexed with Its Receptor, Sialic Acid", *Nature*, 1988, pp. 426-431, vol. 333.

Womble, D. D. "GCG: The Wisconsin Package of Sequence Analysis Programs", *Methods Mol. Biol.*, 2000, pp. 3-22, vol. 132.

Xu, D. et al. "Systemic Induction of a Potato *Pin2* Promoter by Wounding, Methyl Jasmonate, and Abscisic Acid in Transgenic Rice Plants", *Plant Molecular Biology*, 1993, pp. 573-588, vol. 22.

Yang, T-T. et al. "Optimized Codon Usage and Chromophore Mutations Provide Enhanced Sensitivity with the Green Fluorescent Protein", *Nucleic Acid Research*, 1996, pp. 4592-4593, vol. 24, No. 22.

Yoon, K.-Y. et al. "Influenza Virus Infection in Racing Greyhounds", *Emerg. Infect. Dis.*, 2005, pp. 1974-1975, vol. 11, No. 12.

Carey, S. "UF Researchers: Equine Influenza Virus Likely Involved in Recent Respiratory Disease Outbreak in Racing Greyhounds", *HSC News and Communications, University of Florida*, Apr. 22, 2004.

Lai, A. C. K. et al. "Alternate Circulation of Recent Equine-2 Influenza Viruses (H3N8) from Two Distinct Lineages in the United States", *Virus Research*, 2004, pp. 159-164, vol. 100.

Wagener, J. S. "Role of Canine Parainfluenza Virus and *Bordetella bronchiseptica* in Kennel Cough", *Am. J. Vet. Res.*, 1984, pp. 1862-1866, vol. 45, No. 9.

Oxburgh, L. et al. "Evolution of H3N8 Equine Influenza Virus from 1963 to 1991", *Virus Res.* Nov. 1994, pp. 153-165, vol. 34(2). Abstract Only.

McNeil, D.G. and Rubenstein, C. "A New Deadly, Contagious Dog Flu Virus is Detected in 7 States", *The New York Times* (nytimes.com), Sep. 22, 2005.

*Proceedings One Hundred and Eigth Annual Meeting of the United States Animal Health Association*, Oct. 2004, pp. 1, 2, 247, and 296. www.usaha.org/meetings/2004/2004_USAHA_Proceedings.pdf.

Karaca, K. et al. "Evaluation of the Ability of Canarypox-Vectored Equine Influenza Virus Vaccones to Induce Humoral Immune Responses against Canine Influenza Viruses in Dogs", *AJVR*, Feb. 2007, pp. 208-212, vol. 68, No. 2.
Manuguerra, J. C. et al. "Natural infection of dogs by influenza C virus" *Res. Virol.*, 1992, pp. 199-204, vol. 143.
Ohwada, K. et al. "Experimental Infections of Dogs with Type C Influenza Virus" *Microbiol. Immunol.*, 1986, pp. 451-460, vol. 30, No. 5.
Database Biosis, Accession No. PREV200300495526, Cattoli, G. et al., "Plaque morphology of Italian H7N1 LPAI isolates in MDCK cells and in primary cells of different avian species" *Biosciences Information Service*, 2003.
Database EMBL, Accession No. Q3I3U6, "M1", Nov. 8, 2005, pp. 1-2.
Database Medline, Accession No. NLM15782624, Emanuela, F. et al., "Detection of influenza A virus by RT-PCR and standard methods in experimental infection of ducks" *US National Library of Medicine*, Jan. 2005.
Peek, S.F., "Acute respiratory distress syndrome and fatal interstitial pneumonia associated with equine uinfluenza in a neonatal foal" *Journal of Veterinary Internal Medicine*, Jan. 2004, pp. 132-134, vol. 18, No. 1.
Wood, J.M. et al., "The standardization of inactivated equine influenza vaccines by single-radial immunodiffusion" *Journal of Biological Standardization*, Apr. 1983, pp. 133-136, vol. 11, No. 2.
Dubovi, E.J., Crawford, C.W., Donis, R.O., Castleman, W.L., Stephenson, I., Gibbs, E.P.J. "Isolation of equine influenza virus from racing greyhounds with fatal hemorrhagic pneumonia" In: Proceedings of the 47th Annual Meeting of American Association of Veterinary Laboratory Diagnosticians, Oct. 2004, Greensboro, North Carolina, p. 158.

* cited by examiner

SEQUENCE LISTING

```
<160> NUMBER OF SEQ ID NOS: 88

<210> SEQ ID NO 1
<211> LENGTH: 2277
<212> TYPE: DNA
<213> ORGANISM: Influenza virus
<220> FEATURE:
<221> NAME/KEY: CDS
<222> LOCATION: (1)..(2277)

<400> SEQUENCE: 1 atg gag aga ata gaa gaa ctg aga gat ctg atg tta caa tcc cgc acc      48
Met Glu Arg Ile Glu Glu Leu Arg Asp Leu Met Leu Gln Ser Arg Thr
1               5                   10                  15 cgc gag ata cta aca aaa act act gtg gac cac atg gcc ata atc aag      96
Arg Glu Ile Leu Thr Lys Thr Thr Val Asp His Met Ala Ile Ile Lys
            20                  25                  30 aaa tac aca tca gaa aga caa gag aag aac cct gca ctt agg atg aaa     144
Lys Tyr Thr Ser Glu Arg Gln Glu Lys Asn Pro Ala Leu Arg Met Lys
        35                  40                  45 tgg atg atg gca atg aaa tac cca att aca gca gat aag agg ata atg     192
Trp Met Met Ala Met Lys Tyr Pro Ile Thr Ala Asp Lys Arg Ile Met
    50                  55                  60 gag atg att cct gag aga aat gaa cag ggt caa acc ctt tgg agc aaa     240
Glu Met Ile Pro Glu Arg Asn Glu Gln Gly Gln Thr Leu Trp Ser Lys
65                  70                  75                  80 acg aac gat gct ggc tca gac cgc gta atg gta tca cct ctg gca gtg     288
Thr Asn Asp Ala Gly Ser Asp Arg Val Met Val Ser Pro Leu Ala Val
                85                  90                  95 aca tgg tgg aat agg aat gga cca aca acg agc aca att cat tat cca     336
Thr Trp Trp Asn Arg Asn Gly Pro Thr Thr Ser Thr Ile His Tyr Pro
            100                 105                 110 aaa gtc tac aaa act tat ttt gaa aag gtt gaa aga ttg aaa cac gga     384
Lys Val Tyr Lys Thr Tyr Phe Glu Lys Val Glu Arg Leu Lys His Gly
        115                 120                 125 act ttt ggc ccc gtt cat ttt agg aat caa gtc aag ata aga cga aga     432
Thr Phe Gly Pro Val His Phe Arg Asn Gln Val Lys Ile Arg Arg Arg
    130                 135                 140 gtt gat gta aac cct ggt cac gcg gac ctc agt gcc aaa gaa gca caa     480
Val Asp Val Asn Pro Gly His Ala Asp Leu Ser Ala Lys Glu Ala Gln
145                 150                 155                 160 gat gtg atc atg gaa gtt gtt ttc cca aat gaa gtg gga gcc ata att     528
Asp Val Ile Met Glu Val Val Phe Pro Asn Glu Val Gly Ala Ile Ile
                165                 170                 175 cta aca tcg gaa tca caa cta aca ata acc aaa gag aaa aag gaa gaa     576
Leu Thr Ser Glu Ser Gln Leu Thr Ile Thr Lys Glu Lys Lys Glu Glu
            180                 185                 190 ctt cag gac tgc aaa att gct ccc ttg atg gta gca tac atg cta gaa     624
```

```
                                               -continued

Leu Gln Asp Cys Lys Ile Ala Pro Leu Met Val Ala Tyr Met Leu Glu
        195                 200                 205 aga gag ttg gtc cga aaa aca agg ttc ctc cca gta gca ggc gga aca     672
Arg Glu Leu Val Arg Lys Thr Arg Phe Leu Pro Val Ala Gly Gly Thr
    210                 215                 220 agc agt gta tac att gaa gtg ttg cat ctg act cag gga aca tgc tgg     720
Ser Ser Val Tyr Ile Glu Val Leu His Leu Thr Gln Gly Thr Cys Trp
225                 230                 235                 240 gag caa atg tac acc cca gga gga gaa gtt aga aac gat gat att gat     768
Glu Gln Met Tyr Thr Pro Gly Gly Glu Val Arg Asn Asp Asp Ile Asp
                245                 250                 255 caa agt tta att att gca gcc cgg aac ata gtg aga aga gcg aca gta     816
Gln Ser Leu Ile Ile Ala Ala Arg Asn Ile Val Arg Arg Ala Thr Val
            260                 265                 270 tca gca gat cca cta gca tcc cta ctg gaa atg tgc cac agt aca cag     864
Ser Ala Asp Pro Leu Ala Ser Leu Leu Glu Met Cys His Ser Thr Gln
        275                 280                 285 att ggt gga ata agg atg gta gac atc ctt aag cag aat cca aca gag     912
Ile Gly Gly Ile Arg Met Val Asp Ile Leu Lys Gln Asn Pro Thr Glu
    290                 295                 300 gaa caa gct gtg gat ata tgc aaa gca gca atg gga ttg aga att agc     960
Glu Gln Ala Val Asp Ile Cys Lys Ala Ala Met Gly Leu Arg Ile Ser
305                 310                 315                 320 tca tca ttc agc ttt ggt gga ttc acc ttc aaa aga aca agt gga tca    1008
Ser Ser Phe Ser Phe Gly Gly Phe Thr Phe Lys Arg Thr Ser Gly Ser
                325                 330                 335 tca gtc aag aga gaa gaa gaa atg ctt acg ggc aac ctt caa aca ttg    1056
Ser Val Lys Arg Glu Glu Glu Met Leu Thr Gly Asn Leu Gln Thr Leu
            340                 345                 350 aaa ata aga gtg cat gag ggc tat gaa gaa ttc aca atg gtc gga aga    1104
Lys Ile Arg Val His Glu Gly Tyr Glu Glu Phe Thr Met Val Gly Arg
        355                 360                 365 aga gca aca gcc att atc aaa aag gca acc aga aga ttg att caa ttg    1152
Arg Ala Thr Ala Ile Ile Lys Lys Ala Thr Arg Arg Leu Ile Gln Leu
    370                 375                 380 ata gta agt ggg aga gat gaa caa tca att gct gaa gca ata att gta    1200
Ile Val Ser Gly Arg Asp Glu Gln Ser Ile Ala Glu Ala Ile Ile Val
385                 390                 395                 400 gcc atg gtg ttt tcg caa gaa gat tgc atg ata aaa gca gtt cga ggc    1248
Ala Met Val Phe Ser Gln Glu Asp Cys Met Ile Lys Ala Val Arg Gly
                405                 410                 415 gat ttg aac ttt gtt aat aga gca aat cag cgt ttg aac ccc atg cat    1296
Asp Leu Asn Phe Val Asn Arg Ala Asn Gln Arg Leu Asn Pro Met His
            420                 425                 430 caa ctc ttg agg cat ttc caa aaa gat gca aaa gtg ctt ttc cac aat    1344
Gln Leu Leu Arg His Phe Gln Lys Asp Ala Lys Val Leu Phe His Asn
        435                 440                 445 tgg gga att gaa ccc atc gac aat gta atg ggg atg att gga ata ttg    1392
Trp Gly Ile Glu Pro Ile Asp Asn Val Met Gly Met Ile Gly Ile Leu
    450                 455                 460 cct gac atg acc cca agc acc gag atg tca ttg aga gga gtg aga gtc    1440
Pro Asp Met Thr Pro Ser Thr Glu Met Ser Leu Arg Gly Val Arg Val
465                 470                 475                 480 agc aaa atg gga gtg gat gag tac tcc agc act gag aga gtg gtg gtg    1488
Ser Lys Met Gly Val Asp Glu Tyr Ser Ser Thr Glu Arg Val Val Val
                485                 490                 495 agc att gac cgt ttt tta aga gtt cgg gat caa agg gga aac ata cta    1536
Ser Ile Asp Arg Phe Leu Arg Val Arg Asp Gln Arg Gly Asn Ile Leu
            500                 505                 510 ctg tcc cct gaa gaa gtc agt gaa aca caa gga acg gaa aag ctg aca    1584
```

```
Leu Ser Pro Glu Glu Val Ser Glu Thr Gln Gly Thr Glu Lys Leu Thr
        515                 520                 525 ata att tat tcg tca tca atg atg tgg gag att aat ggt ccc gaa tca    1632
Ile Ile Tyr Ser Ser Ser Met Met Trp Glu Ile Asn Gly Pro Glu Ser
530                 535                 540 gtg ttg gtc aat act tat caa tgg atc atc agg aac tgg gaa att gta    1680
Val Leu Val Asn Thr Tyr Gln Trp Ile Ile Arg Asn Trp Glu Ile Val
545                 550                 555                 560 aaa att cag tgg tca cag gac ccc aca atg tta tac aat aag ata gaa    1728
Lys Ile Gln Trp Ser Gln Asp Pro Thr Met Leu Tyr Asn Lys Ile Glu
                565                 570                 575 ttt gag cca ttc caa tcc ctg gtc cct agg gcc acc aga agc caa tac    1776
Phe Glu Pro Phe Gln Ser Leu Val Pro Arg Ala Thr Arg Ser Gln Tyr
            580                 585                 590 agc ggt ttc gta aga acc ctg ttt cag caa atg cga gat gta ctt gga    1824
Ser Gly Phe Val Arg Thr Leu Phe Gln Gln Met Arg Asp Val Leu Gly
        595                 600                 605 aca ttt gat act gct caa ata ata aaa ctc ctc cct ttt gcc gct gct    1872
Thr Phe Asp Thr Ala Gln Ile Ile Lys Leu Leu Pro Phe Ala Ala Ala
610                 615                 620 cct ccg gaa cag agt agg atg cag ttc tct tct ttg act gtt aat gta    1920
Pro Pro Glu Gln Ser Arg Met Gln Phe Ser Ser Leu Thr Val Asn Val
625                 630                 635                 640 aga ggt tcg gga atg agg ata ctt gta aga ggc aat tcc cca gtg ttc    1968
Arg Gly Ser Gly Met Arg Ile Leu Val Arg Gly Asn Ser Pro Val Phe
                645                 650                 655 aac tac aat aaa gcc act aaa agg ctc aca gtc ctc gga aag gat gca    2016
Asn Tyr Asn Lys Ala Thr Lys Arg Leu Thr Val Leu Gly Lys Asp Ala
            660                 665                 670 ggt gcg ctt act gag gac cca gat gaa ggt acg gct gga gta gaa tct    2064
Gly Ala Leu Thr Glu Asp Pro Asp Glu Gly Thr Ala Gly Val Glu Ser
        675                 680                 685 gct gtt cta aga ggg ttt ctc att tta ggt aaa gag aac aag aga tat    2112
Ala Val Leu Arg Gly Phe Leu Ile Leu Gly Lys Glu Asn Lys Arg Tyr
690                 695                 700 ggc cca gca cta agc atc aat gaa cta agc aaa ctt gca aaa ggg gag    2160
Gly Pro Ala Leu Ser Ile Asn Glu Leu Ser Lys Leu Ala Lys Gly Glu
705                 710                 715                 720 aaa gcc aat gta cta att ggg caa ggg gac gta gtg ttg gta atg aaa    2208
Lys Ala Asn Val Leu Ile Gly Gln Gly Asp Val Val Leu Val Met Lys
                725                 730                 735 cgg aaa cgt gac tct agc ata ctt act gac agc cag aca gcg acc aaa    2256
Arg Lys Arg Asp Ser Ser Ile Leu Thr Asp Ser Gln Thr Ala Thr Lys
            740                 745                 750 agg att cgg atg gcc atc aat                                        2277
Arg Ile Arg Met Ala Ile Asn
        755

<210> SEQ ID NO 2
<211> LENGTH: 759
<212> TYPE: PRT
<213> ORGANISM: Influenza virus

<400> SEQUENCE: 2

Met Glu Arg Ile Glu Glu Leu Arg Asp Leu Met Leu Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Glu Arg Gln Glu Lys Asn Pro Ala Leu Arg Met Lys
            35                  40                  45
```

```
Trp Met Met Ala Met Lys Tyr Pro Ile Thr Ala Asp Lys Arg Ile Met
    50                  55                  60
Glu Met Ile Pro Glu Arg Asn Glu Gln Gly Gln Thr Leu Trp Ser Lys
65                      70                  75                  80
Thr Asn Asp Ala Gly Ser Asp Arg Val Met Val Ser Pro Leu Ala Val
                85                  90                  95
Thr Trp Trp Asn Arg Asn Gly Pro Thr Thr Ser Thr Ile His Tyr Pro
                    100                 105                 110
Lys Val Tyr Lys Thr Tyr Phe Glu Lys Val Glu Arg Leu Lys His Gly
            115                 120                 125
Thr Phe Gly Pro Val His Phe Arg Asn Gln Val Lys Ile Arg Arg Arg
    130                 135                 140
Val Asp Val Asn Pro Gly His Ala Asp Leu Ser Ala Lys Glu Ala Gln
145                 150                 155                 160
Asp Val Ile Met Glu Val Val Phe Pro Asn Glu Val Gly Ala Ile Ile
                165                 170                 175
Leu Thr Ser Glu Ser Gln Leu Thr Ile Thr Lys Glu Lys Lys Glu Glu
                    180                 185                 190
Leu Gln Asp Cys Lys Ile Ala Pro Leu Met Val Ala Tyr Met Leu Glu
            195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Ile Asp
                245                 250                 255
Gln Ser Leu Ile Ile Ala Ala Arg Asn Ile Val Arg Arg Ala Thr Val
                    260                 265                 270
Ser Ala Asp Pro Leu Ala Ser Leu Leu Glu Met Cys His Ser Thr Gln
            275                 280                 285
Ile Gly Gly Ile Arg Met Val Asp Ile Leu Lys Gln Asn Pro Thr Glu
    290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Met Leu Thr Gly Asn Leu Gln Thr Leu
                    340                 345                 350
Lys Ile Arg Val His Glu Gly Tyr Glu Glu Phe Thr Met Val Gly Arg
            355                 360                 365
Arg Ala Thr Ala Ile Ile Lys Lys Ala Thr Arg Arg Leu Ile Gln Leu
    370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
                    420                 425                 430
Gln Leu Leu Arg His Phe Gln Lys Asp Ala Lys Val Leu Phe His Asn
            435                 440                 445
Trp Gly Ile Glu Pro Ile Asp Asn Val Met Gly Met Ile Gly Ile Leu
    450                 455                 460
Pro Asp Met Thr Pro Ser Thr Glu Met Ser Leu Arg Gly Val Arg Val
465                 470                 475                 480
```

```
Ser Lys Met Gly Val Asp Glu Tyr Ser Thr Glu Arg Val Val
            485                 490                 495

Ser Ile Asp Arg Phe Leu Arg Val Arg Asp Gln Arg Gly Asn Ile Leu
        500                 505                 510

Leu Ser Pro Glu Val Ser Glu Thr Gln Gly Thr Glu Lys Leu Thr
            515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 3
<211> LENGTH: 2274
<212> TYPE: DNA
<213> ORGANISM: Influenza virus
<220> FEATURE:
<221> NAME/KEY: CDS
<222> LOCATION: (1)..(2274)

<400> SEQUENCE: 3 atg gat gtc aat ccg act cta ctc ttc tta aag gtg cca gcg cag aat    48
Met Asp Val Asn Pro Thr Leu Leu Phe Leu Lys Val Pro Ala Gln Asn
1               5                   10                  15 gct ata agc aca aca ttc cct tat act gga gat cct ccc tac agt cat    96
Ala Ile Ser Thr Thr Phe Pro Tyr Thr Gly Asp Pro Pro Tyr Ser His
            20                  25                  30 gga aca ggg aca gga tac acc atg gat act gtc aac aga aca cac caa   144
Gly Thr Gly Thr Gly Tyr Thr Met Asp Thr Val Asn Arg Thr His Gln
        35                  40                  45 tat tca gaa aaa ggg aaa tgg aca aca aac act gag att gga gca cca   192
Tyr Ser Glu Lys Gly Lys Trp Thr Thr Asn Thr Glu Ile Gly Ala Pro
```

|  |  |  |  |  |  |  |  |  |  |  |  |  |  |  |  |
|---|---|---|---|---|---|---|---|---|---|---|---|---|---|---|---|
| | | 50 | | | | 55 | | | | 60 | | | | | |
| caa | ctt | aat | cca | atc | gat | gga | cca | ctt | cct | gaa | gac | aat | gaa | cca | agc | 240
| Gln | Leu | Asn | Pro | Ile | Asp | Gly | Pro | Leu | Pro | Glu | Asp | Asn | Glu | Pro | Ser |
| 65 | | | | 70 | | | | 75 | | | | 80 | | | |
| ggg | tac | gcc | caa | aca | gat | tgt | gta | ttg | gaa | gca | atg | gct | ttc | ctt | gaa | 288
| Gly | Tyr | Ala | Gln | Thr | Asp | Cys | Val | Leu | Glu | Ala | Met | Ala | Phe | Leu | Glu |
| | | | | 85 | | | | | 90 | | | | | 95 | |
| gaa | tcc | cat | cca | gga | atc | ttt | gaa | aat | tcg | tgt | ctt | gaa | acg | atg | gag | 336
| Glu | Ser | His | Pro | Gly | Ile | Phe | Glu | Asn | Ser | Cys | Leu | Glu | Thr | Met | Glu |
| | | | 100 | | | | | 105 | | | | | 110 | | |
| gtg | att | cag | cag | aca | aga | gtg | gac | aaa | cta | aca | caa | ggc | cga | caa | act | 384
| Val | Ile | Gln | Gln | Thr | Arg | Val | Asp | Lys | Leu | Thr | Gln | Gly | Arg | Gln | Thr |
| | | 115 | | | | | 120 | | | | | 125 | | | |
| tat | gat | tgg | acc | ttg | aat | agg | aat | caa | cct | gcc | gca | aca | gca | ctt | gct | 432
| Tyr | Asp | Trp | Thr | Leu | Asn | Arg | Asn | Gln | Pro | Ala | Ala | Thr | Ala | Leu | Ala |
| | 130 | | | | | 135 | | | | | 140 | | | | |
| aat | acg | att | gaa | gta | ttc | aga | tca | aat | ggt | ctg | act | tcc | aat | gaa | tcg | 480
| Asn | Thr | Ile | Glu | Val | Phe | Arg | Ser | Asn | Gly | Leu | Thr | Ser | Asn | Glu | Ser |
| 145 | | | | | 150 | | | | | 155 | | | | | 160 |
| ggg | aga | ttg | atg | gac | ttc | ctc | aaa | gat | gtc | atg | gag | tcc | atg | aac | aag | 528
| Gly | Arg | Leu | Met | Asp | Phe | Leu | Lys | Asp | Val | Met | Glu | Ser | Met | Asn | Lys |
| | | | | 165 | | | | | 170 | | | | | 175 | |
| gaa | gaa | atg | gaa | ata | aca | aca | cac | ttc | caa | cgg | aag | aga | aga | gta | aga | 576
| Glu | Glu | Met | Glu | Ile | Thr | Thr | His | Phe | Gln | Arg | Lys | Arg | Arg | Val | Arg |
| | | | 180 | | | | | 185 | | | | | 190 | | |
| gac | aac | atg | aca | aag | aga | atg | gta | aca | cag | aga | acc | ata | ggg | aag | aaa | 624
| Asp | Asn | Met | Thr | Lys | Arg | Met | Val | Thr | Gln | Arg | Thr | Ile | Gly | Lys | Lys |
| | | 195 | | | | | 200 | | | | | 205 | | | |
| aaa | caa | cga | tta | aac | aga | aag | agc | tat | cta | atc | aga | aca | tta | acc | cta | 672
| Lys | Gln | Arg | Leu | Asn | Arg | Lys | Ser | Tyr | Leu | Ile | Arg | Thr | Leu | Thr | Leu |
| | 210 | | | | | 215 | | | | | 220 | | | | |
| aac | aca | atg | acc | aag | gac | gct | gag | aga | ggg | aaa | ttg | aaa | cga | cga | gca | 720
| Asn | Thr | Met | Thr | Lys | Asp | Ala | Glu | Arg | Gly | Lys | Leu | Lys | Arg | Arg | Ala |
| 225 | | | | | 230 | | | | | 235 | | | | | 240 |
| atc | gct | acc | cca | ggg | atg | cag | ata | aga | ggg | ttt | gta | tat | ttt | gtt | gaa | 768
| Ile | Ala | Thr | Pro | Gly | Met | Gln | Ile | Arg | Gly | Phe | Val | Tyr | Phe | Val | Glu |
| | | | | 245 | | | | | 250 | | | | | 255 | |
| aca | cta | gct | cga | aga | ata | tgt | gaa | aag | ctt | gaa | caa | tca | gga | ttg | cca | 816
| Thr | Leu | Ala | Arg | Arg | Ile | Cys | Glu | Lys | Leu | Glu | Gln | Ser | Gly | Leu | Pro |
| | | | 260 | | | | | 265 | | | | | 270 | | |
| gtt | ggc | ggt | aat | gag | aaa | aag | gcc | aaa | ctg | gct | aat | gtc | gtc | aga | aaa | 864
| Val | Gly | Gly | Asn | Glu | Lys | Lys | Ala | Lys | Leu | Ala | Asn | Val | Val | Arg | Lys |
| | | 275 | | | | | 280 | | | | | 285 | | | |
| atg | atg | act | aat | tcc | caa | gac | act | gaa | ctc | tcc | ttc | acc | atc | act | ggg | 912
| Met | Met | Thr | Asn | Ser | Gln | Asp | Thr | Glu | Leu | Ser | Phe | Thr | Ile | Thr | Gly |
| | 290 | | | | | 295 | | | | | 300 | | | | |
| gac | aat | acc | aaa | tgg | aat | gaa | aat | cag | aac | cca | cgc | ata | ttc | ctg | gca | 960
| Asp | Asn | Thr | Lys | Trp | Asn | Glu | Asn | Gln | Asn | Pro | Arg | Ile | Phe | Leu | Ala |
| 305 | | | | | 310 | | | | | 315 | | | | | 320 |
| atg | atc | aca | tac | ata | act | aga | aac | cag | cca | gaa | tgg | ttc | aga | aat | gtt | 1008
| Met | Ile | Thr | Tyr | Ile | Thr | Arg | Asn | Gln | Pro | Glu | Trp | Phe | Arg | Asn | Val |
| | | | | 325 | | | | | 330 | | | | | 335 | |
| cta | agc | att | gca | ccg | att | atg | ttc | tca | aat | aaa | atg | gca | aga | ctg | ggg | 1056
| Leu | Ser | Ile | Ala | Pro | Ile | Met | Phe | Ser | Asn | Lys | Met | Ala | Arg | Leu | Gly |
| | | | 340 | | | | | 345 | | | | | 350 | | |
| aaa | gga | tat | atg | ttt | gaa | agc | aaa | agt | atg | aaa | ttg | aga | act | caa | ata | 1104
| Lys | Gly | Tyr | Met | Phe | Glu | Ser | Lys | Ser | Met | Lys | Leu | Arg | Thr | Gln | Ile |
| | | 355 | | | | | 360 | | | | | 365 | | | |
| cca | gca | gaa | atg | cta | gca | agc | att | gac | cta | aaa | tat | ttc | aat | gat | tca | 1152
| Pro | Ala | Glu | Met | Leu | Ala | Ser | Ile | Asp | Leu | Lys | Tyr | Phe | Asn | Asp | Ser |

-continued

```
         370                375                380
aca aaa aag aaa att gag aag ata cga cca ctt ctg gtt gac ggg act    1200
Thr Lys Lys Lys Ile Glu Lys Ile Arg Pro Leu Leu Val Asp Gly Thr
385                 390                395                400 gct tca ctg agt cct ggc atg atg atg gga atg ttc aac atg ttg agc    1248
Ala Ser Leu Ser Pro Gly Met Met Met Gly Met Phe Asn Met Leu Ser
                405                410                415 act gtg ctg ggt gta tcc ata tta aac ctg ggc cag agg aaa tac aca    1296
Thr Val Leu Gly Val Ser Ile Leu Asn Leu Gly Gln Arg Lys Tyr Thr
            420                425                430 aag acc aca tac tgg tgg gat ggt ctg caa tca tcc gat gac ttt gct    1344
Lys Thr Thr Tyr Trp Trp Asp Gly Leu Gln Ser Ser Asp Asp Phe Ala
        435                440                445 ttg ata gtg aat gcg cct aat cat gaa gga gta caa gct gga gta gac    1392
Leu Ile Val Asn Ala Pro Asn His Glu Gly Val Gln Ala Gly Val Asp
    450                455                460 aga ttc tat aga act tgc aaa ctg gtc ggg atc aac atg agc aaa aag    1440
Arg Phe Tyr Arg Thr Cys Lys Leu Val Gly Ile Asn Met Ser Lys Lys
465                 470                475                480 aag tcc tac ata aat aga act gga aca ttc gaa ttc aca agc ttt ttc    1488
Lys Ser Tyr Ile Asn Arg Thr Gly Thr Phe Glu Phe Thr Ser Phe Phe
                485                490                495 tac cgg tat ggt ttt gta gcc aat ttc agc atg gaa cta ccc agt ttt    1536
Tyr Arg Tyr Gly Phe Val Ala Asn Phe Ser Met Glu Leu Pro Ser Phe
            500                505                510 ggg gtt tcc gga ata aat gaa tct gca gac atg agc att gga gtg aca    1584
Gly Val Ser Gly Ile Asn Glu Ser Ala Asp Met Ser Ile Gly Val Thr
        515                520                525 gtc atc aaa aac aac atg ata aat aat gat ctc ggt cct gcc acg gca    1632
Val Ile Lys Asn Asn Met Ile Asn Asn Asp Leu Gly Pro Ala Thr Ala
    530                535                540 caa atg gca ctc caa ctc ttc att aag gat tat cgg tac aca tac cgg    1680
Gln Met Ala Leu Gln Leu Phe Ile Lys Asp Tyr Arg Tyr Thr Tyr Arg
545                 550                555                560 tgc cat aga ggt gat acc cag ata caa acc aga aga tct ttt gag ttg    1728
Cys His Arg Gly Asp Thr Gln Ile Gln Thr Arg Arg Ser Phe Glu Leu
                565                570                575 aag aaa ctg tgg gaa cag act cga tca aag act ggt cta ctg gta tca    1776
Lys Lys Leu Trp Glu Gln Thr Arg Ser Lys Thr Gly Leu Leu Val Ser
            580                585                590 gat ggg ggt cca aac cta tat aac atc aga aac cta cac atc ccg gaa    1824
Asp Gly Gly Pro Asn Leu Tyr Asn Ile Arg Asn Leu His Ile Pro Glu
        595                600                605 gtc tgt tta aaa tgg gag cta atg gat gaa gat tat aag ggg agg cta    1872
Val Cys Leu Lys Trp Glu Leu Met Asp Glu Asp Tyr Lys Gly Arg Leu
    610                615                620 tgc aat cca ttg aat cct ttc gtt agt cac aaa gaa att gaa tca gtc    1920
Cys Asn Pro Leu Asn Pro Phe Val Ser His Lys Glu Ile Glu Ser Val
625                 630                635                640 aac agt gca gta gta atg cct gcg cat ggc cct gcc aaa agc atg gag    1968
Asn Ser Ala Val Val Met Pro Ala His Gly Pro Ala Lys Ser Met Glu
                645                650                655 tat gat gct gtt gca aca aca cat tct tgg atc ccc aag agg aac cgg    2016
Tyr Asp Ala Val Ala Thr Thr His Ser Trp Ile Pro Lys Arg Asn Arg
            660                665                670 tcc ata ttg aac aca agc caa agg gga gta ctc gaa gat gag cag atg    2064
Ser Ile Leu Asn Thr Ser Gln Arg Gly Val Leu Glu Asp Glu Gln Met
        675                680                685 tat cag aaa tgc tgc aac ctg ttt gaa aaa ttc ttc ccc agc agc tca    2112
Tyr Gln Lys Cys Cys Asn Leu Phe Glu Lys Phe Phe Pro Ser Ser Ser
```

-continued

```
           690                     695                     700
tac aga aga cca gtc gga att tct agt atg gtt gag gcc atg gtg tcc    2160
Tyr Arg Arg Pro Val Gly Ile Ser Ser Met Val Glu Ala Met Val Ser
705                 710                     715                 720 agg gcc cgc att gat gca cga att gac ttc gaa tct gga cgg ata aag    2208
Arg Ala Arg Ile Asp Ala Arg Ile Asp Phe Glu Ser Gly Arg Ile Lys
                725                     730                     735 aag gat gag ttc gct gag atc atg aag atc tgt tcc acc att gaa gag    2256
Lys Asp Glu Phe Ala Glu Ile Met Lys Ile Cys Ser Thr Ile Glu Glu
            740                     745                     750 ctc aga cgg caa aaa tag                                            2274
Leu Arg Arg Gln Lys
            755
```

<210> SEQ ID NO 4
<211> LENGTH: 757
<212> TYPE: PRT
<213> ORGANISM: Influenza virus

<400> SEQUENCE: 4

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285
```

```
Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
                355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Arg Lys Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Val Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
                675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720
```

```
Arg Ala Arg Ile Asp Ala Arg Ile Asp Phe Glu Ser Gly Arg Ile Lys
            725                 730                 735
Lys Asp Glu Phe Ala Glu Ile Met Lys Ile Cys Ser Thr Ile Glu Glu
            740                 745                 750
Leu Arg Arg Gln Lys
        755

<210> SEQ ID NO 5
<211> LENGTH: 2151
<212> TYPE: DNA
<213> ORGANISM: Influenza virus
<220> FEATURE:
<221> NAME/KEY: CDS
<222> LOCATION: (1)..(2151)

<400> SEQUENCE: 5

```
tgc att gag agt aag ctt tct caa atg tcc aaa gaa gta aat gcc aga      768
Cys Ile Glu Ser Lys Leu Ser Gln Met Ser Lys Glu Val Asn Ala Arg
            245                 250                 255 atc gaa cca ttt tca aag aca aca ccc cga cca ctc aaa atg cca ggt      816
Ile Glu Pro Phe Ser Lys Thr Thr Pro Arg Pro Leu Lys Met Pro Gly
        260                 265                 270 ggt cca ccc tgc cat cag cga tct aaa ttc ttg cta atg gat gct ctg      864
Gly Pro Pro Cys His Gln Arg Ser Lys Phe Leu Leu Met Asp Ala Leu
            275                 280                 285 aaa ctg agc att gag gac cca agt cac gag gga gag gga ata cca cta      912
Lys Leu Ser Ile Glu Asp Pro Ser His Glu Gly Glu Gly Ile Pro Leu
    290                 295                 300 tat gat gca atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320 agt att gtt aaa cca cat gaa aag ggt ata aac ccg aac tat ctc caa     1008
Ser Ile Val Lys Pro His Glu Lys Gly Ile Asn Pro Asn Tyr Leu Gln
                325                 330                 335 act tgg aag caa gta tta gaa gaa ata caa gac ctt gag aac gaa gaa     1056
Thr Trp Lys Gln Val Leu Glu Glu Ile Gln Asp Leu Glu Asn Glu Glu
            340                 345                 350 agg acc ccc aag acc aag aat atg aaa aaa aca agc caa ttg aaa tgg     1104
Arg Thr Pro Lys Thr Lys Asn Met Lys Lys Thr Ser Gln Leu Lys Trp
        355                 360                 365 gca cta ggt gaa aat atg gca cca gag aaa gtg gat ttt gag gat tgt     1152
Ala Leu Gly Glu Asn Met Ala Pro Glu Lys Val Asp Phe Glu Asp Cys
    370                 375                 380 aaa gac atc aat gat tta aaa caa tat gac agt gat gag cca gaa gca     1200
Lys Asp Ile Asn Asp Leu Lys Gln Tyr Asp Ser Asp Glu Pro Glu Ala
385                 390                 395                 400 agg tct ctt gca agt tgg att caa agt gag ttc aac aaa gct tgt gag     1248
Arg Ser Leu Ala Ser Trp Ile Gln Ser Glu Phe Asn Lys Ala Cys Glu
                405                 410                 415 ctg aca gat tca agc tgg ata gag ctc gat gaa att ggg gag gat gtc     1296
Leu Thr Asp Ser Ser Trp Ile Glu Leu Asp Glu Ile Gly Glu Asp Val
            420                 425                 430 gcc cca ata gaa tac att gcg agc atg agg aga aat tat ttt act gct     1344
Ala Pro Ile Glu Tyr Ile Ala Ser Met Arg Arg Asn Tyr Phe Thr Ala
        435                 440                 445 gag att tcc cat tgt aga gca aca gaa tat ata ata aaa gga gtg tac     1392
Glu Ile Ser His Cys Arg Ala Thr Glu Tyr Ile Ile Lys Gly Val Tyr
    450                 455                 460 atc aac act gct cta ctc aat gca tcc tgt gct gcg atg gat gaa ttt     1440
Ile Asn Thr Ala Leu Leu Asn Ala Ser Cys Ala Ala Met Asp Glu Phe
465                 470                 475                 480 caa tta att ccg atg ata agt aaa tgc agg acc aaa gaa ggg aga agg     1488
Gln Leu Ile Pro Met Ile Ser Lys Cys Arg Thr Lys Glu Gly Arg Arg
                485                 490                 495 aaa aca aat tta tat gga ttc ata ata aag gga agg tcc cat tta aga     1536
Lys Thr Asn Leu Tyr Gly Phe Ile Ile Lys Gly Arg Ser His Leu Arg
            500                 505                 510 aat gat act gac gtg gtg aac ttt gta agt atg gaa ttt tct ctc act     1584
Asn Asp Thr Asp Val Val Asn Phe Val Ser Met Glu Phe Ser Leu Thr
        515                 520                 525 gat cca aga ttt gag cca cac aaa tgg gaa aaa tac tgc gtt cta gaa     1632
Asp Pro Arg Phe Glu Pro His Lys Trp Glu Lys Tyr Cys Val Leu Glu
    530                 535                 540 att gga gac atg ctt cta aga act gct gta ggt caa gtg tca aga ccc     1680
Ile Gly Asp Met Leu Leu Arg Thr Ala Val Gly Gln Val Ser Arg Pro
545                 550                 555                 560
```

| | | | | | | | | | | | | | | | |
|---|---|---|---|---|---|---|---|---|---|---|---|---|---|---|---|
| atg | ttt | ttg | tat | gta | agg | aca | aat | gga | acc | tct | aaa | att | aaa | atg | aaa | 1728 |
| Met | Phe | Leu | Tyr | Val | Arg | Thr | Asn | Gly | Thr | Ser | Lys | Ile | Lys | Met | Lys |
| | | | | 565 | | | | | 570 | | | | | 575 | |

```
atg ttt ttg tat gta agg aca aat gga acc tct aaa att aaa atg aaa      1728
Met Phe Leu Tyr Val Arg Thr Asn Gly Thr Ser Lys Ile Lys Met Lys
                565                 570                 575 tgg gga atg gaa atg agg cgc tgc ctc ctt cag tct ctg caa cag att      1776
Trp Gly Met Glu Met Arg Arg Cys Leu Leu Gln Ser Leu Gln Gln Ile
            580                 585                 590 gaa agc atg atc gaa gct gag tcc tca gtc aaa gaa aag gac atg acc      1824
Glu Ser Met Ile Glu Ala Glu Ser Ser Val Lys Glu Lys Asp Met Thr
        595                 600                 605 aaa gaa ttt ttt gag aac aaa tca gag aca tgg cct ata gga gag tcc      1872
Lys Glu Phe Phe Glu Asn Lys Ser Glu Thr Trp Pro Ile Gly Glu Ser
    610                 615                 620 ccc aaa gga gtg gaa gag ggc tca atc ggg aag gtt tgc agg acc tta      1920
Pro Lys Gly Val Glu Glu Gly Ser Ile Gly Lys Val Cys Arg Thr Leu
625                 630                 635                 640 tta gca aaa tct gtg ttt aac agt tta tat gca tct cca caa ctg gaa      1968
Leu Ala Lys Ser Val Phe Asn Ser Leu Tyr Ala Ser Pro Gln Leu Glu
                645                 650                 655 ggg ttt tca gct gaa tct agg aaa tta ctt ctc att gtt cag gct ctt      2016
Gly Phe Ser Ala Glu Ser Arg Lys Leu Leu Leu Ile Val Gln Ala Leu
            660                 665                 670 aag gat gac ctg gaa cct gga acc ttt gat att ggg ggg tta tat gaa      2064
Lys Asp Asp Leu Glu Pro Gly Thr Phe Asp Ile Gly Gly Leu Tyr Glu
        675                 680                 685 tca att gag gag tgc ctg att aat gat ccc tgg gtt ttg ctt aat gca      2112
Ser Ile Glu Glu Cys Leu Ile Asn Asp Pro Trp Val Leu Leu Asn Ala
    690                 695                 700 tct tgg ttc aac tcc ttc ctt aca cat gca ctg aag tag                  2151
Ser Trp Phe Asn Ser Phe Leu Thr His Ala Leu Lys
705                 710                 715
```

<210> SEQ ID NO 6
<211> LENGTH: 716
<212> TYPE: PRT
<213> ORGANISM: Influenza virus

<400> SEQUENCE: 6

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asn Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
```

-continued

```
                        165                 170                 175
Thr Ile Arg Gln Glu Met Ala Ser Arg Gly Leu Trp Asp Ser Phe Arg
            180                 185                 190
Gln Ser Glu Arg Gly Glu Thr Ile Glu Glu Arg Phe Glu Ile Thr
            195                 200                 205
Gly Thr Met Arg Lys Leu Ala Asn Tyr Ser Leu Pro Pro Asn Phe Ser
            210                 215                 220
Ser Leu Glu Asn Phe Arg Val Tyr Val Asp Gly Phe Glu Pro Asn Gly
225                 230                 235                 240
Cys Ile Glu Ser Lys Leu Ser Gln Met Ser Lys Glu Val Asn Ala Arg
                245                 250                 255
Ile Glu Pro Phe Ser Lys Thr Thr Pro Arg Pro Leu Lys Met Pro Gly
            260                 265                 270
Gly Pro Pro Cys His Gln Arg Ser Lys Phe Leu Leu Met Asp Ala Leu
            275                 280                 285
Lys Leu Ser Ile Glu Asp Pro Ser His Glu Gly Glu Gly Ile Pro Leu
            290                 295                 300
Tyr Asp Ala Ile Lys Cys Met Lys Thr Phe Phe Gly Trp Lys Glu Pro
305                 310                 315                 320
Ser Ile Val Lys Pro His Glu Lys Gly Ile Asn Pro Asn Tyr Leu Gln
                325                 330                 335
Thr Trp Lys Gln Val Leu Glu Glu Ile Gln Asp Leu Glu Asn Glu Glu
            340                 345                 350
Arg Thr Pro Lys Thr Lys Asn Met Lys Lys Thr Ser Gln Leu Lys Trp
            355                 360                 365
Ala Leu Gly Glu Asn Met Ala Pro Glu Lys Val Asp Phe Glu Asp Cys
            370                 375                 380
Lys Asp Ile Asn Asp Leu Lys Gln Tyr Asp Ser Asp Glu Pro Glu Ala
385                 390                 395                 400
Arg Ser Leu Ala Ser Trp Ile Gln Ser Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu Tyr Ile Ala Ser Met Arg Arg Asn Tyr Phe Thr Ala
            435                 440                 445
Glu Ile Ser His Cys Arg Ala Thr Glu Tyr Ile Ile Lys Gly Val Tyr
            450                 455                 460
Ile Asn Thr Ala Leu Leu Asn Ala Ser Cys Ala Ala Met Asp Glu Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
            515                 520                 525
Asp Pro Arg Phe Glu Pro His Lys Trp Glu Lys Tyr Cys Val Leu Glu
            530                 535                 540
Ile Gly Asp Met Leu Leu Arg Thr Ala Val Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
```

```
Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Lys Asp Asp Leu Glu Pro Gly Thr Phe Asp Ile Gly Gly Leu Tyr Glu
    675                 680                 685

Ser Ile Glu Glu Cys Leu Ile Asn Asp Pro Trp Val Leu Leu Asn Ala
690                 695                 700

Ser Trp Phe Asn Ser Phe Leu Thr His Ala Leu Lys
705                 710                 715

<210> SEQ ID NO 7
<211> LENGTH: 838
<212> TYPE: DNA
<213> ORGANISM: Influenza virus
<220> FEATURE:
<221> NAME/KEY: CDS
<222> LOCATION: (1)..(657)

<400> SEQUENCE: 7 atg gat tcc aac act gtg tca agc ttt cag gta gac tgt ttt ctt tgg      48
Met Asp Ser Asn Thr Val Ser Ser Phe Gln Val Asp Cys Phe Leu Trp
1               5                  10                  15 cat gtc cgc aaa cga ttc gca gac caa gaa ctg ggt gat gcc cca ttc      96
His Val Arg Lys Arg Phe Ala Asp Gln Glu Leu Gly Asp Ala Pro Phe
            20                  25                  30 ctt gac cgg ctt cgc cga gac cag aag tcc cta agg gga aga ggt agc     144
Leu Asp Arg Leu Arg Arg Asp Gln Lys Ser Leu Arg Gly Arg Gly Ser
        35                  40                  45 act ctt ggt ctg gac atc gaa aca gcc act cat gca gga aag cag ata     192
Thr Leu Gly Leu Asp Ile Glu Thr Ala Thr His Ala Gly Lys Gln Ile
    50                  55                  60 gtg gag cag att ctg gaa aag gaa tca gat gag gca ctt aaa atg acc     240
Val Glu Gln Ile Leu Glu Lys Glu Ser Asp Glu Ala Leu Lys Met Thr
65                  70                  75                  80 att gcc tct gtt cct act tca ctc tac tta act gac atg act ctt gat     288
Ile Ala Ser Val Pro Thr Ser Leu Tyr Leu Thr Asp Met Thr Leu Asp
                85                  90                  95 gag atg tca aga gac tgg ttc atg ctc atg ccc aag caa aaa gta aca     336
Glu Met Ser Arg Asp Trp Phe Met Leu Met Pro Lys Gln Lys Val Thr
            100                 105                 110 ggc tcc cta tgt ata aga atg gac cag gca atc atg gat aag aac atc     384
Gly Ser Leu Cys Ile Arg Met Asp Gln Ala Ile Met Asp Lys Asn Ile
        115                 120                 125 ata ctt aaa gca aac ttt agt gtg att ttc gaa ggg ctg gaa aca cta     432
Ile Leu Lys Ala Asn Phe Ser Val Ile Phe Glu Gly Leu Glu Thr Leu
    130                 135                 140 ata cta ctt aga gcc ttc acc gaa gaa gga gca gtt gtt ggc gaa att     480
Ile Leu Leu Arg Ala Phe Thr Glu Glu Gly Ala Val Val Gly Glu Ile
145                 150                 155                 160 tca cca tta cct tct ctt cca gga cat act aat gag gat gtc aaa aat     528
Ser Pro Leu Pro Ser Leu Pro Gly His Thr Asn Glu Asp Val Lys Asn
                165                 170                 175 gca att ggg gtc ctc atc gga gga ctt aaa tgg aat gat aat acg gtt     576
Ala Ile Gly Val Leu Ile Gly Gly Leu Lys Trp Asn Asp Asn Thr Val
```

```
Ala Ile Gly Val Leu Ile Gly Gly Leu Lys Trp Asn Asp Asn Thr Val
        180                 185                 190 aga atc tct gaa act cta cag aga ttc gct tgg aga agc agt cat gag    624
Arg Ile Ser Glu Thr Leu Gln Arg Phe Ala Trp Arg Ser Ser His Glu
        195                 200                 205 aat ggg aga cct tca ttc cct tca aag cag aaa tgaaaaatgg agagaacaat  677
Asn Gly Arg Pro Ser Phe Pro Ser Lys Gln Lys
        210                 215 taagccagaa atttgaagaa ataagatggt tgattgaaga agtgcgacat agattgaaaa   737
atacagaaaa tagttttgaa caaataacat ttatgcaagc cttacaacta ttgcttgaag   797
tagaacaaga gataagaact ttctcgtttc agcttattta a                       838

<210> SEQ ID NO 8
<211> LENGTH: 219
<212> TYPE: PRT
<213> ORGANISM: Influenza virus

<400> SEQUENCE: 8

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
65                  70                  75                  80

Ile Ala Ser Val Pro Thr Ser Leu Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Gly Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Ser Lys Gln Lys
    210                 215

<210> SEQ ID NO 9
<211> LENGTH: 1497
<212> TYPE: DNA
<213> ORGANISM: Influenza virus
<220> FEATURE:
<221> NAME/KEY: CDS
<222> LOCATION: (1)..(1497)

<400> SEQUENCE: 9 atg gcg tct caa ggc acc aaa cga tcc tat gaa cag atg gaa act gat     48
Met Ala Ser Gln Gly Thr Lys Arg Ser Tyr Glu Gln Met Glu Thr Asp
```

```
1               5                  10                 15
ggg gaa cgc cag aat gca act gaa atc aga gca tct gtc gga agg atg         96
Gly Glu Arg Gln Asn Ala Thr Glu Ile Arg Ala Ser Val Gly Arg Met
             20                  25                 30 gtg gga gga atc ggc cga ttt tat gtt cag atg tgt act gag ctt aaa        144
Val Gly Gly Ile Gly Arg Phe Tyr Val Gln Met Cys Thr Glu Leu Lys
         35                  40                 45 cta aac gac cat gaa ggg cgg ctg att cag aac agc ata aca ata gaa        192
Leu Asn Asp His Glu Gly Arg Leu Ile Gln Asn Ser Ile Thr Ile Glu
     50                  55                 60 agg atg gta ctt tcg gca ttc gac gaa aga aga aac aag tat ctc gag        240
Arg Met Val Leu Ser Ala Phe Asp Glu Arg Arg Asn Lys Tyr Leu Glu
65                  70                 75                 80 gag cat ccc agt gct ggg aaa gac cct aag aaa acg gga ggc ccg ata        288
Glu His Pro Ser Ala Gly Lys Asp Pro Lys Lys Thr Gly Gly Pro Ile
                 85                  90                 95 tac aga agg aaa gat ggg aaa tgg atg agg gaa ctc atc ctc cat gat        336
Tyr Arg Arg Lys Asp Gly Lys Trp Met Arg Glu Leu Ile Leu His Asp
             100                 105                110 aaa gaa gaa atc atg aga atc tgg cgt cag gcc aac aat ggt gaa gac        384
Lys Glu Glu Ile Met Arg Ile Trp Arg Gln Ala Asn Asn Gly Glu Asp
         115                 120                125 gct act gct ggt ctt act cat atg atg atc tgg cac tcc aat ctc aat        432
Ala Thr Ala Gly Leu Thr His Met Met Ile Trp His Ser Asn Leu Asn
     130                 135                140 gac acc aca tac caa aga aca agg gct ctt gtt cgg act ggg atg gat        480
Asp Thr Thr Tyr Gln Arg Thr Arg Ala Leu Val Arg Thr Gly Met Asp
145                 150                 155                160 ccc aga atg tgc tct ctg atg caa ggc tca acc ctc cca cgg aga tct        528
Pro Arg Met Cys Ser Leu Met Gln Gly Ser Thr Leu Pro Arg Arg Ser
                 165                 170                175 gga gcc gct ggt gct gca gta aaa ggt gtt gga aca atg gta atg gaa        576
Gly Ala Ala Gly Ala Ala Val Lys Gly Val Gly Thr Met Val Met Glu
             180                 185                190 ctc atc aga atg atc aaa cgc gga ata aat gat cgg aat ttc tgg aga        624
Leu Ile Arg Met Ile Lys Arg Gly Ile Asn Asp Arg Asn Phe Trp Arg
         195                 200                205 ggt gaa aat ggt cga aaa acc aga att gct tat gaa aga atg tgc aat        672
Gly Glu Asn Gly Arg Lys Thr Arg Ile Ala Tyr Glu Arg Met Cys Asn
     210                 215                220 atc ctc aaa ggg aaa ttt cag aca gca gca caa cgg gct atg atg gac        720
Ile Leu Lys Gly Lys Phe Gln Thr Ala Ala Gln Arg Ala Met Met Asp
225                 230                 235                240 cag gtg agg gaa ggc cgc aat cct gga aac gct gag att gag gat ctc        768
Gln Val Arg Glu Gly Arg Asn Pro Gly Asn Ala Glu Ile Glu Asp Leu
                 245                 250                255 att ttc ttg gca cga tca gca ctt att ttg aga gga tca gta gcc cat        816
Ile Phe Leu Ala Arg Ser Ala Leu Ile Leu Arg Gly Ser Val Ala His
             260                 265                270 aaa tca tgc cta cct gcc tgt gtt tat ggc ctt gca ata acc agt ggg        864
Lys Ser Cys Leu Pro Ala Cys Val Tyr Gly Leu Ala Ile Thr Ser Gly
         275                 280                285 tat gac ttt gag aag gaa gga tac tct ctg gtt gga att gat cct ttc        912
Tyr Asp Phe Glu Lys Glu Gly Tyr Ser Leu Val Gly Ile Asp Pro Phe
     290                 295                300 aaa cta ctc cag aac agt caa att ttc agt cta atc aga cca aaa gaa        960
Lys Leu Leu Gln Asn Ser Gln Ile Phe Ser Leu Ile Arg Pro Lys Glu
305                 310                 315                320 aac cca gca cac aag agc cag ttg gtg tgg atg gca tgc cat tct gca       1008
Asn Pro Ala His Lys Ser Gln Leu Val Trp Met Ala Cys His Ser Ala
```

```
                325                 330                 335
gca ttt gag gac ctg aga gtt tta aat ttc att aga gga acc aaa gta     1056
Ala Phe Glu Asp Leu Arg Val Leu Asn Phe Ile Arg Gly Thr Lys Val
            340                 345                 350 atc cca aga gga cag tta aca acc aga gga gtt caa att gct tca aat     1104
Ile Pro Arg Gly Gln Leu Thr Thr Arg Gly Val Gln Ile Ala Ser Asn
                355                 360                 365 gaa aac atg gag aca ata aat tct agc aca ctt gaa ctg aga agc aaa     1152
Glu Asn Met Glu Thr Ile Asn Ser Ser Thr Leu Glu Leu Arg Ser Lys
        370                 375                 380 tat tgg gca ata agg acc aga agc gga gga aac acc agt caa cag aga     1200
Tyr Trp Ala Ile Arg Thr Arg Ser Gly Gly Asn Thr Ser Gln Gln Arg
385                 390                 395                 400 gca tct gca gga cag ata agt gtg caa cct act ttc tca gta cag aga     1248
Ala Ser Ala Gly Gln Ile Ser Val Gln Pro Thr Phe Ser Val Gln Arg
                405                 410                 415 aat cta ccc ttt gag aga gcg acc att atg gct gca ttc act ggt aac     1296
Asn Leu Pro Phe Glu Arg Ala Thr Ile Met Ala Ala Phe Thr Gly Asn
            420                 425                 430 act gaa ggg agg act tcc gac atg aga acg gaa atc ata agg atg atg     1344
Thr Glu Gly Arg Thr Ser Asp Met Arg Thr Glu Ile Ile Arg Met Met
                435                 440                 445 gaa aat gcc aaa tca gaa gat gtg tct ttc cag ggg cgg gga gtc ttc     1392
Glu Asn Ala Lys Ser Glu Asp Val Ser Phe Gln Gly Arg Gly Val Phe
        450                 455                 460 gag ctc tcg gac gaa aag gca acg aac ccg atc gtg cct tcc ttt gac     1440
Glu Leu Ser Asp Glu Lys Ala Thr Asn Pro Ile Val Pro Ser Phe Asp
465                 470                 475                 480 atg agc aat gaa ggg tct tat ttc ttc gga gac aat gct gag gag ttt     1488
Met Ser Asn Glu Gly Ser Tyr Phe Phe Gly Asp Asn Ala Glu Glu Phe
                485                 490                 495 gac agt taa                                                         1497
Asp Ser <210> SEQ ID NO 10
<211> LENGTH: 498
<212> TYPE: PRT
<213> ORGANISM: Influenza virus

<400> SEQUENCE: 10

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140
```

```
Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
            165                 170                 175

Gly Ala Ala Gly Ala Ala Val Lys Gly Val Gly Thr Met Val Met Glu
        180                 185                 190

Leu Ile Arg Met Ile Lys Arg Gly Ile Asn Asp Arg Asn Phe Trp Arg
    195                 200                 205

Gly Glu Asn Gly Arg Lys Thr Arg Ile Ala Tyr Glu Arg Met Cys Asn
210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
            245                 250                 255

Ile Phe Leu Ala Arg Ser Ala Leu Ile Leu Arg Gly Ser Val Ala His
        260                 265                 270

Lys Ser Cys Leu Pro Ala Cys Val Tyr Gly Leu Ala Ile Thr Ser Gly
    275                 280                 285

Tyr Asp Phe Glu Lys Glu Gly Tyr Ser Leu Val Gly Ile Asp Pro Phe
290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
            325                 330                 335

Ala Phe Glu Asp Leu Arg Val Leu Asn Phe Ile Arg Gly Thr Lys Val
        340                 345                 350

Ile Pro Arg Gly Gln Leu Thr Thr Arg Gly Val Gln Ile Ala Ser Asn
    355                 360                 365

Glu Asn Met Glu Thr Ile Asn Ser Ser Thr Leu Glu Leu Arg Ser Lys
370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
            405                 410                 415

Asn Leu Pro Phe Glu Arg Ala Thr Ile Met Ala Ala Phe Thr Gly Asn
        420                 425                 430

Thr Glu Gly Arg Thr Ser Asp Met Arg Thr Glu Ile Ile Arg Met Met
    435                 440                 445

Glu Asn Ala Lys Ser Glu Asp Val Ser Phe Gln Gly Arg Gly Val Phe
450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
            485                 490                 495

Asp Ser

<210> SEQ ID NO 11
<211> LENGTH: 1413
<212> TYPE: DNA
<213> ORGANISM: Influenza virus
<220> FEATURE:
<221> NAME/KEY: CDS
<222> LOCATION: (1)..(1413)

<400> SEQUENCE: 11 atg aat cca aat caa aag ata ata gca att gga ttt gca tca ttg ggg      48
```

```
    Met Asn Pro Asn Gln Lys Ile Ile Ala Ile Gly Phe Ala Ser Leu Gly
    1               5                   10                  15 ata tta atc att aat gtc att ctc cat gta gtc agc att ata gta aca    96
    Ile Leu Ile Ile Asn Val Ile Leu His Val Val Ser Ile Ile Val Thr
                    20                  25                  30 gta ctg gtc ctc aat aac aat aga aca gat ctg aac tgc aaa ggg acg   144
    Val Leu Val Leu Asn Asn Asn Arg Thr Asp Leu Asn Cys Lys Gly Thr
                35                  40                  45 atc ata aga aag tac aat gaa aca gta aga gta gaa aaa att act caa   192
    Ile Ile Arg Lys Tyr Asn Glu Thr Val Arg Val Glu Lys Ile Thr Gln
            50                  55                  60 tgg tat aat acc agt aca att aag tac ata gag aga cct tca aat gaa   240
    Trp Tyr Asn Thr Ser Thr Ile Lys Tyr Ile Glu Arg Pro Ser Asn Glu
    65                  70                  75                  80 tac tac atg aac aac act gaa cca ctt tgt gag gcc caa ggc ttt gca   288
    Tyr Tyr Met Asn Asn Thr Glu Pro Leu Cys Glu Ala Gln Gly Phe Ala
                    85                  90                  95 cca ttt tcc aaa gat aat gga ata cga att ggg tcg aga ggc cat gtt   336
    Pro Phe Ser Lys Asp Asn Gly Ile Arg Ile Gly Ser Arg Gly His Val
                100                 105                 110 ttt gtg ata aga gaa cct ttt gta tca tgt tcg ccc tca gaa tgt aga   384
    Phe Val Ile Arg Glu Pro Phe Val Ser Cys Ser Pro Ser Glu Cys Arg
            115                 120                 125 acc ttt ttc ctc aca cag ggc tca tta ctc aat gac aaa cat tct aac   432
    Thr Phe Phe Leu Thr Gln Gly Ser Leu Leu Asn Asp Lys His Ser Asn
    130                 135                 140 ggc aca gta aag gac cga agt ccg tat agg act ttg atg agt gtc aaa   480
    Gly Thr Val Lys Asp Arg Ser Pro Tyr Arg Thr Leu Met Ser Val Lys
    145                 150                 155                 160 ata ggg caa tca cct aat gta tat caa gct aga ttt gaa tcg gta gca   528
    Ile Gly Gln Ser Pro Asn Val Tyr Gln Ala Arg Phe Glu Ser Val Ala
                    165                 170                 175 tgg tca gca aca gca tgc cat gat gga aaa aaa tgg atg aca gtt gga   576
    Trp Ser Ala Thr Ala Cys His Asp Gly Lys Lys Trp Met Thr Val Gly
                180                 185                 190 gtc aca ggg ccc gac aat caa gca att gca gta gtg aac tat gga ggt   624
    Val Thr Gly Pro Asp Asn Gln Ala Ile Ala Val Val Asn Tyr Gly Gly
            195                 200                 205 gtt ccg gtt gat att att aat tca tgg gca ggg gat att tta aga acc   672
    Val Pro Val Asp Ile Ile Asn Ser Trp Ala Gly Asp Ile Leu Arg Thr
    210                 215                 220 caa gaa tca tca tgc acc tgc att aaa gga gac tgt tat tgg gta atg   720
    Gln Glu Ser Ser Cys Thr Cys Ile Lys Gly Asp Cys Tyr Trp Val Met
    225                 230                 235                 240 act gat gga ccg gca aat agg caa gct aaa tat agg ata ttc aaa gca   768
    Thr Asp Gly Pro Ala Asn Arg Gln Ala Lys Tyr Arg Ile Phe Lys Ala
                    245                 250                 255 aaa gat gga aga gta att gga cag act gat ata agt ttc aat ggg gga   816
    Lys Asp Gly Arg Val Ile Gly Gln Thr Asp Ile Ser Phe Asn Gly Gly
                260                 265                 270 cac ata gag gag tgt tct tgt tac ccc aat gaa ggg aag gtg gaa tgc   864
    His Ile Glu Glu Cys Ser Cys Tyr Pro Asn Glu Gly Lys Val Glu Cys
            275                 280                 285 ata tgc agg gac aat tgg act gga aca aat aga cca gtt ctg gta ata   912
    Ile Cys Arg Asp Asn Trp Thr Gly Thr Asn Arg Pro Val Leu Val Ile
    290                 295                 300 tct tct gat cta tcg tac aca gtt gga tat ttg tgt gct ggc att ccc   960
    Ser Ser Asp Leu Ser Tyr Thr Val Gly Tyr Leu Cys Ala Gly Ile Pro
    305                 310                 315                 320 act gac act cct agg gga gag gat agt caa ttc aca ggc tca tgt aca  1008
```

```
Thr Asp Thr Pro Arg Gly Glu Asp Ser Gln Phe Thr Gly Ser Cys Thr
                325                 330                 335 agt cct ttg gga aat aaa gga tac ggt gta aaa ggt ttc ggg ttt cga      1056
Ser Pro Leu Gly Asn Lys Gly Tyr Gly Val Lys Gly Phe Gly Phe Arg
            340                 345                 350 caa gga act gac gta tgg gcc gga agg aca att agt agg act tca aga      1104
Gln Gly Thr Asp Val Trp Ala Gly Arg Thr Ile Ser Arg Thr Ser Arg
            355                 360                 365 tca gga ttc gaa ata ata aaa atc agg aat ggt tgg aca cag aac agt      1152
Ser Gly Phe Glu Ile Ile Lys Ile Arg Asn Gly Trp Thr Gln Asn Ser
        370                 375                 380 aaa gac caa atc agg agg caa gtg att atc gat gac cca aat tgg tca      1200
Lys Asp Gln Ile Arg Arg Gln Val Ile Ile Asp Asp Pro Asn Trp Ser
385                 390                 395                 400 gga tat agc ggt tct ttc aca ttg ccg gtt gaa cta aca aaa aag gga      1248
Gly Tyr Ser Gly Ser Phe Thr Leu Pro Val Glu Leu Thr Lys Lys Gly
                405                 410                 415 tgt ttg gtc ccc tgt ttc tgg gtt gaa atg att aga ggt aaa cct gaa      1296
Cys Leu Val Pro Cys Phe Trp Val Glu Met Ile Arg Gly Lys Pro Glu
            420                 425                 430 gaa aca aca ata tgg acc tct agt agc tcc att gtg atg tgt gga gta      1344
Glu Thr Thr Ile Trp Thr Ser Ser Ser Ser Ile Val Met Cys Gly Val
            435                 440                 445 gat cat aaa att gcc agt tgg tca tgg cac gat gga gct att ctt ccc      1392
Asp His Lys Ile Ala Ser Trp Ser Trp His Asp Gly Ala Ile Leu Pro
450                 455                 460 ttt gac atc gat aag atg taa                                          1413
Phe Asp Ile Asp Lys Met
465                 470

<210> SEQ ID NO 12
<211> LENGTH: 470
<212> TYPE: PRT
<213> ORGANISM: Influenza virus

<400> SEQUENCE: 12

Met Asn Pro Asn Gln Lys Ile Ile Ala Ile Gly Phe Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Lys Tyr Asn Glu Thr Val Arg Val Glu Lys Ile Thr Gln
    50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175
```

```
Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
            195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
                260                 265                 270

His Ile Glu Glu Cys Ser Cys Tyr Pro Asn Glu Gly Lys Val Glu Cys
            275                 280                 285

Ile Cys Arg Asp Asn Trp Thr Gly Thr Asn Arg Pro Val Leu Val Ile
        290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470

<210> SEQ ID NO 13
<211> LENGTH: 982
<212> TYPE: DNA
<213> ORGANISM: Influenza virus
<220> FEATURE:
<221> NAME/KEY: CDS
<222> LOCATION: (1)..(756)

<400> SEQUENCE: 13 atg agt ctt cta acc gag gtc gaa acg tac gtt ctc tct atc gta cca      48
Met Ser Leu Leu Thr Glu Val Glu Thr Tyr Val Leu Ser Ile Val Pro
1               5                   10                  15 tca ggc ccc ctc aaa gcc gag atc gcg cag aga ctt gaa gat gtc ttt      96
Ser Gly Pro Leu Lys Ala Glu Ile Ala Gln Arg Leu Glu Asp Val Phe
                20                  25                  30 gca gga aag aac acc gat ctt gag gca ctc atg gaa tgg cta aag aca     144
Ala Gly Lys Asn Thr Asp Leu Glu Ala Leu Met Glu Trp Leu Lys Thr
            35                  40                  45
```

```
aga cca atc ctg tca cct ctg act aaa ggg att tta gga ttt gta ttc    192
Arg Pro Ile Leu Ser Pro Leu Thr Lys Gly Ile Leu Gly Phe Val Phe
    50              55                  60 acg ctc acc gtg ccc agt gag cga gga ctg cag cgt aga cgc ttt gtc    240
Thr Leu Thr Val Pro Ser Glu Arg Gly Leu Gln Arg Arg Arg Phe Val
65              70                  75                  80 caa aat gcc ctt agt gga aac gga gat cca aac aac atg gac aga gca    288
Gln Asn Ala Leu Ser Gly Asn Gly Asp Pro Asn Asn Met Asp Arg Ala
                85                  90                  95 gta aaa ctg tac agg aag ctt aaa aga gaa ata aca ttc cat ggg gca    336
Val Lys Leu Tyr Arg Lys Leu Lys Arg Glu Ile Thr Phe His Gly Ala
            100                 105                 110 aaa gag gta gca ctc agc tat tcc act ggt gca cta gcc agc tgc atg    384
Lys Glu Val Ala Leu Ser Tyr Ser Thr Gly Ala Leu Ala Ser Cys Met
        115                 120                 125 gga ctc ata tac aac aga atg gga act gtt aca acc gaa gtg gca ttt    432
Gly Leu Ile Tyr Asn Arg Met Gly Thr Val Thr Thr Glu Val Ala Phe
    130                 135                 140 ggc ctg gta tgc gcc aca tgt gaa cag att gct gat tcc cag cat cga    480
Gly Leu Val Cys Ala Thr Cys Glu Gln Ile Ala Asp Ser Gln His Arg
145                 150                 155                 160 gct cac agg cag atg gtg aca aca acc aac cca ttg atc aga cat gaa    528
Ala His Arg Gln Met Val Thr Thr Thr Asn Pro Leu Ile Arg His Glu
                165                 170                 175 aac aga atg gta tta gcc agt acc acg gct aaa gcc atg gaa cag atg    576
Asn Arg Met Val Leu Ala Ser Thr Thr Ala Lys Ala Met Glu Gln Met
            180                 185                 190 gca gga tcg agt gag cag gca gca gag gcc atg gag gtt gct agt agg    624
Ala Gly Ser Ser Glu Gln Ala Ala Glu Ala Met Glu Val Ala Ser Arg
        195                 200                 205 gct agg cag atg gta cag gca atg aga acc att ggg acc cac cct agc    672
Ala Arg Gln Met Val Gln Ala Met Arg Thr Ile Gly Thr His Pro Ser
    210                 215                 220 tcc agt gcc ggt ttg aaa gat gat ctc ctt gaa aat tta cag gcc tac    720
Ser Ser Ala Gly Leu Lys Asp Asp Leu Leu Glu Asn Leu Gln Ala Tyr
225                 230                 235                 240 cag aaa cgg atg gga gtg caa atg cag cga ttc aag tgatcctctc         766
Gln Lys Arg Met Gly Val Gln Met Gln Arg Phe Lys
                245                 250 gttattgcag caagtatcat tgggatcttg cacttgatat tgtggattct tgatcgtctt   826
ttcttcaaat tcatttatcg tcgccttaaa tacgggttga aaagagggcc ttctacggaa   886
ggagtacctg agtctatgag gaagaatat cggcaggaac agcagaatgc tgtggatgtt    946
gacgatggtc atttgtcaa catagagctg gagtaa                              982

<210> SEQ ID NO 14
<211> LENGTH: 252
<212> TYPE: PRT
<213> ORGANISM: Influenza virus

<400> SEQUENCE: 14

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60
```

```
Thr Leu Thr Val Pro Ser Glu Arg Gly Leu Gln Arg Arg Phe Val
 65                  70                  75                  80

Gln Asn Ala Leu Ser Gly Asn Gly Asp Pro Asn Asn Met Asp Arg Ala
                 85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Glu Val Ala Phe
130                 135                 140

Gly Leu Val Cys Ala Thr Cys Glu Gln Ile Ala Asp Ser Gln His Arg
145                 150                 155                 160

Ala His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 15
<211> LENGTH: 1698
<212> TYPE: DNA
<213> ORGANISM: Influenza virus
<220> FEATURE:
<221> NAME/KEY: CDS
<222> LOCATION: (1)..(1698)

<400> SEQUENCE: 15 atg aag aca acc att att ttg ata cta cta acc cat tgg gcc tac agt      48
Met Lys Thr Thr Ile Ile Leu Ile Leu Leu Thr His Trp Ala Tyr Ser
1               5                   10                  15 caa aac cca atc agt ggc aac aac aca gcc aca ctg tgt ctg gga cac      96
Gln Asn Pro Ile Ser Gly Asn Asn Thr Ala Thr Leu Cys Leu Gly His
            20                  25                  30 cat gca gta gca aat gga aca ttg gta aaa aca atg agt gat gat caa     144
His Ala Val Ala Asn Gly Thr Leu Val Lys Thr Met Ser Asp Asp Gln
        35                  40                  45 att gag gtg aca aat gct aca gaa tta gtt cag agc att tca atg ggg     192
Ile Glu Val Thr Asn Ala Thr Glu Leu Val Gln Ser Ile Ser Met Gly
    50                  55                  60 aaa ata tgc aac aaa tca tat aga att cta gat gga aga aat tgc aca     240
Lys Ile Cys Asn Lys Ser Tyr Arg Ile Leu Asp Gly Arg Asn Cys Thr
65                  70                  75                  80 tta ata gat gca atg cta gga gac ccc cac tgt gac gcc ttt cag tat     288
Leu Ile Asp Ala Met Leu Gly Asp Pro His Cys Asp Ala Phe Gln Tyr
                85                  90                  95 gag agt tgg gac ctc ttc ata gaa aga agc aac gct ttc agc aat tgc     336
Glu Ser Trp Asp Leu Phe Ile Glu Arg Ser Asn Ala Phe Ser Asn Cys
            100                 105                 110 tac cca tat gac atc cct gac tat gca tcg ctc cga tcc att gta gca     384
Tyr Pro Tyr Asp Ile Pro Asp Tyr Ala Ser Leu Arg Ser Ile Val Ala
        115                 120                 125 tcc tca gga aca ttg gaa ttc aca gca gag gga ttc aca tgg aca ggt     432
```

-continued

```
            Ser Ser Gly Thr Leu Glu Phe Thr Ala Glu Gly Phe Thr Trp Thr Gly
                130                 135                 140 gtc act caa aac gga aga agt gga gcc tgc aaa agg gga tca gcc gat        480
Val Thr Gln Asn Gly Arg Ser Gly Ala Cys Lys Arg Gly Ser Ala Asp
145                 150                 155                 160 agt ttc ttt agc cga ctg aat tgg cta aca aaa tct gga agc tct tac        528
Ser Phe Phe Ser Arg Leu Asn Trp Leu Thr Lys Ser Gly Ser Ser Tyr
                165                 170                 175 ccc aca ttg aat gtg aca atg cct aac aat aaa aat ttc gac aag cta        576
Pro Thr Leu Asn Val Thr Met Pro Asn Asn Lys Asn Phe Asp Lys Leu
            180                 185                 190 tac atc tgg ggg att cat cac ccg agc tca aat caa gag cag aca aaa        624
Tyr Ile Trp Gly Ile His His Pro Ser Ser Asn Gln Glu Gln Thr Lys
        195                 200                 205 ttg tac atc caa gaa tca gga cga gta aca gtc tca aca aaa aga agt        672
Leu Tyr Ile Gln Glu Ser Gly Arg Val Thr Val Ser Thr Lys Arg Ser
210                 215                 220 caa caa aca ata atc cct aac atc gga tct aga ccg ttg gtc aga ggt        720
Gln Gln Thr Ile Ile Pro Asn Ile Gly Ser Arg Pro Leu Val Arg Gly
225                 230                 235                 240 caa tca ggc agg ata agc ata tac tgg acc att gta aaa cct gga gat        768
Gln Ser Gly Arg Ile Ser Ile Tyr Trp Thr Ile Val Lys Pro Gly Asp
                245                 250                 255 atc cta atg ata aac agt aat ggc aac tta gtt gca ccg cgg gga tat        816
Ile Leu Met Ile Asn Ser Asn Gly Asn Leu Val Ala Pro Arg Gly Tyr
            260                 265                 270 ttt aaa ttg aaa aca ggg aaa agc tct gta atg aga tca gat gca ccc        864
Phe Lys Leu Lys Thr Gly Lys Ser Ser Val Met Arg Ser Asp Ala Pro
        275                 280                 285 ata gac att tgt gtg tct gaa tgt att aca cca aat gga agc atc tcc        912
Ile Asp Ile Cys Val Ser Glu Cys Ile Thr Pro Asn Gly Ser Ile Ser
290                 295                 300 aac gac aag cca ttc caa aat gtg aac aaa gtt aca tat gga aaa tgc        960
Asn Asp Lys Pro Phe Gln Asn Val Asn Lys Val Thr Tyr Gly Lys Cys
305                 310                 315                 320 cct aag tat atc agg caa aac act tta aag ctg gcc act ggg atg agg       1008
Pro Lys Tyr Ile Arg Gln Asn Thr Leu Lys Leu Ala Thr Gly Met Arg
                325                 330                 335 aat gta cca gaa aag caa acc aga gga atc ttt gga gca ata gcg gga       1056
Asn Val Pro Glu Lys Gln Thr Arg Gly Ile Phe Gly Ala Ile Ala Gly
            340                 345                 350 ttc atc gaa aac ggc tgg gaa gga atg gtt gat ggg tgg tat ggg ttc       1104
Phe Ile Glu Asn Gly Trp Glu Gly Met Val Asp Gly Trp Tyr Gly Phe
        355                 360                 365 cga tat caa aac tct gaa gga aca ggg caa gct gca gat cta aag agc       1152
Arg Tyr Gln Asn Ser Glu Gly Thr Gly Gln Ala Ala Asp Leu Lys Ser
370                 375                 380 act caa gca gcc atc gac cag att aat gga aag tta aac aga gtg att       1200
Thr Gln Ala Ala Ile Asp Gln Ile Asn Gly Lys Leu Asn Arg Val Ile
385                 390                 395                 400 gaa aga acc aat gag aaa ttc cat caa ata gag aag gaa ttc tca gaa       1248
Glu Arg Thr Asn Glu Lys Phe His Gln Ile Glu Lys Glu Phe Ser Glu
                405                 410                 415 gta gaa gga aga att cag gac ctg gag aaa tat gta gaa gac acc aaa       1296
Val Glu Gly Arg Ile Gln Asp Leu Glu Lys Tyr Val Glu Asp Thr Lys
            420                 425                 430 ata gac cta tgg tcc tac aat gca gaa ttg ctg gtg gct cta gaa aat       1344
Ile Asp Leu Trp Ser Tyr Asn Ala Glu Leu Leu Val Ala Leu Glu Asn
        435                 440                 445 caa cat aca att gac tta aca gat gca gaa atg aat aaa tta ttt gag       1392
```

```
Gln His Thr Ile Asp Leu Thr Asp Ala Glu Met Asn Lys Leu Phe Glu
    450                 455                 460 aag act aga cgc cag tta aga gaa aac gca gaa gac atg gga ggt gga      1440
Lys Thr Arg Arg Gln Leu Arg Glu Asn Ala Glu Asp Met Gly Gly Gly
465                 470                 475                 480 tgt ttc aag att tac cac aaa tgt gat aat gca tgc att gga tca ata      1488
Cys Phe Lys Ile Tyr His Lys Cys Asp Asn Ala Cys Ile Gly Ser Ile
                485                 490                 495 aga act ggg aca tat gac cat tac ata tac aga gat gaa gca tta aac      1536
Arg Thr Gly Thr Tyr Asp His Tyr Ile Tyr Arg Asp Glu Ala Leu Asn
            500                 505                 510 aac cga ttt cag atc aaa ggt gta gag ttg aaa tca ggc tac aaa gat      1584
Asn Arg Phe Gln Ile Lys Gly Val Glu Leu Lys Ser Gly Tyr Lys Asp
        515                 520                 525 tgg ata ttg tgg att tca ttc gcc ata tca tgc ttc tta att tgc gtt      1632
Trp Ile Leu Trp Ile Ser Phe Ala Ile Ser Cys Phe Leu Ile Cys Val
    530                 535                 540 gtt cta ttg ggt ttc att atg tgg gct tgc caa aga ggc aac atc aga      1680
Val Leu Leu Gly Phe Ile Met Trp Ala Cys Gln Arg Gly Asn Ile Arg
545                 550                 555                 560 tgc aac att tgc att tga                                              1698
Cys Asn Ile Cys Ile
                565

<210> SEQ ID NO 16
<211> LENGTH: 565
<212> TYPE: PRT
<213> ORGANISM: Influenza virus

<400> SEQUENCE: 16

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220
```

-continued

```
Gln Gln Thr Ile Ile Pro Asn Ile Gly Ser Arg Pro Leu Val Arg Gly
225                 230                 235                 240

Gln Ser Gly Arg Ile Ser Ile Tyr Trp Thr Ile Val Lys Pro Gly Asp
            245                 250                 255

Ile Leu Met Ile Asn Ser Asn Gly Asn Leu Val Ala Pro Arg Gly Tyr
        260                 265                 270

Phe Lys Leu Lys Thr Gly Lys Ser Ser Val Met Arg Ser Asp Ala Pro
    275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
            325                 330                 335

Asn Val Pro Glu Lys Gln Thr Arg Gly Ile Phe Gly Ala Ile Ala Gly
        340                 345                 350

Phe Ile Glu Asn Gly Trp Glu Gly Met Val Asp Gly Trp Tyr Gly Phe
    355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
        420                 425                 430

Ile Asp Leu Trp Ser Tyr Asn Ala Glu Leu Leu Val Ala Leu Glu Asn
    435                 440                 445

Gln His Thr Ile Asp Leu Thr Asp Ala Glu Met Asn Lys Leu Phe Glu
450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
            485                 490                 495

Arg Thr Gly Thr Tyr Asp His Tyr Ile Tyr Arg Asp Glu Ala Leu Asn
        500                 505                 510

Asn Arg Phe Gln Ile Lys Gly Val Glu Leu Lys Ser Gly Tyr Lys Asp
    515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Arg Gly Asn Ile Arg
545                 550                 555                 560

Cys Asn Ile Cys Ile
                565

<210> SEQ ID NO 17
<211> LENGTH: 2277
<212> TYPE: DNA
<213> ORGANISM: Influenza virus
<220> FEATURE:
<221> NAME/KEY: CDS
<222> LOCATION: (1)..(2277)
<220> FEATURE:
<221> NAME/KEY: misc_feature
<222> LOCATION: (731)..(731)
<223> OTHER INFORMATION: The 'Xaa' at location 731 stands for Val

<400> SEQUENCE: 17

```
atg gag aga ata aaa gaa ctg aga gat ctg atg tta caa tcc cgc acc       48
Met Glu Arg Ile Lys Glu Leu Arg Asp Leu Met Leu Gln Ser Arg Thr
 1               5                  10                  15 cgc gag ata cta aca aaa act act gtg gac cac atg gcc ata atc aag       96
Arg Glu Ile Leu Thr Lys Thr Thr Val Asp His Met Ala Ile Ile Lys
             20                  25                  30 aaa tac aca tca gga aga caa gag aag aac cct gca ctt agg atg aaa      144
Lys Tyr Thr Ser Gly Arg Gln Glu Lys Asn Pro Ala Leu Arg Met Lys
         35                  40                  45 tgg atg atg gca atg aaa tac cca att aca gca gat aag agg ata atg      192
Trp Met Met Ala Met Lys Tyr Pro Ile Thr Ala Asp Lys Arg Ile Met
 50                  55                  60 gag atg att cct gag aga aat gaa cag gga caa acc ctt tgg agc aaa      240
Glu Met Ile Pro Glu Arg Asn Glu Gln Gly Gln Thr Leu Trp Ser Lys
 65                  70                  75                  80 acg aac gat gct ggc tca gac cgc gta atg gta tca cct ctg gca gtg      288
Thr Asn Asp Ala Gly Ser Asp Arg Val Met Val Ser Pro Leu Ala Val
                 85                  90                  95 aca tgg tgg aat agg aat gga cca aca acg agc aca att cat tat cca      336
Thr Trp Trp Asn Arg Asn Gly Pro Thr Thr Ser Thr Ile His Tyr Pro
            100                 105                 110 aaa gtc tac aaa act tat ttt gaa aag gtt gaa aga ttg aaa cac gga      384
Lys Val Tyr Lys Thr Tyr Phe Glu Lys Val Glu Arg Leu Lys His Gly
        115                 120                 125 acc ttt ggc ccc gtt cat ttt agg aat caa gtc aag ata aga cga aga      432
Thr Phe Gly Pro Val His Phe Arg Asn Gln Val Lys Ile Arg Arg Arg
    130                 135                 140 gtt gat gta aac cct ggt cac gcg gac ctc agt gcc aaa gaa gca caa      480
Val Asp Val Asn Pro Gly His Ala Asp Leu Ser Ala Lys Glu Ala Gln
145                 150                 155                 160 gat gtg atc atg gaa gtt gtt ttc cca aat gaa gtg gga gcc aga att      528
Asp Val Ile Met Glu Val Val Phe Pro Asn Glu Val Gly Ala Arg Ile
                165                 170                 175 cta aca tcg gaa tca caa cta aca ata acc aaa gag aaa aag gaa gaa      576
Leu Thr Ser Glu Ser Gln Leu Thr Ile Thr Lys Glu Lys Lys Glu Glu
            180                 185                 190 ctt cag gac tgc aaa att gct ccc ttg atg gta gca tac atg cta gaa      624
Leu Gln Asp Cys Lys Ile Ala Pro Leu Met Val Ala Tyr Met Leu Glu
        195                 200                 205 aga gag ttg gtc cga aaa aca agg ttc ctc cca gta gca ggc gga aca      672
Arg Glu Leu Val Arg Lys Thr Arg Phe Leu Pro Val Ala Gly Gly Thr
    210                 215                 220 agc agt gta tac att gaa gtg ttg cat ctg act cag gga aca tgc tgg      720
Ser Ser Val Tyr Ile Glu Val Leu His Leu Thr Gln Gly Thr Cys Trp
225                 230                 235                 240 gag caa atg tac acc cca gga gga gaa gtt aga aac gat gat att gat      768
Glu Gln Met Tyr Thr Pro Gly Gly Glu Val Arg Asn Asp Asp Ile Asp
                245                 250                 255 caa agt tta att att gca gcc cgg aac ata gtg aga aga gcg aca gta      816
Gln Ser Leu Ile Ile Ala Ala Arg Asn Ile Val Arg Arg Ala Thr Val
            260                 265                 270 tca gca gat cca cta gca tcc cta ctg gaa atg tgc cac agt aca cag      864
Ser Ala Asp Pro Leu Ala Ser Leu Leu Glu Met Cys His Ser Thr Gln
        275                 280                 285 att ggt gga ata agg atg gta gac atc ctt aag cag aat cca aca gag      912
Ile Gly Gly Ile Arg Met Val Asp Ile Leu Lys Gln Asn Pro Thr Glu
    290                 295                 300 gaa caa gct gtg gat ata tgc aaa gca gca atg gga ttg aga att agc      960
Glu Gln Ala Val Asp Ile Cys Lys Ala Ala Met Gly Leu Arg Ile Ser
```

|  |  |  |  |  |  |  |  |  |  |  |  |  |  |  |  |
|---|---|---|---|---|---|---|---|---|---|---|---|---|---|---|---|
| Glu | Gln | Ala | Val | Asp | Ile | Cys | Lys | Ala | Ala | Met | Gly | Leu | Arg | Ile | Ser |
| 305 |  |  |  | 310 |  |  |  |  | 315 |  |  |  |  | 320 |  |

```
tca tca ttc agc ttt ggt gga ttc acc ttc aaa aga aca agt gga tca      1008
Ser Ser Phe Ser Phe Gly Gly Phe Thr Phe Lys Arg Thr Ser Gly Ser
                325                 330                 335 tca gtc aag aga gaa gaa gaa atg ctt acg ggc aac ctt caa aca ttg      1056
Ser Val Lys Arg Glu Glu Glu Met Leu Thr Gly Asn Leu Gln Thr Leu
        340                 345                 350 aaa ata aga gtg cat gag ggc tat gaa gaa ttc aca atg gtc gga aga      1104
Lys Ile Arg Val His Glu Gly Tyr Glu Glu Phe Thr Met Val Gly Arg
                355                 360                 365 aga gca aca gcc att atc aga aag gca acc aga aga ttg att caa ttg      1152
Arg Ala Thr Ala Ile Ile Arg Lys Ala Thr Arg Arg Leu Ile Gln Leu
        370                 375                 380 ata gta agt ggg aga gat gaa caa tca att gct gaa gca ata att gta      1200
Ile Val Ser Gly Arg Asp Glu Gln Ser Ile Ala Glu Ala Ile Ile Val
385                 390                 395                 400 gcc atg gtg ttt tcg caa gaa gat tgc atg ata aaa gca gtt cga ggc      1248
Ala Met Val Phe Ser Gln Glu Asp Cys Met Ile Lys Ala Val Arg Gly
                405                 410                 415 gat ttg aac ttt gtt aat aga gca aat cag cgt ttg aac ccc atg cat      1296
Asp Leu Asn Phe Val Asn Arg Ala Asn Gln Arg Leu Asn Pro Met His
        420                 425                 430 caa ctc ttg agg cat ttc caa aaa gat gca aaa gtg ctt ttc caa aat      1344
Gln Leu Leu Arg His Phe Gln Lys Asp Ala Lys Val Leu Phe Gln Asn
                435                 440                 445 tgg gga att gaa ccc atc gac aat gta atg ggg atg att gga ata ttg      1392
Trp Gly Ile Glu Pro Ile Asp Asn Val Met Gly Met Ile Gly Ile Leu
        450                 455                 460 cct gac atg acc cca agc acc gag atg tca ttg aga gga gtg aga gtc      1440
Pro Asp Met Thr Pro Ser Thr Glu Met Ser Leu Arg Gly Val Arg Val
465                 470                 475                 480 agc aaa atg gga gtg gat gag tac tcc agc act gag aga gtg gtg gtg      1488
Ser Lys Met Gly Val Asp Glu Tyr Ser Ser Thr Glu Arg Val Val Val
                485                 490                 495 agc att gac cgt ttt tta aga gtt cgg gat caa agg gga aac ata cta      1536
Ser Ile Asp Arg Phe Leu Arg Val Arg Asp Gln Arg Gly Asn Ile Leu
        500                 505                 510 ctg tcc cct gaa gaa gtc agt gaa aca caa gga acg gaa aag ctg aca      1584
Leu Ser Pro Glu Glu Val Ser Glu Thr Gln Gly Thr Glu Lys Leu Thr
        515                 520                 525 ata att tat tcg tca tca atg atg tgg gag att aat ggt ccc gaa tca      1632
Ile Ile Tyr Ser Ser Ser Met Met Trp Glu Ile Asn Gly Pro Glu Ser
530                 535                 540 gtg ttg gtc aat act tat caa tgg atc atc agg aac tgg gaa att gta      1680
Val Leu Val Asn Thr Tyr Gln Trp Ile Ile Arg Asn Trp Glu Ile Val
545                 550                 555                 560 aaa att cag tgg tca cag gac ccc aca atg tta tac aat aag ata gaa      1728
Lys Ile Gln Trp Ser Gln Asp Pro Thr Met Leu Tyr Asn Lys Ile Glu
                565                 570                 575 ttt gag cca ttc caa tcc ctg gtc cct agg gcc acc aga agc caa tac      1776
Phe Glu Pro Phe Gln Ser Leu Val Pro Arg Ala Thr Arg Ser Gln Tyr
        580                 585                 590 agc ggt ttc gta aga acc ctg ttt cag caa atg cga gat gta ctt gga      1824
Ser Gly Phe Val Arg Thr Leu Phe Gln Gln Met Arg Asp Val Leu Gly
            595                 600                 605 aca ttt gat act gct caa ata ata aaa ctc ctc cct ttt gcc gct gct      1872
Thr Phe Asp Thr Ala Gln Ile Ile Lys Leu Leu Pro Phe Ala Ala Ala
610                 615                 620 cct ccg gaa cag agt agg atg cag ttc tct tct ttg act gtt aat gta      1920
```

```
Pro Pro Glu Gln Ser Arg Met Gln Phe Ser Ser Leu Thr Val Asn Val
625                 630                 635                 640 aga ggt tcg gga atg agg ata ctt gta aga ggc aat tcc cca gtg ttc     1968
Arg Gly Ser Gly Met Arg Ile Leu Val Arg Gly Asn Ser Pro Val Phe
                    645                 650                 655 aac tac aat aaa gcc act aaa agg ctc aca gtc ctc gga aag gat gca     2016
Asn Tyr Asn Lys Ala Thr Lys Arg Leu Thr Val Leu Gly Lys Asp Ala
                660                 665                 670 ggt gcg ctt act gag gac cca gat gaa ggt acg gct gga gta gaa tct     2064
Gly Ala Leu Thr Glu Asp Pro Asp Glu Gly Thr Ala Gly Val Glu Ser
            675                 680                 685 gct gtt cta aga ggg ttt ctc att tta ggt aaa gaa aac aag aga tat     2112
Ala Val Leu Arg Gly Phe Leu Ile Leu Gly Lys Glu Asn Lys Arg Tyr
        690                 695                 700 ggc cca gca cta agc atc aat gaa cta agc aaa ctt gca aaa ggg gag     2160
Gly Pro Ala Leu Ser Ile Asn Glu Leu Ser Lys Leu Ala Lys Gly Glu
705                 710                 715                 720 aaa gcc aat gta cta att ggg caa ggg gac rta gtg ttg gta atg aaa     2208
Lys Ala Asn Val Leu Ile Gly Gln Gly Asp Xaa Val Leu Val Met Lys
                725                 730                 735 cgg aaa cgt gac tct agc ata ctt act gac agc cag aca gcg acc aaa     2256
Arg Lys Arg Asp Ser Ser Ile Leu Thr Asp Ser Gln Thr Ala Thr Lys
                740                 745                 750 agg att cgg atg gcc atc aat                                         2277
Arg Ile Arg Met Ala Ile Asn
            755

<210> SEQ ID NO 18
<211> LENGTH: 759
<212> TYPE: PRT
<213> ORGANISM: Influenza virus
<220> FEATURE:
<221> NAME/KEY: misc_feature
<222> LOCATION: (731)..(731)
<223> OTHER INFORMATION: The 'Xaa' at location 731 stands for Val, or
      Ile.

<400> SEQUENCE: 18

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175
```

```
Leu Thr Ser Glu Ser Gln Leu Thr Ile Thr Lys Glu Lys Glu Glu
            180                 185                 190

Leu Gln Asp Cys Lys Ile Ala Pro Leu Met Val Ala Tyr Met Leu Glu
            195                 200                 205

Arg Glu Leu Val Arg Lys Thr Arg Phe Leu Pro Val Ala Gly Gly Thr
210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
            245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
            275                 280                 285

Ile Gly Gly Ile Arg Met Val Asp Ile Leu Lys Gln Asn Pro Thr Glu
            290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
            355                 360                 365

Arg Ala Thr Ala Ile Ile Arg Lys Ala Thr Arg Arg Leu Ile Gln Leu
            370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
            405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
            435                 440                 445

Trp Gly Ile Glu Pro Ile Asp Asn Val Met Gly Met Ile Gly Ile Leu
450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
            485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
            515                 520                 525

Ile Ile Tyr Ser Ser Ser Met Met Trp Glu Ile Asn Gly Pro Glu Ser
            530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
            565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
```

```
                    595                 600                 605
Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Xaa Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 19
<211> LENGTH: 2274
<212> TYPE: DNA
<213> ORGANISM: Influenza virus
<220> FEATURE:
<221> NAME/KEY: CDS
<222> LOCATION: (1)..(2274)

<400> SEQUENCE: 19 atg gat gtc aat ccg act cta ctt ttc tta aag gtg cca gcg caa aat      48
Met Asp Val Asn Pro Thr Leu Leu Phe Leu Lys Val Pro Ala Gln Asn
1               5                  10                  15 gct ata agc aca aca ttc cct tat act gga gat cct ccc tac agt cat      96
Ala Ile Ser Thr Thr Phe Pro Tyr Thr Gly Asp Pro Pro Tyr Ser His
                20                  25                  30 gga aca ggg aca gga tac acc atg gat act gtc aac aga aca cac caa     144
Gly Thr Gly Thr Gly Tyr Thr Met Asp Thr Val Asn Arg Thr His Gln
            35                  40                  45 tat tca gaa aaa ggg aaa tgg aca aca aac act gag att gga gca cca     192
Tyr Ser Glu Lys Gly Lys Trp Thr Thr Asn Thr Glu Ile Gly Ala Pro
        50                  55                  60 caa ctt aat cca atc gat gga cca ctt cct gaa gac aat gaa cca agt     240
Gln Leu Asn Pro Ile Asp Gly Pro Leu Pro Glu Asp Asn Glu Pro Ser
65                  70                  75                  80 ggg tac gcc caa aca gat tgt gta ttg gaa gca atg gct ttc ctt gaa     288
Gly Tyr Ala Gln Thr Asp Cys Val Leu Glu Ala Met Ala Phe Leu Glu
                85                  90                  95 gaa tcc cat ccc gga atc ttt gaa aat tcg tgt ctt gaa acg atg gag     336
Glu Ser His Pro Gly Ile Phe Glu Asn Ser Cys Leu Glu Thr Met Glu
                100                 105                 110 gtg att cag cag aca aga gtg gac aaa cta aca caa ggc cga caa act     384
Val Ile Gln Gln Thr Arg Val Asp Lys Leu Thr Gln Gly Arg Gln Thr
            115                 120                 125 tat gat tgg acc ttg aat agg aat caa cct gcc gca aca gca ctt gct     432
Tyr Asp Trp Thr Leu Asn Arg Asn Gln Pro Ala Ala Thr Ala Leu Ala
        130                 135                 140 aat acg att gaa gta ttc aga tca aat ggt ctg act tcc aat gaa tcg     480
```

-continued

```
Asn Thr Ile Glu Val Phe Arg Ser Asn Gly Leu Thr Ser Asn Glu Ser
145                 150                 155                 160 ggg aga ttg atg gac ttc ctc aaa gat gtc atg gag tcc atg aac aag     528
Gly Arg Leu Met Asp Phe Leu Lys Asp Val Met Glu Ser Met Asn Lys
                165                 170                 175 gaa gaa atg gaa ata aca aca cac ttc caa cgg aag aga aga gta aga     576
Glu Glu Met Glu Ile Thr Thr His Phe Gln Arg Lys Arg Arg Val Arg
            180                 185                 190 gac aac atg aca aag aga atg gta aca cag aga acc ata ggg aag aaa     624
Asp Asn Met Thr Lys Arg Met Val Thr Gln Arg Thr Ile Gly Lys Lys
        195                 200                 205 aaa caa cga tta aac aga aag agc tat cta atc aga aca tta acc cta     672
Lys Gln Arg Leu Asn Arg Lys Ser Tyr Leu Ile Arg Thr Leu Thr Leu
210                 215                 220 aac aca atg acc aag gac gct gag aga ggg aaa ttg aaa cga cga gca     720
Asn Thr Met Thr Lys Asp Ala Glu Arg Gly Lys Leu Lys Arg Arg Ala
225                 230                 235                 240 atc gct acc cca ggg atg cag ata aga ggg ttt gta tat ttt gtt gaa     768
Ile Ala Thr Pro Gly Met Gln Ile Arg Gly Phe Val Tyr Phe Val Glu
                245                 250                 255 aca cta gcc cga aga ata tgt gaa aag ctt gaa caa tca gga ttg cca     816
Thr Leu Ala Arg Arg Ile Cys Glu Lys Leu Glu Gln Ser Gly Leu Pro
            260                 265                 270 gtt ggc ggt aat gag aaa aag gcc aaa ctg gct aat gtc gtc aga aaa     864
Val Gly Gly Asn Glu Lys Lys Ala Lys Leu Ala Asn Val Val Arg Lys
        275                 280                 285 atg atg act aat tcc caa gac act gaa ctc tcc ttc acc atc act ggg     912
Met Met Thr Asn Ser Gln Asp Thr Glu Leu Ser Phe Thr Ile Thr Gly
290                 295                 300 gac aat acc aaa tgg aat gaa aat cag aac cca cgc ata ttc ctg gca     960
Asp Asn Thr Lys Trp Asn Glu Asn Gln Asn Pro Arg Ile Phe Leu Ala
305                 310                 315                 320 atg atc aca tac ata act aga aac cag cca gaa tgg ttc aga aat gtt    1008
Met Ile Thr Tyr Ile Thr Arg Asn Gln Pro Glu Trp Phe Arg Asn Val
                325                 330                 335 cta agc att gca ccg att atg ttc tca aat aaa atg gca aga ctg ggg    1056
Leu Ser Ile Ala Pro Ile Met Phe Ser Asn Lys Met Ala Arg Leu Gly
            340                 345                 350 aaa gga tat atg ttt gaa agc aaa agt atg aaa ttg aga act caa ata    1104
Lys Gly Tyr Met Phe Glu Ser Lys Ser Met Lys Leu Arg Thr Gln Ile
        355                 360                 365 cca gca gaa atg cta gca agc att gac cta aaa tat ttc aat gat tca    1152
Pro Ala Glu Met Leu Ala Ser Ile Asp Leu Lys Tyr Phe Asn Asp Ser
370                 375                 380 aca aaa aag aaa att gaa aag ata cga cca ctt ctg gtt gac ggg act    1200
Thr Lys Lys Lys Ile Glu Lys Ile Arg Pro Leu Leu Val Asp Gly Thr
385                 390                 395                 400 gct tca ctg agt cct ggc atg atg atg gga atg ttc aac atg ttg agc    1248
Ala Ser Leu Ser Pro Gly Met Met Met Gly Met Phe Asn Met Leu Ser
                405                 410                 415 act gtg ctg ggt gta tcc ata tta aac ctg ggc cag agg aaa tac aca    1296
Thr Val Leu Gly Val Ser Ile Leu Asn Leu Gly Gln Arg Lys Tyr Thr
            420                 425                 430 aag acc aca tac tgg tgg gat ggt ctg caa tca tcc gat gac ttt gct    1344
Lys Thr Thr Tyr Trp Trp Asp Gly Leu Gln Ser Ser Asp Asp Phe Ala
        435                 440                 445 ttg ata gtg aat gcg cct aat cat gaa gga ata caa gct gga gta gac    1392
Leu Ile Val Asn Ala Pro Asn His Glu Gly Ile Gln Ala Gly Val Asp
450                 455                 460 aga ttc tat aga act tgc aaa ctg gtc ggg atc aac atg agc aaa aag    1440
```

```
                                            -continued

Arg Phe Tyr Arg Thr Cys Lys Leu Val Gly Ile Asn Met Ser Lys Lys
465                 470                 475                 480 aaa tcc tac ata aat aga act gga aca ttc gaa ttc aca agc ttt ttc      1488
Lys Ser Tyr Ile Asn Arg Thr Gly Thr Phe Glu Phe Thr Ser Phe Phe
                        485                 490                 495 tac cgg tat ggt ttt gta gcc aat ttc agc atg gaa cta ccc agt ttt      1536
Tyr Arg Tyr Gly Phe Val Ala Asn Phe Ser Met Glu Leu Pro Ser Phe
            500                 505                 510 ggg gtt tcc gga ata aat gaa tct gca gac atg agc att gga gtg aca      1584
Gly Val Ser Gly Ile Asn Glu Ser Ala Asp Met Ser Ile Gly Val Thr
        515                 520                 525 gtc atc aaa aac aac atg ata aat aat gat ctc ggt cct gcc acg gca      1632
Val Ile Lys Asn Asn Met Ile Asn Asn Asp Leu Gly Pro Ala Thr Ala
530                 535                 540 caa atg gca ctc caa ctc ttc att aag gat tat cgg tac aca tac cgg      1680
Gln Met Ala Leu Gln Leu Phe Ile Lys Asp Tyr Arg Tyr Thr Tyr Arg
545                 550                 555                 560 tgc cat aga ggt gat acc cag ata caa acc aga aga tct ttt gag ttg      1728
Cys His Arg Gly Asp Thr Gln Ile Gln Thr Arg Arg Ser Phe Glu Leu
                565                 570                 575 aag aaa ctg tgg gaa cag act cga tca aag act ggt cta ctg gta tca      1776
Lys Lys Leu Trp Glu Gln Thr Arg Ser Lys Thr Gly Leu Leu Val Ser
            580                 585                 590 gat ggg ggt cca aac cta tat aac atc aga aac cta cac atc ccg gaa      1824
Asp Gly Gly Pro Asn Leu Tyr Asn Ile Arg Asn Leu His Ile Pro Glu
        595                 600                 605 gtc tgt tta aaa tgg gag cta atg gat gaa gat tat aag ggg agg cta      1872
Val Cys Leu Lys Trp Glu Leu Met Asp Glu Asp Tyr Lys Gly Arg Leu
610                 615                 620 tgc aat cca ttg aat cct ttc gtt agt cac aaa gaa att gaa tca gtc      1920
Cys Asn Pro Leu Asn Pro Phe Val Ser His Lys Glu Ile Glu Ser Val
625                 630                 635                 640 aac agt gca gta gta atg cct gcg cat ggc cct gcc aaa agc atg gag      1968
Asn Ser Ala Val Val Met Pro Ala His Gly Pro Ala Lys Ser Met Glu
                645                 650                 655 tat gat gct gtt gca aca aca cat tct tgg atc ccc aag agg aac cgg      2016
Tyr Asp Ala Val Ala Thr Thr His Ser Trp Ile Pro Lys Arg Asn Arg
            660                 665                 670 tcc ata ttg aac aca agc caa agg gga ata ctc gaa gat gag cag atg      2064
Ser Ile Leu Asn Thr Ser Gln Arg Gly Ile Leu Glu Asp Glu Gln Met
        675                 680                 685 tat cag aaa tgc tgc aac ctg ttt gaa aaa ttc ttc ccc agc agc tca      2112
Tyr Gln Lys Cys Cys Asn Leu Phe Glu Lys Phe Phe Pro Ser Ser Ser
690                 695                 700 tac aga aga cca gtc gga att tct agt atg gtt gag gcc atg gtg tcc      2160
Tyr Arg Arg Pro Val Gly Ile Ser Ser Met Val Glu Ala Met Val Ser
705                 710                 715                 720 agg gcc cgc att gat gca cga att gac ttc gaa tct gga cgg ata aag      2208
Arg Ala Arg Ile Asp Ala Arg Ile Asp Phe Glu Ser Gly Arg Ile Lys
                725                 730                 735 aag gat gag ttc gct gag atc atg aag atc tgt tcc acc att gaa gag      2256
Lys Asp Glu Phe Ala Glu Ile Met Lys Ile Cys Ser Thr Ile Glu Glu
            740                 745                 750 ctc aga cgg caa aaa tag                                              2274
Leu Arg Arg Gln Lys
        755

<210> SEQ ID NO 20
<211> LENGTH: 757
<212> TYPE: PRT
<213> ORGANISM: Influenza virus
```

<400> SEQUENCE: 20

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415
```

```
Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755

<210> SEQ ID NO 21
<211> LENGTH: 2151
<212> TYPE: DNA
<213> ORGANISM: Influenza virus
<220> FEATURE:
<221> NAME/KEY: CDS
<222> LOCATION: (1)..(2151)

<400> SEQUENCE: 21 atg gaa gac ttt gtg cga cag tgc ttc aat cca atg atc gtc gag ctt       48
Met Glu Asp Phe Val Arg Gln Cys Phe Asn Pro Met Ile Val Glu Leu

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
gcg aaa aag gca atg aaa gaa tat gga gag aac ccg aaa atc gaa aca            96
Ala Glu Lys Ala Met Lys Glu Tyr Gly Glu Asn Pro Lys Ile Glu Thr
                20                  25                  30 aac aaa ttt gca gca ata tgc act cac ttg gaa gtc tgc ttc atg tac          144
Asn Lys Phe Ala Ala Ile Cys Thr His Leu Glu Val Cys Phe Met Tyr
        35                  40                  45 tcg gat ttt cac ttt att aat gaa ctg ggt gag tca gtg gtc ata gag          192
Ser Asp Phe His Phe Ile Asn Glu Leu Gly Glu Ser Val Val Ile Glu
    50                  55                  60 tct ggt gac cca aat gct ctt ttg aaa cac aga ttt gaa atc att gag          240
Ser Gly Asp Pro Asn Ala Leu Leu Lys His Arg Phe Glu Ile Ile Glu
65                  70                  75                  80 ggg aga gat cga aca atg gca tgg aca gta gta aac agc atc tgc aac          288
Gly Arg Asp Arg Thr Met Ala Trp Thr Val Val Asn Ser Ile Cys Asn
                85                  90                  95 acc aca aga gct gaa aaa cct aaa ttt ctt cca gat tta tac gac tat          336
Thr Thr Arg Ala Glu Lys Pro Lys Phe Leu Pro Asp Leu Tyr Asp Tyr
            100                 105                 110 aag gag aac aga ttt gtt gaa att ggt gtg aca agg aga gaa gtt cac          384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat          432
Ile Tyr Tyr Leu Glu Lys Ala Asn Lys Ile Lys Ser Glu Lys Thr His
    130                 135                 140 atc cac att ttc tca ttt aca gga gag gaa atg gct aca aaa gcg gac          480
Ile His Ile Phe Ser Phe Thr Gly Glu Glu Met Ala Thr Lys Ala Asp
145                 150                 155                 160 tat act ctt gat gaa gag agt aga gcc agg atc aag acc aga cta ttc          528
Tyr Thr Leu Asp Glu Glu Ser Arg Ala Arg Ile Lys Thr Arg Leu Phe
                165                 170                 175 act ata aga caa gaa atg gcc agt aga ggc ctc tgg gat tcc ttt cgt          576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca          624
Gln Ser Glu Arg Gly Glu Glu Thr Ile Glu Glu Arg Phe Glu Ile Thr
        195                 200                 205 ggg acg atg cgc aag ctt gcc aat tac agt ctc cca ccg aac ttc tcc          672
Gly Thr Met Arg Lys Leu Ala Asn Tyr Ser Leu Pro Pro Asn Phe Ser
    210                 215                 220 agc ctt gaa aat ttt aga gtc tat gtg gat gga ttc gaa ccg aac ggc          720
Ser Leu Glu Asn Phe Arg Val Tyr Val Asp Gly Phe Glu Pro Asn Gly
225                 230                 235                 240 tgc att gag agt aag ctt tct caa atg tcc aaa gaa gta aat gcc aga          768
Cys Ile Glu Ser Lys Leu Ser Gln Met Ser Lys Glu Val Asn Ala Arg
                245                 250                 255 atc gaa cca ttt tca aag aca aca ccc cga cca ctc aaa atg cca ggt          816
Ile Glu Pro Phe Ser Lys Thr Thr Pro Arg Pro Leu Lys Met Pro Gly
            260                 265                 270 ggt cca ccc tgc cat cag cga tct aaa ttc ttg cta atg gat gct ctg          864
Gly Pro Pro Cys His Gln Arg Ser Lys Phe Leu Leu Met Asp Ala Leu
        275                 280                 285 aaa ctg agc att gag gac cca agt cac gag gga gag gga ata cca cta          912
Lys Leu Ser Ile Glu Asp Pro Ser His Glu Gly Glu Gly Ile Pro Leu
    290                 295                 300 tat gat gca atc aaa tgc atg aaa act ttc ttt gga tgg aaa gag ccc          960
Tyr Asp Ala Ile Lys Cys Met Lys Thr Phe Phe Gly Trp Lys Glu Pro
305                 310                 315                 320 agt att gtt aaa cca cat gaa aag ggt ata aac ccg aac tat ctc caa         1008
Ser Ile Val Lys Pro His Glu Lys Gly Ile Asn Pro Asn Tyr Leu Gln
```

```
                                 325                 330                 335
act tgg aag caa gta tta gaa gaa ata caa gac ctt gag aac gaa gaa       1056
Thr Trp Lys Gln Val Leu Glu Glu Ile Gln Asp Leu Glu Asn Glu Glu
                340                 345                 350 agg acc ccc aag acc aag aat atg aaa aaa aca agc caa ttg aaa tgg       1104
Arg Thr Pro Lys Thr Lys Asn Met Lys Lys Thr Ser Gln Leu Lys Trp
            355                 360                 365 gca cta ggt gaa aat atg gca cca gag aaa gtg gat ttt gag gat tgt       1152
Ala Leu Gly Glu Asn Met Ala Pro Glu Lys Val Asp Phe Glu Asp Cys
        370                 375                 380 aaa gac atc aat gat tta aaa caa tat gac agt gat gag cca gaa aca       1200
Lys Asp Ile Asn Asp Leu Lys Gln Tyr Asp Ser Asp Glu Pro Glu Thr
385                 390                 395                 400 agg tct ctt gca agt tgg att caa agt gag ttc aac aaa gct tgt gag       1248
Arg Ser Leu Ala Ser Trp Ile Gln Ser Glu Phe Asn Lys Ala Cys Glu
                405                 410                 415 ctg aca gat tca agc tgg ata gag ctc gat gaa att ggg gag gat gtc       1296
Leu Thr Asp Ser Ser Trp Ile Glu Leu Asp Glu Ile Gly Glu Asp Val
            420                 425                 430 gcc cca ata gaa tac att gcg agc atg agg aga aat tat ttt act gct       1344
Ala Pro Ile Glu Tyr Ile Ala Ser Met Arg Arg Asn Tyr Phe Thr Ala
        435                 440                 445 gag att tcc cat tgt aga gca aca gaa tat ata atg aaa gga gtg tac       1392
Glu Ile Ser His Cys Arg Ala Thr Glu Tyr Ile Met Lys Gly Val Tyr
450                 455                 460 atc aac act gct cta ctc aat gca tcc tgt gct gcg atg gat gaa ttt       1440
Ile Asn Thr Ala Leu Leu Asn Ala Ser Cys Ala Ala Met Asp Glu Phe
465                 470                 475                 480 caa tta att ccg atg ata agt aaa tgc agg acc aaa gaa ggg aga agg       1488
Gln Leu Ile Pro Met Ile Ser Lys Cys Arg Thr Lys Glu Gly Arg Arg
                485                 490                 495 aaa aca aat tta tat gga ttc ata ata aag gga agg tcc cat tta aga       1536
Lys Thr Asn Leu Tyr Gly Phe Ile Ile Lys Gly Arg Ser His Leu Arg
            500                 505                 510 aat gat act gac gtg gtg aac ttt gta agt atg gaa ttt tct ctc act       1584
Asn Asp Thr Asp Val Val Asn Phe Val Ser Met Glu Phe Ser Leu Thr
        515                 520                 525 gat cca aga ttt gag cca cac aaa tgg gaa aaa tac tgc gtt cta gaa       1632
Asp Pro Arg Phe Glu Pro His Lys Trp Glu Lys Tyr Cys Val Leu Glu
    530                 535                 540 att gga gac atg ctt cta aga act gct gta ggt caa gtg tca aga ccc       1680
Ile Gly Asp Met Leu Leu Arg Thr Ala Val Gly Gln Val Ser Arg Pro
545                 550                 555                 560 atg ttt ttg tat gta agg aca aat gga acc tct aaa att aaa atg aaa       1728
Met Phe Leu Tyr Val Arg Thr Asn Gly Thr Ser Lys Ile Lys Met Lys
                565                 570                 575 tgg gga atg gaa atg agg cgc tgc ctc ctt cag tct ctg caa cag att       1776
Trp Gly Met Glu Met Arg Arg Cys Leu Leu Gln Ser Leu Gln Gln Ile
            580                 585                 590 gaa agc atg atc gaa gct gag tcc tca gtc aaa gaa aag gac atg acc       1824
Glu Ser Met Ile Glu Ala Glu Ser Ser Val Lys Glu Lys Asp Met Thr
        595                 600                 605 aaa gaa ttt ttt gag aac aaa tca gag aca tgg cct ata gga gag tcc       1872
Lys Glu Phe Phe Glu Asn Lys Ser Glu Thr Trp Pro Ile Gly Glu Ser
    610                 615                 620 ccc aaa gga gtg gaa gag ggc tca atc ggg aag gtt tgc agg acc tta       1920
Pro Lys Gly Val Glu Glu Gly Ser Ile Gly Lys Val Cys Arg Thr Leu
625                 630                 635                 640 tta gca aaa tct gtg ttt aac agt tta tat gca tct cca caa ctg gaa       1968
Leu Ala Lys Ser Val Phe Asn Ser Leu Tyr Ala Ser Pro Gln Leu Glu
```

-continued

```
                            645                 650                 655
ggg ttt tca gct gaa tct agg aaa tta ctc att gtt cag gct ctt         2016
Gly Phe Ser Ala Glu Ser Arg Lys Leu Leu Ile Val Gln Ala Leu
            660                 665                 670 agg gat gac ctg gaa cct gga acc ttt gat att ggg gga tta tat gaa     2064
Arg Asp Asp Leu Glu Pro Gly Thr Phe Asp Ile Gly Gly Leu Tyr Glu
        675                 680                 685 tca att gag gag tgc ctg att aat gat ccc tgg gtt ttg ctt aat gca     2112
Ser Ile Glu Glu Cys Leu Ile Asn Asp Pro Trp Val Leu Leu Asn Ala
    690                 695                 700 tct tgg ttc aac tcc ttc ctt aca cat gca ctg aag tag                 2151
Ser Trp Phe Asn Ser Phe Leu Thr His Ala Leu Lys
705                 710                 715
```

<210> SEQ ID NO 22
<211> LENGTH: 716
<212> TYPE: PRT
<213> ORGANISM: Influenza virus

<400> SEQUENCE: 22

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asn Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285
```

```
Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Ile Val Lys Pro His Glu Lys Gly Ile Asn Pro Asn Tyr Leu Gln
                325                 330                 335

Thr Trp Lys Gln Val Leu Glu Glu Ile Gln Asp Leu Glu Asn Glu Glu
            340                 345                 350

Arg Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
        435                 440                 445

Glu Ile Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
    530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asp Leu Glu Pro Gly Thr Phe Asp Ile Gly Gly Leu Tyr Glu
        675                 680                 685

Ser Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715
```

<210> SEQ ID NO 23
<211> LENGTH: 838
<212> TYPE: DNA
<213> ORGANISM: Influenza virus
<220> FEATURE:
<221> NAME/KEY: CDS
<222> LOCATION: (1)..(657)

<400> SEQUENCE: 23

| atg gat tcc aac act gtg tca agc ttt cag gta gac tgt ttt ctt tgg | 48 |
| Met Asp Ser Asn Thr Val Ser Ser Phe Gln Val Asp Cys Phe Leu Trp | |
| 1               5                   10                  15      | |

| cat gtc cgc aaa cga ttc gca gac caa gaa ctg ggt gat gcc cca ttc | 96 |
| His Val Arg Lys Arg Phe Ala Asp Gln Glu Leu Gly Asp Ala Pro Phe | |
|             20                  25                  30          | |

| ctt gac cgg ctt cgc cga gac cag aag tcc cta agg gga aga ggt agc | 144 |
| Leu Asp Arg Leu Arg Arg Asp Gln Lys Ser Leu Arg Gly Arg Gly Ser | |
|         35                  40                  45              | |

| act ctt ggt ctg gac atc gaa aca gcc act cat gca gga aag cag ata | 192 |
| Thr Leu Gly Leu Asp Ile Glu Thr Ala Thr His Ala Gly Lys Gln Ile | |
|     50                  55                  60                  | |

| gtg gag cag att ctg gaa aag gaa tca gat gag gca ctt aaa atg acc | 240 |
| Val Glu Gln Ile Leu Glu Lys Glu Ser Asp Glu Ala Leu Lys Met Thr | |
| 65                  70                  75                  80  | |

| att gcc tct gtt cct act tca cgc tac tta act gac atg act ctt gat | 288 |
| Ile Ala Ser Val Pro Thr Ser Arg Tyr Leu Thr Asp Met Thr Leu Asp | |
|                 85                  90                  95      | |

| gag atg tca aga gac tgg ttc atg ctc atg ccc aag caa aaa gta aca | 336 |
| Glu Met Ser Arg Asp Trp Phe Met Leu Met Pro Lys Gln Lys Val Thr | |
|             100                 105                 110         | |

| ggc tcc cta tgt ata aga atg gac cag gca atc atg gat aag aac atc | 384 |
| Gly Ser Leu Cys Ile Arg Met Asp Gln Ala Ile Met Asp Lys Asn Ile | |
|         115                 120                 125             | |

| ata ctt aaa gca aac ttt agt gtg att ttc gaa ggg ctg gaa aca cta | 432 |
| Ile Leu Lys Ala Asn Phe Ser Val Ile Phe Glu Gly Leu Glu Thr Leu | |
|     130                 135                 140                 | |

| ata cta ctt aga gcc ttc acc gaa gaa gga gca gtc gtt ggc gaa att | 480 |
| Ile Leu Leu Arg Ala Phe Thr Glu Glu Gly Ala Val Val Gly Glu Ile | |
| 145                 150                 155                 160 | |

| tca cca tta cct tct ctt cca gga cat act aat gag gat gtc aaa aat | 528 |
| Ser Pro Leu Pro Ser Leu Pro Gly His Thr Asn Glu Asp Val Lys Asn | |
|                 165                 170                 175     | |

| gca att ggg gtc ctc atc gga gga ctt aaa tgg aat gat aat acg gtt | 576 |
| Ala Ile Gly Val Leu Ile Gly Gly Leu Lys Trp Asn Asp Asn Thr Val | |
|             180                 185                 190         | |

| aga atc tct gaa act cta cag aga ttc gct tgg aga agc agt cat gag | 624 |
| Arg Ile Ser Glu Thr Leu Gln Arg Phe Ala Trp Arg Ser Ser His Glu | |
|         195                 200                 205             | |

| aat ggg aga cct tca ttc cct tca aag cag aaa tgaaaaatgg agagaacaat | 677 |
| Asn Gly Arg Pro Ser Phe Pro Ser Lys Gln Lys | |
|     210                 215 | | taagccagaa atttgaagaa ataagatggt tgattgaaga agtgcgacat agattgaaaa     737 atacagaaaa tagttttgaa caaataacat ttatgcaagc cttacaacta ttgcttgaag     797 tagaacaaga gataagaact ttctcgtttc agcttattta a                        838

<210> SEQ ID NO 24
<211> LENGTH: 219
<212> TYPE: PRT
<213> ORGANISM: Influenza virus -continued

```
<400> SEQUENCE: 24

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
65                  70                  75                  80

Ile Ala Ser Val Pro Thr Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Gly Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Ser Lys Gln Lys
    210                 215

<210> SEQ ID NO 25
<211> LENGTH: 1497
<212> TYPE: DNA
<213> ORGANISM: Influenza virus
<220> FEATURE:
<221> NAME/KEY: CDS
<222> LOCATION: (1)..(1497)

<400> SEQUENCE: 25 atg gcg tct caa ggc acc aaa cga tcc tat gaa cag atg gaa act gat      48
Met Ala Ser Gln Gly Thr Lys Arg Ser Tyr Glu Gln Met Glu Thr Asp
1               5                   10                  15 ggg gaa cgc cag aat gca act gaa atc aga gca tct gtc gga agg atg      96
Gly Glu Arg Gln Asn Ala Thr Glu Ile Arg Ala Ser Val Gly Arg Met
            20                  25                  30 gtg gga gga atc ggc cgg ttt tat gtt cag atg tgt act gag ctt aaa     144
Val Gly Gly Ile Gly Arg Phe Tyr Val Gln Met Cys Thr Glu Leu Lys
        35                  40                  45 cta aac gac cat gaa ggg cgg ctg att cag aac agc ata aca ata gaa     192
Leu Asn Asp His Glu Gly Arg Leu Ile Gln Asn Ser Ile Thr Ile Glu
    50                  55                  60 agg atg gta ctt tcg gca ttc gac gaa aga aga aac aag tat ctc gag     240
Arg Met Val Leu Ser Ala Phe Asp Glu Arg Arg Asn Lys Tyr Leu Glu
65                  70                  75                  80 gag cat ccc agt gct ggg aaa gac cct aag aaa acg gga ggc ccg ata     288
Glu His Pro Ser Ala Gly Lys Asp Pro Lys Lys Thr Gly Gly Pro Ile
                85                  90                  95 tac aga agg aaa gat ggg aaa tgg atg agg gaa ctc atc ctc cat gat     336
```

-continued

```
                Tyr Arg Arg Lys Asp Gly Lys Trp Met Arg Glu Leu Ile Leu His Asp
                                100                 105                 110 aaa gaa gaa atc atg aga atc tgg cgt cag gcc aac aat ggt gaa gac        384
Lys Glu Glu Ile Met Arg Ile Trp Arg Gln Ala Asn Asn Gly Glu Asp
            115                 120                 125 gct act gct ggt ctt act cat atg atg atc tgg cac tcc aat ctc aat        432
Ala Thr Ala Gly Leu Thr His Met Met Ile Trp His Ser Asn Leu Asn
130                 135                 140 gac acc aca tac caa aga aca agg gct ctt gtt cgg act ggg atg gat        480
Asp Thr Thr Tyr Gln Arg Thr Arg Ala Leu Val Arg Thr Gly Met Asp
145                 150                 155                 160 ccc aga atg tgc tct ctg atg caa ggc tca acc ctc cca cgg aga tct        528
Pro Arg Met Cys Ser Leu Met Gln Gly Ser Thr Leu Pro Arg Arg Ser
                165                 170                 175 gga gcc gct ggt gct gca gta aaa ggt gtt gga aca atg gta atg gaa        576
Gly Ala Ala Gly Ala Ala Val Lys Gly Val Gly Thr Met Val Met Glu
                180                 185                 190 ctc atc aga atg atc aaa cgc gga ata aat gat cgg aat ttc tgg aga        624
Leu Ile Arg Met Ile Lys Arg Gly Ile Asn Asp Arg Asn Phe Trp Arg
            195                 200                 205 ggt gaa aat ggt cga aga acc aga att gct tat gaa aga atg tgc aat        672
Gly Glu Asn Gly Arg Arg Thr Arg Ile Ala Tyr Glu Arg Met Cys Asn
        210                 215                 220 atc ctc aaa ggg aaa ttt cag aca gca gca caa cgg gct atg atg gac        720
Ile Leu Lys Gly Lys Phe Gln Thr Ala Ala Gln Arg Ala Met Met Asp
225                 230                 235                 240 cag gtg agg gaa ggc cgc aat cct gga aac gct gag att gag gat ctc        768
Gln Val Arg Glu Gly Arg Asn Pro Gly Asn Ala Glu Ile Glu Asp Leu
                245                 250                 255 att ttc ttg gca cga tca gca ctt att ttg aga gga tca gta gcc cat        816
Ile Phe Leu Ala Arg Ser Ala Leu Ile Leu Arg Gly Ser Val Ala His
                260                 265                 270 aaa tca tgc cta cct gcc tgt gtt tat ggc ctt gca gta acc agt ggg        864
Lys Ser Cys Leu Pro Ala Cys Val Tyr Gly Leu Ala Val Thr Ser Gly
            275                 280                 285 tat gac ttt gag aag gaa gga tac tct ctg gtt gga att gat cct ttc        912
Tyr Asp Phe Glu Lys Glu Gly Tyr Ser Leu Val Gly Ile Asp Pro Phe
        290                 295                 300 aaa cta ctc cag aac agt caa att ttc agt cta atc aga cca aaa gaa        960
Lys Leu Leu Gln Asn Ser Gln Ile Phe Ser Leu Ile Arg Pro Lys Glu
305                 310                 315                 320 aac cca gca cac aag agc cag ttg gtg tgg atg gca tgc cat tct gca       1008
Asn Pro Ala His Lys Ser Gln Leu Val Trp Met Ala Cys His Ser Ala
                325                 330                 335 gca ttt gag gac ctg aga gtt tta aat ttc att aga gga acc aaa gta       1056
Ala Phe Glu Asp Leu Arg Val Leu Asn Phe Ile Arg Gly Thr Lys Val
                340                 345                 350 atc cca aga gga cag tta aca acc aga gga gtt caa att gct tca aat       1104
Ile Pro Arg Gly Gln Leu Thr Thr Arg Gly Val Gln Ile Ala Ser Asn
            355                 360                 365 gaa aac atg gag aca ata gat tct agc aca ctt gaa ctg aga agc aaa       1152
Glu Asn Met Glu Thr Ile Asp Ser Ser Thr Leu Glu Leu Arg Ser Lys
        370                 375                 380 tat tgg gca ata agg acc aga agc gga gga aac acc agt caa cag aga       1200
Tyr Trp Ala Ile Arg Thr Arg Ser Gly Gly Asn Thr Ser Gln Gln Arg
385                 390                 395                 400 gca tct gca gga cag ata agt gtg caa cct act ttc tca gta cag aga       1248
Ala Ser Ala Gly Gln Ile Ser Val Gln Pro Thr Phe Ser Val Gln Arg
                405                 410                 415 aat ctt ccc ttt gag aga gca acc att atg gct gca ttc act ggt aac       1296
Asn Leu Pro Phe Glu Arg Ala Thr Ile Met Ala Ala Phe Thr Gly Asn
```

```
Asn Leu Pro Phe Glu Arg Ala Thr Ile Met Ala Ala Phe Thr Gly Asn
            420                 425                 430 act gaa ggg agg act tcc gac atg aga acg gaa atc ata agg atg atg   1344
Thr Glu Gly Arg Thr Ser Asp Met Arg Thr Glu Ile Ile Arg Met Met
            435                 440                 445 gaa aat gcc aaa tca gaa gat gtg tct ttc cag ggg cgg gga gtc ttc   1392
Glu Asn Ala Lys Ser Glu Asp Val Ser Phe Gln Gly Arg Gly Val Phe
450                 455                 460 gag ctc tcg gac gaa aag gca acg aac ccg atc gtg cct tcc ttt gac   1440
Glu Leu Ser Asp Glu Lys Ala Thr Asn Pro Ile Val Pro Ser Phe Asp
465                 470                 475                 480 atg agc aat gaa ggg tct tat ttc ttc gga gac aat gct gag gag ttt   1488
Met Ser Asn Glu Gly Ser Tyr Phe Phe Gly Asp Asn Ala Glu Glu Phe
            485                 490                 495 gac agt taa                                                       1497
Asp Ser

<210> SEQ ID NO 26
<211> LENGTH: 498
<212> TYPE: PRT
<213> ORGANISM: Influenza virus

<400> SEQUENCE: 26

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270
```

```
Lys Ser Cys Leu Pro Ala Cys Val Tyr Gly Leu Ala Val Thr Ser Gly
            275                 280                 285

Tyr Asp Phe Glu Lys Glu Gly Tyr Ser Leu Val Gly Ile Asp Pro Phe
        290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
        355                 360                 365

Glu Asn Met Glu Thr Ile Asp Ser Ser Thr Leu Glu Leu Arg Ser Lys
    370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Lys Ser Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Ser

<210> SEQ ID NO 27
<211> LENGTH: 1410
<212> TYPE: DNA
<213> ORGANISM: Influenza virus
<220> FEATURE:
<221> NAME/KEY: CDS
<222> LOCATION: (1)..(1410)

<400> SEQUENCE: 27 atg aat cca aat caa aag ata ata aca att gga ttt gca tca ttg ggg      48
Met Asn Pro Asn Gln Lys Ile Ile Thr Ile Gly Phe Ala Ser Leu Gly
1               5                   10                  15 ata tta atc att aat gtc att ctc cat gta gtc agc att ata gta aca      96
Ile Leu Ile Ile Asn Val Ile Leu His Val Val Ser Ile Ile Val Thr
            20                  25                  30 gta ctg gtc ctc aat aac aat aga aca gat ctg aac tgc aaa ggg acg     144
Val Leu Val Leu Asn Asn Asn Arg Thr Asp Leu Asn Cys Lys Gly Thr
        35                  40                  45 atc ata aga gag tac aat gaa aca gta aga gta gaa aaa att act caa     192
Ile Ile Arg Glu Tyr Asn Glu Thr Val Arg Val Glu Lys Ile Thr Gln
    50                  55                  60 tgg tat aat acc agt aca att aag tac ata gag aga cct tca aat gaa     240
Trp Tyr Asn Thr Ser Thr Ile Lys Tyr Ile Glu Arg Pro Ser Asn Glu
65                  70                  75                  80 tac tac atg aac aac act gaa cca ctt tgt gag gcc caa ggc ttt gca     288
Tyr Tyr Met Asn Asn Thr Glu Pro Leu Cys Glu Ala Gln Gly Phe Ala
                85                  90                  95
```

```
cca ttt tcc aaa gat aat gga ata cga att ggg tcg aga ggc cat gtt      336
Pro Phe Ser Lys Asp Asn Gly Ile Arg Ile Gly Ser Arg Gly His Val
            100                 105                 110 ttt gtg ata aga gaa cct ttt gta tca tgt tcg ccc tca gaa tgt aga      384
Phe Val Ile Arg Glu Pro Phe Val Ser Cys Ser Pro Ser Glu Cys Arg
            115                 120                 125 acc ttt ttc ctc aca cag ggc tca tta ctc aat gac aaa cat tct aac      432
Thr Phe Phe Leu Thr Gln Gly Ser Leu Leu Asn Asp Lys His Ser Asn
            130                 135                 140 ggc aca gta aag gac cga agt ccg tat agg act ttg atg agt gtc aaa      480
Gly Thr Val Lys Asp Arg Ser Pro Tyr Arg Thr Leu Met Ser Val Lys
145                 150                 155                 160 ata ggg caa tca cct aat gta tat caa gct agg ttt gaa tcg gtg gca      528
Ile Gly Gln Ser Pro Asn Val Tyr Gln Ala Arg Phe Glu Ser Val Ala
                165                 170                 175 tgg tca gca aca gca tgc cat gat gga aaa aaa tgg atg aca gtt gga      576
Trp Ser Ala Thr Ala Cys His Asp Gly Lys Lys Trp Met Thr Val Gly
                180                 185                 190 gtc aca ggg ccc gac aat caa gca att gca gta gtg aac tat gga ggt      624
Val Thr Gly Pro Asp Asn Gln Ala Ile Ala Val Val Asn Tyr Gly Gly
            195                 200                 205 gtt ccg gtt gat att att aat tca tgg gca ggg gat att tta aga acc      672
Val Pro Val Asp Ile Ile Asn Ser Trp Ala Gly Asp Ile Leu Arg Thr
210                 215                 220 caa gaa tca tca tgc acc tgc att aaa gga gac tgt tat tgg gta atg      720
Gln Glu Ser Ser Cys Thr Cys Ile Lys Gly Asp Cys Tyr Trp Val Met
225                 230                 235                 240 act gat gga ccg gca aat agg caa gct aaa tat agg ata ttc aaa gca      768
Thr Asp Gly Pro Ala Asn Arg Gln Ala Lys Tyr Arg Ile Phe Lys Ala
                245                 250                 255 aaa gat gga aga gta att gga cag act gat ata agt ttc aat ggg gga      816
Lys Asp Gly Arg Val Ile Gly Gln Thr Asp Ile Ser Phe Asn Gly Gly
            260                 265                 270 cac ata gag gag tgt tct tgt tac ccc aat gaa ggg aag gtg gaa tgc      864
His Ile Glu Glu Cys Ser Cys Tyr Pro Asn Glu Gly Lys Val Glu Cys
            275                 280                 285 ata tgc agg gac aat tgg act gga aca aat aga cca att ctg gta ata      912
Ile Cys Arg Asp Asn Trp Thr Gly Thr Asn Arg Pro Ile Leu Val Ile
290                 295                 300 tct tct gat cta tcg tac aca gtt gga tat ttg tgt gct ggc att ccc      960
Ser Ser Asp Leu Ser Tyr Thr Val Gly Tyr Leu Cys Ala Gly Ile Pro
305                 310                 315                 320 act gac act cct agg gga gag gat agt caa ttc aca ggc tca tgt aca     1008
Thr Asp Thr Pro Arg Gly Glu Asp Ser Gln Phe Thr Gly Ser Cys Thr
                325                 330                 335 agt cct ttg gga aat aaa gga tac ggt gta aaa ggt ttc ggg ttt cga     1056
Ser Pro Leu Gly Asn Lys Gly Tyr Gly Val Lys Gly Phe Gly Phe Arg
            340                 345                 350 caa gga act gac gta tgg gcc gga agg aca att agt agg act tca aga     1104
Gln Gly Thr Asp Val Trp Ala Gly Arg Thr Ile Ser Arg Thr Ser Arg
            355                 360                 365 tca gga ttc gaa ata ata aaa atc agg aat ggt tgg aca cag aac agt     1152
Ser Gly Phe Glu Ile Ile Lys Ile Arg Asn Gly Trp Thr Gln Asn Ser
370                 375                 380 aaa gac caa atc agg agg caa gtg att atc gat gac cca aat tgg tca     1200
Lys Asp Gln Ile Arg Arg Gln Val Ile Ile Asp Asp Pro Asn Trp Ser
385                 390                 395                 400 gga tat agc ggt tct ttc aca ttg ccg gtt gaa cta aca aaa aag gga     1248
Gly Tyr Ser Gly Ser Phe Thr Leu Pro Val Glu Leu Thr Lys Lys Gly
                405                 410                 415
```

```
tgt ttg gtc ccc tgt ttc tgg gtt gaa atg att aga ggt aaa cct gaa   1296
Cys Leu Val Pro Cys Phe Trp Val Glu Met Ile Arg Gly Lys Pro Glu
        420                 425                 430 gaa aca aca ata tgg acc tct agc agc tcc att gtg atg tgt gga gta   1344
Glu Thr Thr Ile Trp Thr Ser Ser Ser Ile Val Met Cys Gly Val
    435                 440                 445 gat cat aaa att gcc agt tgg tca tgg cac gat gga gct att ctt ccc   1392
Asp His Lys Ile Ala Ser Trp Ser Trp His Asp Gly Ala Ile Leu Pro
450                 455                 460 ttt gac atc gat aag atg                                           1410
Phe Asp Ile Asp Lys Met
465                 470

<210> SEQ ID NO 28
<211> LENGTH: 470
<212> TYPE: PRT
<213> ORGANISM: Influenza virus

<400> SEQUENCE: 28

Met Asn Pro Asn Gln Lys Ile Ile Thr Ile Gly Phe Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Ile Thr Gln
    50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300
```

```
Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
            325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
                435                 440                 445

Asp His Lys Ile Ala Ser Trp Ser Trp His Asp Gly Ala Ile Leu Pro
450                 455                 460

Phe Asp Ile Asp Lys Met
465                 470

<210> SEQ ID NO 29
<211> LENGTH: 982
<212> TYPE: DNA
<213> ORGANISM: Influenza virus
<220> FEATURE:
<221> NAME/KEY: CDS
<222> LOCATION: (1)..(756)

<400> SEQUENCE: 29 atg agt ctt cta acc gag gtc gaa acg tac gtt ctc tct atc gta cca     48
Met Ser Leu Leu Thr Glu Val Glu Thr Tyr Val Leu Ser Ile Val Pro
1               5                   10                  15 tca ggc ccc ctc aaa gcc gag atc gcg cag aga ctt gaa gat gtc ttt     96
Ser Gly Pro Leu Lys Ala Glu Ile Ala Gln Arg Leu Glu Asp Val Phe
                20                  25                  30 gca ggg aag aac acc gat ctt gag gca ctc atg gaa tgg cta aag aca    144
Ala Gly Lys Asn Thr Asp Leu Glu Ala Leu Met Glu Trp Leu Lys Thr
            35                  40                  45 aga cca atc ctg tca cct ctg act aaa ggg att tta gga ttt gta ttc    192
Arg Pro Ile Leu Ser Pro Leu Thr Lys Gly Ile Leu Gly Phe Val Phe
        50                  55                  60 acg ctc acc gtg ccc agt gag cga gga ctg cag cgt aga cgc ttt gtc    240
Thr Leu Thr Val Pro Ser Glu Arg Gly Leu Gln Arg Arg Arg Phe Val
65                  70                  75                  80 caa aat gcc ctt agt gga aac gga gat cca aac aac atg gac aga gca    288
Gln Asn Ala Leu Ser Gly Asn Gly Asp Pro Asn Asn Met Asp Arg Ala
                85                  90                  95 gta aaa ctg tac agg aag ctt aaa aga gaa ata aca ttc cat ggg gca    336
Val Lys Leu Tyr Arg Lys Leu Lys Arg Glu Ile Thr Phe His Gly Ala
                100                 105                 110 aaa gag gtg gca ctc agc tat tcc act ggt gca cta gcc agc tgc atg    384
Lys Glu Val Ala Leu Ser Tyr Ser Thr Gly Ala Leu Ala Ser Cys Met
            115                 120                 125 gga ctc ata tac aac aga atg gga act gtt aca acc gaa gtg gca ttt    432
Gly Leu Ile Tyr Asn Arg Met Gly Thr Val Thr Thr Glu Val Ala Phe
        130                 135                 140
```

```
ggc ctg gta tgc gcc aca tgt gaa cag att gct gat tcc cag cat cga      480
Gly Leu Val Cys Ala Thr Cys Glu Gln Ile Ala Asp Ser Gln His Arg
145                 150                 155                 160 tct cac agg cag atg gtg aca aca acc aac cca tta atc aga cat gaa      528
Ser His Arg Gln Met Val Thr Thr Thr Asn Pro Leu Ile Arg His Glu
                165                 170                 175 aac aga atg gta tta gcc agt acc acg gct aaa gcc atg gaa cag atg      576
Asn Arg Met Val Leu Ala Ser Thr Thr Ala Lys Ala Met Glu Gln Met
            180                 185                 190 gca gga tcg agt gag cag gca gca gag gcc atg gag gtt gct agt agg      624
Ala Gly Ser Ser Glu Gln Ala Ala Glu Ala Met Glu Val Ala Ser Arg
        195                 200                 205 gct agg cag atg gta cag gca atg aga acc att ggg acc cac cct agc      672
Ala Arg Gln Met Val Gln Ala Met Arg Thr Ile Gly Thr His Pro Ser
    210                 215                 220 tcc agt gcc ggt ttg aaa gat gat ctc ctt gaa aat tta cag gcc tac      720
Ser Ser Ala Gly Leu Lys Asp Asp Leu Leu Glu Asn Leu Gln Ala Tyr
225                 230                 235                 240 cag aaa cgg atg gga gtg caa atg cag cga ttc aag tgatcctctc           766
Gln Lys Arg Met Gly Val Gln Met Gln Arg Phe Lys
                245                 250 gttattgcag caagtatcat tgggatcttg cacttgatat tgtggattct tgatcgtctt    826
ttcttcaaat tcatttatcg tcgccttaaa tacgggttga aaagagggcc ttctacggaa    886
ggagtacctg agtctatgag ggaagaatat cggcaggaac agcagaatgc tgtggatgtt    946
gacgatggtc attttgtcaa catagagctg agtaa                              982

<210> SEQ ID NO 30
<211> LENGTH: 252
<212> TYPE: PRT
<213> ORGANISM: Influenza virus

<400> SEQUENCE: 30

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

```
Ala Gly Ser Ser Glu Gln Ala Ala Glu Ala Met Glu Val Ala Ser Arg
            195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 31
<211> LENGTH: 1698
<212> TYPE: DNA
<213> ORGANISM: Influenza virus
<220> FEATURE:
<221> NAME/KEY: CDS
<222> LOCATION: (1)..(1698)

<400> SEQUENCE: 31 atg aag aca acc att att ttg ata cta ctg acc cat tgg gcc tac agt      48
Met Lys Thr Thr Ile Ile Leu Ile Leu Leu Thr His Trp Ala Tyr Ser
1               5                   10                  15 caa aac cca atc agt gac aac aac aca gcc aca ctg tgt ctg gga cac      96
Gln Asn Pro Ile Ser Asp Asn Asn Thr Ala Thr Leu Cys Leu Gly His
            20                  25                  30 cat gca gta gca aat gga aca ttg gta aaa aca ata agt gat gat caa     144
His Ala Val Ala Asn Gly Thr Leu Val Lys Thr Ile Ser Asp Asp Gln
        35                  40                  45 att gag gtg aca aat gct aca gaa tta gtt cag agc att tca atg ggg     192
Ile Glu Val Thr Asn Ala Thr Glu Leu Val Gln Ser Ile Ser Met Gly
    50                  55                  60 aaa ata tgc aac aaa tca tat aga att cta gat gga aga aat tgc aca     240
Lys Ile Cys Asn Lys Ser Tyr Arg Ile Leu Asp Gly Arg Asn Cys Thr
65                  70                  75                  80 tta ata gat gca atg cta gga gac ccc cac tgt gac gcc ttt cag tat     288
Leu Ile Asp Ala Met Leu Gly Asp Pro His Cys Asp Ala Phe Gln Tyr
                85                  90                  95 gag agt tgg gac ctc ttt ata gaa aga agc agc gct ttc agc aat tgc     336
Glu Ser Trp Asp Leu Phe Ile Glu Arg Ser Ser Ala Phe Ser Asn Cys
            100                 105                 110 tac cca tat gac atc cct gac tat gca tcg ctc cga tcc att gta gca     384
Tyr Pro Tyr Asp Ile Pro Asp Tyr Ala Ser Leu Arg Ser Ile Val Ala
        115                 120                 125 tcc tca gga aca ttg gaa ttc aca gca gag gga ttc aca tgg aca ggt     432
Ser Ser Gly Thr Leu Glu Phe Thr Ala Glu Gly Phe Thr Trp Thr Gly
    130                 135                 140 gtc act caa aac gga aga agt gga gcc tgc aaa agg gga tca gcc gat     480
Val Thr Gln Asn Gly Arg Ser Gly Ala Cys Lys Arg Gly Ser Ala Asp
145                 150                 155                 160 agt ttc ttt agc cga ctg aat tgg cta aca aaa tct gga agc tct tac     528
Ser Phe Phe Ser Arg Leu Asn Trp Leu Thr Lys Ser Gly Ser Ser Tyr
                165                 170                 175 ccc aca ttg aat gtg aca atg cct aac aat aaa aat ttc gac aag cta     576
Pro Thr Leu Asn Val Thr Met Pro Asn Asn Lys Asn Phe Asp Lys Leu
            180                 185                 190 tac atc tgg ggg att cat cac ccg agc tca aat caa gag cag aca aaa     624
Tyr Ile Trp Gly Ile His His Pro Ser Ser Asn Gln Glu Gln Thr Lys
        195                 200                 205 ttg tac atc caa gaa tca gga cga gta aca gtc tca aca aaa aga agt     672
Leu Tyr Ile Gln Glu Ser Gly Arg Val Thr Val Ser Thr Lys Arg Ser
    210                 215                 220
```

-continued

```
caa caa aca ata atc cct aac atc gga tct aga ccg ttg gtc aga ggt      720
Gln Gln Thr Ile Ile Pro Asn Ile Gly Ser Arg Pro Leu Val Arg Gly
225             230                 235                 240 caa tca ggc agg ata agc ata tac tgg acc att gta aaa cct gga gat      768
Gln Ser Gly Arg Ile Ser Ile Tyr Trp Thr Ile Val Lys Pro Gly Asp
                245                 250                 255 atc cta atg ata aac agt aat ggc aac tta gtt gca ccg cgg gga tat      816
Ile Leu Met Ile Asn Ser Asn Gly Asn Leu Val Ala Pro Arg Gly Tyr
            260                 265                 270 ttt aaa ttg aaa aca ggg aaa agc tct gta atg aga tca gat gta ccc      864
Phe Lys Leu Lys Thr Gly Lys Ser Ser Val Met Arg Ser Asp Val Pro
        275                 280                 285 ata gac att tgt gtg tct gaa tgt att aca cca aat gga agc atc tcc      912
Ile Asp Ile Cys Val Ser Glu Cys Ile Thr Pro Asn Gly Ser Ile Ser
    290                 295                 300 aac gac aag cca ttc caa aat gtg aac aaa gtt aca tat gga aaa tgc      960
Asn Asp Lys Pro Phe Gln Asn Val Asn Lys Val Thr Tyr Gly Lys Cys
305                 310                 315                 320 ccc aag tat atc agg caa aac act tta aag ctg gcc act ggg atg agg     1008
Pro Lys Tyr Ile Arg Gln Asn Thr Leu Lys Leu Ala Thr Gly Met Arg
                325                 330                 335 aat gta cca gaa aag caa acc aga gga atc ttt gga gca ata gcg gga     1056
Asn Val Pro Glu Lys Gln Thr Arg Gly Ile Phe Gly Ala Ile Ala Gly
            340                 345                 350 ttc atc gaa aac ggc tgg gaa gga atg gtt gat ggg tgg tat ggg ttc     1104
Phe Ile Glu Asn Gly Trp Glu Gly Met Val Asp Gly Trp Tyr Gly Phe
        355                 360                 365 cga tat caa aac tct gaa gga aca ggg caa gct gca gat cta aag agc     1152
Arg Tyr Gln Asn Ser Glu Gly Thr Gly Gln Ala Ala Asp Leu Lys Ser
    370                 375                 380 act caa gca gcc atc gac cag att aat gga aag tta aac aga gtg att     1200
Thr Gln Ala Ala Ile Asp Gln Ile Asn Gly Lys Leu Asn Arg Val Ile
385                 390                 395                 400 gaa aga acc aat gag aaa ttc cat caa ata gag aag gaa ttc tca gaa     1248
Glu Arg Thr Asn Glu Lys Phe His Gln Ile Glu Lys Glu Phe Ser Glu
                405                 410                 415 gta gaa gga aga att cag gac ttg gag aaa tat gta gaa gac acc aaa     1296
Val Glu Gly Arg Ile Gln Asp Leu Glu Lys Tyr Val Glu Asp Thr Lys
            420                 425                 430 ata gac cta tgg tcc tac aat gca gaa ttg ctg gtg gct cta gaa aat     1344
Ile Asp Leu Trp Ser Tyr Asn Ala Glu Leu Leu Val Ala Leu Glu Asn
        435                 440                 445 caa cat aca att gac tta aca gat gca gaa atg aat aaa tta ttt gag     1392
Gln His Thr Ile Asp Leu Thr Asp Ala Glu Met Asn Lys Leu Phe Glu
    450                 455                 460 aag act aga cgc cag tta aga gaa aac gca gaa gac atg gga ggt gga     1440
Lys Thr Arg Arg Gln Leu Arg Glu Asn Ala Glu Asp Met Gly Gly Gly
465                 470                 475                 480 tgt ttc aag att tac cac aaa tgt gat aat gca tgc att gga tca ata     1488
Cys Phe Lys Ile Tyr His Lys Cys Asp Asn Ala Cys Ile Gly Ser Ile
                485                 490                 495 aga act ggg aca tat gac cat tac ata tac aga gat gaa gca tta aac     1536
Arg Thr Gly Thr Tyr Asp His Tyr Ile Tyr Arg Asp Glu Ala Leu Asn
            500                 505                 510 aac cga ttt cag atc aaa ggt gta gag ttg aaa tca ggc tac aaa gat     1584
Asn Arg Phe Gln Ile Lys Gly Val Glu Leu Lys Ser Gly Tyr Lys Asp
        515                 520                 525 tgg ata ctg tgg att tca ttc gcc ata tca tgc ttc tta att tgc gtt     1632
Trp Ile Leu Trp Ile Ser Phe Ala Ile Ser Cys Phe Leu Ile Cys Val
    530                 535                 540
```

```
gtt cta ttg ggt ttc att atg tgg gct tgc caa aaa ggc aac atc a

```
                340                 345                 350
Phe Ile Glu Asn Gly Trp Glu Gly Met Val Asp Gly Trp Tyr Gly Phe
            355                 360                 365
Arg Tyr Gln Asn Ser Glu Gly Thr Gly Gln Ala Ala Asp Leu Lys Ser
            370                 375                 380
Thr Gln Ala Ala Ile Asp Gln Ile Asn Gly Lys Leu Asn Arg Val Ile
385                 390                 395                 400
Glu Arg Thr Asn Glu Lys Phe His Gln Ile Glu Lys Glu Phe Ser Glu
                405                 410                 415
Val Glu Gly Arg Ile Gln Asp Leu Glu Lys Tyr Val Glu Asp Thr Lys
            420                 425                 430
Ile Asp Leu Trp Ser Tyr Asn Ala Glu Leu Leu Val Ala Leu Glu Asn
            435                 440                 445
Gln His Thr Ile Asp Leu Thr Asp Ala Glu Met Asn Lys Leu Phe Glu
            450                 455                 460
Lys Thr Arg Arg Gln Leu Arg Glu Asn Ala Glu Asp Met Gly Gly Gly
465                 470                 475                 480
Cys Phe Lys Ile Tyr His Lys Cys Asp Asn Ala Cys Ile Gly Ser Ile
                485                 490                 495
Arg Thr Gly Thr Tyr Asp His Tyr Ile Tyr Arg Asp Glu Ala Leu Asn
            500                 505                 510
Asn Arg Phe Gln Ile Lys Gly Val Glu Leu Lys Ser Gly Tyr Lys Asp
            515                 520                 525
Trp Ile Leu Trp Ile Ser Phe Ala Ile Ser Cys Phe Leu Ile Cys Val
            530                 535                 540
Val Leu Leu Gly Phe Ile Met Trp Ala Cys Gln Lys Gly Asn Ile Arg
545                 550                 555                 560
Cys Asn Ile Cys Ile
                565

<210> SEQ ID NO 33
<211> LENGTH: 549
<212> TYPE: PRT
<213> ORGANISM: Influenza virus

<400> SEQUENCE: 33

Gln Asn Pro Ile Ser Gly Asn Asn Thr Ala Thr Leu Cys Leu Gly His
1               5                   10                  15
His Ala Val Ala Asn Gly Thr Leu Val Lys Thr Met Ser Asp Asp Gln
            20                  25                  30
Ile Glu Val Thr Asn Ala Thr Glu Leu Val Gln Ser Ile Ser Met Gly
            35                  40                  45
Lys Ile Cys Asn Lys Ser Tyr Arg Ile Leu Asp Gly Arg Asn Cys Thr
        50                  55                  60
Leu Ile Asp Ala Met Leu Gly Asp Pro His Cys Asp Ala Phe Gln Tyr
65                  70                  75                  80
Glu Ser Trp Asp Leu Phe Ile Glu Arg Ser Asn Ala Phe Ser Asn Cys
                85                  90                  95
Tyr Pro Tyr Asp Ile Pro Asp Tyr Ala Ser Leu Arg Ser Ile Val Ala
            100                 105                 110
Ser Ser Gly Thr Leu Glu Phe Thr Ala Glu Gly Phe Thr Trp Thr Gly
            115                 120                 125
Val Thr Gln Asn Gly Arg Ser Gly Ala Cys Lys Arg Gly Ser Ala Asp
            130                 135                 140
Ser Phe Phe Ser Arg Leu Asn Trp Leu Thr Lys Ser Gly Ser Ser Tyr
```

```
              145                 150                 155                 160
        Pro Thr Leu Asn Val Thr Met Pro Asn Asn Lys Asn Phe Asp Lys Leu
                            165                 170                 175

Tyr Ile Trp Gly Ile His His Pro Ser Ser Asn Gln Glu Gln Thr Lys
                            180                 185                 190

Leu Tyr Ile Gln Glu Ser Gly Arg Val Thr Val Ser Thr Lys Arg Ser
                            195                 200                 205

Gln Gln Thr Ile Ile Pro Asn Ile Gly Ser Arg Pro Leu Val Arg Gly
                210                 215                 220

Gln Ser Gly Arg Ile Ser Ile Tyr Trp Thr Ile Val Lys Pro Gly Asp
        225                 230                 235                 240

Ile Leu Met Ile Asn Ser Asn Gly Asn Leu Val Ala Pro Arg Gly Tyr
                            245                 250                 255

Phe Lys Leu Lys Thr Gly Lys Ser Ser Val Met Arg Ser Asp Ala Pro
                            260                 265                 270

Ile Asp Ile Cys Val Ser Glu Cys Ile Thr Pro Asn Gly Ser Ile Ser
                        275                 280                 285

Asn Asp Lys Pro Phe Gln Asn Val Asn Lys Val Thr Tyr Gly Lys Cys
                290                 295                 300

Pro Lys Tyr Ile Arg Gln Asn Thr Leu Lys Leu Ala Thr Gly Met Arg
        305                 310                 315                 320

Asn Val Pro Glu Lys Gln Thr Arg Gly Ile Phe Gly Ala Ile Ala Gly
                            325                 330                 335

Phe Ile Glu Asn Gly Trp Glu Gly Met Val Asp Gly Trp Tyr Gly Phe
                        340                 345                 350

Arg Tyr Gln Asn Ser Glu Gly Thr Gly Gln Ala Ala Asp Leu Lys Ser
                        355                 360                 365

Thr Gln Ala Ala Ile Asp Gln Ile Asn Gly Lys Leu Asn Arg Val Ile
                370                 375                 380

Glu Arg Thr Asn Glu Lys Phe His Gln Ile Glu Lys Glu Phe Ser Glu
        385                 390                 395                 400

Val Glu Gly Arg Ile Gln Asp Leu Glu Lys Tyr Val Glu Asp Thr Lys
                            405                 410                 415

Ile Asp Leu Trp Ser Tyr Asn Ala Glu Leu Leu Val Ala Leu Glu Asn
                        420                 425                 430

Gln His Thr Ile Asp Leu Thr Asp Ala Glu Met Asn Lys Leu Phe Glu
                        435                 440                 445

Lys Thr Arg Arg Gln Leu Arg Glu Asn Ala Glu Asp Met Gly Gly Gly
                450                 455                 460

Cys Phe Lys Ile Tyr His Lys Cys Asp Asn Ala Cys Ile Gly Ser Ile
        465                 470                 475                 480

Arg Thr Gly Thr Tyr Asp His Tyr Ile Tyr Arg Asp Glu Ala Leu Asn
                        485                 490                 495

Asn Arg Phe Gln Ile Lys Gly Val Glu Leu Lys Ser Gly Tyr Lys Asp
                        500                 505                 510

Trp Ile Leu Trp Ile Ser Phe Ala Ile Ser Cys Phe Leu Ile Cys Val
                        515                 520                 525

Val Leu Leu Gly Phe Ile Met Trp Ala Cys Gln Arg Gly Asn Ile Arg
                530                 535                 540

Cys Asn Ile Cys Ile
        545

<210> SEQ ID NO 34
<211> LENGTH: 549
```

<212> TYPE: PRT
<213> ORGANISM: Influenza virus

<400> SEQUENCE: 34

```
Gln Asn Pro Ile Ser Asp Asn Asn Thr Ala Thr Leu Cys Leu Gly His
1               5                   10                  15

His Ala Val Ala Asn Gly Thr Leu Val Lys Thr Ile Ser Asp Asp Gln
            20                  25                  30

Ile Glu Val Thr Asn Ala Thr Glu Leu Val Gln Ser Ile Ser Met Gly
        35                  40                  45

Lys Ile Cys Asn Lys Ser Tyr Arg Ile Leu Asp Gly Arg Asn Cys Thr
50                  55                  60

Leu Ile Asp Ala Met Leu Gly Asp Pro His Cys Asp Ala Phe Gln Tyr
65                  70                  75                  80

Glu Ser Trp Asp Leu Phe Ile Glu Arg Ser Ser Ala Phe Ser Asn Cys
                85                  90                  95

Tyr Pro Tyr Asp Ile Pro Asp Tyr Ala Ser Leu Arg Ser Ile Val Ala
            100                 105                 110

Ser Ser Gly Thr Leu Glu Phe Thr Ala Glu Gly Phe Thr Trp Thr Gly
        115                 120                 125

Val Thr Gln Asn Gly Arg Ser Gly Ala Cys Lys Arg Gly Ser Ala Asp
130                 135                 140

Ser Phe Phe Ser Arg Leu Asn Trp Leu Thr Lys Ser Gly Ser Ser Tyr
145                 150                 155                 160

Pro Thr Leu Asn Val Thr Met Pro Asn Asn Lys Asn Phe Asp Lys Leu
                165                 170                 175

Tyr Ile Trp Gly Ile His His Pro Ser Ser Asn Gln Glu Gln Thr Lys
            180                 185                 190

Leu Tyr Ile Gln Glu Ser Gly Arg Val Thr Val Ser Thr Lys Arg Ser
        195                 200                 205

Gln Gln Thr Ile Ile Pro Asn Ile Gly Ser Arg Pro Leu Val Arg Gly
210                 215                 220

Gln Ser Gly Arg Ile Ser Ile Tyr Trp Thr Ile Val Lys Pro Gly Asp
225                 230                 235                 240

Ile Leu Met Ile Asn Ser Asn Gly Asn Leu Val Ala Pro Arg Gly Tyr
                245                 250                 255

Phe Lys Leu Lys Thr Gly Lys Ser Ser Val Met Arg Ser Asp Val Pro
            260                 265                 270

Ile Asp Ile Cys Val Ser Glu Cys Ile Thr Pro Asn Gly Ser Ile Ser
        275                 280                 285

Asn Asp Lys Pro Phe Gln Asn Val Asn Lys Val Thr Tyr Gly Lys Cys
290                 295                 300

Pro Lys Tyr Ile Arg Gln Asn Thr Leu Lys Leu Ala Thr Gly Met Arg
305                 310                 315                 320

Asn Val Pro Glu Lys Gln Thr Arg Gly Ile Phe Gly Ala Ile Ala Gly
                325                 330                 335

Phe Ile Glu Asn Gly Trp Glu Gly Met Val Asp Gly Trp Tyr Gly Phe
            340                 345                 350

Arg Tyr Gln Asn Ser Glu Gly Thr Gly Gln Ala Ala Asp Leu Lys Ser
        355                 360                 365

Thr Gln Ala Ala Ile Asp Gln Ile Asn Gly Lys Leu Asn Arg Val Ile
370                 375                 380

Glu Arg Thr Asn Glu Lys Phe His Gln Ile Glu Lys Glu Phe Ser Glu
385                 390                 395                 400
```

```
Val Glu Gly Arg Ile Gln Asp Leu Glu Lys Tyr Val Glu Asp Thr Lys
            405                 410                 415
Ile Asp Leu Trp Ser Tyr Asn Ala Glu Leu Leu Val Ala Leu Glu Asn
        420                 425                 430
Gln His Thr Ile Asp Leu Thr Asp Ala Glu Met Asn Lys Leu Phe Glu
    435                 440                 445
Lys Thr Arg Arg Gln Leu Arg Glu Asn Ala Glu Asp Met Gly Gly Gly
450                 455                 460
Cys Phe Lys Ile Tyr His Lys Cys Asp Asn Ala Cys Ile Gly Ser Ile
465                 470                 475                 480
Arg Thr Gly Thr Tyr Asp His Tyr Ile Tyr Arg Asp Glu Ala Leu Asn
            485                 490                 495
Asn Arg Phe Gln Ile Lys Gly Val Glu Leu Lys Ser Gly Tyr Lys Asp
        500                 505                 510
Trp Ile Leu Trp Ile Ser Phe Ala Ile Ser Cys Phe Leu Ile Cys Val
    515                 520                 525
Val Leu Leu Gly Phe Ile Met Trp Ala Cys Gln Lys Gly Asn Ile Arg
530                 535                 540
Cys Asn Ile Cys Ile
545

<210> SEQ ID NO 35
<211> LENGTH: 9
<212> TYPE: DNA
<213> ORGANISM: Influenza virus

<400> SEQUENCE: 35 gagagttgg                                                                   9

<210> SEQ ID NO 36
<211> LENGTH: 9
<212> TYPE: DNA
<213> ORGANISM: Influenza virus

<400> SEQUENCE: 36 ccgttggtc                                                                   9

<210> SEQ ID NO 37
<211> LENGTH: 9
<212> TYPE: DNA
<213> ORGANISM: Influenza virus

<400> SEQUENCE: 37 caaaccaga                                                                   9

<210> SEQ ID NO 38
<211> LENGTH: 9
<212> TYPE: DNA
<213> ORGANISM: Influenza virus

<400> SEQUENCE: 38 agaactggg                                                                   9

<210> SEQ ID NO 39
<211> LENGTH: 15
<212> TYPE: DNA
<213> ORGANISM: Influenza virus

<400> SEQUENCE: 39
tatgagagtt gggac                                                           15
```

```
<210> SEQ ID NO 40
<211> LENGTH: 15
<212> TYPE: DNA
<213> ORGANISM: Influenza virus

<400> SEQUENCE: 40
agaccgttgg tcaga                                                    15

<210> SEQ ID NO 41
<211> LENGTH: 15
<212> TYPE: DNA
<213> ORGANISM: Influenza virus

<400> SEQUENCE: 41
aagcaaacca gagga                                                    15

<210> SEQ ID NO 42
<211> LENGTH: 15
<212> TYPE: DNA
<213> ORGANISM: Influenza virus

<400> SEQUENCE: 42
ataagaactg ggaca                                                    15

<210> SEQ ID NO 43
<211> LENGTH: 9
<212> TYPE: DNA
<213> ORGANISM: Influenza virus

<400> SEQUENCE: 43 acaatgagt                                                            9

<210> SEQ ID NO 44
<211> LENGTH: 15
<212> TYPE: DNA
<213> ORGANISM: Influenza virus

<400> SEQUENCE: 44
aaaacaatga gtgat                                                    15

<210> SEQ ID NO 45
<211> LENGTH: 9
<212> TYPE: DNA
<213> ORGANISM: Influenza virus

<400> SEQUENCE: 45 gatgtaccc                                                            9

<210> SEQ ID NO 46
<211> LENGTH: 15
<212> TYPE: DNA
<213> ORGANISM: Influenza virus

<400> SEQUENCE: 46
tcagatgtac ccata                                                    15

<210> SEQ ID NO 47
<211> LENGTH: 2280
<212> TYPE: DNA
<213> ORGANISM: Influenza virus
<220> FEATURE:
<221> NAME/KEY: CDS
<222> LOCATION: (1)..(2280)

<400> SEQUENCE: 47
```

```
atg gag aga ata aaa gaa ctg aga gat ctg atg tta caa tcc cgc acc      48
Met Glu Arg Ile Lys Glu Leu Arg Asp Leu Met Leu Gln Ser Arg Thr
1               5                   10                  15 cgc gag ata cta aca aaa act act gtg gac cac atg gcc ata atc aag      96
Arg Glu Ile Leu Thr Lys Thr Thr Val Asp His Met Ala Ile Ile Lys
                20                  25                  30 aaa tac aca tca gga aga caa gag aag aac cct gca ctt agg atg aaa     144
Lys Tyr Thr Ser Gly Arg Gln Glu Lys Asn Pro Ala Leu Arg Met Lys
            35                  40                  45 tgg atg atg gca atg aaa tac cca att aca gca gat aag agg ata atg     192
Trp Met Met Ala Met Lys Tyr Pro Ile Thr Ala Asp Lys Arg Ile Met
50                  55                  60 gag atg att cct gag aga aat gaa cag gga caa acc ctt tgg agc aaa     240
Glu Met Ile Pro Glu Arg Asn Glu Gln Gly Gln Thr Leu Trp Ser Lys
65                  70                  75                  80 acg aac gat gct ggc tca gac cgc gta atg gta tca cct ctg gca gtg     288
Thr Asn Asp Ala Gly Ser Asp Arg Val Met Val Ser Pro Leu Ala Val
                85                  90                  95 aca tgg tgg aat agg aat gga cca aca acg aac aca att cat tat cca     336
Thr Trp Trp Asn Arg Asn Gly Pro Thr Thr Asn Thr Ile His Tyr Pro
            100                 105                 110 aaa gtc tac aaa act tat ttt gaa aag gtt gaa aga ttg aaa cac gga     384
Lys Val Tyr Lys Thr Tyr Phe Glu Lys Val Glu Arg Leu Lys His Gly
        115                 120                 125 acc ttt ggc ccc gtt cat ttt agg aat caa gtc aag ata aga cga aga     432
Thr Phe Gly Pro Val His Phe Arg Asn Gln Val Lys Ile Arg Arg Arg
130                 135                 140 gtt gat gta aac cct ggt cac gcg gac ctc agt gct aaa gaa gca caa     480
Val Asp Val Asn Pro Gly His Ala Asp Leu Ser Ala Lys Glu Ala Gln
145                 150                 155                 160 gat gtg atc atg gaa gtt gtt ttc cca aat gaa gtg gga gcc aga att     528
Asp Val Ile Met Glu Val Val Phe Pro Asn Glu Val Gly Ala Arg Ile
                165                 170                 175 cta aca tca gaa tca caa cta aca ata acc aaa gag aaa aag gaa gaa     576
Leu Thr Ser Glu Ser Gln Leu Thr Ile Thr Lys Glu Lys Lys Glu Glu
            180                 185                 190 ctt cag gac tgc aaa att gct ccc ttg atg gta gca tac atg cta gaa     624
Leu Gln Asp Cys Lys Ile Ala Pro Leu Met Val Ala Tyr Met Leu Glu
        195                 200                 205 aga gag ttg gtc cga aaa aca agg ttc ctc cca gta gta ggc gga aca     672
Arg Glu Leu Val Arg Lys Thr Arg Phe Leu Pro Val Val Gly Gly Thr
210                 215                 220 agc agt gta tac att gaa gtg ttg cat ctg act cag gga aca tgc tgg     720
Ser Ser Val Tyr Ile Glu Val Leu His Leu Thr Gln Gly Thr Cys Trp
225                 230                 235                 240 gag caa atg tac acc cca gga gga aaa gtt aga aac gat gat att gat     768
Glu Gln Met Tyr Thr Pro Gly Gly Lys Val Arg Asn Asp Asp Ile Asp
                245                 250                 255 caa agt tta att att gca gcc cgg aac ata gtg aga aga gca aca gta     816
Gln Ser Leu Ile Ile Ala Ala Arg Asn Ile Val Arg Arg Ala Thr Val
            260                 265                 270 tca gca gat cca cta gca tcc cta ctg gaa atg tgc cac agt aca cag     864
Ser Ala Asp Pro Leu Ala Ser Leu Leu Glu Met Cys His Ser Thr Gln
        275                 280                 285 att ggt gga aca agg atg gta gac atc ctt aag cag aac cca aca gag     912
Ile Gly Gly Thr Arg Met Val Asp Ile Leu Lys Gln Asn Pro Thr Glu
290                 295                 300 gaa caa gct gtg gat ata tgc aaa gca gca atg gga ttg aga att agc     960
Glu Gln Ala Val Asp Ile Cys Lys Ala Ala Met Gly Leu Arg Ile Ser
305                 310                 315                 320
```

| | |
|---|---|
| tca tca ttc agc ttt ggt gga ttc acc ttc aaa agg aca agt gga tca<br>Ser Ser Phe Ser Phe Gly Gly Phe Thr Phe Lys Arg Thr Ser Gly Ser<br>　　　　　　　325　　　　　　　　　330　　　　　　　　　335 | 1008 |
| tca gtc aag aga gaa gaa gaa atg ctt acg ggc aac ctt caa aca ttg<br>Ser Val Lys Arg Glu Glu Glu Met Leu Thr Gly Asn Leu Gln Thr Leu<br>340　　　　　　　　　345　　　　　　　　　350 | 1056 |
| aaa ata aga gtg cat gag ggc tat gaa gaa ttc aca atg gtc gga aga<br>Lys Ile Arg Val His Glu Gly Tyr Glu Glu Phe Thr Met Val Gly Arg<br>　　　355　　　　　　　　　360　　　　　　　　　365 | 1104 |
| aga gca aca gcc att atc aga aag gca acc aga aga ttg att caa ttg<br>Arg Ala Thr Ala Ile Ile Arg Lys Ala Thr Arg Arg Leu Ile Gln Leu<br>　　　　　　　370　　　　　　　　　375　　　　　　　　　380 | 1152 |
| ata gta agt ggg aga gat gaa caa tca att gct gaa gca ata att gta<br>Ile Val Ser Gly Arg Asp Glu Gln Ser Ile Ala Glu Ala Ile Ile Val<br>385　　　　　　　　　390　　　　　　　　　395　　　　　　　　　400 | 1200 |
| gcc atg gtg ttt tcg caa gaa gat tgc atg ata aaa gca gtt cga ggc<br>Ala Met Val Phe Ser Gln Glu Asp Cys Met Ile Lys Ala Val Arg Gly<br>　　　　　　　　　405　　　　　　　　　410　　　　　　　　　415 | 1248 |
| gat ttg aac ttt gtt aat aga gca aat cag cgt ttg aac ccc atg cat<br>Asp Leu Asn Phe Val Asn Arg Ala Asn Gln Arg Leu Asn Pro Met His<br>　　　　　420　　　　　　　　　425　　　　　　　　　430 | 1296 |
| caa ctc ttg agg cat ttc caa aaa gat gca aaa gtg ctt ttc caa aat<br>Gln Leu Leu Arg His Phe Gln Lys Asp Ala Lys Val Leu Phe Gln Asn<br>　　　　　　　　　435　　　　　　　　　440　　　　　　　　　445 | 1344 |
| tgg gga att gaa ccc atc gac aat gta atg ggg atg att gga ata ttg<br>Trp Gly Ile Glu Pro Ile Asp Asn Val Met Gly Met Ile Gly Ile Leu<br>　　　　　450　　　　　　　　　455　　　　　　　　　460 | 1392 |
| cct gac atg acc cca agc acc gag atg tca ttg aga gga gtg aga gtc<br>Pro Asp Met Thr Pro Ser Thr Glu Met Ser Leu Arg Gly Val Arg Val<br>465　　　　　　　　　470　　　　　　　　　475　　　　　　　　　480 | 1440 |
| agc aaa atg gga gtg gat gag tac tcc agc act gag aga gtg gtg gtg<br>Ser Lys Met Gly Val Asp Glu Tyr Ser Ser Thr Glu Arg Val Val Val<br>　　　　　　　　　485　　　　　　　　　490　　　　　　　　　495 | 1488 |
| agc att gac cgt ttt tta aga gtt cgg gat caa agg gga aac ata cta<br>Ser Ile Asp Arg Phe Leu Arg Val Arg Asp Gln Arg Gly Asn Ile Leu<br>　　　　　500　　　　　　　　　505　　　　　　　　　510 | 1536 |
| ctg tcc cct gaa gaa gtc agt gaa aca caa gga acg gaa aag ctg aca<br>Leu Ser Pro Glu Glu Val Ser Glu Thr Gln Gly Thr Glu Lys Leu Thr<br>　　　　　　　　　515　　　　　　　　　520　　　　　　　　　525 | 1584 |
| ata att tat tcg tca tca atg atg tgg gag att aat ggt ccc gaa tca<br>Ile Ile Tyr Ser Ser Ser Met Met Trp Glu Ile Asn Gly Pro Glu Ser<br>　　　　　530　　　　　　　　　535　　　　　　　　　540 | 1632 |
| gtg ttg gtc aat act tat caa tgg atc atc aga aac tgg gaa att gta<br>Val Leu Val Asn Thr Tyr Gln Trp Ile Ile Arg Asn Trp Glu Ile Val<br>545　　　　　　　　　550　　　　　　　　　555　　　　　　　　　560 | 1680 |
| aaa att cag tgg tca cag gac ccc aca atg tta tac aat aag ata gaa<br>Lys Ile Gln Trp Ser Gln Asp Pro Thr Met Leu Tyr Asn Lys Ile Glu<br>　　　　　　　　　565　　　　　　　　　570　　　　　　　　　575 | 1728 |
| ttt gaa cca ttc caa tcc ctg gtc cct agg gcc acc aga agc caa tac<br>Phe Glu Pro Phe Gln Ser Leu Val Pro Arg Ala Thr Arg Ser Gln Tyr<br>　　　　　580　　　　　　　　　585　　　　　　　　　590 | 1776 |
| agc ggt ttc gta aga acc ctg ttt cag caa atg cga gat gta ctt gga<br>Ser Gly Phe Val Arg Thr Leu Phe Gln Gln Met Arg Asp Val Leu Gly<br>　　　　　　　　　595　　　　　　　　　600　　　　　　　　　605 | 1824 |
| aca ttt gat act gct caa ata ata aaa ctc ctc cct ttt gcc gct gct<br>Thr Phe Asp Thr Ala Gln Ile Ile Lys Leu Leu Pro Phe Ala Ala Ala<br>　　　　　610　　　　　　　　　615　　　　　　　　　620 | 1872 |
| cct cog gaa cag agt agg atg cag ttc tct tct ttg act gtt aat gta<br>Pro Pro Glu Gln Ser Arg Met Gln Phe Ser Ser Leu Thr Val Asn Val<br>625　　　　　　　　　630　　　　　　　　　635　　　　　　　　　640 | 1920 |

```
aga ggt tcg gga atg agg ata ctt gta aga ggc aat tcc cca gtg ttc    1968
Arg Gly Ser Gly Met Arg Ile Leu Val Arg Gly Asn Ser Pro Val Phe
                645                 650                 655 aac tac aat aaa gtc act aaa agg ctc aca gtc ctc gga aag gat gca    2016
Asn Tyr Asn Lys Val Thr Lys Arg Leu Thr Val Leu Gly Lys Asp Ala
            660                 665                 670 ggt gcg ctt act gag gac cca gat gaa ggt acg gct gga gta gag tct    2064
Gly Ala Leu Thr Glu Asp Pro Asp Glu Gly Thr Ala Gly Val Glu Ser
        675                 680                 685 gct gtt cta aga ggg ttt ctc att tta ggt aaa gaa aac aag aga tat    2112
Ala Val Leu Arg Gly Phe Leu Ile Leu Gly Lys Glu Asn Lys Arg Tyr
    690                 695                 700 ggc cca gca cta agc atc aat gaa ctt agc aaa ctt gca aaa ggg gag    2160
Gly Pro Ala Leu Ser Ile Asn Glu Leu Ser Lys Leu Ala Lys Gly Glu
705                 710                 715                 720 aaa gcc aat gta cta att ggg caa ggg gac gta gtg ttg gta atg aaa    2208
Lys Ala Asn Val Leu Ile Gly Gln Gly Asp Val Val Leu Val Met Lys
                725                 730                 735 cgg aaa cgt gac tct agc ata ctt act gac agc cag aca gcg acc aaa    2256
Arg Lys Arg Asp Ser Ser Ile Leu Thr Asp Ser Gln Thr Ala Thr Lys
            740                 745                 750 agg att cgg atg gcc atc aat tag                                    2280
Arg Ile Arg Met Ala Ile Asn
        755

<210> SEQ ID NO 48
<211> LENGTH: 759
<212> TYPE: PRT
<213> ORGANISM: Influenza virus

<400> SEQUENCE: 48

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205
```

-continued

```
Arg Glu Leu Val Arg Lys Thr Arg Phe Leu Pro Val Val Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Lys Val Arg Asn Asp Asp Ile Asp
                245                 250                 255
Gln Ser Leu Ile Ile Ala Ala Arg Asn Ile Val Arg Arg Ala Thr Val
            260                 265                 270
Ser Ala Asp Pro Leu Ala Ser Leu Leu Glu Met Cys His Ser Thr Gln
        275                 280                 285
Ile Gly Gly Thr Arg Met Val Asp Ile Leu Lys Gln Asn Pro Thr Glu
    290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Met Leu Thr Gly Asn Leu Gln Thr Leu
            340                 345                 350
Lys Ile Arg Val His Gly Tyr Glu Glu Phe Thr Met Val Gly Arg
    355                 360                 365
Arg Ala Thr Ala Ile Ile Arg Lys Ala Thr Arg Leu Ile Gln Leu
    370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Ile Glu Pro Ile Asp Asn Val Met Gly Met Ile Gly Ile Leu
    450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Ile Leu
            500                 505                 510
Leu Ser Pro Glu Glu Val Ser Glu Thr Gln Gly Thr Glu Lys Leu Thr
        515                 520                 525
Ile Ile Tyr Ser Ser Ser Met Met Trp Glu Ile Asn Gly Pro Glu Ser
    530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
            580                 585                 590
Ser Gly Phe Val Arg Thr Leu Phe Gln Gln Met Arg Asp Val Leu Gly
        595                 600                 605
Thr Phe Asp Thr Ala Gln Ile Ile Lys Leu Leu Pro Phe Ala Ala Ala
    610                 615                 620
Pro Pro Glu Gln Ser Arg Met Gln Phe Ser Ser Leu Thr Val Asn Val
625                 630                 635                 640
```

```
Arg Gly Ser Gly Met Arg Ile Leu Val Arg Gly Asn Ser Pro Val Phe
            645                 650                 655

Asn Tyr Asn Lys Val Thr Lys Arg Leu Thr Val Leu Gly Lys Asp Ala
        660                 665                 670

Gly Ala Leu Thr Glu Asp Pro Asp Glu Gly Thr Ala Gly Val Glu Ser
            675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 49
<211> LENGTH: 2274
<212> TYPE: DNA
<213> ORGANISM: Influenza virus
<220> FEATURE:
<221> NAME/KEY: CDS
<222> LOCATION: (1)..(2274)

<400> SEQUENCE: 49
```

| | | | | | | | | | | | | | | | | |
|---|---|---|---|---|---|---|---|---|---|---|---|---|---|---|---|---|
| atg | gat | gtc | aat | ccg | act | cta | ctt | ttc | tta | aag | gtg | cca | gcg | caa | aat | 48 |
| Met | Asp | Val | Asn | Pro | Thr | Leu | Leu | Phe | Leu | Lys | Val | Pro | Ala | Gln | Asn | |
| 1 | | | | 5 | | | | | 10 | | | | | 15 | | |
| gct | ata | agc | aca | aca | ttc | cct | tat | act | gga | gat | cct | ccc | tac | agt | cat | 96 |
| Ala | Ile | Ser | Thr | Thr | Phe | Pro | Tyr | Thr | Gly | Asp | Pro | Pro | Tyr | Ser | His | |
| | | | 20 | | | | | 25 | | | | | 30 | | | |
| gga | aca | ggg | aca | gga | tac | acc | atg | gat | act | gtc | aac | aga | aca | cac | caa | 144 |
| Gly | Thr | Gly | Thr | Gly | Tyr | Thr | Met | Asp | Thr | Val | Asn | Arg | Thr | His | Gln | |
| | | 35 | | | | | 40 | | | | | 45 | | | | |
| tat | tca | gaa | aaa | ggg | aaa | tgg | aca | aca | aac | act | gag | att | gga | gca | cca | 192 |
| Tyr | Ser | Glu | Lys | Gly | Lys | Trp | Thr | Thr | Asn | Thr | Glu | Ile | Gly | Ala | Pro | |
| 50 | | | | | 55 | | | | | 60 | | | | | | |
| caa | ctt | aat | cca | atc | gat | gga | cca | ctt | cct | gaa | gac | aat | gaa | cca | agt | 240 |
| Gln | Leu | Asn | Pro | Ile | Asp | Gly | Pro | Leu | Pro | Glu | Asp | Asn | Glu | Pro | Ser | |
| 65 | | | | | 70 | | | | | 75 | | | | | 80 | |
| ggg | tac | gcc | caa | aca | gat | tgt | gta | ttg | gaa | gca | atg | gct | ttc | ctt | gaa | 288 |
| Gly | Tyr | Ala | Gln | Thr | Asp | Cys | Val | Leu | Glu | Ala | Met | Ala | Phe | Leu | Glu | |
| | | | | 85 | | | | | 90 | | | | | 95 | | |
| gaa | tcc | cat | ccc | gga | atc | ttt | gaa | aat | tcg | tgt | ctt | gaa | acg | atg | gag | 336 |
| Glu | Ser | His | Pro | Gly | Ile | Phe | Glu | Asn | Ser | Cys | Leu | Glu | Thr | Met | Glu | |
| | | | 100 | | | | | 105 | | | | | 110 | | | |
| gtg | att | cag | cag | aca | aga | gtg | gac | aaa | cta | aca | caa | ggc | cga | caa | act | 384 |
| Val | Ile | Gln | Gln | Thr | Arg | Val | Asp | Lys | Leu | Thr | Gln | Gly | Arg | Gln | Thr | |
| | | 115 | | | | | 120 | | | | | 125 | | | | |
| tat | gat | tgg | acc | ttg | aat | agg | aat | caa | cct | gcc | gca | aca | gca | ctt | gct | 432 |
| Tyr | Asp | Trp | Thr | Leu | Asn | Arg | Asn | Gln | Pro | Ala | Ala | Thr | Ala | Leu | Ala | |
| 130 | | | | | 135 | | | | | 140 | | | | | | |
| aat | acg | att | gaa | gta | ttc | aga | tca | aat | ggt | ctg | acc | tcc | aat | gaa | tcg | 480 |
| Asn | Thr | Ile | Glu | Val | Phe | Arg | Ser | Asn | Gly | Leu | Thr | Ser | Asn | Glu | Ser | |
| 145 | | | | | 150 | | | | | 155 | | | | | 160 | |
| ggg | aga | ttg | atg | gac | ttc | ctc | aaa | gat | gtc | atg | gag | tcc | atg | aac | aag | 528 |
| Gly | Arg | Leu | Met | Asp | Phe | Leu | Lys | Asp | Val | Met | Glu | Ser | Met | Asn | Lys | |
| | | | | 165 | | | | | 170 | | | | | 175 | | |

```
gag gaa atg gaa ata aca aca cac ttc caa cgg aag aga aga gta aga      576
Glu Glu Met Glu Ile Thr Thr His Phe Gln Arg Lys Arg Arg Val Arg
            180                 185                 190 gac aac atg aca aag aga atg ata aca cag aga acc ata gga aag aaa      624
Asp Asn Met Thr Lys Arg Met Ile Thr Gln Arg Thr Ile Gly Lys Lys
        195                 200                 205 aaa caa cga tta agc aga aag agc tat cta atc aga aca tta acc cta      672
Lys Gln Arg Leu Ser Arg Lys Ser Tyr Leu Ile Arg Thr Leu Thr Leu
    210                 215                 220 aac aca atg acc aag gac gct gag aga ggg aaa ttg aaa cga cga gca      720
Asn Thr Met Thr Lys Asp Ala Glu Arg Gly Lys Leu Lys Arg Arg Ala
225                 230                 235                 240 atc gct acc cca ggg atg cag ata aga gga ttt gta tat ttt gtt gaa      768
Ile Ala Thr Pro Gly Met Gln Ile Arg Gly Phe Val Tyr Phe Val Glu
                245                 250                 255 aca cta gct cga aga ata tgt gaa aag ctt gaa caa tca gga ttg cca      816
Thr Leu Ala Arg Arg Ile Cys Glu Lys Leu Glu Gln Ser Gly Leu Pro
            260                 265                 270 gtt ggc ggt aat gag aaa aag gcc aaa ctg gct aat gtc gtc aga aaa      864
Val Gly Gly Asn Glu Lys Lys Ala Lys Leu Ala Asn Val Val Arg Lys
        275                 280                 285 atg atg act aat tcc caa gac act gaa ctc tcc ttc acc atc act ggg      912
Met Met Thr Asn Ser Gln Asp Thr Glu Leu Ser Phe Thr Ile Thr Gly
    290                 295                 300 gac aat acc aaa tgg aat gaa aat cag aac cca cgc ata ttc ctg gca      960
Asp Asn Thr Lys Trp Asn Glu Asn Gln Asn Pro Arg Ile Phe Leu Ala
305                 310                 315                 320 atg atc aca tac ata act aga gat cag cca gaa tgg ttc aga aat gtt     1008
Met Ile Thr Tyr Ile Thr Arg Asp Gln Pro Glu Trp Phe Arg Asn Val
                325                 330                 335 cta agc att gca ccg att atg ttc tca aat aaa atg gca aga ctg ggg     1056
Leu Ser Ile Ala Pro Ile Met Phe Ser Asn Lys Met Ala Arg Leu Gly
            340                 345                 350 aaa gga tat atg ttt gaa agc aaa agt atg aaa ttg aga act caa ata     1104
Lys Gly Tyr Met Phe Glu Ser Lys Ser Met Lys Leu Arg Thr Gln Ile
        355                 360                 365 cca gca gaa atg cta gca agc att gac cta aaa tat ttc aat gat tca     1152
Pro Ala Glu Met Leu Ala Ser Ile Asp Leu Lys Tyr Phe Asn Asp Ser
    370                 375                 380 aca aaa aag aaa att gaa aag ata cga cca ctc ctg gtt gac ggg act     1200
Thr Lys Lys Lys Ile Glu Lys Ile Arg Pro Leu Leu Val Asp Gly Thr
385                 390                 395                 400 gct tca ctg agt cct ggc atg atg atg gga atg ttc aac atg ttg agc     1248
Ala Ser Leu Ser Pro Gly Met Met Met Gly Met Phe Asn Met Leu Ser
                405                 410                 415 act gtg ctg ggt gta tcc ata tta aac ctg ggc cag agg aaa tat aca     1296
Thr Val Leu Gly Val Ser Ile Leu Asn Leu Gly Gln Arg Lys Tyr Thr
            420                 425                 430 aag acc aca tac tgg tgg gat ggt ctg caa tca tcc gat gac ttt gct     1344
Lys Thr Thr Tyr Trp Trp Asp Gly Leu Gln Ser Ser Asp Asp Phe Ala
        435                 440                 445 ttg ata gtg aat gcg cct aat cat gaa gga ata caa gct gga gta gac     1392
Leu Ile Val Asn Ala Pro Asn His Glu Gly Ile Gln Ala Gly Val Asp
    450                 455                 460 aga ttc tat aga act tgc aaa ctg gtc ggg atc aac atg agc aaa aag     1440
Arg Phe Tyr Arg Thr Cys Lys Leu Val Gly Ile Asn Met Ser Lys Lys
465                 470                 475                 480 aag tcc tac ata aat aga act gga aca ttc gaa ttc aca agc ttt ttc     1488
Lys Ser Tyr Ile Asn Arg Thr Gly Thr Phe Glu Phe Thr Ser Phe Phe
                485                 490                 495
```

```
tac cgg tat ggt ttt gta gcc aat ttc agc atg gaa cta ccc agt ttt    1536
Tyr Arg Tyr Gly Phe Val Ala Asn Phe Ser Met Glu Leu Pro Ser Phe
            500                 505                 510 ggg gtt tcc gga ata aat gaa tct gca gac atg agc att gga gtg aca    1584
Gly Val Ser Gly Ile Asn Glu Ser Ala Asp Met Ser Ile Gly Val Thr
        515                 520                 525 gtc atc aaa aac aac atg ata aat aat gat ctc ggt cct gcc acg gca    1632
Val Ile Lys Asn Asn Met Ile Asn Asn Asp Leu Gly Pro Ala Thr Ala
    530                 535                 540 caa atg gca ctc caa ctc ttc att aag gat tat cgg tac aca tac cgg    1680
Gln Met Ala Leu Gln Leu Phe Ile Lys Asp Tyr Arg Tyr Thr Tyr Arg
545                 550                 555                 560 tgc cat aga ggt gat acc cag ata caa acc aga aga tct ttt gag ttg    1728
Cys His Arg Gly Asp Thr Gln Ile Gln Thr Arg Arg Ser Phe Glu Leu
                565                 570                 575 aag aaa ctg tgg gaa cag act cga tca aag act ggt cta ctg gta tca    1776
Lys Lys Leu Trp Glu Gln Thr Arg Ser Lys Thr Gly Leu Leu Val Ser
            580                 585                 590 gat ggg ggt cca aac cta tat aac atc aga aac cta cac atc ccg gaa    1824
Asp Gly Gly Pro Asn Leu Tyr Asn Ile Arg Asn Leu His Ile Pro Glu
        595                 600                 605 gtc tgt tta aaa tgg gag cta atg gat gaa gat tat aag ggg agg cta    1872
Val Cys Leu Lys Trp Glu Leu Met Asp Glu Asp Tyr Lys Gly Arg Leu
    610                 615                 620 tgc aat cca ttg aat cct ttc gtt agt cac aaa gaa att gaa tca gtc    1920
Cys Asn Pro Leu Asn Pro Phe Val Ser His Lys Glu Ile Glu Ser Val
625                 630                 635                 640 aac agt gca gta gta atg cct gct cat ggc cct gcc aaa agc atg gag    1968
Asn Ser Ala Val Val Met Pro Ala His Gly Pro Ala Lys Ser Met Glu
                645                 650                 655 tat gat gct gtt gca aca aca cat tct tgg atc ccc aag agg aac cgg    2016
Tyr Asp Ala Val Ala Thr Thr His Ser Trp Ile Pro Lys Arg Asn Arg
            660                 665                 670 tcc ata ttg aac aca agc caa agg gga ata cta gaa gat gag cag atg    2064
Ser Ile Leu Asn Thr Ser Gln Arg Gly Ile Leu Glu Asp Glu Gln Met
        675                 680                 685 tat cag aaa tgc tgc aac ctg ttt gaa aaa ttc ttc ccc agc agc tca    2112
Tyr Gln Lys Cys Cys Asn Leu Phe Glu Lys Phe Phe Pro Ser Ser Ser
    690                 695                 700 tac aga aga cca gtc gga att tct agt atg gtt gag gcc atg gta tcc    2160
Tyr Arg Arg Pro Val Gly Ile Ser Ser Met Val Glu Ala Met Val Ser
705                 710                 715                 720 agg gcc cgc att gat gca cga att gac ttc gaa tct gga cgg ata aag    2208
Arg Ala Arg Ile Asp Ala Arg Ile Asp Phe Glu Ser Gly Arg Ile Lys
                725                 730                 735 aag gat gag ttc gct gag atc atg aag atc tgt tcc acc att gaa gag    2256
Lys Asp Glu Phe Ala Glu Ile Met Lys Ile Cys Ser Thr Ile Glu Glu
            740                 745                 750 ctc aga cgg caa aaa tag                                            2274
Leu Arg Arg Gln Lys
                755

<210> SEQ ID NO 50
<211> LENGTH: 757
<212> TYPE: PRT
<213> ORGANISM: Influenza virus

<400> SEQUENCE: 50

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
```

-continued

```
                20                  25                  30
Gly Thr Gly Thr Gly Tyr Thr Met Asp Thr Val Asn Arg Thr His Gln
            35                  40                  45
Tyr Ser Glu Lys Gly Lys Trp Thr Thr Asn Thr Glu Ile Gly Ala Pro
        50                  55                  60
Gln Leu Asn Pro Ile Asp Gly Pro Leu Pro Glu Asp Asn Glu Pro Ser
65                  70                  75                  80
Gly Tyr Ala Gln Thr Asp Cys Val Leu Glu Ala Met Ala Phe Leu Glu
                85                  90                  95
Glu Ser His Pro Gly Ile Phe Glu Asn Ser Cys Leu Glu Thr Met Glu
            100                 105                 110
Val Ile Gln Gln Thr Arg Val Asp Lys Leu Thr Gln Gly Arg Gln Thr
        115                 120                 125
Tyr Asp Trp Thr Leu Asn Arg Asn Gln Pro Ala Ala Thr Ala Leu Ala
    130                 135                 140
Asn Thr Ile Glu Val Phe Arg Ser Asn Gly Leu Thr Ser Asn Glu Ser
145                 150                 155                 160
Gly Arg Leu Met Asp Phe Leu Lys Asp Val Met Glu Ser Met Asn Lys
                165                 170                 175
Glu Glu Met Glu Ile Thr Thr His Phe Gln Arg Lys Arg Arg Val Arg
            180                 185                 190
Asp Asn Met Thr Lys Arg Met Ile Thr Gln Arg Thr Ile Gly Lys Lys
        195                 200                 205
Lys Gln Arg Leu Ser Arg Lys Ser Tyr Leu Ile Arg Thr Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Arg Ile Cys Gly Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
    290                 295                 300
Asp Asn Thr Lys Trp Asn Glu Asn Gln Asn Pro Arg Ile Phe Leu Ala
305                 310                 315                 320
Met Ile Thr Tyr Ile Thr Arg Asp Gln Pro Glu Trp Phe Arg Asn Val
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
        355                 360                 365
Pro Ala Glu Met Leu Ala Ser Ile Asp Leu Lys Tyr Phe Asn Asp Ser
    370                 375                 380
Thr Lys Lys Lys Ile Glu Lys Ile Arg Pro Leu Leu Val Asp Gly Thr
385                 390                 395                 400
Ala Ser Leu Ser Pro Gly Met Met Gly Met Phe Asn Met Leu Ser
                405                 410                 415
Thr Val Leu Gly Val Ser Ile Leu Asn Leu Gly Gln Arg Lys Tyr Thr
            420                 425                 430
Lys Thr Thr Tyr Trp Trp Asp Gly Leu Gln Ser Ser Asp Asp Phe Ala
        435                 440                 445
```

```
Leu Ile Val Asn Ala Pro Asn His Glu Gly Ile Gln Ala Gly Val Asp
    450                 455                 460
Arg Phe Tyr Arg Thr Cys Lys Leu Val Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
        515                 520                 525
Val Ile Lys Asn Asn Met Ile Asn Asn Asp Leu Gly Pro Ala Thr Ala
    530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Leu
                565                 570                 575
Lys Lys Leu Trp Glu Gln Thr Arg Ser Lys Thr Gly Leu Leu Val Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Lys Gly Arg Leu
    610                 615                 620
Cys Asn Pro Leu Asn Pro Phe Val Ser His Lys Glu Ile Glu Ser Val
625                 630                 635                 640
Asn Ser Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Ile Leu Glu Asp Glu Gln Met
        675                 680                 685
Tyr Gln Lys Cys Cys Asn Leu Phe Glu Lys Phe Phe Pro Ser Ser Ser
    690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Asp Glu Phe Ala Glu Ile Met Lys Ile Cys Ser Thr Ile Glu Glu
            740                 745                 750
Leu Arg Arg Gln Lys
        755

<210> SEQ ID NO 51
<211> LENGTH: 2151
<212> TYPE: DNA
<213> ORGANISM: Influenza virus
<220> FEATURE:
<221> NAME/KEY: CDS
<222> LOCATION: (1)..(2151)

<400> SEQUENCE: 51 atg gaa gac ttt gtg cga cag tgc ttc aat cca atg atc gtc gag ctt      48
Met Glu Asp Phe Val Arg Gln Cys Phe Asn Pro Met Ile Val Glu Leu
1               5                   10                  15 gcg gaa aag gca atg aaa gaa tat gga gag aac ccg aaa atc gaa aca      96
Ala Glu Lys Ala Met Lys Glu Tyr Gly Glu Asn Pro Lys Ile Glu Thr
                20                  25                  30 aac aaa ttt gca gca ata tgc act cac ttg gaa gtc tgc ttc atg tac     144
Asn Lys Phe Ala Ala Ile Cys Thr His Leu Glu Val Cys Phe Met Tyr
```

```
Asn Lys Phe Ala Ala Ile Cys Thr His Leu Glu Val Cys Phe Met Tyr
        35                  40                  45 tcg gat ttc cac ttt ata aat gaa ctg ggt gag tca gtg gtc ata gag    192
Ser Asp Phe His Phe Ile Asn Glu Leu Gly Glu Ser Val Val Ile Glu
 50                  55                  60 tct ggt gac cca aat gct ctt ttg aaa cac aga ttt gaa atc att gag    240
Ser Gly Asp Pro Asn Ala Leu Leu Lys His Arg Phe Glu Ile Ile Glu
 65                  70                  75                  80 ggg aga gat cga aca atg gca tgg aca gta gta aac agc atc tgc aac    288
Gly Arg Asp Arg Thr Met Ala Trp Thr Val Val Asn Ser Ile Cys Asn
                 85                  90                  95 acc aca aga gct gaa aaa cct aaa ttt ctt cca gat tta tac gac tat    336
Thr Thr Arg Ala Glu Lys Pro Lys Phe Leu Pro Asp Leu Tyr Asp Tyr
            100                 105                 110 aaa gag aac aga ttt gtt gaa att ggt gtg aca agg aga gaa gtt cac    384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat    432
Ile Tyr Tyr Leu Glu Lys Ala Asn Lys Ile Lys Ser Glu Lys Thr His
130                 135                 140 atc cac att ttc tca ttt aca gga gaa gaa atg gct aca aaa gcg gac    480
Ile His Ile Phe Ser Phe Thr Gly Glu Glu Met Ala Thr Lys Ala Asp
145                 150                 155                 160 tat act ctt gat gaa gag agt aga gcc agg atc aag acc aga cta ttc    528
Tyr Thr Leu Asp Glu Glu Ser Arg Ala Arg Ile Lys Thr Arg Leu Phe
                165                 170                 175 act ata aga caa gaa atg gcc agt aga ggc ctc tgg gat tcc ttt cgt    576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca    624
Gln Ser Glu Arg Gly Glu Glu Thr Ile Glu Glu Arg Phe Glu Ile Thr
        195                 200                 205 ggg acg atg cgc aag ctt gcc aat tac agt ctc cca ccg aac ttc tcc    672
Gly Thr Met Arg Lys Leu Ala Asn Tyr Ser Leu Pro Pro Asn Phe Ser
210                 215                 220 agc ctt gaa aat ttt aga gtc tat ata gat gga ttc gaa ccg aac ggc    720
Ser Leu Glu Asn Phe Arg Val Tyr Ile Asp Gly Phe Glu Pro Asn Gly
225                 230                 235                 240 tgc att gag agt aag ctt tct caa atg tcc aaa gaa gta aat gcc aaa    768
Cys Ile Glu Ser Lys Leu Ser Gln Met Ser Lys Glu Val Asn Ala Lys
                245                 250                 255 ata gaa cca ttt tca aag aca aca ccc cga cca ctc aaa atg cca ggt    816
Ile Glu Pro Phe Ser Lys Thr Thr Pro Arg Pro Leu Lys Met Pro Gly
            260                 265                 270 ggt cca ccc tgc cat cag cga tcc aaa ttc ttg cta atg gat gct ctg    864
Gly Pro Pro Cys His Gln Arg Ser Lys Phe Leu Leu Met Asp Ala Leu
        275                 280                 285 aaa ctg agc att gag gac cca agt cac gag gga gag ggg ata cca cta    912
Lys Leu Ser Ile Glu Asp Pro Ser His Glu Gly Glu Gly Ile Pro Leu
290                 295                 300 tat gat gca atc aaa tgc atg aaa act ttc ttt gga tgg aaa gag ccc    960
Tyr Asp Ala Ile Lys Cys Met Lys Thr Phe Phe Gly Trp Lys Glu Pro
305                 310                 315                 320 agt att gtt aaa cca cat aaa aag ggt ata aac ccg aac tat ctc caa   1008
Ser Ile Val Lys Pro His Lys Lys Gly Ile Asn Pro Asn Tyr Leu Gln
                325                 330                 335 act tgg aag caa gta tta gaa gaa ata caa gac ctt gag aac gaa gaa   1056
Thr Trp Lys Gln Val Leu Glu Glu Ile Gln Asp Leu Glu Asn Glu Glu
            340                 345                 350 agg acc ccc aag acc aag aat atg aaa aaa aca agc caa ttg aaa tgg   1104
```

-continued

| | | |
|---|---|---|
| Arg Thr Pro Lys Thr Lys Asn Met Lys Lys Thr Ser Gln Leu Lys Trp<br>355 360 365 | | |
| gca cta ggt gaa aat atg gca cca gag aaa gtg gat ttt gag gat tgt<br>Ala Leu Gly Glu Asn Met Ala Pro Glu Lys Val Asp Phe Glu Asp Cys<br>370 375 380 | | 1152 |
| aaa gac atc aat gat tta aaa caa tat gac agt gat gag cca gaa gca<br>Lys Asp Ile Asn Asp Leu Lys Gln Tyr Asp Ser Asp Glu Pro Glu Ala<br>385 390 395 400 | | 1200 |
| agg tct ctt gca agt tgg att caa agt gag ttc aac aag gct tgt gag<br>Arg Ser Leu Ala Ser Trp Ile Gln Ser Glu Phe Asn Lys Ala Cys Glu<br>405 410 415 | | 1248 |
| ctg aca gat tca agc tgg ata gag ctc gat gaa att ggg gag gat gtc<br>Leu Thr Asp Ser Ser Trp Ile Glu Leu Asp Glu Ile Gly Glu Asp Val<br>420 425 430 | | 1296 |
| gcc cca ata gaa tac att gcg agc atg agg aga aat tat ttt act gct<br>Ala Pro Ile Glu Tyr Ile Ala Ser Met Arg Arg Asn Tyr Phe Thr Ala<br>435 440 445 | | 1344 |
| gag att tcc cat tgt aga gca aca gaa tat ata atg aaa gga gtg tac<br>Glu Ile Ser His Cys Arg Ala Thr Glu Tyr Ile Met Lys Gly Val Tyr<br>450 455 460 | | 1392 |
| atc aac act gct cta ctc aat gca tcc tgt gct gcg atg gat gaa ttt<br>Ile Asn Thr Ala Leu Leu Asn Ala Ser Cys Ala Ala Met Asp Glu Phe<br>465 470 475 480 | | 1440 |
| caa tta att ccg atg ata agt aaa tgc agg acc aaa gaa ggg aga agg<br>Gln Leu Ile Pro Met Ile Ser Lys Cys Arg Thr Lys Glu Gly Arg Arg<br>485 490 495 | | 1488 |
| aaa aca aat tta tat gga ttc ata ata aag gga agg tcc cat tta aga<br>Lys Thr Asn Leu Tyr Gly Phe Ile Ile Lys Gly Arg Ser His Leu Arg<br>500 505 510 | | 1536 |
| aat gat act gac gtg gtg aac ttt gta agt atg gaa ttt tct ctc act<br>Asn Asp Thr Asp Val Val Asn Phe Val Ser Met Glu Phe Ser Leu Thr<br>515 520 525 | | 1584 |
| gat cca aga ttt gag cca cac aaa tgg gaa aaa tac tgc gtt cta gaa<br>Asp Pro Arg Phe Glu Pro His Lys Trp Glu Lys Tyr Cys Val Leu Glu<br>530 535 540 | | 1632 |
| att gga gac atg ctt tta aga act gct gta ggt caa gtg tca aga ccc<br>Ile Gly Asp Met Leu Leu Arg Thr Ala Val Gly Gln Val Ser Arg Pro<br>545 550 555 560 | | 1680 |
| atg ttt ttg tat gta agg aca aat gga acc tct aaa att aaa atg aaa<br>Met Phe Leu Tyr Val Arg Thr Asn Gly Thr Ser Lys Ile Lys Met Lys<br>565 570 575 | | 1728 |
| tgg gga atg gaa atg agg cgc tgc ctc ctt cag tct ctg caa cag att<br>Trp Gly Met Glu Met Arg Arg Cys Leu Leu Gln Ser Leu Gln Gln Ile<br>580 585 590 | | 1776 |
| gaa agc atg atc gaa gct gag tcc tca gtc aaa gaa aag gac atg acc<br>Glu Ser Met Ile Glu Ala Glu Ser Ser Val Lys Glu Lys Asp Met Thr<br>595 600 605 | | 1824 |
| aaa gaa ttt ttt gag aac aaa tca gag aca tgg cct ata gga gag tcc<br>Lys Glu Phe Phe Glu Asn Lys Ser Glu Thr Trp Pro Ile Gly Glu Ser<br>610 615 620 | | 1872 |
| ccc aaa gga gtg gaa gag ggc tca atc ggg aag gtt tgc agg acc tta<br>Pro Lys Gly Val Glu Glu Gly Ser Ile Gly Lys Val Cys Arg Thr Leu<br>625 630 635 640 | | 1920 |
| tta gca aaa tct gtg ttt aac agt tta tat gca tct cca caa ctg gaa<br>Leu Ala Lys Ser Val Phe Asn Ser Leu Tyr Ala Ser Pro Gln Leu Glu<br>645 650 655 | | 1968 |
| gga ttt tca gct gaa tct agg aaa tta ctt ctc att gtt cag gct ctt<br>Gly Phe Ser Ala Glu Ser Arg Lys Leu Leu Leu Ile Val Gln Ala Leu<br>660 665 670 | | 2016 |
| aga gat gac ctg gaa cct gga acc ttt gat att ggg ggg tta tat gaa | | 2064 |

```
Arg Asp Asp Leu Glu Pro Gly Thr Phe Asp Ile Gly Gly Leu Tyr Glu
            675                 680                 685 tca att gag gag tgc ctg att aat gat ccc tgg gtt ttg ctt aat gca      2112
Ser Ile Glu Glu Cys Leu Ile Asn Asp Pro Trp Val Leu Leu Asn Ala
            690                 695                 700 tct tgg ttc aac tcc ttc ctc aca cat gca ctg aag tag                  2151
Ser Trp Phe Asn Ser Phe Leu Thr His Ala Leu Lys
705                 710                 715
```

<210> SEQ ID NO 52
<211> LENGTH: 716
<212> TYPE: PRT
<213> ORGANISM: Influenza virus

<400> SEQUENCE: 52

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asn Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asn Tyr Ser Leu Pro Pro Asn Phe Ser
    210                 215                 220

Ser Leu Glu Asn Phe Arg Val Tyr Ile Asp Gly Phe Glu Pro Asn Gly
225                 230                 235                 240

Cys Ile Glu Ser Lys Leu Ser Gln Met Ser Lys Glu Val Asn Ala Lys
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Ile Val Lys Pro His Lys Lys Gly Ile Asn Pro Asn Tyr Leu Gln
```

```
                     325                 330                 335
Thr Trp Lys Gln Val Leu Glu Glu Ile Gln Asp Leu Glu Asn Glu Glu
                340                 345                 350

Arg Thr Pro Lys Thr Lys Asn Met Lys Lys Thr Ser Gln Leu Lys Trp
            355                 360                 365

Ala Leu Gly Glu Asn Met Ala Pro Glu Lys Val Asp Phe Glu Asp Cys
        370                 375                 380

Lys Asp Ile Asn Asp Leu Lys Gln Tyr Asp Ser Asp Glu Pro Glu Ala
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
        435                 440                 445

Glu Ile Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
    530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asp Leu Glu Pro Gly Thr Phe Asp Ile Gly Gly Leu Tyr Glu
        675                 680                 685

Ser Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 53
<211> LENGTH: 844
<212> TYPE: DNA
<213> ORGANISM: Influenza virus
<220> FEATURE:
```

<221> NAME/KEY: CDS
<222> LOCATION: (1)..(690)

<400> SEQUENCE: 53

| | | | | | | | | | | | | | | | | |
|---|---|---|---|---|---|---|---|---|---|---|---|---|---|---|---|---|
| atg | gat | tcc | aac | act | gtg | tca | agc | ttt | cag | gta | gac | tgt | ttt | ctt | tgg | 48 |
| Met | Asp | Ser | Asn | Thr | Val | Ser | Ser | Phe | Gln | Val | Asp | Cys | Phe | Leu | Trp | |
| 1 | | | | 5 | | | | | 10 | | | | | 15 | | |
| cat | gtc | cgt | aaa | cga | ttc | gca | gac | caa | gaa | ctg | ggt | gat | gcc | cca | ttc | 96 |
| His | Val | Arg | Lys | Arg | Phe | Ala | Asp | Gln | Glu | Leu | Gly | Asp | Ala | Pro | Phe | |
| | | | 20 | | | | | 25 | | | | | 30 | | | |
| ctt | gac | cgg | ctt | cgc | cga | gac | cag | aag | tcc | cta | agg | gga | aga | ggt | agc | 144 |
| Leu | Asp | Arg | Leu | Arg | Arg | Asp | Gln | Lys | Ser | Leu | Arg | Gly | Arg | Gly | Ser | |
| | | 35 | | | | | 40 | | | | | 45 | | | | |
| act | ctt | ggt | ctg | gac | atc | gaa | aca | gcc | act | cat | gca | gga | aag | cag | ata | 192 |
| Thr | Leu | Gly | Leu | Asp | Ile | Glu | Thr | Ala | Thr | His | Ala | Gly | Lys | Gln | Ile | |
| 50 | | | | | 55 | | | | | 60 | | | | | | |
| gtg | gag | cag | att | ctg | gaa | aag | gaa | tca | gat | gag | gca | ctt | aaa | atg | acc | 240 |
| Val | Glu | Gln | Ile | Leu | Glu | Lys | Glu | Ser | Asp | Glu | Ala | Leu | Lys | Met | Thr | |
| 65 | | | | | 70 | | | | | 75 | | | | | 80 | |
| att | gcc | tct | gtt | cct | gct | tca | cgc | tac | tta | act | gac | atg | act | ctt | gat | 288 |
| Ile | Ala | Ser | Val | Pro | Ala | Ser | Arg | Tyr | Leu | Thr | Asp | Met | Thr | Leu | Asp | |
| | | | | 85 | | | | | 90 | | | | | 95 | | |
| gag | atg | tca | aga | gac | tgg | ttc | atg | ctc | atg | ccc | aag | caa | aaa | gta | aca | 336 |
| Glu | Met | Ser | Arg | Asp | Trp | Phe | Met | Leu | Met | Pro | Lys | Gln | Lys | Val | Thr | |
| | | | 100 | | | | | 105 | | | | | 110 | | | |
| ggc | tcc | cta | tgt | ata | aga | atg | gac | cag | gca | atc | atg | gat | aag | aac | atc | 384 |
| Gly | Ser | Leu | Cys | Ile | Arg | Met | Asp | Gln | Ala | Ile | Met | Asp | Lys | Asn | Ile | |
| | | 115 | | | | | 120 | | | | | 125 | | | | |
| ata | ctt | aaa | gca | aac | ttt | agt | gtg | att | ttc | gaa | agg | ctg | gaa | aca | cta | 432 |
| Ile | Leu | Lys | Ala | Asn | Phe | Ser | Val | Ile | Phe | Glu | Arg | Leu | Glu | Thr | Leu | |
| 130 | | | | | 135 | | | | | 140 | | | | | | |
| ata | cta | ctt | aga | gcc | ttc | acc | gaa | gaa | gga | gca | gtc | gtt | ggc | gaa | att | 480 |
| Ile | Leu | Leu | Arg | Ala | Phe | Thr | Glu | Glu | Gly | Ala | Val | Val | Gly | Glu | Ile | |
| 145 | | | | | 150 | | | | | 155 | | | | | 160 | |
| tca | cca | tta | cct | tct | ctt | cca | gga | cat | act | aat | gag | gat | gtc | aaa | aat | 528 |
| Ser | Pro | Leu | Pro | Ser | Leu | Pro | Gly | His | Thr | Asn | Glu | Asp | Val | Lys | Asn | |
| | | | | 165 | | | | | 170 | | | | | 175 | | |
| gca | att | ggg | gtc | ctc | atc | gga | gga | ctt | aaa | tgg | aat | gat | aat | acg | gtt | 576 |
| Ala | Ile | Gly | Val | Leu | Ile | Gly | Gly | Leu | Lys | Trp | Asn | Asp | Asn | Thr | Val | |
| | | | 180 | | | | | 185 | | | | | 190 | | | |
| aga | atc | tct | gaa | act | cta | cag | aga | ttc | gct | tgg | aga | agc | agt | cat | gaa | 624 |
| Arg | Ile | Ser | Glu | Thr | Leu | Gln | Arg | Phe | Ala | Trp | Arg | Ser | Ser | His | Glu | |
| | | 195 | | | | | 200 | | | | | 205 | | | | |
| aat | ggg | aga | cct | tca | ttc | cct | tca | aaa | cag | aaa | cga | aaa | atg | gag | aga | 672 |
| Asn | Gly | Arg | Pro | Ser | Phe | Pro | Ser | Lys | Gln | Lys | Arg | Lys | Met | Glu | Arg | |
| | 210 | | | | | 215 | | | | | 220 | | | | | |
| aca | att | aag | cca | gaa | att | tgaagaaata agatggttga ttgaagaagt | | | | | | | | | | 720 |
| Thr | Ile | Lys | Pro | Glu | Ile | | | | | | | | | | | |
| 225 | | | | 230 | | | | | | | | | | | | | gcgacataga ttgaaaaata cagaaaatag ttttgaacaa ataacattta tgcaagcctt        780 acaactattg cttgaagtag aacaagagat aagaactttc tcgtttcagc ttatttaatg        840 ataa                                                                     844

<210> SEQ ID NO 54
<211> LENGTH: 230
<212> TYPE: PRT
<213> ORGANISM: Influenza virus

<400> SEQUENCE: 54

Met Asp Ser Asn Thr Val Ser Ser Phe Gln Val Asp Cys Phe Leu Trp

```
                1               5              10              15
           His Val Arg Lys Arg Phe Ala Asp Gln Glu Leu Gly Asp Ala Pro Phe
                          20                  25                  30

Leu Asp Arg Leu Arg Arg Asp Gln Lys Ser Leu Arg Gly Arg Gly Ser
                          35                  40                  45

Thr Leu Gly Leu Asp Ile Glu Thr Ala Thr His Ala Gly Lys Gln Ile
            50                  55                  60

Val Glu Gln Ile Leu Glu Lys Glu Ser Asp Glu Ala Leu Lys Met Thr
            65                  70                  75                  80

Ile Ala Ser Val Pro Ala Ser Arg Tyr Leu Thr Asp Met Thr Leu Asp
                          85                  90                  95

Glu Met Ser Arg Asp Trp Phe Met Leu Met Pro Lys Gln Lys Val Thr
                          100                 105                 110

Gly Ser Leu Cys Ile Arg Met Asp Gln Ala Ile Met Asp Lys Asn Ile
                          115                 120                 125

Ile Leu Lys Ala Asn Phe Ser Val Ile Phe Glu Arg Leu Glu Thr Leu
                          130                 135                 140

Ile Leu Leu Arg Ala Phe Thr Glu Glu Gly Ala Val Val Gly Glu Ile
           145                 150                 155                 160

Ser Pro Leu Pro Ser Leu Pro Gly His Thr Asn Glu Asp Val Lys Asn
                          165                 170                 175

Ala Ile Gly Val Leu Ile Gly Gly Leu Lys Trp Asn Asp Asn Thr Val
                          180                 185                 190

Arg Ile Ser Glu Thr Leu Gln Arg Phe Ala Trp Arg Ser Ser His Glu
                          195                 200                 205

Asn Gly Arg Pro Ser Phe Pro Ser Lys Gln Lys Arg Lys Met Glu Arg
                          210                 215                 220

Thr Ile Lys Pro Glu Ile
           225                 230

<210> SEQ ID NO 55
           <211> LENGTH: 1497
           <212> TYPE: DNA
           <213> ORGANISM: Influenza virus
           <220> FEATURE:
           <221> NAME/KEY: CDS
           <222> LOCATION: (1)..(1497)

<400> SEQUENCE: 55 atg gcg tct caa ggc acc aaa cga tcc tat gaa cag atg gaa act gat        48
           Met Ala Ser Gln Gly Thr Lys Arg Ser Tyr Glu Gln Met Glu Thr Asp
            1               5                  10                  15 ggg gaa cgc cag aat gca act gaa atc aga gca tct gtc gga agg atg        96
           Gly Glu Arg Gln Asn Ala Thr Glu Ile Arg Ala Ser Val Gly Arg Met
                          20                  25                  30 gtg gga gga atc gga cgg ttt tat gtc cag atg tgt act gag ctt aaa       144
           Val Gly Gly Ile Gly Arg Phe Tyr Val Gln Met Cys Thr Glu Leu Lys
                      35                  40                  45 cta aac gac cat gaa ggg cgg ctg att cag aac agc ata aca ata gaa       192
           Leu Asn Asp His Glu Gly Arg Leu Ile Gln Asn Ser Ile Thr Ile Glu
            50                  55                  60 agg atg gtg ctt tcg gca ttc gac gaa aga aga aac aag tat ctc gag       240
           Arg Met Val Leu Ser Ala Phe Asp Glu Arg Arg Asn Lys Tyr Leu Glu
           65                  70                  75                  80 gag cat ccc agt gct ggg aaa gac cct aag aaa acg gga ggc ccg ata       288
           Glu His Pro Ser Ala Gly Lys Asp Pro Lys Lys Thr Gly Gly Pro Ile
                          85                  90                  95 tac aga aga aaa gat ggg aaa tgg atg agg gaa ctc atc ctc cat gat       336
```

```
                Tyr Arg Arg Lys Asp Gly Lys Trp Met Arg Glu Leu Ile Leu His Asp
                                100                 105                 110 aaa gaa gaa atc atg aga atc tgg cgt cag gcc aac aat ggt gaa gac            384
Lys Glu Glu Ile Met Arg Ile Trp Arg Gln Ala Asn Asn Gly Glu Asp
            115                 120                 125 gct act gct ggt ctt act cat atg atg atc tgg cac tcc aat ctc aat            432
Ala Thr Ala Gly Leu Thr His Met Met Ile Trp His Ser Asn Leu Asn
        130                 135                 140 gac acc aca tac caa aga aca agg gct ctt gtt cgg act ggg atg gat            480
Asp Thr Thr Tyr Gln Arg Thr Arg Ala Leu Val Arg Thr Gly Met Asp
145                 150                 155                 160 ccc aga atg tgc tct ctg atg caa ggc tca acc ctc cca cgg aga tct            528
Pro Arg Met Cys Ser Leu Met Gln Gly Ser Thr Leu Pro Arg Arg Ser
                165                 170                 175 gga gcc gct ggt gct gca gta aaa ggc gtt gga aca atg gta atg gaa            576
Gly Ala Ala Gly Ala Ala Val Lys Gly Val Gly Thr Met Val Met Glu
            180                 185                 190 ctc atc aga atg atc aag cgc gga ata aat gat cgg aat ttc tgg aga            624
Leu Ile Arg Met Ile Lys Arg Gly Ile Asn Asp Arg Asn Phe Trp Arg
        195                 200                 205 ggt gaa aat ggt cga aga acc aga att gct tat gaa aga atg tgc aat            672
Gly Glu Asn Gly Arg Arg Thr Arg Ile Ala Tyr Glu Arg Met Cys Asn
210                 215                 220 atc ctc aaa ggg aaa ttt cag aca gca gca caa cgg gct atg atg gac            720
Ile Leu Lys Gly Lys Phe Gln Thr Ala Ala Gln Arg Ala Met Met Asp
225                 230                 235                 240 cag gtg agg gaa ggc cgc aat cct gga aac gct gag att gag gat ctc            768
Gln Val Arg Glu Gly Arg Asn Pro Gly Asn Ala Glu Ile Glu Asp Leu
                245                 250                 255 att ttc ttg gca cga tca gca ctt att ttg aga gga tca gta gcc cat            816
Ile Phe Leu Ala Arg Ser Ala Leu Ile Leu Arg Gly Ser Val Ala His
            260                 265                 270 aaa tca tgc cta cct gcc tgt gtt tat ggc ctt gca gta acc agt ggg            864
Lys Ser Cys Leu Pro Ala Cys Val Tyr Gly Leu Ala Val Thr Ser Gly
        275                 280                 285 tat gac ttt gag aag gaa gga tac tct ctg gtt gga att gat cct ttc            912
Tyr Asp Phe Glu Lys Glu Gly Tyr Ser Leu Val Gly Ile Asp Pro Phe
    290                 295                 300 aaa cta ctc cag aac agt caa att ttc agt cta atc aga cca aaa gaa            960
Lys Leu Leu Gln Asn Ser Gln Ile Phe Ser Leu Ile Arg Pro Lys Glu
305                 310                 315                 320 aac cca gca cac aaa agc cag ttg gtg tgg atg gca tgc cat tct gca           1008
Asn Pro Ala His Lys Ser Gln Leu Val Trp Met Ala Cys His Ser Ala
                325                 330                 335 gca ttt gag gat ctg aga gtt tta aat ttc att aga gga acc aaa gta           1056
Ala Phe Glu Asp Leu Arg Val Leu Asn Phe Ile Arg Gly Thr Lys Val
            340                 345                 350 atc cca aga gga cag tta aca acc aga gga gtt caa att gct tca aat           1104
Ile Pro Arg Gly Gln Leu Thr Thr Arg Gly Val Gln Ile Ala Ser Asn
        355                 360                 365 gaa aac atg gag aca ata aat tct agc aca ctt gaa ctg aga agc aaa           1152
Glu Asn Met Glu Thr Ile Asn Ser Ser Thr Leu Glu Leu Arg Ser Lys
    370                 375                 380 tat tgg gca ata agg acc aga agc gga gga aac acc agt caa cag aga           1200
Tyr Trp Ala Ile Arg Thr Arg Ser Gly Gly Asn Thr Ser Gln Gln Arg
385                 390                 395                 400 gca tct gca gga cag ata agt gtg caa cct act ttc tca gta cag aga           1248
Ala Ser Ala Gly Gln Ile Ser Val Gln Pro Thr Phe Ser Val Gln Arg
                405                 410                 415 aat ctt ccc ttt gag aga gca acc att atg gct gca ttc act ggt aac           1296
Asn Leu Pro Phe Glu Arg Ala Thr Ile Met Ala Ala Phe Thr Gly Asn
```

-continued

```
Asn Leu Pro Phe Glu Arg Ala Thr Ile Met Ala Ala Phe Thr Gly Asn
            420                 425                 430 act gaa gga agg act tcc gac atg aga acg gaa atc ata agg atg atg      1344
Thr Glu Gly Arg Thr Ser Asp Met Arg Thr Glu Ile Ile Arg Met Met
        435                 440                 445 gaa aat gcc aaa tca gaa gat gtg tct ttc cag ggg cgg gga gtc ttc      1392
Glu Asn Ala Lys Ser Glu Asp Val Ser Phe Gln Gly Arg Gly Val Phe
    450                 455                 460 gag ctc tcg gac gaa aag gca acg aac ccg atc gtg cct tcc ttt gac      1440
Glu Leu Ser Asp Glu Lys Ala Thr Asn Pro Ile Val Pro Ser Phe Asp
465                 470                 475                 480 atg agc aat gaa ggg tct tat ttc ttc gga gac aat gct gag gag ttt      1488
Met Ser Asn Glu Gly Ser Tyr Phe Phe Gly Asp Asn Ala Glu Glu Phe
                485                 490                 495 gac agt taa                                                          1497
Asp Ser <210> SEQ ID NO 56
<211> LENGTH: 498
<212> TYPE: PRT
<213> ORGANISM: Influenza virus

<400> SEQUENCE: 56

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270
```

```
Lys Ser Cys Leu Pro Ala Cys Val Tyr Gly Leu Ala Val Thr Ser Gly
            275                 280                 285

Tyr Asp Phe Glu Lys Glu Gly Tyr Ser Leu Val Gly Ile Asp Pro Phe
        290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
        355                 360                 365

Glu Asn Met Glu Thr Ile Asn Ser Ser Thr Leu Glu Leu Arg Ser Lys
    370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Lys Ser Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Ser

<210> SEQ ID NO 57
<211> LENGTH: 1413
<212> TYPE: DNA
<213> ORGANISM: Influenza virus
<220> FEATURE:
<221> NAME/KEY: CDS
<222> LOCATION: (1)..(1413)

<400> SEQUENCE: 57 atg aat cca aat caa aag ata ata gca att gga ttt gca tca ttg ggg    48
Met Asn Pro Asn Gln Lys Ile Ile Ala Ile Gly Phe Ala Ser Leu Gly
1               5                  10                  15 ata tta atc att aat gtc att ctc cat gta gtc agc att ata gta aca    96
Ile Leu Ile Ile Asn Val Ile Leu His Val Val Ser Ile Ile Val Thr
                20                  25                  30 gta ctg gtc ctc aat aac aat aga aca gat ctg aac tgc aaa ggg acg   144
Val Leu Val Leu Asn Asn Asn Arg Thr Asp Leu Asn Cys Lys Gly Thr
            35                  40                  45 atc ata aga gaa tac aat gaa aca gta aga gta gaa aaa ctt act caa   192
Ile Ile Arg Glu Tyr Asn Glu Thr Val Arg Val Glu Lys Leu Thr Gln
        50                  55                  60 tgg tat aat acc agt aca att aag tac ata gag aga cct tca aat gaa   240
Trp Tyr Asn Thr Ser Thr Ile Lys Tyr Ile Glu Arg Pro Ser Asn Glu
65                  70                  75                  80 tac tac atg aat aac act gaa cca ctt tgt gag gcc caa ggc ttt gca   288
Tyr Tyr Met Asn Asn Thr Glu Pro Leu Cys Glu Ala Gln Gly Phe Ala
                85                  90                  95
```

| | | | | | | | | | | | | | | | | |
|---|---|---|---|---|---|---|---|---|---|---|---|---|---|---|---|---|
| cca | ttt | tcc | aaa | gat | aat | gga | ata | cga | att | ggg | tcg | aga | ggc | cat | gtt | 336 |
| Pro | Phe | Ser | Lys | Asp | Asn | Gly | Ile | Arg | Ile | Gly | Ser | Arg | Gly | His | Val | |
| | | | 100 | | | | 105 | | | | | 110 | | | | |
| ttt | gtg | ata | aga | gaa | cct | ttt | gta | tca | tgt | tcg | ccc | tca | gaa | tgt | aga | 384 |
| Phe | Val | Ile | Arg | Glu | Pro | Phe | Val | Ser | Cys | Ser | Pro | Ser | Glu | Cys | Arg | |
| | | 115 | | | | | 120 | | | | | 125 | | | | |
| acc | ttt | ttc | ctc | aca | cag | ggc | tca | tta | ctc | aat | gac | aaa | cat | tct | aac | 432 |
| Thr | Phe | Phe | Leu | Thr | Gln | Gly | Ser | Leu | Leu | Asn | Asp | Lys | His | Ser | Asn | |
| | 130 | | | | | 135 | | | | | 140 | | | | | |
| ggc | aca | ata | aag | gat | cga | agt | ccg | tat | agg | act | ttg | atg | agt | gtc | aaa | 480 |
| Gly | Thr | Ile | Lys | Asp | Arg | Ser | Pro | Tyr | Arg | Thr | Leu | Met | Ser | Val | Lys | |
| 145 | | | | | 150 | | | | | 155 | | | | | 160 | |
| ata | ggg | caa | tca | cct | aat | gta | tat | caa | gct | agg | ttt | gaa | tcg | gtg | gca | 528 |
| Ile | Gly | Gln | Ser | Pro | Asn | Val | Tyr | Gln | Ala | Arg | Phe | Glu | Ser | Val | Ala | |
| | | | | 165 | | | | | 170 | | | | | 175 | | |
| tgg | tca | gca | aca | gca | tgc | cat | gat | gga | aaa | aaa | tgg | atg | aca | gtt | gga | 576 |
| Trp | Ser | Ala | Thr | Ala | Cys | His | Asp | Gly | Lys | Lys | Trp | Met | Thr | Val | Gly | |
| | | | 180 | | | | | 185 | | | | | 190 | | | |
| gtc | aca | ggg | ccc | gac | aat | caa | gca | att | gca | gta | gtg | aac | tat | gga | ggt | 624 |
| Val | Thr | Gly | Pro | Asp | Asn | Gln | Ala | Ile | Ala | Val | Val | Asn | Tyr | Gly | Gly | |
| | | 195 | | | | | 200 | | | | | 205 | | | | |
| gtt | ccg | gtt | gat | att | att | aat | tca | tgg | gca | ggg | gat | att | tta | aga | acc | 672 |
| Val | Pro | Val | Asp | Ile | Ile | Asn | Ser | Trp | Ala | Gly | Asp | Ile | Leu | Arg | Thr | |
| | 210 | | | | | 215 | | | | | 220 | | | | | |
| caa | gaa | tca | tca | tgc | acc | tgc | att | aaa | gga | gac | tgt | tat | tgg | gta | atg | 720 |
| Gln | Glu | Ser | Ser | Cys | Thr | Cys | Ile | Lys | Gly | Asp | Cys | Tyr | Trp | Val | Met | |
| 225 | | | | | 230 | | | | | 235 | | | | | 240 | |
| act | gat | gga | ccg | gca | aat | agg | caa | gct | aaa | tat | agg | ata | ttc | aaa | gca | 768 |
| Thr | Asp | Gly | Pro | Ala | Asn | Arg | Gln | Ala | Lys | Tyr | Arg | Ile | Phe | Lys | Ala | |
| | | | | 245 | | | | | 250 | | | | | 255 | | |
| aaa | gat | gga | aga | gta | att | gga | caa | act | gat | ata | agt | ttc | aat | ggg | gga | 816 |
| Lys | Asp | Gly | Arg | Val | Ile | Gly | Gln | Thr | Asp | Ile | Ser | Phe | Asn | Gly | Gly | |
| | | | 260 | | | | | 265 | | | | | 270 | | | |
| cac | ata | gag | gag | tgt | tct | tgt | tac | ccc | aat | gaa | ggg | aag | gtg | gaa | tgc | 864 |
| His | Ile | Glu | Glu | Cys | Ser | Cys | Tyr | Pro | Asn | Glu | Gly | Lys | Val | Glu | Cys | |
| | | 275 | | | | | 280 | | | | | 285 | | | | |
| ata | tgc | agg | gac | aat | tgg | act | gga | aca | aat | aga | cca | att | ctg | gta | ata | 912 |
| Ile | Cys | Arg | Asp | Asn | Trp | Thr | Gly | Thr | Asn | Arg | Pro | Ile | Leu | Val | Ile | |
| | 290 | | | | | 295 | | | | | 300 | | | | | |
| tct | tct | gat | cta | tcg | tac | aca | gtt | gga | tat | ttg | tgt | gct | ggc | att | ccc | 960 |
| Ser | Ser | Asp | Leu | Ser | Tyr | Thr | Val | Gly | Tyr | Leu | Cys | Ala | Gly | Ile | Pro | |
| 305 | | | | | 310 | | | | | 315 | | | | | 320 | |
| act | gac | act | cct | agg | gga | gag | gat | agt | caa | ttc | aca | ggc | tca | tgt | aca | 1008 |
| Thr | Asp | Thr | Pro | Arg | Gly | Glu | Asp | Ser | Gln | Phe | Thr | Gly | Ser | Cys | Thr | |
| | | | | 325 | | | | | 330 | | | | | 335 | | |
| agt | cct | ttg | gga | aat | aaa | gga | tac | ggt | gta | aaa | ggc | ttc | ggg | ttt | cga | 1056 |
| Ser | Pro | Leu | Gly | Asn | Lys | Gly | Tyr | Gly | Val | Lys | Gly | Phe | Gly | Phe | Arg | |
| | | | 340 | | | | | 345 | | | | | 350 | | | |
| caa | gga | act | gac | gta | tgg | gcc | gga | agg | aca | att | agt | agg | act | tca | aga | 1104 |
| Gln | Gly | Thr | Asp | Val | Trp | Ala | Gly | Arg | Thr | Ile | Ser | Arg | Thr | Ser | Arg | |
| | | 355 | | | | | 360 | | | | | 365 | | | | |
| tca | gga | ttc | gaa | ata | ata | aaa | atc | agg | aat | ggt | tgg | aca | cag | aac | agt | 1152 |
| Ser | Gly | Phe | Glu | Ile | Ile | Lys | Ile | Arg | Asn | Gly | Trp | Thr | Gln | Asn | Ser | |
| | 370 | | | | | 375 | | | | | 380 | | | | | |
| aag | gac | caa | atc | agg | agg | caa | gtg | att | atc | gat | gac | cca | aat | tgg | tca | 1200 |
| Lys | Asp | Gln | Ile | Arg | Arg | Gln | Val | Ile | Ile | Asp | Asp | Pro | Asn | Trp | Ser | |
| 385 | | | | | 390 | | | | | 395 | | | | | 400 | |
| gga | tat | agc | ggt | tct | ttc | aca | ttg | ccg | gtt | gaa | ctg | aca | aaa | aag | gga | 1248 |
| Gly | Tyr | Ser | Gly | Ser | Phe | Thr | Leu | Pro | Val | Glu | Leu | Thr | Lys | Lys | Gly | |
| | | | | 405 | | | | | 410 | | | | | 415 | | |

```
tgt ttg gtc ccc tgt ttc tgg gtt gaa atg att aga ggt aaa cct gaa    1296
Cys Leu Val Pro Cys Phe Trp Val Glu Met Ile Arg Gly Lys Pro Glu
        420                 425                 430 gaa aca aca ata tgg acc tct agc agc tcc att gtg atg tgt gga gta    1344
Glu Thr Thr Ile Trp Thr Ser Ser Ser Ile Val Met Cys Gly Val
            435                 440                 445 gat cat aaa att gcc agt tgg tca tgg cac gat gga gct att ctt ccc    1392
Asp His Lys Ile Ala Ser Trp Ser Trp His Asp Gly Ala Ile Leu Pro
        450                 455                 460 ttt gac atc gat aag atg taa                                        1413
Phe Asp Ile Asp Lys Met
465             470

<210> SEQ ID NO 58
<211> LENGTH: 470
<212> TYPE: PRT
<213> ORGANISM: Influenza virus

<400> SEQUENCE: 58

Met Asn Pro Asn Gln Lys Ile Ile Ala Ile Gly Phe Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Leu Thr Gln
    50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300
```

```
Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
            325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
            405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
        435                 440                 445

Asp His Lys Ile Ala Ser Trp Ser Trp His Asp Gly Ala Ile Leu Pro
450                 455                 460

Phe Asp Ile Asp Lys Met
465                 470

<210> SEQ ID NO 59
<211> LENGTH: 981
<212> TYPE: DNA
<213> ORGANISM: Influenza virus
<220> FEATURE:
<221> NAME/KEY: CDS
<222> LOCATION: (1)..(756)

<400> SEQUENCE: 59 atg agt ctt cta acc gag gtc gaa acg tac gtt ctc tct atc gta cca      48
Met Ser Leu Leu Thr Glu Val Glu Thr Tyr Val Leu Ser Ile Val Pro
1               5                   10                  15 tca ggc ccc ctc aaa gcc gag atc gcg cag aga ctt gaa gat gtc ttt      96
Ser Gly Pro Leu Lys Ala Glu Ile Ala Gln Arg Leu Glu Asp Val Phe
            20                  25                  30 gcg gga aag aac acc gat ctt gag gca ctc atg gaa tgg cta aag aca     144
Ala Gly Lys Asn Thr Asp Leu Glu Ala Leu Met Glu Trp Leu Lys Thr
        35                  40                  45 aga cca atc ctg tca cct ctg act aaa ggg att tta gga ttt gta ttc     192
Arg Pro Ile Leu Ser Pro Leu Thr Lys Gly Ile Leu Gly Phe Val Phe
    50                  55                  60 acg ctc acc gtg ccc agt gag cga gga ctg cag cgt aga cgc ttt gtc     240
Thr Leu Thr Val Pro Ser Glu Arg Gly Leu Gln Arg Arg Arg Phe Val
65                  70                  75                  80 caa aat gcc ctt agt gga aac gga gat cca aac aac atg gac aga gca     288
Gln Asn Ala Leu Ser Gly Asn Gly Asp Pro Asn Asn Met Asp Arg Ala
            85                  90                  95 gta aaa ctg tac agg aag ctt aaa aga gaa ata aca ttc cat ggg gca     336
Val Lys Leu Tyr Arg Lys Leu Lys Arg Glu Ile Thr Phe His Gly Ala
        100                 105                 110 aaa gag gtg gca ctc agc tat tcc act ggt gca cta gcc agc tgc atg     384
Lys Glu Val Ala Leu Ser Tyr Ser Thr Gly Ala Leu Ala Ser Cys Met
    115                 120                 125 gga ctc ata tac aac aga atg gga act gtt aca acc gaa gtg gca ttt     432
Gly Leu Ile Tyr Asn Arg Met Gly Thr Val Thr Thr Glu Val Ala Phe
130                 135                 140
```

```
ggc ctg gta tgc gcc aca tgt gaa cag att gct gat tcc cag cat cga      480
Gly Leu Val Cys Ala Thr Cys Glu Gln Ile Ala Asp Ser Gln His Arg
145                 150                 155                 160 tct cac agg cag atg gtg aca aca acc aac cca tta atc aga cat gaa      528
Ser His Arg Gln Met Val Thr Thr Thr Asn Pro Leu Ile Arg His Glu
                165                 170                 175 aac aga atg gta tta gcc agt acc acg gct aaa gcc atg gaa cag atg      576
Asn Arg Met Val Leu Ala Ser Thr Thr Ala Lys Ala Met Glu Gln Met
            180                 185                 190 gca gga tcg agt gag cag gca gca gag gcc atg gag gtt gct agt agg      624
Ala Gly Ser Ser Glu Gln Ala Ala Glu Ala Met Glu Val Ala Ser Arg
        195                 200                 205 gct agg cag atg gta cag gca atg aga acc att ggg acc cac cct agc      672
Ala Arg Gln Met Val Gln Ala Met Arg Thr Ile Gly Thr His Pro Ser
    210                 215                 220 tcc agt gcc ggt ttg aaa gat gat ctc ctt gaa aat tta cag gcc tac      720
Ser Ser Ala Gly Leu Lys Asp Asp Leu Leu Glu Asn Leu Gln Ala Tyr
225                 230                 235                 240 cag aaa cgg atg gga gtg caa atg cag cga ttc aag tgatcctctc           766
Gln Lys Arg Met Gly Val Gln Met Gln Arg Phe Lys
                245                 250 gtcattgcag caagtatcat tgggatcttg cacttgatat tgtggattct tgatcgtctt    826
ttcttcaaat tcatttatcg tcgccttaaa tacgggttga aaagagggcc ttctacggaa    886
ggagtacctg agtctatgag ggaagaatat cggcaggaac agcagaatgc tgtggatgtt    946
gacgatggtc attttgtcaa catagagctg gagta                               981

<210> SEQ ID NO 60
<211> LENGTH: 252
<212> TYPE: PRT
<213> ORGANISM: Influenza virus

<400> SEQUENCE: 60

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

```
Ala Gly Ser Ser Glu Gln Ala Ala Glu Ala Met Glu Val Ala Ser Arg
            195                 200                 205

Ala Arg Gln Met Val Gln Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 61
<211> LENGTH: 1698
<212> TYPE: DNA
<213> ORGANISM: Influenza virus
<220> FEATURE:
<221> NAME/KEY: CDS
<222> LOCATION: (1)..(1698)

<400> SEQUENCE: 61 atg aag aca acc att att tta ata cta ctg acc cat tgg gcc tac agt      48
Met Lys Thr Thr Ile Ile Leu Ile Leu Leu Thr His Trp Ala Tyr Ser
1               5                   10                  15 caa aac cca atc agt ggc aat aac aca gcc aca ctg tgt ctg gga cac      96
Gln Asn Pro Ile Ser Gly Asn Asn Thr Ala Thr Leu Cys Leu Gly His
                20                  25                  30 cat gca gta gca aat gga aca ttg gta aaa aca atg agt gat gat caa     144
His Ala Val Ala Asn Gly Thr Leu Val Lys Thr Met Ser Asp Asp Gln
            35                  40                  45 att gag gtg aca aat gct aca gaa tta gtt cag agc att tca atg ggg     192
Ile Glu Val Thr Asn Ala Thr Glu Leu Val Gln Ser Ile Ser Met Gly
        50                  55                  60 aaa ata tgc aac aaa tca tat aga att cta gat gga aga aat tgc aca     240
Lys Ile Cys Asn Lys Ser Tyr Arg Ile Leu Asp Gly Arg Asn Cys Thr
65                  70                  75                  80 tta ata gat gca atg cta gga gac ccc cac tgt gac gcc ttt cag tat     288
Leu Ile Asp Ala Met Leu Gly Asp Pro His Cys Asp Ala Phe Gln Tyr
                85                  90                  95 gag agt tgg gac ctc ttt ata gaa aga agc agc gct ttc agc aat tgc     336
Glu Ser Trp Asp Leu Phe Ile Glu Arg Ser Ser Ala Phe Ser Asn Cys
            100                 105                 110 tac cca tat gac atc cct gac tat gca tcg ctc cga tcc att gta gca     384
Tyr Pro Tyr Asp Ile Pro Asp Tyr Ala Ser Leu Arg Ser Ile Val Ala
        115                 120                 125 tcc tca ggg aca gtg gaa ttc aca gca gag gga ttc acg tgg aca ggt     432
Ser Ser Gly Thr Val Glu Phe Thr Ala Glu Gly Phe Thr Trp Thr Gly
130                 135                 140 gta act caa aac gga aga agt gga gcc tgc aaa agg gga tca gcc gat     480
Val Thr Gln Asn Gly Arg Ser Gly Ala Cys Lys Arg Gly Ser Ala Asp
145                 150                 155                 160 agt ttc ttt agc cga ctg aat tgg cta aca aaa tct gga agc tct tac     528
Ser Phe Phe Ser Arg Leu Asn Trp Leu Thr Lys Ser Gly Ser Ser Tyr
                165                 170                 175 ccc aca ttg aat gtg aca atg cct aac aat aaa aat ttc gac aag cta     576
Pro Thr Leu Asn Val Thr Met Pro Asn Asn Lys Asn Phe Asp Lys Leu
            180                 185                 190 tac atc tgg ggg att cat cac ccg agc tca aat caa gag cag aca aaa     624
Tyr Ile Trp Gly Ile His His Pro Ser Ser Asn Gln Glu Gln Thr Lys
        195                 200                 205 ttg tac atc caa gaa tca gga cga gta aca gtc tca aca aaa aga agt     672
Leu Tyr Ile Gln Glu Ser Gly Arg Val Thr Val Ser Thr Lys Arg Ser
210                 215                 220
```

```
caa caa aca ata atc cct aac atc gga tct aga ccg ttg gtc aga ggt    720
Gln Gln Thr Ile Ile Pro Asn Ile Gly Ser Arg Pro Leu Val Arg Gly
225                 230                 235                 240 caa tca ggc agg ata agc ata tac tgg acc att gta aaa cct gga gat    768
Gln Ser Gly Arg Ile Ser Ile Tyr Trp Thr Ile Val Lys Pro Gly Asp
            245                 250                 255 atc cta atg ata aac agt aat ggc aac tta gtt gca ccg cgg gga tat    816
Ile Leu Met Ile Asn Ser Asn Gly Asn Leu Val Ala Pro Arg Gly Tyr
        260                 265                 270 ttt aaa ttg aac aca ggg aaa agc tct gta atg aga tcc gat gta ccc    864
Phe Lys Leu Asn Thr Gly Lys Ser Ser Val Met Arg Ser Asp Val Pro
    275                 280                 285 ata gac att tgt gtg tct gaa tgt att aca cca aat gga agc atc tcc    912
Ile Asp Ile Cys Val Ser Glu Cys Ile Thr Pro Asn Gly Ser Ile Ser
290                 295                 300 aac gac aag cca ttc caa aat gtg aac aaa gtt aca tat gga aaa tgc    960
Asn Asp Lys Pro Phe Gln Asn Val Asn Lys Val Thr Tyr Gly Lys Cys
305                 310                 315                 320 ccc aag tat atc agg caa aac act tta aag ctg gcc act ggg atg agg   1008
Pro Lys Tyr Ile Arg Gln Asn Thr Leu Lys Leu Ala Thr Gly Met Arg
            325                 330                 335 aat gta cca gaa aag caa acc aga gga atc ttt gga gca ata gcg gga   1056
Asn Val Pro Glu Lys Gln Thr Arg Gly Ile Phe Gly Ala Ile Ala Gly
        340                 345                 350 ttc atc gaa aac ggc tgg gaa gga atg gtt gat ggg tgg tat ggg ttc   1104
Phe Ile Glu Asn Gly Trp Glu Gly Met Val Asp Gly Trp Tyr Gly Phe
    355                 360                 365 cga tat caa aac tct gaa gga aca ggg caa gct gca gat cta aag agc   1152
Arg Tyr Gln Asn Ser Glu Gly Thr Gly Gln Ala Ala Asp Leu Lys Ser
370                 375                 380 act caa gca gcc atc gac cag att aat gga aag tta aac aga gtg att   1200
Thr Gln Ala Ala Ile Asp Gln Ile Asn Gly Lys Leu Asn Arg Val Ile
385                 390                 395                 400 gaa aga acc aat gag aaa ttc cat caa ata gag aag gaa ttc tca gaa   1248
Glu Arg Thr Asn Glu Lys Phe His Gln Ile Glu Lys Glu Phe Ser Glu
            405                 410                 415 gta gaa gga aga att cag gac ttg gag aaa tat gta gaa gac acc aaa   1296
Val Glu Gly Arg Ile Gln Asp Leu Glu Lys Tyr Val Glu Asp Thr Lys
        420                 425                 430 ata gac cta tgg tcc tac aat gca gaa ttg ctg gtg gct cta gaa aat   1344
Ile Asp Leu Trp Ser Tyr Asn Ala Glu Leu Leu Val Ala Leu Glu Asn
    435                 440                 445 caa cat aca att gac tta aca gat gca gaa atg aat aaa tta ttt gag   1392
Gln His Thr Ile Asp Leu Thr Asp Ala Glu Met Asn Lys Leu Phe Glu
450                 455                 460 aag act aga cgc cag tta aga gaa aac gca gaa gac atg gga ggt gga   1440
Lys Thr Arg Arg Gln Leu Arg Glu Asn Ala Glu Asp Met Gly Gly Gly
465                 470                 475                 480 tgt ttc aag att tac cac aaa tgt gat aat gca tgc att gaa tca ata   1488
Cys Phe Lys Ile Tyr His Lys Cys Asp Asn Ala Cys Ile Glu Ser Ile
            485                 490                 495 aga act ggg aca tat gac cat tac ata tac aaa gat gaa gca tta aac   1536
Arg Thr Gly Thr Tyr Asp His Tyr Ile Tyr Lys Asp Glu Ala Leu Asn
        500                 505                 510 aat cga ttt cag atc aaa ggt gta gag ttg aaa tca ggc tac aaa gat   1584
Asn Arg Phe Gln Ile Lys Gly Val Glu Leu Lys Ser Gly Tyr Lys Asp
    515                 520                 525 tgg ata ctg tgg att tca ttc gcc ata tca tgc ttc tta att tgc gtt   1632
Trp Ile Leu Trp Ile Ser Phe Ala Ile Ser Cys Phe Leu Ile Cys Val
530                 535                 540
```

```
gtt cta ttg ggt ttc att atg tgg gct tgc caa aaa ggc aac at

```
                 340                 345                 350
Phe Ile Glu Asn Gly Trp Glu Gly Met Val Asp Gly Trp Tyr Gly Phe
            355                 360                 365

Arg Tyr Gln Asn Ser Glu Gly Thr Gly Gln Ala Ala Asp Leu Lys Ser
            370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
            435                 440                 445

Gln His Thr Ile Asp Leu Thr Asp Ala Glu Met Asn Lys Leu Phe Glu
            450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
            485                 490                 495

Arg Thr Gly Thr Tyr Asp His Tyr Ile Tyr Lys Asp Glu Ala Leu Asn
            500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
            530                 535                 540

Val Leu Leu Gly Phe Ile Met Trp Ala Cys Gln Lys Gly Asn Ile Arg
545                 550                 555                 560

Cys Asn Ile Cys Ile
            565

<210> SEQ ID NO 63
<211> LENGTH: 2280
<212> TYPE: DNA
<213> ORGANISM: Influenza virus
<220> FEATURE:
<221> NAME/KEY: CDS
<222> LOCATION: (1)..(2280)

<400> SEQUENCE: 63 atg gag aga ata aaa gaa ctg aga gat ctg atg tta caa tcc cgc acc       48
Met Glu Arg Ile Lys Glu Leu Arg Asp Leu Met Leu Gln Ser Arg Thr
1               5                   10                  15 cgc gag ata cta aca aaa act act gtg gac cac atg gcc ata atc aag       96
Arg Glu Ile Leu Thr Lys Thr Thr Val Asp His Met Ala Ile Ile Lys
                20                  25                  30 aaa tac aca tca gga aga caa gag aag aac cct gca ctt agg atg aaa      144
Lys Tyr Thr Ser Gly Arg Gln Glu Lys Asn Pro Ala Leu Arg Met Lys
            35                  40                  45 tgg atg atg gca atg aaa tac cca att aca gca gat aag agg ata atg      192
Trp Met Met Ala Met Lys Tyr Pro Ile Thr Ala Asp Lys Arg Ile Met
        50                  55                  60 gag atg att cct gag aga aat gaa cag gga caa acc ctt tgg agc aaa      240
Glu Met Ile Pro Glu Arg Asn Glu Gln Gly Gln Thr Leu Trp Ser Lys
65                  70                  75                  80 acg aac gat gct ggc tca gac cgc gta atg gta tca cct ctg gca gtg      288
Thr Asn Asp Ala Gly Ser Asp Arg Val Met Val Ser Pro Leu Ala Val
                85                  90                  95 aca tgg tgg aat agg aat gga cca aca acg aac aca att cat tat cca      336
```

```
Thr Trp Trp Asn Arg Asn Gly Pro Thr Thr Asn Thr Ile His Tyr Pro
            100                 105                 110 aaa gtc tac aaa act tat ttt gaa aag gtt gaa aga ttg aaa cac gga    384
Lys Val Tyr Lys Thr Tyr Phe Glu Lys Val Glu Arg Leu Lys His Gly
            115                 120                 125 acc ttt ggc ccc gtt cat ttt agg aat caa gtc aag ata aga cga aga    432
Thr Phe Gly Pro Val His Phe Arg Asn Gln Val Lys Ile Arg Arg Arg
            130                 135                 140 gtt gat gta aac cct ggt cac gcg gac ctc agt gct aaa gaa gca caa    480
Val Asp Val Asn Pro Gly His Ala Asp Leu Ser Ala Lys Glu Ala Gln
145             150                 155                 160 gat gtg atc atg gaa gtt gtt ttc cca aat gaa gtg gga gcc aga att    528
Asp Val Ile Met Glu Val Val Phe Pro Asn Glu Val Gly Ala Arg Ile
                165                 170                 175 cta aca tca gaa tca caa cta aca ata acc aaa gag aaa aag gaa gaa    576
Leu Thr Ser Glu Ser Gln Leu Thr Ile Thr Lys Glu Lys Lys Glu Glu
                180                 185                 190 ctt cag gac tgc aaa att gct ccc ttg atg gta gca tac atg cta gaa    624
Leu Gln Asp Cys Lys Ile Ala Pro Leu Met Val Ala Tyr Met Leu Glu
            195                 200                 205 aga gag ttg gtc cga aaa aca agg ttc ctc cca gta gta ggc gga aca    672
Arg Glu Leu Val Arg Lys Thr Arg Phe Leu Pro Val Val Gly Gly Thr
            210                 215                 220 agc agt gta tac att gaa gtg ttg cat ctg act cag gga aca tgc tgg    720
Ser Ser Val Tyr Ile Glu Val Leu His Leu Thr Gln Gly Thr Cys Trp
225             230                 235                 240 gag caa atg tac acc cca gga gga aaa gtt aga aac gat gat att gat    768
Glu Gln Met Tyr Thr Pro Gly Gly Lys Val Arg Asn Asp Asp Ile Asp
                245                 250                 255 caa agt tta att att gca gcc cgg aac ata gtg aga aga gca aca gta    816
Gln Ser Leu Ile Ile Ala Ala Arg Asn Ile Val Arg Arg Ala Thr Val
            260                 265                 270 tca gca gat cca cta gca tcc cta ctg gaa atg tgc cac agt aca cag    864
Ser Ala Asp Pro Leu Ala Ser Leu Leu Glu Met Cys His Ser Thr Gln
            275                 280                 285 att ggt gga aca agg atg gta gac atc ctt aag cag aac cca aca gag    912
Ile Gly Gly Thr Arg Met Val Asp Ile Leu Lys Gln Asn Pro Thr Glu
            290                 295                 300 gaa caa gct gtg gat ata tgc aaa gca gca atg gga ttg aga att agc    960
Glu Gln Ala Val Asp Ile Cys Lys Ala Ala Met Gly Leu Arg Ile Ser
305             310                 315                 320 tca tca ttc agc ttt ggt gga ttc acc ttc aaa agg aca agt gga tca   1008
Ser Ser Phe Ser Phe Gly Gly Phe Thr Phe Lys Arg Thr Ser Gly Ser
            325                 330                 335 tca gtc aag aga gaa gaa gaa atg ctt acg ggc aac ctt caa aca ttg   1056
Ser Val Lys Arg Glu Glu Glu Met Leu Thr Gly Asn Leu Gln Thr Leu
            340                 345                 350 aaa ata aga gtg cat gag ggc tat gaa gaa ttc aca atg gtc gga aga   1104
Lys Ile Arg Val His Glu Gly Tyr Glu Glu Phe Thr Met Val Gly Arg
            355                 360                 365 aga gca aca gcc att atc aga aag gca acc aga aga ttg att caa ttg   1152
Arg Ala Thr Ala Ile Ile Arg Lys Ala Thr Arg Arg Leu Ile Gln Leu
            370                 375                 380 ata gta agt ggg aga gat gaa caa tca att gct gaa gca ata att gta   1200
Ile Val Ser Gly Arg Asp Glu Gln Ser Ile Ala Glu Ala Ile Ile Val
385             390                 395                 400 gcc atg gtg ttt tcg caa gaa gat tgc atg ata aaa gca gtt cga ggc   1248
Ala Met Val Phe Ser Gln Glu Asp Cys Met Ile Lys Ala Val Arg Gly
                405                 410                 415 gat ttg aac ttt gtt aat aga gca aat cag cgt ttg aac ccc atg cat   1296
```

```
                                    -continued

Asp Leu Asn Phe Val Asn Arg Ala Asn Gln Arg Leu Asn Pro Met His
            420                 425                 430 caa ctc ttg agg cat ttc caa aaa gat gca aaa gtg ctt ttc caa aat       1344
Gln Leu Leu Arg His Phe Gln Lys Asp Ala Lys Val Leu Phe Gln Asn
            435                 440                 445 tgg gga att gaa ccc atc gac aat gta atg ggg atg att gga ata ttg       1392
Trp Gly Ile Glu Pro Ile Asp Asn Val Met Gly Met Ile Gly Ile Leu
            450                 455                 460 cct gac atg acc cca agc acc gag atg tca ttg aga gga gtg aga gtc       1440
Pro Asp Met Thr Pro Ser Thr Glu Met Ser Leu Arg Gly Val Arg Val
465             470                 475                 480 agc aaa atg gga gtg gat gag tac tcc agc act gag aga gtg gtg gtg       1488
Ser Lys Met Gly Val Asp Glu Tyr Ser Ser Thr Glu Arg Val Val Val
                        485                 490                 495 agc att gac cgt ttt tta aga gtt cgg gat caa agg gga aac ata cta       1536
Ser Ile Asp Arg Phe Leu Arg Val Arg Asp Gln Arg Gly Asn Ile Leu
                500                 505                 510 ctg tcc cct gaa gaa gtc agt gaa aca caa gga acg gaa aag ctg aca       1584
Leu Ser Pro Glu Glu Val Ser Glu Thr Gln Gly Thr Glu Lys Leu Thr
            515                 520                 525 ata att tat tcg tca tca atg atg tgg gag att aat ggt ccc gaa tca       1632
Ile Ile Tyr Ser Ser Ser Met Met Trp Glu Ile Asn Gly Pro Glu Ser
530             535                 540 gtg ttg gtc aat act tat caa tgg atc atc aga aac tgg gaa att gta       1680
Val Leu Val Asn Thr Tyr Gln Trp Ile Ile Arg Asn Trp Glu Ile Val
545             550                 555                 560 aaa att cag tgg tca cag gac ccc aca atg tta tac aat aag ata gaa       1728
Lys Ile Gln Trp Ser Gln Asp Pro Thr Met Leu Tyr Asn Lys Ile Glu
                565                 570                 575 ttt gaa cca ttc caa tcc ctg gtc cct agg gcc acc aga agc caa tac       1776
Phe Glu Pro Phe Gln Ser Leu Val Pro Arg Ala Thr Arg Ser Gln Tyr
            580                 585                 590 agc ggt ttc gta aga acc ctg ttt cag caa atg cga gat gta ctt gga       1824
Ser Gly Phe Val Arg Thr Leu Phe Gln Gln Met Arg Asp Val Leu Gly
        595                 600                 605 aca ttt gat act gct caa ata ata aaa ctc ctc cct ttt gcc gct gct       1872
Thr Phe Asp Thr Ala Gln Ile Ile Lys Leu Leu Pro Phe Ala Ala Ala
610             615                 620 cct ccg gaa cag agt agg atg cag ttc tct tct ttg act gtt aat gta       1920
Pro Pro Glu Gln Ser Arg Met Gln Phe Ser Ser Leu Thr Val Asn Val
625             630                 635                 640 aga ggt tcg gga atg agg ata ctt gta aga ggc aat tcc cca gtg ttc       1968
Arg Gly Ser Gly Met Arg Ile Leu Val Arg Gly Asn Ser Pro Val Phe
                645                 650                 655 aac tac aat aaa gtc act aaa agg ctc aca gtc ctc gga aag gat gca       2016
Asn Tyr Asn Lys Val Thr Lys Arg Leu Thr Val Leu Gly Lys Asp Ala
            660                 665                 670 ggt gcg ctt act gag gac cca gat gaa ggt acg gct gga gta gag tct       2064
Gly Ala Leu Thr Glu Asp Pro Asp Glu Gly Thr Ala Gly Val Glu Ser
        675                 680                 685 gct gtt cta aga ggg ttt ctc att tta ggt aaa gaa aac aag aga tat       2112
Ala Val Leu Arg Gly Phe Leu Ile Leu Gly Lys Glu Asn Lys Arg Tyr
    690                 695                 700 ggc cca gca cta agc atc aat gaa ctt agc aaa ctt gca aaa ggg gag       2160
Gly Pro Ala Leu Ser Ile Asn Glu Leu Ser Lys Leu Ala Lys Gly Glu
705             710                 715                 720 aaa gcc aat gta cta att ggg caa ggg gac gta gtg ttg gta atg aaa       2208
Lys Ala Asn Val Leu Ile Gly Gln Gly Asp Val Val Leu Val Met Lys
                725                 730                 735 cgg aaa cgt gac tct agc ata ctt act gac agc cag aca gcg acc aaa       2256
```

```
Arg Lys Arg Asp Ser Ser Ile Leu Thr Asp Ser Gln Thr Ala Thr Lys
                740                 745                 750 agg att cgg atg gcc atc aat tag                                      2280
Arg Ile Arg Met Ala Ile Asn
        755

<210> SEQ ID NO 64
<211> LENGTH: 759
<212> TYPE: PRT
<213> ORGANISM: Influenza virus

<400> SEQUENCE: 64

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Val Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Lys Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350
```

```
Lys Ile Arg Val His Glu Gly Tyr Glu Phe Thr Met Val Gly Arg
        355                 360                 365
Arg Ala Thr Ala Ile Ile Arg Lys Ala Thr Arg Arg Leu Ile Gln Leu
        370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
                420                 425                 430
Gln Leu Leu Arg His Phe Gln Lys Asp Ala Lys Val Leu Phe Gln Asn
            435                 440                 445
Trp Gly Ile Glu Pro Ile Asp Asn Val Met Gly Met Ile Gly Ile Leu
        450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Ile Leu
                500                 505                 510
Leu Ser Pro Glu Glu Val Ser Glu Thr Gln Gly Thr Glu Lys Leu Thr
            515                 520                 525
Ile Ile Tyr Ser Ser Ser Met Met Trp Glu Ile Asn Gly Pro Glu Ser
        530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
                580                 585                 590
Ser Gly Phe Val Arg Thr Leu Phe Gln Gln Met Arg Asp Val Leu Gly
            595                 600                 605
Thr Phe Asp Thr Ala Gln Ile Ile Lys Leu Leu Pro Phe Ala Ala Ala
        610                 615                 620
Pro Pro Glu Gln Ser Arg Met Gln Phe Ser Ser Leu Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Val Thr Lys Arg Leu Thr Val Leu Gly Lys Asp Ala
                660                 665                 670
Gly Ala Leu Thr Glu Asp Pro Asp Glu Gly Thr Ala Gly Val Glu Ser
            675                 680                 685
Ala Val Leu Arg Gly Phe Leu Ile Leu Gly Lys Glu Asn Lys Arg Tyr
        690                 695                 700
Gly Pro Ala Leu Ser Ile Asn Glu Leu Ser Lys Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
                740                 745                 750
Arg Ile Arg Met Ala Ile Asn
            755
```

<210> SEQ ID NO 65
<211> LENGTH: 2274
<212> TYPE: DNA
<213> ORGANISM: Influenza virus
<220> FEATURE:
<221> NAME/KEY: CDS
<222> LOCATION: (1)..(2274)

<400> SEQUENCE: 65

| | | | | | | | | | | | | | | | | |
|---|---|---|---|---|---|---|---|---|---|---|---|---|---|---|---|---|
| atg | gat | gtc | aat | ccg | act | cta | ctt | ttc | tta | aag | gtg | cca | gcg | caa | aat | 48 |
| Met | Asp | Val | Asn | Pro | Thr | Leu | Leu | Phe | Leu | Lys | Val | Pro | Ala | Gln | Asn | |
| 1 | | | | 5 | | | | | 10 | | | | | 15 | | |
| gct | ata | agc | aca | aca | ttc | cct | tat | act | gga | gat | cct | ccc | tac | agt | cat | 96 |
| Ala | Ile | Ser | Thr | Thr | Phe | Pro | Tyr | Thr | Gly | Asp | Pro | Pro | Tyr | Ser | His | |
| | | | 20 | | | | | 25 | | | | | 30 | | | |
| gga | aca | ggg | aca | gga | tac | acc | atg | gat | act | gtc | aac | aga | aca | cac | caa | 144 |
| Gly | Thr | Gly | Thr | Gly | Tyr | Thr | Met | Asp | Thr | Val | Asn | Arg | Thr | His | Gln | |
| | | 35 | | | | | 40 | | | | | 45 | | | | |
| tat | tca | gaa | aaa | ggg | aaa | tgg | aca | aca | aac | act | gag | att | gga | gca | cca | 192 |
| Tyr | Ser | Glu | Lys | Gly | Lys | Trp | Thr | Thr | Asn | Thr | Glu | Ile | Gly | Ala | Pro | |
| 50 | | | | | 55 | | | | | 60 | | | | | | |
| caa | ctt | aat | cca | atc | gat | gga | cca | ctt | cct | gaa | gac | aat | gaa | cca | agt | 240 |
| Gln | Leu | Asn | Pro | Ile | Asp | Gly | Pro | Leu | Pro | Glu | Asp | Asn | Glu | Pro | Ser | |
| 65 | | | | | 70 | | | | | 75 | | | | | 80 | |
| ggg | tac | gcc | caa | aca | gat | tgt | gta | ttg | gaa | gca | atg | gct | ttc | ctt | gaa | 288 |
| Gly | Tyr | Ala | Gln | Thr | Asp | Cys | Val | Leu | Glu | Ala | Met | Ala | Phe | Leu | Glu | |
| | | | | 85 | | | | | 90 | | | | | 95 | | |
| gaa | tcc | cat | ccc | gga | atc | ttt | gaa | aat | tcg | tgt | ctt | gaa | acg | atg | gag | 336 |
| Glu | Ser | His | Pro | Gly | Ile | Phe | Glu | Asn | Ser | Cys | Leu | Glu | Thr | Met | Glu | |
| | | | 100 | | | | | 105 | | | | | 110 | | | |
| gtg | att | cag | cag | aca | aga | gtg | gac | aaa | cta | aca | caa | ggc | cga | caa | act | 384 |
| Val | Ile | Gln | Gln | Thr | Arg | Val | Asp | Lys | Leu | Thr | Gln | Gly | Arg | Gln | Thr | |
| | | 115 | | | | | 120 | | | | | 125 | | | | |
| tat | gat | tgg | acc | ttg | aat | agg | aat | caa | cct | gcc | gca | aca | gca | ctt | gct | 432 |
| Tyr | Asp | Trp | Thr | Leu | Asn | Arg | Asn | Gln | Pro | Ala | Ala | Thr | Ala | Leu | Ala | |
| 130 | | | | | 135 | | | | | 140 | | | | | | |
| aat | acg | att | gaa | gta | ttc | aga | tca | aat | ggt | ctg | acc | tcc | aat | gaa | tcg | 480 |
| Asn | Thr | Ile | Glu | Val | Phe | Arg | Ser | Asn | Gly | Leu | Thr | Ser | Asn | Glu | Ser | |
| 145 | | | | | 150 | | | | | 155 | | | | | 160 | |
| ggg | aga | ttg | atg | gac | ttc | ctc | aaa | gat | gtc | atg | gag | tcc | atg | aac | aag | 528 |
| Gly | Arg | Leu | Met | Asp | Phe | Leu | Lys | Asp | Val | Met | Glu | Ser | Met | Asn | Lys | |
| | | | | 165 | | | | | 170 | | | | | 175 | | |
| gag | gaa | atg | gaa | ata | aca | aca | cac | ttc | caa | cgg | aag | aga | aga | gta | aga | 576 |
| Glu | Glu | Met | Glu | Ile | Thr | Thr | His | Phe | Gln | Arg | Lys | Arg | Arg | Val | Arg | |
| | | | 180 | | | | | 185 | | | | | 190 | | | |
| gac | aac | atg | aca | aag | aga | atg | ata | aca | cag | aga | acc | ata | gga | aag | aaa | 624 |
| Asp | Asn | Met | Thr | Lys | Arg | Met | Ile | Thr | Gln | Arg | Thr | Ile | Gly | Lys | Lys | |
| | | 195 | | | | | 200 | | | | | 205 | | | | |
| aaa | caa | cga | tta | agc | aga | aag | agc | tat | cta | atc | aga | aca | tta | acc | cta | 672 |
| Lys | Gln | Arg | Leu | Ser | Arg | Lys | Ser | Tyr | Leu | Ile | Arg | Thr | Leu | Thr | Leu | |
| 210 | | | | | 215 | | | | | 220 | | | | | | |
| aac | aca | atg | acc | aag | gac | gct | gag | aga | ggg | aaa | ttg | aaa | cga | cga | gca | 720 |
| Asn | Thr | Met | Thr | Lys | Asp | Ala | Glu | Arg | Gly | Lys | Leu | Lys | Arg | Arg | Ala | |
| 225 | | | | | 230 | | | | | 235 | | | | | 240 | |
| atc | gct | acc | cca | ggg | atg | cag | ata | aga | gga | ttt | gta | tat | ttt | gtt | gaa | 768 |
| Ile | Ala | Thr | Pro | Gly | Met | Gln | Ile | Arg | Gly | Phe | Val | Tyr | Phe | Val | Glu | |
| | | | | 245 | | | | | 250 | | | | | 255 | | |
| aca | cta | gct | cga | aga | ata | tgt | gaa | aag | ctt | gaa | caa | tca | gga | ttg | cca | 816 |
| Thr | Leu | Ala | Arg | Arg | Ile | Cys | Glu | Lys | Leu | Glu | Gln | Ser | Gly | Leu | Pro | |
| | | | 260 | | | | | 265 | | | | | 270 | | | |
| gtt | ggc | ggt | aat | gag | aaa | aag | gcc | aaa | ctg | gca | aat | gtc | gtc | aga | aaa | 864 |
| Val | Gly | Gly | Asn | Glu | Lys | Lys | Ala | Lys | Leu | Ala | Asn | Val | Val | Arg | Lys | |

```
                275              280               285
atg atg act aat tcc caa gac act gaa ctc tcc ttc acc atc act ggg      912
Met Met Thr Asn Ser Gln Asp Thr Glu Leu Ser Phe Thr Ile Thr Gly
    290              295               300 gac aat acc aaa tgg aat gaa aat cag aac cca cgc ata ttc ctg gca      960
Asp Asn Thr Lys Trp Asn Glu Asn Gln Asn Pro Arg Ile Phe Leu Ala
305              310              315                  320 atg atc aca tac ata act aga gat cag cca gaa tgg ttc aga aat gtt     1008
Met Ile Thr Tyr Ile Thr Arg Asp Gln Pro Glu Trp Phe Arg Asn Val
                325              330              335 cta agc att gca ccg att atg ttc tca aat aaa atg gca aga ctg ggg     1056
Leu Ser Ile Ala Pro Ile Met Phe Ser Asn Lys Met Ala Arg Leu Gly
            340              345              350 aaa gga tat atg ttt gaa agc aaa agt atg aaa ttg aga act caa ata     1104
Lys Gly Tyr Met Phe Glu Ser Lys Ser Met Lys Leu Arg Thr Gln Ile
        355              360              365 cca gca gaa atg cta gca agc att gac cta aaa tat ttc aat gat tca     1152
Pro Ala Glu Met Leu Ala Ser Ile Asp Leu Lys Tyr Phe Asn Asp Ser
370              375              380 aca aaa aag aaa att gaa aag ata cga cca ctc ctg gtt gac ggg act     1200
Thr Lys Lys Lys Ile Glu Lys Ile Arg Pro Leu Leu Val Asp Gly Thr
385              390              395              400 gct tca ctg agt cct ggc atg atg atg gga atg ttc aac atg ttg agc     1248
Ala Ser Leu Ser Pro Gly Met Met Met Gly Met Phe Asn Met Leu Ser
                405              410              415 act gtg ctg ggt gta tcc ata tta aac ctg ggc cag agg aaa tat aca     1296
Thr Val Leu Gly Val Ser Ile Leu Asn Leu Gly Gln Arg Lys Tyr Thr
            420              425              430 aag acc aca tac tgg tgg gat ggt ctg caa tca tcc gat gac ttt gct     1344
Lys Thr Thr Tyr Trp Trp Asp Gly Leu Gln Ser Ser Asp Asp Phe Ala
        435              440              445 ttg ata gtg aat gcg cct aat cat gaa gga ata caa gct gga gta gac     1392
Leu Ile Val Asn Ala Pro Asn His Glu Gly Ile Gln Ala Gly Val Asp
450              455              460 aga ttc tat aga act tgc aaa ctg gtc ggg atc aac atg agc aaa aag     1440
Arg Phe Tyr Arg Thr Cys Lys Leu Val Gly Ile Asn Met Ser Lys Lys
465              470              475              480 aag tcc tac ata aat aga act gga aca ttc gaa ttc aca agc ttt ttc     1488
Lys Ser Tyr Ile Asn Arg Thr Gly Thr Phe Glu Phe Thr Ser Phe Phe
                485              490              495 tac cgg tat ggt ttt gta gcc aat ttc agc atg gaa cta ccc agt ttt     1536
Tyr Arg Tyr Gly Phe Val Ala Asn Phe Ser Met Glu Leu Pro Ser Phe
            500              505              510 ggg gtt tcc gga ata aat gaa tct gca gac atg agc att gga gtg aca     1584
Gly Val Ser Gly Ile Asn Glu Ser Ala Asp Met Ser Ile Gly Val Thr
        515              520              525 gtc atc aaa aac aac atg ata aat aat gat ctc ggt cct gcc acg gca     1632
Val Ile Lys Asn Asn Met Ile Asn Asn Asp Leu Gly Pro Ala Thr Ala
530              535              540 caa atg gca ctc caa ctc ttc att aag gat tat cgg tac aca tac cgg     1680
Gln Met Ala Leu Gln Leu Phe Ile Lys Asp Tyr Arg Tyr Thr Tyr Arg
545              550              555              560 tgc cat aga ggt gat acc cag ata caa acc aga aga tct ttt gag ttg     1728
Cys His Arg Gly Asp Thr Gln Ile Gln Thr Arg Arg Ser Phe Glu Leu
                565              570              575 aag aaa ctg tgg gaa cag act cga tca aag act ggt cta ctg gta tca     1776
Lys Lys Leu Trp Glu Gln Thr Arg Ser Lys Thr Gly Leu Leu Val Ser
            580              585              590 gat ggg ggt cca aac cta tat aac atc aga aac cta cac atc ccg gaa     1824
Asp Gly Gly Pro Asn Leu Tyr Asn Ile Arg Asn Leu His Ile Pro Glu
```

```
                 595                 600                 605
gtc tgt tta aaa tgg gag cta atg gat gaa gat tat aag ggg agg cta    1872
Val Cys Leu Lys Trp Glu Leu Met Asp Glu Asp Tyr Lys Gly Arg Leu
610                 615                 620 tgc aat cca ttg aat cct ttc gtt agt cac aaa gaa att gaa tca gtc    1920
Cys Asn Pro Leu Asn Pro Phe Val Ser His Lys Glu Ile Glu Ser Val
625                 630                 635                 640 aac agt gca gta gta atg cct gct cat ggc cct gcc aaa agc atg gag    1968
Asn Ser Ala Val Val Met Pro Ala His Gly Pro Ala Lys Ser Met Glu
                645                 650                 655 tat gat gct gtt gca aca aca cat tct tgg atc ccc aag agg aac cgg    2016
Tyr Asp Ala Val Ala Thr Thr His Ser Trp Ile Pro Lys Arg Asn Arg
            660                 665                 670 tcc ata ttg aac aca agc caa agg gga ata cta gaa gat gag cag atg    2064
Ser Ile Leu Asn Thr Ser Gln Arg Gly Ile Leu Glu Asp Glu Gln Met
        675                 680                 685 tat cag aaa tgc tgc aac ctg ttt gaa aaa ttc ttc ccc agc agc tca    2112
Tyr Gln Lys Cys Cys Asn Leu Phe Glu Lys Phe Phe Pro Ser Ser Ser
    690                 695                 700 tac aga aga cca gtc gga att tct agt atg gtt gag gcc atg gta tcc    2160
Tyr Arg Arg Pro Val Gly Ile Ser Ser Met Val Glu Ala Met Val Ser
705                 710                 715                 720 agg gcc cgc att gat gca cga att gac ttc gaa tct gga cgg ata aag    2208
Arg Ala Arg Ile Asp Ala Arg Ile Asp Phe Glu Ser Gly Arg Ile Lys
                725                 730                 735 aag gat gag ttc gct gag atc atg aag atc tgt tcc acc att gaa gag    2256
Lys Asp Glu Phe Ala Glu Ile Met Lys Ile Cys Ser Thr Ile Glu Glu
            740                 745                 750 ctc aga cgg caa aaa tag                                             2274
Leu Arg Arg Gln Lys
        755

<210> SEQ ID NO 66
<211> LENGTH: 757
<212> TYPE: PRT
<213> ORGANISM: Influenza virus

<400> SEQUENCE: 66

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Ile Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160
```

-continued

```
Gly Arg Leu Met Asp Phe Leu Lys Asp Val Met Glu Ser Met Asn Lys
            165                 170                 175

Glu Glu Met Glu Ile Thr Thr His Phe Gln Arg Lys Arg Arg Val Arg
            180                 185                 190

Asp Asn Met Thr Lys Arg Met Ile Thr Gln Arg Thr Ile Gly Lys Lys
            195                 200                 205

Lys Gln Arg Leu Ser Arg Lys Ser Tyr Leu Ile Arg Thr Leu Thr Leu
            210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
            245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
            325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
            405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
            485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
            565                 570                 575

Lys Lys Leu Trp Glu Gln Thr Arg Ser Lys Thr Gly Leu Leu Val Ser
            580                 585                 590
```

```
Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
                740                 745                 750

Leu Arg Arg Gln Lys
        755

<210> SEQ ID NO 67
<211> LENGTH: 2151
<212> TYPE: DNA
<213> ORGANISM: Influenza virus
<220> FEATURE:
<221> NAME/KEY: CDS
<222> LOCATION: (1)..(2151)

<400> SEQUENCE: 67 atg gaa gac ttt gtg cga cag tgc ttc aat cca atg atc gtc gag ctt      48
Met Glu Asp Phe Val Arg Gln Cys Phe Asn Pro Met Ile Val Glu Leu
1               5                   10                  15 gcg gaa aag gca atg aaa gaa tat gga gag aac ccg aaa atc gaa aca      96
Ala Glu Lys Ala Met Lys Glu Tyr Gly Glu Asn Pro Lys Ile Glu Thr
                20                  25                  30 aac aaa ttt gca gca ata tgc act cac ttg gaa gtc tgc ttc atg tac     144
Asn Lys Phe Ala Ala Ile Cys Thr His Leu Glu Val Cys Phe Met Tyr
            35                  40                  45 tcg gat ttc cac ttt ata aat gaa ctg ggt gag tca gtg gtc ata gag     192
Ser Asp Phe His Phe Ile Asn Glu Leu Gly Glu Ser Val Val Ile Glu
        50                  55                  60 tct ggt gac cca aat gct ctt ttg aaa cac aga ttt gaa atc att gag     240
Ser Gly Asp Pro Asn Ala Leu Leu Lys His Arg Phe Glu Ile Ile Glu
65                  70                  75                  80 ggg aga gat cga aca atg gca tgg aca gta gta aac agc atc tgc aac     288
Gly Arg Asp Arg Thr Met Ala Trp Thr Val Val Asn Ser Ile Cys Asn
                85                  90                  95 acc aca aga gct gaa aaa cct aaa ttt ctt cca gat tta tac gac tat     336
Thr Thr Arg Ala Glu Lys Pro Lys Phe Leu Pro Asp Leu Tyr Asp Tyr
            100                 105                 110 aaa gag aac aga ttt gtt gaa att ggt gtg aca agg aga gaa gtt cac     384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat     432
Ile Tyr Tyr Leu Glu Lys Ala Asn Lys Ile Lys Ser Glu Lys Thr His
    130                 135                 140
```

```
atc cac att ttc tca ttt aca gga gaa gaa atg gct aca aaa gcg gac      480
Ile His Ile Phe Ser Phe Thr Gly Glu Glu Met Ala Thr Lys Ala Asp
145                 150                 155                 160 tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175 act ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205 ggg acg atg cgc aag ctt gcc aat tac agt ctc cca ccg aac ttc tcc      672
Gly Thr Met Arg Lys Leu Ala Asn Tyr Ser Leu Pro Pro Asn Phe Ser
    210                 215                 220 agc ctt gaa aat ttt aga gtc tat ata gat gga ttc gaa ccg aac ggc      720
Ser Leu Glu Asn Phe Arg Val Tyr Ile Asp Gly Phe Glu Pro Asn Gly
225                 230                 235                 240 tgc att gag agt aag ctt tct caa atg tcc aaa gaa gta aat gcc aaa      768
Cys Ile Glu Ser Lys Leu Ser Gln Met Ser Lys Glu Val Asn Ala Lys
                245                 250                 255 ata gaa cca ttt tca aag aca aca ccc cga cca ctc aaa atg cca ggt      816
Ile Glu Pro Phe Ser Lys Thr Thr Pro Arg Pro Leu Lys Met Pro Gly
                260                 265                 270 ggt cca ccc tgc cat cag cga tcc aaa ttc ttg cta atg gat gct ctg      864
Gly Pro Pro Cys His Gln Arg Ser Lys Phe Leu Leu Met Asp Ala Leu
            275                 280                 285 aaa ctg agc att gag gac cca agt cac gag gga gag ggg ata cca cta      912
Lys Leu Ser Ile Glu Asp Pro Ser His Glu Gly Glu Gly Ile Pro Leu
290                 295                 300 tat gat gca atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320 agt att gtt aaa cca cat aaa aag ggt ata aac ccg aac tat ctc caa      1008
Ser Ile Val Lys Pro His Lys Lys Gly Ile Asn Pro Asn Tyr Leu Gln
                325                 330                 335 act tgg aag caa gta tta gaa gaa ata caa gac ctt gag aac gaa gaa      1056
Thr Trp Lys Gln Val Leu Glu Glu Ile Gln Asp Leu Glu Asn Glu Glu
                340                 345                 350 agg acc ccc aag acc aag aat atg aaa aaa aca agc caa ttg aaa tgg      1104
Arg Thr Pro Lys Thr Lys Asn Met Lys Lys Thr Ser Gln Leu Lys Trp
            355                 360                 365 gca cta ggt gaa aat atg gca cca gag aaa gtg gat ttt gag gat tgt      1152
Ala Leu Gly Glu Asn Met Ala Pro Glu Lys Val Asp Phe Glu Asp Cys
        370                 375                 380 aaa gac atc aat gat tta aaa caa tat gac agt gat gag cca gaa gca      1200
Lys Asp Ile Asn Asp Leu Lys Gln Tyr Asp Ser Asp Glu Pro Glu Ala
385                 390                 395                 400 agg tct ctt gca agt tgg att caa agt gag ttc aac aag gct tgt gag      1248
Arg Ser Leu Ala Ser Trp Ile Gln Ser Glu Phe Asn Lys Ala Cys Glu
                405                 410                 415 ctg aca gat tca agc tgg ata gag ctc gat gaa att ggg gag gat gtc      1296
Leu Thr Asp Ser Ser Trp Ile Glu Leu Asp Glu Ile Gly Glu Asp Val
                420                 425                 430 gcc cca ata gaa tac att gcg agc atg agg aga aat tat ttt act gct      1344
Ala Pro Ile Glu Tyr Ile Ala Ser Met Arg Arg Asn Tyr Phe Thr Ala
            435                 440                 445 gag att tcc cat tgt aga gca aca gaa tat ata atg aaa gga gtg tac      1392
Glu Ile Ser His Cys Arg Ala Thr Glu Tyr Ile Met Lys Gly Val Tyr
        450                 455                 460
```

```
atc aac act gct cta ctc aat gca tcc tgt gct gcg atg gat g

```
                 35                  40                  45
Ser Asp Phe His Phe Ile Asn Glu Leu Gly Glu Ser Val Val Ile Glu
 50                  55                  60

Ser Gly Asp Pro Asn Ala Leu Leu Lys His Arg Phe Glu Ile Ile Glu
 65                  70                  75                  80

Gly Arg Asp Arg Thr Met Ala Trp Thr Val Val Asn Ser Ile Cys Asn
                     85                  90                  95

Thr Thr Arg Ala Glu Lys Pro Lys Phe Leu Pro Asp Leu Tyr Asp Tyr
                100                 105                 110

Lys Glu Asn Arg Phe Val Glu Ile Gly Val Thr Arg Arg Glu Val His
                115                 120                 125

Ile Tyr Tyr Leu Glu Lys Ala Asn Lys Ile Lys Ser Glu Lys Thr His
                130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
                180                 185                 190

Gln Ser Glu Arg Gly Glu Glu Thr Ile Glu Glu Arg Phe Glu Ile Thr
                195                 200                 205

Gly Thr Met Arg Lys Leu Ala Asn Tyr Ser Leu Pro Pro Asn Phe Ser
                210                 215                 220

Ser Leu Glu Asn Phe Arg Val Tyr Ile Asp Gly Phe Glu Pro Asn Gly
225                 230                 235                 240

Cys Ile Glu Ser Lys Leu Ser Gln Met Ser Lys Glu Val Asn Ala Lys
                245                 250                 255

Ile Glu Pro Phe Ser Lys Thr Thr Pro Arg Pro Leu Lys Met Pro Gly
                260                 265                 270

Gly Pro Pro Cys His Gln Arg Ser Lys Phe Leu Leu Met Asp Ala Leu
                275                 280                 285

Lys Leu Ser Ile Glu Asp Pro Ser His Glu Gly Glu Gly Ile Pro Leu
290                 295                 300

Tyr Asp Ala Ile Lys Cys Met Lys Thr Phe Phe Gly Trp Lys Glu Pro
305                 310                 315                 320

Ser Ile Val Lys Pro His Lys Lys Gly Ile Asn Pro Asn Tyr Leu Gln
                325                 330                 335

Thr Trp Lys Gln Val Leu Glu Glu Ile Gln Asp Leu Glu Asn Glu Glu
                340                 345                 350

Arg Thr Pro Lys Thr Lys Asn Met Lys Lys Thr Ser Gln Leu Lys Trp
                355                 360                 365

Ala Leu Gly Glu Asn Met Ala Pro Glu Lys Val Asp Phe Glu Asp Cys
                370                 375                 380

Lys Asp Ile Asn Asp Leu Lys Gln Tyr Asp Ser Asp Glu Pro Glu Ala
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
                420                 425                 430

Ala Pro Ile Glu Tyr Ile Ala Ser Met Arg Arg Asn Tyr Phe Thr Ala
                435                 440                 445

Glu Ile Ser His Cys Arg Ala Thr Glu Tyr Ile Met Lys Gly Val Tyr
                450                 455                 460
```

```
Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
            485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Phe Glu Pro His Lys Trp Glu Lys Tyr Cys Val Leu Glu
530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asp Leu Glu Pro Gly Thr Phe Asp Ile Gly Gly Leu Tyr Glu
                675                 680                 685

Ser Ile Glu Glu Cys Leu Ile Asn Asp Pro Trp Val Leu Leu Asn Ala
            690                 695                 700

Ser Trp Phe Asn Ser Phe Leu Thr His Ala Leu Lys
705                 710                 715

<210> SEQ ID NO 69
<211> LENGTH: 844
<212> TYPE: DNA
<213> ORGANISM: Influenza virus
<220> FEATURE:
<221> NAME/KEY: CDS
<222> LOCATION: (1)..(690)

<400> SEQUENCE: 69 atg gat tcc aac act gtg tca agc ttt cag gta gac tgt ttt ctt tgg    48
Met Asp Ser Asn Thr Val Ser Ser Phe Gln Val Asp Cys Phe Leu Trp
1               5                   10                  15 cat gtc cgt aaa cga ttc gca gac caa gaa ctg ggt gat gcc cca ttc    96
His Val Arg Lys Arg Phe Ala Asp Gln Glu Leu Gly Asp Ala Pro Phe
            20                  25                  30 ctt gac cgg ctt cgc cga gac cag aag tcc cta agg gga aga ggt agc    144
Leu Asp Arg Leu Arg Arg Asp Gln Lys Ser Leu Arg Gly Arg Gly Ser
        35                  40                  45 act ctt ggt ctg gac atc gaa aca gcc act cat gca gga aag cag ata    192
Thr Leu Gly Leu Asp Ile Glu Thr Ala Thr His Ala Gly Lys Gln Ile
    50                  55                  60 gtg gag cag att ctg gaa aag gaa tca gat gag gca ctt aaa atg acc    240
Val Glu Gln Ile Leu Glu Lys Glu Ser Asp Glu Ala Leu Lys Met Thr
65                  70                  75                  80 att gcc tct gtt cct gct tca cgc tac tta act gac atg act ctt gat    288
Ile Ala Ser Val Pro Ala Ser Arg Tyr Leu Thr Asp Met Thr Leu Asp
```

```
Ile Ala Ser Val Pro Ala Ser Arg Tyr Leu Thr Asp Met Thr Leu Asp
                85                  90                  95 gag atg tca aga gac tgg ttc atg ctc atg ccc aag caa aaa gta aca        336
Glu Met Ser Arg Asp Trp Phe Met Leu Met Pro Lys Gln Lys Val Thr
            100                 105                 110 ggc tcc cta tgt ata aga atg gac cag gca atc atg gat aag aac atc       384
Gly Ser Leu Cys Ile Arg Met Asp Gln Ala Ile Met Asp Lys Asn Ile
            115                 120                 125 ata ctt aaa gca aac ttt agt gtg att ttc gaa agg ctg gaa aca cta       432
Ile Leu Lys Ala Asn Phe Ser Val Ile Phe Glu Arg Leu Glu Thr Leu
        130                 135                 140 ata cta ctt aga gcc ttc acc gaa gaa gga gca gtc gtt ggc gaa att       480
Ile Leu Leu Arg Ala Phe Thr Glu Glu Gly Ala Val Val Gly Glu Ile
145                 150                 155                 160 tca cca tta cct tct ctt cca gga cat act aat gag gat gtc aaa aat      528
Ser Pro Leu Pro Ser Leu Pro Gly His Thr Asn Glu Asp Val Lys Asn
                165                 170                 175 gca att ggg gtc ctc atc gga gga ctt aaa tgg aat gat aat acg gtt      576
Ala Ile Gly Val Leu Ile Gly Gly Leu Lys Trp Asn Asp Asn Thr Val
            180                 185                 190 aga atc tct gaa act cta cag aga ttc gct tgg aga agc agt cat gaa      624
Arg Ile Ser Glu Thr Leu Gln Arg Phe Ala Trp Arg Ser Ser His Glu
            195                 200                 205 aat ggg aga cct tca ttc cct tca aaa cag aaa cga aaa atg gag aga      672
Asn Gly Arg Pro Ser Phe Pro Ser Lys Gln Lys Arg Lys Met Glu Arg
        210                 215                 220 aca att aag cca gaa att tgaagaaata agatggttga ttgaagaagt             720
Thr Ile Lys Pro Glu Ile
225                 230 gcgacataga ttgaaaaata cagaaaatag ttttgaacaa ataacattta tgcaagcctt    780
acaactattg cttgaagtag aacaagagat aagaactttc tcgtttcagc ttatttaatg   840
ataa                                                                 844

<210> SEQ ID NO 70
<211> LENGTH: 230
<212> TYPE: PRT
<213> ORGANISM: Influenza virus

<400> SEQUENCE: 70

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
            115                 120                 125

Ile Leu Lys Ala Asn Phe Ser Val Ile Phe Glu Arg Leu Glu Thr Leu
        130                 135                 140
```

```
Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Ser Lys Gln Lys Arg Lys Met Glu Arg
    210                 215                 220

Thr Ile Lys Pro Glu Ile
225                 230

<210> SEQ ID NO 71
<211> LENGTH: 1497
<212> TYPE: DNA
<213> ORGANISM: Influenza virus
<220> FEATURE:
<221> NAME/KEY: CDS
<222> LOCATION: (1)..(1497)

<400> SEQUENCE: 71 atg gcg tct caa ggc acc aaa cga tcc tat gaa cag atg gaa act gat         48
Met Ala Ser Gln Gly Thr Lys Arg Ser Tyr Glu Gln Met Glu Thr Asp
1               5                   10                  15 ggg gaa cgc cag aat gca act gaa atc aga gca tct gtc gga agg atg         96
Gly Glu Arg Gln Asn Ala Thr Glu Ile Arg Ala Ser Val Gly Arg Met
            20                  25                  30 gtg gga gga atc gga cgg ttt tat gtc cag atg tgt act gag ctt aaa        144
Val Gly Gly Ile Gly Arg Phe Tyr Val Gln Met Cys Thr Glu Leu Lys
        35                  40                  45 cta aac gac cat gaa ggg cgg ctg att cag aac agc ata aca ata gaa        192
Leu Asn Asp His Glu Gly Arg Leu Ile Gln Asn Ser Ile Thr Ile Glu
    50                  55                  60 agg atg gtg ctt tcg gca ttc gac gaa aga aga aac aag tat ctc gag        240
Arg Met Val Leu Ser Ala Phe Asp Glu Arg Arg Asn Lys Tyr Leu Glu
65                  70                  75                  80 gag cat ccc agt gct ggg aaa gac cct aag aaa acg gga ggc ccg ata        288
Glu His Pro Ser Ala Gly Lys Asp Pro Lys Lys Thr Gly Gly Pro Ile
                85                  90                  95 tac aga aga aaa gat ggg aaa tgg atg agg gaa ctc atc ctc cat gat        336
Tyr Arg Arg Lys Asp Gly Lys Trp Met Arg Glu Leu Ile Leu His Asp
            100                 105                 110 aaa gaa gaa atc atg aga atc tgg cgt cag gcc aac aat ggt gaa gac        384
Lys Glu Glu Ile Met Arg Ile Trp Arg Gln Ala Asn Asn Gly Glu Asp
        115                 120                 125 gct act gct ggt ctt act cat atg atg atc tgg cac tcc aat ctc aat        432
Ala Thr Ala Gly Leu Thr His Met Met Ile Trp His Ser Asn Leu Asn
    130                 135                 140 gac acc aca tac caa aga aca agg gct ctt gtt cgg act ggg atg gat        480
Asp Thr Thr Tyr Gln Arg Thr Arg Ala Leu Val Arg Thr Gly Met Asp
145                 150                 155                 160 ccc aga atg tgc tct ctg atg caa ggc tca acc ctc cca cgg aga tct        528
Pro Arg Met Cys Ser Leu Met Gln Gly Ser Thr Leu Pro Arg Arg Ser
                165                 170                 175 gga gcc gct ggt gct gca gta aaa ggc gtt gga aca atg gta atg gaa        576
Gly Ala Ala Gly Ala Ala Val Lys Gly Val Gly Thr Met Val Met Glu
            180                 185                 190 ctc atc aga atg atc aag cgc gga ata aat gat cgg aat ttc tgg aga        624
Leu Ile Arg Met Ile Lys Arg Gly Ile Asn Asp Arg Asn Phe Trp Arg
        195                 200                 205
```

| | | |
|---|---|---|
| ggt gaa aat ggt cga aga acc aga att gct tat gaa aga atg tgc aat<br>Gly Glu Asn Gly Arg Arg Thr Arg Ile Ala Tyr Glu Arg Met Cys Asn<br>210               215                  220 | | 672 |
| atc ctc aaa ggg aaa ttt cag aca gca gca caa cgg gct atg atg gac<br>Ile Leu Lys Gly Lys Phe Gln Thr Ala Ala Gln Arg Ala Met Met Asp<br>225               230              235              240 | | 720 |
| cag gtg agg gaa ggc cgc aat cct gga aac gct gag att gag gat ctc<br>Gln Val Arg Glu Gly Arg Asn Pro Gly Asn Ala Glu Ile Glu Asp Leu<br>             245              250              255 | | 768 |
| att ttc ttg gca cga tca gca ctt att ttg aga gga tca gta gcc cat<br>Ile Phe Leu Ala Arg Ser Ala Leu Ile Leu Arg Gly Ser Val Ala His<br>260               265                  270 | | 816 |
| aaa tca tgc cta cct gcc tgt gtt tat ggc ctt gca cta acc agt ggg<br>Lys Ser Cys Leu Pro Ala Cys Val Tyr Gly Leu Ala Leu Thr Ser Gly<br>             275              280              285 | | 864 |
| tat gac ttt gag aag gaa gga tac tct ctg gtt gga att gat cct ttc<br>Tyr Asp Phe Glu Lys Glu Gly Tyr Ser Leu Val Gly Ile Asp Pro Phe<br>290               295                  300 | | 912 |
| aaa cta ctc cag aac agt caa att ttc agt cta atc aga cca aaa gaa<br>Lys Leu Leu Gln Asn Ser Gln Ile Phe Ser Leu Ile Arg Pro Lys Glu<br>305               310              315              320 | | 960 |
| aac cca gca cac aaa agc cag ttg gtg tgg atg gca tgc cat tct gca<br>Asn Pro Ala His Lys Ser Gln Leu Val Trp Met Ala Cys His Ser Ala<br>             325              330              335 | | 1008 |
| gca ttt gag gat ctg aga gtt tta aat ttc att aga gga acc aaa gta<br>Ala Phe Glu Asp Leu Arg Val Leu Asn Phe Ile Arg Gly Thr Lys Val<br>340               345                  350 | | 1056 |
| atc cca aga gga cag tta aca acc aga gga gtt caa att gct tca aat<br>Ile Pro Arg Gly Gln Leu Thr Thr Arg Gly Val Gln Ile Ala Ser Asn<br>             355              360              365 | | 1104 |
| gaa aac atg gag aca ata aat tct agc aca ctt gaa ctg aga agc aaa<br>Glu Asn Met Glu Thr Ile Asn Ser Ser Thr Leu Glu Leu Arg Ser Lys<br>370               375                  380 | | 1152 |
| tat tgg gca ata agg acc aga agc gga gga aac acc agt caa cag aga<br>Tyr Trp Ala Ile Arg Thr Arg Ser Gly Gly Asn Thr Ser Gln Gln Arg<br>385               390              395              400 | | 1200 |
| gca tct gca gga cag ata agt gtg caa cct act ttc tca gta cag aga<br>Ala Ser Ala Gly Gln Ile Ser Val Gln Pro Thr Phe Ser Val Gln Arg<br>             405              410              415 | | 1248 |
| aat ctt ccc ttt gag aga gca acc att atg gct gca ttc act ggt aac<br>Asn Leu Pro Phe Glu Arg Ala Thr Ile Met Ala Ala Phe Thr Gly Asn<br>420               425                  430 | | 1296 |
| act gaa gga agg act tcc gac atg aga acg gaa atc ata agg atg atg<br>Thr Glu Gly Arg Thr Ser Asp Met Arg Thr Glu Ile Ile Arg Met Met<br>             435              440              445 | | 1344 |
| gaa aat gcc aaa tca gaa gat gtg tct ttc cag ggg cgg gga gtc ttc<br>Glu Asn Ala Lys Ser Glu Asp Val Ser Phe Gln Gly Arg Gly Val Phe<br>450               455                  460 | | 1392 |
| gag ctc tcg gac gaa aag gca acg aac ccg atc gtg cct tcc ttt gac<br>Glu Leu Ser Asp Glu Lys Ala Thr Asn Pro Ile Val Pro Ser Phe Asp<br>465               470              475              480 | | 1440 |
| atg agc aat gaa ggg tct tat ttc ttc gga gac aat gct gag gag ttt<br>Met Ser Asn Glu Gly Ser Tyr Phe Phe Gly Asp Asn Ala Glu Glu Phe<br>             485              490              495 | | 1488 |
| gac agt taa<br>Asp Ser | | 1497 |

<210> SEQ ID NO 72
<211> LENGTH: 498
<212> TYPE: PRT

<213> ORGANISM: Influenza virus

<400> SEQUENCE: 72

```
Met Ala Ser Gln Gly Thr Lys Arg Ser Tyr Gl

```
                         405                 410                 415
Asn Leu Pro Phe Glu Arg Ala Thr Ile Met Ala Ala Phe Thr Gly Asn
                420                 425                 430

Thr Glu Gly Arg Thr Ser Asp Met Arg Thr Glu Ile Ile Arg Met Met
            435                 440                 445

Glu Asn Ala Lys Ser Glu Asp Val Ser Phe Gln Gly Arg Gly Val Phe
        450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Ser

<210> SEQ ID NO 73
<211> LENGTH: 1413
<212> TYPE: DNA
<213> ORGANISM: Influenza virus
<220> FEATURE:
<221> NAME/KEY: CDS
<222> LOCATION: (1)..(1413)

<400> SEQUENCE: 73 atg aat cca aat caa aag ata ata gca att gga ttt gca tca ttg ggg      48
Met Asn Pro Asn Gln Lys Ile Ile Ala Ile Gly Phe Ala Ser Leu Gly
1               5                   10                  15 ata tta atc att aat gtc att ctc cat gta gtc agc att ata gta aca      96
Ile Leu Ile Ile Asn Val Ile Leu His Val Val Ser Ile Ile Val Thr
                20                  25                  30 gta ctg gtc ctc aat aac aat aga aca gat ctg aac tgc aaa ggg acg     144
Val Leu Val Leu Asn Asn Asn Arg Thr Asp Leu Asn Cys Lys Gly Thr
            35                  40                  45 atc ata aga gaa tac aat gaa aca gta aga gta gaa aaa ctt act caa     192
Ile Ile Arg Glu Tyr Asn Glu Thr Val Arg Val Glu Lys Leu Thr Gln
        50                  55                  60 tgg tat aat acc agt aca att aag tac ata gag aga cct tca aat gaa     240
Trp Tyr Asn Thr Ser Thr Ile Lys Tyr Ile Glu Arg Pro Ser Asn Glu
65                  70                  75                  80 tac tac atg aat aac act gaa cca ctt tgt gag gcc caa ggc ttt gca     288
Tyr Tyr Met Asn Asn Thr Glu Pro Leu Cys Glu Ala Gln Gly Phe Ala
                85                  90                  95 cca ttt tcc aaa gat aat gga ata cga att ggg tcg aga ggc cat gtt     336
Pro Phe Ser Lys Asp Asn Gly Ile Arg Ile Gly Ser Arg Gly His Val
                100                 105                 110 ttt gtg ata aga gaa cct ttt gta tca tgt tcg ccc tca gaa tgt aga     384
Phe Val Ile Arg Glu Pro Phe Val Ser Cys Ser Pro Ser Glu Cys Arg
            115                 120                 125 acc ttt ttc ctc aca cag ggc tca tta ctc aat gac aaa cat tct aac     432
Thr Phe Phe Leu Thr Gln Gly Ser Leu Leu Asn Asp Lys His Ser Asn
        130                 135                 140 ggc aca ata aag gat cga agt ccg tat agg act ttg atg agt gtc aaa     480
Gly Thr Ile Lys Asp Arg Ser Pro Tyr Arg Thr Leu Met Ser Val Lys
145                 150                 155                 160 ata ggg caa tca cct aat gta tat caa gct agg ttt gaa tcg gtg gca     528
Ile Gly Gln Ser Pro Asn Val Tyr Gln Ala Arg Phe Glu Ser Val Ala
                165                 170                 175 tgg tca gca aca gca tgc cat gat gga aaa aaa tgg atg aca gtt gga     576
Trp Ser Ala Thr Ala Cys His Asp Gly Lys Lys Trp Met Thr Val Gly
                180                 185                 190 gtc aca ggg ccc gac aat caa gca att gca gta gtg aac tat gga ggt     624
Val Thr Gly Pro Asp Asn Gln Ala Ile Ala Val Val Asn Tyr Gly Gly
```

```
            195                 200                 205
gtt ccg gtt gat att att aat tca tgg gca ggg gat att tta aga acc    672
Val Pro Val Asp Ile Ile Asn Ser Trp Ala Gly Asp Ile Leu Arg Thr
210                 215                 220 caa gaa tca tca tgc acc tgc att aaa gga gac tgt tat tgg gta atg    720
Gln Glu Ser Ser Cys Thr Cys Ile Lys Gly Asp Cys Tyr Trp Val Met
225                 230                 235                 240 act gat gga ccg gca aat agg caa gct aaa tat agg ata ttc aaa gca    768
Thr Asp Gly Pro Ala Asn Arg Gln Ala Lys Tyr Arg Ile Phe Lys Ala
                245                 250                 255 aaa gat gga aga gta att gga caa act gat ata agt ttc aat ggg gga    816
Lys Asp Gly Arg Val Ile Gly Gln Thr Asp Ile Ser Phe Asn Gly Gly
            260                 265                 270 cac ata gag gag tgt tct tgt tac ccc aat gaa ggg aag gtg gaa tgc    864
His Ile Glu Glu Cys Ser Cys Tyr Pro Asn Glu Gly Lys Val Glu Cys
        275                 280                 285 ata tgc agg gac aat tgg act gga aca aat aga cca att ctg gta ata    912
Ile Cys Arg Asp Asn Trp Thr Gly Thr Asn Arg Pro Ile Leu Val Ile
    290                 295                 300 tct tct gat cta tcg tac aca gtt gga tat ttg tgt gct ggc att ccc    960
Ser Ser Asp Leu Ser Tyr Thr Val Gly Tyr Leu Cys Ala Gly Ile Pro
305                 310                 315                 320 act gac act cct agg gga gag gat agt caa ttc aca ggc tca tgt aca   1008
Thr Asp Thr Pro Arg Gly Glu Asp Ser Gln Phe Thr Gly Ser Cys Thr
                325                 330                 335 agt cct ttg gga aat aaa gga tac ggt gta aaa ggc ttc ggg ttt cga   1056
Ser Pro Leu Gly Asn Lys Gly Tyr Gly Val Lys Gly Phe Gly Phe Arg
            340                 345                 350 caa gga act gac gta tgg gcc gga agg aca att agt agg act tca aga   1104
Gln Gly Thr Asp Val Trp Ala Gly Arg Thr Ile Ser Arg Thr Ser Arg
        355                 360                 365 tca gga ttc gaa ata ata aaa atc agg aat ggt tgg aca cag aac agt   1152
Ser Gly Phe Glu Ile Ile Lys Ile Arg Asn Gly Trp Thr Gln Asn Ser
    370                 375                 380 aag gac caa atc agg agg caa gtg att atc gat gac cca aat tgg tca   1200
Lys Asp Gln Ile Arg Arg Gln Val Ile Ile Asp Asp Pro Asn Trp Ser
385                 390                 395                 400 gga tat agc ggt tct ttc aca ttg ccg gtt gaa ctg aca aaa aag gga   1248
Gly Tyr Ser Gly Ser Phe Thr Leu Pro Val Glu Leu Thr Lys Lys Gly
                405                 410                 415 tgt ttg gtc ccc tgt ttc tgg gtt gaa atg att aga ggt aaa cct gaa   1296
Cys Leu Val Pro Cys Phe Trp Val Glu Met Ile Arg Gly Lys Pro Glu
            420                 425                 430 gaa aca aca ata tgg acc tct agc agc tcc att gtg atg tgt gga gta   1344
Glu Thr Thr Ile Trp Thr Ser Ser Ser Ser Ile Val Met Cys Gly Val
        435                 440                 445 gat cat aaa att gcc agt tgg tca tgg cac gat gga gct att ctt ccc   1392
Asp His Lys Ile Ala Ser Trp Ser Trp His Asp Gly Ala Ile Leu Pro
    450                 455                 460 ttt gac atc gat aag atg taa                                       1413
Phe Asp Ile Asp Lys Met
465                 470

<210> SEQ ID NO 74
<211> LENGTH: 470
<212> TYPE: PRT
<213> ORGANISM: Influenza virus

<400> SEQUENCE: 74

Met Asn Pro Asn Gln Lys Ile Ile Ala Ile Gly Phe Ala Ser Leu Gly
1               5                   10                  15
```

```
Ile Leu Ile Ile Asn Val Ile Leu His Val Val Ser Ile Ile Val Thr
            20                  25                  30
Val Leu Val Leu Asn Asn Asn Arg Thr Asp Leu Asn Cys Lys Gly Thr
            35                  40                  45
Ile Ile Arg Glu Tyr Asn Glu Thr Val Arg Val Glu Lys Leu Thr Gln
        50                  55                  60
Trp Tyr Asn Thr Ser Thr Ile Lys Tyr Ile Glu Arg Pro Ser Asn Glu
 65                  70                  75                  80
Tyr Tyr Met Asn Asn Thr Glu Pro Leu Cys Glu Ala Gln Gly Phe Ala
                85                  90                  95
Pro Phe Ser Lys Asp Asn Gly Ile Arg Ile Gly Ser Arg Gly His Val
               100                 105                 110
Phe Val Ile Arg Glu Pro Phe Val Ser Cys Ser Pro Ser Glu Cys Arg
               115                 120                 125
Thr Phe Phe Leu Thr Gln Gly Ser Leu Leu Asn Asp Lys His Ser Asn
           130                 135                 140
Gly Thr Ile Lys Asp Arg Ser Pro Tyr Arg Thr Leu Met Ser Val Lys
145                 150                 155                 160
Ile Gly Gln Ser Pro Asn Val Tyr Gln Ala Arg Phe Glu Ser Val Ala
               165                 170                 175
Trp Ser Ala Thr Ala Cys His Asp Gly Lys Lys Trp Met Thr Val Gly
               180                 185                 190
Val Thr Gly Pro Asp Asn Gln Ala Ile Ala Val Val Asn Tyr Gly Gly
           195                 200                 205
Val Pro Val Asp Ile Ile Asn Ser Trp Ala Gly Asp Ile Leu Arg Thr
210                 215                 220
Gln Glu Ser Ser Cys Thr Cys Ile Lys Gly Asp Cys Tyr Trp Val Met
225                 230                 235                 240
Thr Asp Gly Pro Ala Asn Arg Gln Ala Lys Tyr Arg Ile Phe Lys Ala
               245                 250                 255
Lys Asp Gly Arg Val Ile Gly Gln Thr Asp Ile Ser Phe Asn Gly Gly
               260                 265                 270
His Ile Glu Glu Cys Ser Cys Tyr Pro Asn Glu Gly Lys Val Glu Cys
           275                 280                 285
Ile Cys Arg Asp Asn Trp Thr Gly Thr Asn Arg Pro Ile Leu Val Ile
290                 295                 300
Ser Ser Asp Leu Ser Tyr Thr Val Gly Tyr Leu Cys Ala Gly Ile Pro
305                 310                 315                 320
Thr Asp Thr Pro Arg Gly Glu Asp Ser Gln Phe Thr Gly Ser Cys Thr
               325                 330                 335
Ser Pro Leu Gly Asn Lys Gly Tyr Gly Val Lys Gly Phe Gly Phe Arg
           340                 345                 350
Gln Gly Thr Asp Val Trp Ala Gly Arg Thr Ile Ser Arg Thr Ser Arg
           355                 360                 365
Ser Gly Phe Glu Ile Ile Lys Ile Arg Asn Gly Trp Thr Gln Asn Ser
370                 375                 380
Lys Asp Gln Ile Arg Arg Gln Val Ile Ile Asp Asp Pro Asn Trp Ser
385                 390                 395                 400
Gly Tyr Ser Gly Ser Phe Thr Leu Pro Val Glu Leu Thr Lys Lys Gly
               405                 410                 415
Cys Leu Val Pro Cys Phe Trp Val Glu Met Ile Arg Gly Lys Pro Glu
           420                 425                 430
Glu Thr Thr Ile Trp Thr Ser Ser Ser Ile Val Met Cys Gly Val
```

```
                        435                 440                 445
Asp His Lys Ile Ala Ser Trp Ser Trp His As

```
Gln Lys Arg Met Gly Val Gln Met Gln Arg Phe Lys
            245                 250 gtcattgcag caagtatcat tgggatcttg cacttgatat tgtggattct tgatcgtctt      826
ttcttcaaat tcatttatcg tcgccttaaa tacgggttga aaagagggcc ttctacggaa      886
ggagtacctg agtctatgag ggaagaatat cggcaggaac agcagaatgc tgtggatgtt      946
gacgatggtc attttgtcaa catagagctg agta                                  981

<210> SEQ ID NO 76
<211> LENGTH: 252
<212> TYPE: PRT
<213> ORGANISM: Influenza virus

<400> SEQUENCE: 76

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 77
<211> LENGTH: 1698
<212> TYPE: DNA
<213> ORGANISM: Influenza virus
<220> FEATURE:
<221> NAME/KEY: CDS
<222> LOCATION: (1)..(1698)

<400> SEQUENCE: 77 atg aag aca acc att att tta ata cta ctg acc cat tgg gcc tac agt      48
Met Lys Thr Thr Ile Ile Leu Ile Leu Leu Thr His Trp Ala Tyr Ser
```

```
                                    -continued
1           5               10              15 caa aac cca atc agt ggc aat aac aca gcc aca ctg tgt ctg gga cac     96
Gln Asn Pro Ile Ser Gly Asn Asn Thr Ala Thr Leu Cys Leu Gly His
            20              25              30 cat gca gta gca aat gga aca ttg gta aaa aca atg agt gat gat caa    144
His Ala Val Ala Asn Gly Thr Leu Val Lys Thr Met Ser Asp Asp Gln
            35              40              45 att gag gtg aca aat gct aca gaa tta gtt cag agc att tca atg ggg    192
Ile Glu Val Thr Asn Ala Thr Glu Leu Val Gln Ser Ile Ser Met Gly
            50              55              60 aaa ata tgc aac aaa tca tat aga att cta gat gga aga aat tgc aca    240
Lys Ile Cys Asn Lys Ser Tyr Arg Ile Leu Asp Gly Arg Asn Cys Thr
65              70              75              80 tta ata gat gca atg cta gga gac ccc cac tgt gac gcc ttt cag tat    288
Leu Ile Asp Ala Met Leu Gly Asp Pro His Cys Asp Ala Phe Gln Tyr
                85              90              95 gag agt tgg gac ctc ttt ata gaa aga agc agc gct ttc agc aat tgc    336
Glu Ser Trp Asp Leu Phe Ile Glu Arg Ser Ser Ala Phe Ser Asn Cys
                100             105             110 tac cca tat gac atc cct gac tat gca ccg ctc cga tcc att gta gca    384
Tyr Pro Tyr Asp Ile Pro Asp Tyr Ala Pro Leu Arg Ser Ile Val Ala
                115             120             125 tcc tca ggg aca gtg gaa ttc aca gca gag gga ttc aca tgg aca ggt    432
Ser Ser Gly Thr Val Glu Phe Thr Ala Glu Gly Phe Thr Trp Thr Gly
130             135             140 gta act caa aac gga aga agt gga gcc tgc aaa agg gga tca gcc gat    480
Val Thr Gln Asn Gly Arg Ser Gly Ala Cys Lys Arg Gly Ser Ala Asp
145             150             155             160 agt ttc ttt agc cga ctg aat tgg cta aca aaa tct gga agc tct tac    528
Ser Phe Phe Ser Arg Leu Asn Trp Leu Thr Lys Ser Gly Ser Ser Tyr
                165             170             175 ccc aca ttg aat gtg aca atg cct aac aat aaa aat ttc gac aag cta    576
Pro Thr Leu Asn Val Thr Met Pro Asn Asn Lys Asn Phe Asp Lys Leu
                180             185             190 tac atc tgg ggg att cat cac ccg agc tca aat caa gag cag aca aaa    624
Tyr Ile Trp Gly Ile His His Pro Ser Ser Asn Gln Glu Gln Thr Lys
                195             200             205 ttg tac atc caa gaa tca gga cga gta aca gtc tca aca aaa aga agt    672
Leu Tyr Ile Gln Glu Ser Gly Arg Val Thr Val Ser Thr Lys Arg Ser
210             215             220 caa caa aca ata atc cct aac atc gga tct aga ccg ttg gtc aga ggt    720
Gln Gln Thr Ile Ile Pro Asn Ile Gly Ser Arg Pro Leu Val Arg Gly
225             230             235             240 caa tca ggc agg ata agc ata tac tgg acc att gta aaa cct gga gat    768
Gln Ser Gly Arg Ile Ser Ile Tyr Trp Thr Ile Val Lys Pro Gly Asp
                245             250             255 atc cta atg ata aac agt aat ggc aac tta gtt gca ccg cgg gga tat    816
Ile Leu Met Ile Asn Ser Asn Gly Asn Leu Val Ala Pro Arg Gly Tyr
                260             265             270 ttt aaa ttg aac aca ggg aaa agc tct gta atg aga tca gat gta ccc    864
Phe Lys Leu Asn Thr Gly Lys Ser Ser Val Met Arg Ser Asp Val Pro
                275             280             285 ata gac att tgt gtg tct gaa tgt att aca cca aat gga agc atc tcc    912
Ile Asp Ile Cys Val Ser Glu Cys Ile Thr Pro Asn Gly Ser Ile Ser
                290             295             300 aac gac aag cca ttc caa aat gtg aac aaa gtt aca tat gga aaa tgc    960
Asn Asp Lys Pro Phe Gln Asn Val Asn Lys Val Thr Tyr Gly Lys Cys
305             310             315             320 ccc aag tat atc agg caa aac act tta aag ctg gcc act ggg atg agg   1008
Pro Lys Tyr Ile Arg Gln Asn Thr Leu Lys Leu Ala Thr Gly Met Arg
```

```
                    325                 330                 335
aat gta cca gaa aag caa acc aga gga atc ttt gga gca ata gcg gga       1056
Asn Val Pro Glu Lys Gln Thr Arg Gly Ile Phe Gly Ala Ile Ala Gly
            340                 345                 350 ttc atc gaa aac ggc tgg gaa gga atg gtt gat ggg tgg tat ggg ttc       1104
Phe Ile Glu Asn Gly Trp Glu Gly Met Val Asp Gly Trp Tyr Gly Phe
                355                 360                 365 cga tat caa aac tct gaa gga aca ggg caa gct gca gat cta aag agc       1152
Arg Tyr Gln Asn Ser Glu Gly Thr Gly Gln Ala Ala Asp Leu Lys Ser
            370                 375                 380 act caa gca gcc atc gac cag att aat gga aag tta aac aga gtg att       1200
Thr Gln Ala Ala Ile Asp Gln Ile Asn Gly Lys Leu Asn Arg Val Ile
385                 390                 395                 400 gaa aga acc aat gag aaa ttc cat caa ata gag aag gaa ttc tca gaa       1248
Glu Arg Thr Asn Glu Lys Phe His Gln Ile Glu Lys Glu Phe Ser Glu
                405                 410                 415 gta gaa gga aga att cag gac ttg gag aaa tat gta gaa gac acc aaa       1296
Val Glu Gly Arg Ile Gln Asp Leu Glu Lys Tyr Val Glu Asp Thr Lys
            420                 425                 430 ata gac cta tgg tcc tac aat gca gaa ttg ctg gtg gct cta gaa aat       1344
Ile Asp Leu Trp Ser Tyr Asn Ala Glu Leu Leu Val Ala Leu Glu Asn
                435                 440                 445 caa cat aca att gac tta aca gat gca gaa atg aat aaa tta ttt gag       1392
Gln His Thr Ile Asp Leu Thr Asp Ala Glu Met Asn Lys Leu Phe Glu
        450                 455                 460 aag act aga cgc cag tta aga gaa aac gca gaa gac atg gga ggt gga       1440
Lys Thr Arg Arg Gln Leu Arg Glu Asn Ala Glu Asp Met Gly Gly Gly
465                 470                 475                 480 tgt ttc aag att tac cac aaa tgt gat aat gca tgc att gaa tca ata       1488
Cys Phe Lys Ile Tyr His Lys Cys Asp Asn Ala Cys Ile Glu Ser Ile
                485                 490                 495 aga act ggg aca tat gac cat tac ata tac aaa gat gaa gca tta aac       1536
Arg Thr Gly Thr Tyr Asp His Tyr Ile Tyr Lys Asp Glu Ala Leu Asn
            500                 505                 510 aat cga ttt cag atc aaa ggt gta gag ttg aaa tca ggc tac aaa gat       1584
Asn Arg Phe Gln Ile Lys Gly Val Glu Leu Lys Ser Gly Tyr Lys Asp
                515                 520                 525 tgg ata ctg tgg att tca ttc gcc ata tca tgc ttc tta att tgc gtt       1632
Trp Ile Leu Trp Ile Ser Phe Ala Ile Ser Cys Phe Leu Ile Cys Val
        530                 535                 540 gtt cta ttg ggt ttc att atg tgg gct tgc caa aaa ggc aac atc aga       1680
Val Leu Leu Gly Phe Ile Met Trp Ala Cys Gln Lys Gly Asn Ile Arg
545                 550                 555                 560 tgc aac att tgc att tga                                               1698
Cys Asn Ile Cys Ile
                565

<210> SEQ ID NO 78
<211> LENGTH: 565
<212> TYPE: PRT
<213> ORGANISM: Influenza virus

<400> SEQUENCE: 78

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
```

```
                50                  55                  60
Lys Ile Cys Asn Lys Ser Tyr Arg Ile Leu Asp Gly Arg Asn Cys Thr
 65                  70                  75                  80

Leu Ile Asp Ala Met Leu Gly Asp Pro His Cys Asp Ala Phe Gln Tyr
                 85                  90                  95

Glu Ser Trp Asp Leu Phe Ile Glu Arg Ser Ser Ala Phe Ser Asn Cys
                100                 105                 110

Tyr Pro Tyr Asp Ile Pro Asp Tyr Ala Pro Leu Arg Ser Ile Val Ala
                115                 120                 125

Ser Ser Gly Thr Val Glu Phe Thr Ala Glu Gly Phe Thr Trp Thr Gly
130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
                180                 185                 190

Tyr Ile Trp Gly Ile His His Pro Ser Ser Asn Gln Glu Gln Thr Lys
                195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Leu Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
                260                 265                 270

Phe Lys Leu Asn Thr Gly Lys Ser Ser Val Met Arg Ser Asp Val Pro
                275                 280                 285

Ile Asp Ile Cys Val Ser Glu Cys Ile Thr Pro Asn Gly Ser Ile Ser
                290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
                340                 345                 350

Phe Ile Glu Asn Gly Trp Glu Gly Met Val Asp Gly Trp Tyr Gly Phe
                355                 360                 365

Arg Tyr Gln Asn Ser Glu Gly Thr Gly Gln Ala Ala Asp Leu Lys Ser
                370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
                420                 425                 430

Ile Asp Leu Trp Ser Tyr Asn Ala Glu Leu Leu Val Ala Leu Glu Asn
                435                 440                 445

Gln His Thr Ile Asp Leu Thr Asp Ala Glu Met Asn Lys Leu Phe Glu
                450                 455                 460

Lys Thr Arg Arg Gln Leu Arg Glu Asn Ala Glu Asp Met Gly Gly Gly
465                 470                 475                 480
```

-continued

```
Cys Phe Lys Ile Tyr His Lys Cys Asp Asn Ala Cys Ile Glu Ser Ile
            485                 490                 495

Arg Thr Gly Thr Tyr Asp His Tyr Ile Tyr Lys Asp Glu Ala Leu Asn
        500                 505                 510

Asn Arg Phe Gln Ile Lys Gly Val Glu Leu Lys Ser Gly Tyr Lys Asp
    515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 79
<211> LENGTH: 20
<212> TYPE: DNA
<213> ORGANISM: Influenza virus

<400> SEQUENCE: 79
tatgcatcgc tccgatccat                                         20

<210> SEQ ID NO 80
<211> LENGTH: 21
<212> TYPE: DNA
<213> ORGANISM: Influenza virus

<400> SEQUENCE: 80
gctccacttc ttccgttttg a                                       21

<210> SEQ ID NO 81
<211> LENGTH: 30
<212> TYPE: DNA
<213> ORGANISM: Influenza virus

<400> SEQUENCE: 81
aattcacagc agagggattc acatggacag                              30

<210> SEQ ID NO 82
<211> LENGTH: 24
<212> TYPE: DNA
<213> ORGANISM: Influenza Virus
<220> FEATURE:
<221> NAME/KEY: variation
<222> LOCATION: (7)..(7)
<223> OTHER INFORMATION: r = a or g

<400> SEQUENCE: 82
catggartgg ctaaagacaa gacc                                    24

<210> SEQ ID NO 83
<211> LENGTH: 24
<212> TYPE: DNA
<213> ORGANISM: Influenza virus
<220> FEATURE:
<221> NAME/KEY: variation
<222> LOCATION: (18)..(18)
<223> OTHER INFORMATION: k = g or t

<400> SEQUENCE: 83
agggcatttt ggacaaakcg tcta                                    24

<210> SEQ ID NO 84
<211> LENGTH: 18
<212> TYPE: DNA
```

```
<213> ORGANISM: Influenza virus

<400> SEQUENCE: 84
acgctcaccg tgcccagt                                                 18

<210> SEQ ID NO 85
<211> LENGTH: 28
<212> TYPE: DNA
<213> ORGANISM: Influenza virus

<400> SEQUENCE: 85
tattcgtctc agggagcaaa agcagggg                                      28

<210> SEQ ID NO 86
<211> LENGTH: 42
<212> TYPE: DNA
<213> ORGANISM: Influenza virus

<400> SEQUENCE: 86
tgtaatacga ctcactatag ggctccactt cttccgtttt ga                      42

<210> SEQ ID NO 87
<211> LENGTH: 30
<212> TYPE: DNA
<213> ORGANISM: Influenza virus

<400> SEQUENCE: 87
gatcgctctt cagggagcaa aagcaggtag                                    30

<210> SEQ ID NO 88
<211> LENGTH: 40
<212> TYPE: DNA
<213> ORGANISM: Influenza virus

<400> SEQUENCE: 88
tgtaatacga ctcactatag ggcattttgg acaaagcgtc                         40
```

MATERIALS AND METHODS FOR RESPIRATORY DISEASE CONTROL IN CANINES

CROSS-REFERENCE TO RELATED APPLICATION

This application is a continuation-in-part of application U.S. Ser. No. 11/409,416, filed Apr. 21, 2006, now abandoned which claims priority from U.S. Ser. No. 60/673,443, filed Apr. 21, 2005; and this application claims priority to U.S. Ser. Nos. 60/728,449, filed Oct. 19, 2005; 60/754,881, filed Dec. 29, 2005; 60/759,162, filed Jan. 14, 2006; 60/761,451, filed Jan. 23, 2006; and 60/779,080, filed Mar. 3, 2006, the disclosure of each of which is hereby incorporated by reference herein in its entirety, including any brief summary, detailed descriptions of the invention, examples, claims, abstract, figures, tables, nucleic acid sequences, amino acid sequences, and drawings.

The Sequence Listing for this application is on duplicate compact discs labeled "Copy 1" and "Copy 2." Copy 1 and Copy 2 each contain only one file named "Sequence-Listing-as-filed.txt" which was created on Oct. 19, 2006, and is 399 KB. The entire contents of each of the computer discs are incorporated herein by reference in their entireties.

BACKGROUND OF THE INVENTION

"Kennel cough" or infectious tracheobronchitis (ITB) is an acute, contagious respiratory infection in dogs characterized mainly by coughing (Ford et al, 1998). Canine ITB is considered one of the most prevalent infectious respiratory diseases of dogs worldwide, and outbreaks can reach epidemic proportions when dogs are housed in high-density population environments such as kennels. Most outbreaks are due to direct dog-to-dog contact or aerosolization of respiratory secretions (Ford et al, 1998). The clinical signs are caused by infection with one or a combination of bacterial and viral agents that colonize the epithelium of the upper and lower respiratory tract. Canine parainfluenza virus (CPiV) and *Bordetella bronchiseptica* bacteria are the most common organisms isolated from affected dogs, but several other viruses such as canine distemper virus (CDV) and canine adenoviruses-1 and -2 (CAV-1, CAV-2), along with bacteria such as *Streptococcus* sp., *Pasteurella multicoda* and *Escherichia coli*, can influence the clinical course and outcome (Ford et al, 1998). While outbreaks occur most efficiently and rapidly in high-density populations with high morbidity, complicated respiratory infections and death are uncommon. Although life-threatening secondary bacterial pneumonia can develop, the majority of ITB cases are self-limiting and resolve without any treatment (Ford et al, 1998).

In July 1992, a respiratory infection presumed to be "kennel cough" became epidemic at several greyhound tracks in New England, Florida, West Virginia, Wisconsin, Kansas, Colorado, Oklahoma and Arizona. According to veterinarians, most of the affected dogs had a mild cough that resolved, but more than a dozen greyhounds developed an acute hemorrhagic pneumonia followed by rapid death (Greyhound Daily News, 1999).

In late 1998 to early 1999, several outbreaks of "kennel cough" occurred in racing greyhound kennels across the country, resulting in mandatory closure of tracks and quarantine of all racing greyhounds in the U.S. for several weeks (Greyhound Daily News, 1999). At one track in Florida (Palm Beach Kennel Club), coughing was recorded in nearly 40% of the dog population on a single day (Personal communication from Dr. William Duggar). Similar to the outbreak in 1992, the coughing resolved in most greyhounds, but 10 dogs in Florida died from a hemorrhagic pneumonia syndrome uncharacteristic of "kennel cough" (Putnam, 1999).

In March-April 2003, another outbreak of "kennel cough" occurred at greyhound tracks in the eastern U.S. The outbreak is believed to have originated in kennels at four tracks in Florida and caused the suspension of racing and quarantine of dogs for almost three weeks. Nearly 25% of the dogs at the track in West Palm Beach were affected, while almost 50% of the 1400 dogs at Derby Lane in St. Petersburg developed coughing. Again, most dogs recovered, but several dogs have died from the respiratory infection. The estimated economic impact of the respiratory outbreak at the Derby Lane track alone was $2 million.

There are no published reports documenting the etiology or clinicopathology of the "kennel cough" epidemics in racing greyhound kennels in 1992, 1998-1999, or 2003. The assumption has been that the infections were due to CPiV and/or *B. bronchiseptica*, the two most common causes of kennel cough. Unsubstantiated communications such as web sites have attributed the fatal hemorrhagic pneumonias reported in some of the coughing dogs to infection with β-hemolytic *Streptococcus equi* subspecies *zooepidemicus*, and refer to the syndrome as "canine streptococcal toxic shock."

Transmission of virus from one host species to another is a crucial feature of the ecology and epidemiology of influenza virus (Webster, 1998). Two basic mechanisms of interspecies transmission of influenza virus are possible (Webster et al., 1992; Lipatov et al., 2004). One is the direct transfer of an essentially unaltered virus from one species to another. Examples of this mechanism include the recent human infections with the H5N1 subtype of avian influenza virus (Subbarao et al., 1998; Peiris et al., 2004; Guan et al., 2004) and possibly the pandemic of 1918, known as Spanish flu (Reid et al., 2004). The second mechanism is a consequence of the segmented nature of the influenza genome. Co-infection of a host with viruses from different species can result in reassortment of the segmented viral genes and the generation of a recombinant with the ability to infect other species. For example, novel viruses generated by gene reassortment between avian and human influenza viruses resulted in human influenza pandemics in 1957 and 1968 (Webster et al., 1992; Lipatov et al., 2004; Kawaoka et al., 1989).

Most direct transmissions of unaltered influenza viruses from the natural host species to a different species are terminal events because sustained transmission between individuals of the new species fails to occur. Multiple virus-host interactions are necessary for replication and horizontal transmission and provide a formidable barrier to perpetuation of influenza viruses in the new host (Webby et al., 2004). Therefore, establishment of new host-specific lineages of influenza virus is uncommon and has only occurred in domestic poultry, pigs, horses, and humans (Webster et al., 1992; Lipatov et al., 2004).

Because of the serious nature of influenza virus infection, there remains a need for methods for diagnosing, preventing, and treating infection by influenza virus.

BRIEF SUMMARY OF THE INVENTION

The subject invention pertains to isolated influenza virus that is capable of infecting canids and causing respiratory disease in the canid. The subject invention also pertains to compositions and methods for inducing an immune response against an influenza virus of the present invention. The subject invention also pertains to compositions and methods for identifying a virus of the invention and diagnosing infection of an animal with a virus of the invention.

One aspect of the invention relates to vaccines and methods for protecting canines from canine influenza, kits comprising such vaccines, and methods for using such vaccines. This protection includes preventing, reducing the risk of, delaying the onset of, reducing the spread of, ameliorating, suppressing, and/or eradicating the influenza and/or one or more (typically two or more) of its symptoms. It is believed that the vaccines, kits, and methods of this invention are generally suitable for use with canines. Canines include wild, zoo, and domestic canines, such as wolves, coyotes, and foxes. Canines also include dogs, particularly domestic dogs, such as, for example, pure-bred and/or mongrel companion dogs, show dogs, working dogs, herding dogs, hunting dogs, guard dogs, police dogs, racing dogs, and/or laboratory dogs.

This invention is also directed, in part, to a method for protecting a canine from an influenza virus infection (i.e., preventing, reducing the risk of, delaying the onset of, suppressing, ameliorating, or eradicating an influenza virus infection). The method comprises administering a therapeutically effective amount of a vaccine that comprises at least one equine influenza virus antigen, at least one H3 influenza virus antigen, and/or at least one H7 influenza virus antigen.

This invention also is directed, in part, to a method for protecting a canine from respiratory lesions (i.e., preventing, reducing the risk of, delaying the onset of, suppressing, ameliorating, or eradicating respiratory lesions) caused by canine influenza virus. The method comprises administering to the canine a therapeutically effective amount of a vaccine that comprises at least one equine influenza virus antigen, at least one H3 influenza virus antigen, and/or at least one H7 influenza virus antigen.

This invention also is directed, in part, to a method for protecting a canine from having canine influenza virus in nasal or oral secretion (i.e., preventing, reducing the risk of, delaying the onset of, suppressing, ameliorating, or eradicating canine influenza virus in nasal or oral secretion) caused by canine influenza virus infection. The method comprises administering to the canine a therapeutically effective amount of a vaccine that comprises at least one equine influenza virus antigen, at least one H3 influenza virus antigen, and/or at least one H7 influenza virus antigen.

This invention also is directed, in part, to a canine influenza vaccine. In some embodiments, for example, the vaccine comprises a therapeutically effective amount of at least one equine influenza virus antigen, at least one H3 influenza virus antigen, and/or at least one H7 influenza virus antigen.

This invention also is directed, in part, to a kit for protecting a canine from influenza virus infection. The kit comprises a therapeutically effective amount of a vaccine that comprises at least one equine influenza virus antigen, at least one H3 influenza virus antigen, and/or at least one H7 influenza virus antigen. In addition, the kit comprises at least one of the following:
- an apparatus for administering the vaccine to the canine,
- a pharmaceutically acceptable excipient that aids in administering the vaccine to the canine,
- a pharmaceutically acceptable excipient that enhances the canine's immune response to the vaccine,
- a food to be consumed by the canine simultaneously with the vaccine, and/or
- a treat to be consumed by the canine simultaneously with the vaccine.

Further benefits of Applicants' invention will be apparent to one skilled in the art from reading this specification.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

FIG. 1A shows a tree of HA genes from representative canine, human, avian, swine, and equine isolates, including A/Budgerigar/Hokkaido/1/77 (H4) as outgroup. FIG. 1B shows a tree of the canine influenza virus HA genes with contemporary and older equine HA genes, using A/Duck/Ukraine/63 (H3) as outgroup. Phylogenetic trees were inferred from nucleotide sequences by the neighbor joining method and bootstrap analysis values ≧90% are shown. The bar denotes the number of nucleotide changes per unit length of the horizontal tree branches.

FIG. 2A shows bronchial epithelium from a greyhound with spontaneous disease. Viral H3 antigen was detected in bronchial epithelial cell cytoplasm and in macrophages in airway lumens and in alveolar spaces. FIG. 2B shows bronchial epithelium from a dog 5 days after inoculation with A/canine/Florida/43/2004 (H3N8). Viral H3 antigen was detected in bronchial epithelial cell cytoplasm. Scale bar, 66 µm.

FIG. 4A shows a phylogenetic tree of the canine influenza virus HA genes with contemporary and older equine HA genes. FIG. 4B shows a phylogenetic tree of the canine influenza virus HA protein with contemporary and older equine HA. Phylogenetic trees were inferred from genetic or amino acid sequences by the neighbor joining method and bootstrap analysis values ≧80% are shown. The bar denotes the number of amino acid changes per unit length of the horizontal tree branches.

BRIEF DESCRIPTION OF THE SEQUENCES

Figure 1A:
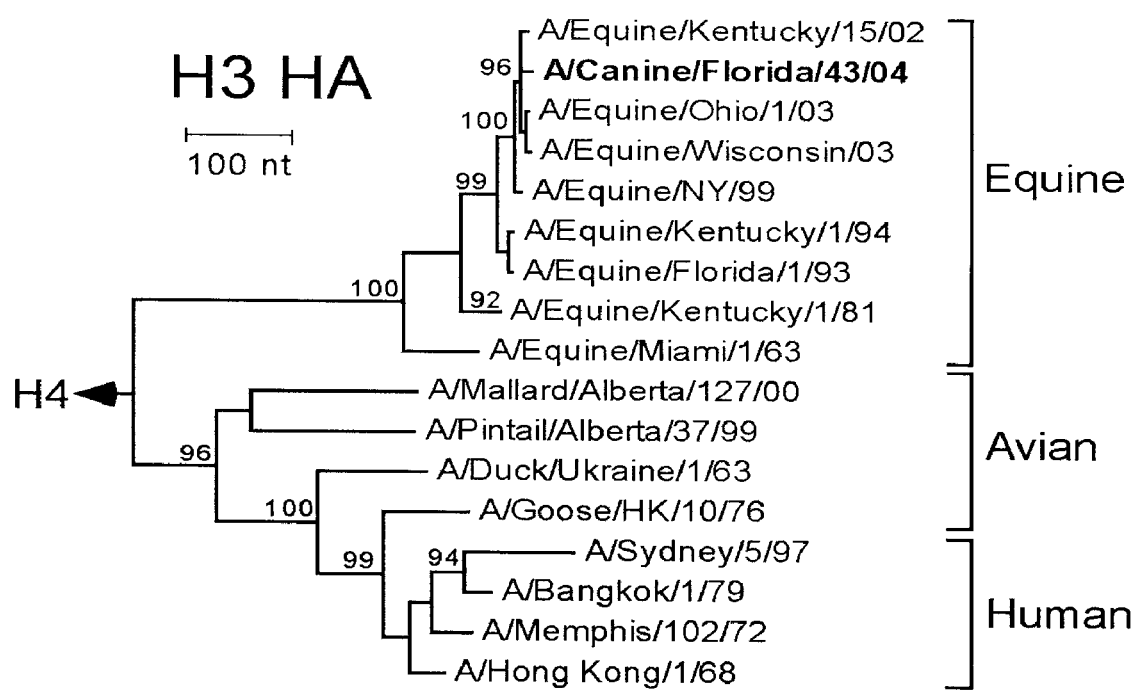
FIGS. 1A-1B show phylogenetic relationships among the hemagglutinin genes.

SEQ ID NO: 1 is a nucleotide sequence of a canine influenza virus (Florida/43/04) encoding a PB2 protein that can be used according to the present invention.

SEQ ID NO: 2 is the amino acid sequence encoded by SEQ ID NO: 1.

SEQ ID NO: 3 is a nucleotide sequence of a canine influenza virus (Florida/43/04) encoding a PB1 protein that can be used according to the present invention.

SEQ ID NO: 4 is the amino acid sequence encoded by SEQ ID NO: 3.

SEQ ID NO: 5 is a nucleotide sequence of a canine influenza virus (Florida/43/04) encoding a PA protein that can be used according to the present invention.

SEQ ID NO: 6 is the amino acid sequence encoded by SEQ ID NO: 5.

SEQ ID NO: 7 is a nucleotide sequence of a canine influenza virus (Florida/43/04) encoding an NS protein that can be used according to the present invention.

SEQ ID NO: 8 is the amino acid sequence encoded by SEQ ID NO: 7.

SEQ ID NO: 9 is a nucleotide sequence of a canine influenza virus (Florida/43/04) encoding an NP protein that can be used according to the present invention.

SEQ ID NO: 10 is the amino acid sequence encoded by SEQ ID NO: 9.

SEQ ID NO: 11 is a nucleotide sequence of a canine influenza virus (Florida/43/04) encoding an NA protein that can be used according to the present invention.

SEQ ID NO: 12 is the amino acid sequence encoded by SEQ ID NO: 11.

SEQ ID NO: 13 is a nucleotide sequence of a canine influenza virus (Florida/43/04) encoding an MA protein that can be used according to the present invention.

SEQ ID NO: 14 is the amino acid sequence encoded by SEQ ID NO: 13.

SEQ ID NO: 15 is a nucleotide sequence of a canine influenza virus (Florida/43/04) encoding an HA protein that can be used according to the present invention.

SEQ ID NO: 16 is the amino acid sequence encoded by SEQ ID NO: 15.

SEQ ID NO: 17 is a nucleotide sequence of a canine influenza virus (FL/242/03) encoding a PB2 protein that can be used according to the present invention.

SEQ ID NO: 18 is the amino acid sequence encoded by SEQ ID NO: 17.

SEQ ID NO: 19 is a nucleotide sequence of a canine influenza virus (FL/242/03) encoding a PB 1 protein that can be used according to the present invention.

SEQ ID NO: 20 is the amino acid sequence encoded by SEQ ID NO: 19.

SEQ ID NO: 21 is a nucleotide sequence of a canine influenza virus (FL/242/03) encoding a PA protein that can be used according to the present invention.

SEQ ID NO: 22 is the amino acid sequence encoded by SEQ ID NO: 21.

SEQ ID NO: 23 is a nucleotide sequence of a canine influenza virus (FL/242/03) encoding an NS protein that can be used according to the present invention.

SEQ ID NO: 24 is the amino acid sequence encoded by SEQ ID NO: 23.

SEQ ID NO: 25 is a nucleotide sequence of a canine influenza virus (FL/242/03) encoding an NP protein that can be used according to the present invention.

SEQ ID NO: 26 is the amino acid sequence encoded by SEQ ID NO: 25.

SEQ ID NO: 27 is a nucleotide sequence of a canine influenza virus (FL/242/03) encoding an NA protein that can be used according to the present invention.

SEQ ID NO: 28 is the amino acid sequence encoded by SEQ ID NO: 27.

SEQ ID NO: 29 is a nucleotide sequence of a canine influenza virus (FL/242/03) encoding an MA protein that can be used according to the present invention.

SEQ ID NO: 30 is the amino acid sequence encoded by SEQ ID NO: 29.

SEQ ID NO: 31 is a nucleotide sequence of a canine influenza virus (FL/242/03) encoding an HA protein that can be used according to the present invention.

SEQ ID NO: 32 is the amino acid sequence encoded by SEQ ID NO: 31.

SEQ ID NO: 33 is the mature form of the HA protein shown in SEQ ID NO: 16 wherein the N-terminal 16 amino acid signal sequence has been removed.

SEQ ID NO: 34 is the mature form of the HA protein shown in SEQ ID NO: 32 wherein the N-terminal 16 amino acid signal sequence has been removed.

SEQ ID NO: 35 is an oligonucleotide that can be used according to the present invention.

SEQ ID NO: 36 is an oligonucleotide that can be used according to the present invention.

SEQ ID NO: 37 is an oligonucleotide that can be used according to the present invention.

SEQ ID NO: 38 is an oligonucleotide that can be used according to the present invention.

SEQ ID NO: 39 is an oligonucleotide that can be used according to the present invention.

SEQ ID NO: 41 is an oligonucleotide that can be used according to the present invention.

SEQ ID NO: 42 is an oligonucleotide that can be used according to the present invention.

SEQ ID NO: 43 is an oligonucleotide that can be used according to the present invention.

SEQ ID NO: 44 is an oligonucleotide that can be used according to the present invention.

SEQ ID NO: 45 is an oligonucleotide that can be used according to the present invention.

SEQ ID NO: 46 is an oligonucleotide that can be used according to the present invention.

SEQ ID NO: 47 is a nucleotide sequence of a canine influenza virus (Miami/2005) encoding a PB2 protein that can be used according to the present invention.

SEQ ID NO: 48 is the amino acid sequence encoded by SEQ ID NO: 47.

SEQ ID NO: 49 is a nucleotide sequence of a canine influenza virus (Miami/2005) encoding a PB1 protein that can be used according to the present invention.

SEQ ID NO: 50 is the amino acid sequence encoded by SEQ ID NO: 49.

SEQ ID NO: 51 is a nucleotide sequence of a canine influenza virus (Miami/2005) encoding a PA protein that can be used according to the present invention.

SEQ ID NO: 52 is the amino acid sequence encoded by SEQ ID NO: 51.

SEQ ID NO: 53 is a nucleotide sequence of a canine influenza virus (Miami/2005) encoding an NS protein that can be used according to the present invention.

SEQ ID NO: 54 is the amino acid sequence encoded by SEQ ID NO: 53.

SEQ ID NO: 55 is a nucleotide sequence of a canine influenza virus (Miami/2005) encoding an NP protein that can be used according to the present invention.

SEQ ID NO: 56 is the amino acid sequence encoded by SEQ ID NO: 55.

SEQ ID NO: 57 is a nucleotide sequence of a canine influenza virus (Miami/2005) encoding an NA protein that can be used according to the present invention.

SEQ ID NO: 58 is the amino acid sequence encoded by SEQ ID NO: 57.

SEQ ID NO: 59 is a nucleotide sequence of a canine influenza virus (Miami/2005) encoding an MA protein that can be used according to the present invention.

SEQ ID NO: 60 is the amino acid sequence encoded by SEQ ID NO: 59.

SEQ ID NO: 61 is a nucleotide sequence of a canine influenza virus (Miami/2005) encoding an HA protein that can be used according to the present invention.

SEQ ID NO: 62 is the amino acid sequence encoded by SEQ ID NO: 61.

SEQ ID NO: 63 is a nucleotide sequence of a canine influenza virus (Jacksonville/2005) encoding a PB2 protein that can be used according to the present invention.

SEQ ID NO: 64 is the amino acid sequence encoded by SEQ ID NO: 63.

SEQ ID NO: 65 is a nucleotide sequence of a canine influenza virus (Jacksonville/2005) encoding a PB1 protein that can be used according to the present invention.

SEQ ID NO: 66 is the amino acid sequence encoded by SEQ ID NO: 65.

SEQ ID NO: 67 is a nucleotide sequence of a canine influenza virus (Jacksonville/2005) encoding a PA protein that can be used according to the present invention.

SEQ ID NO: 68 is the amino acid sequence encoded by SEQ ID NO: 67.

SEQ ID NO: 69 is a nucleotide sequence of a canine influenza virus (Jacksonville/2005) encoding an NS protein that can be used according to the present invention.

SEQ ID NO: 70 is the amino acid sequence encoded by SEQ ID NO: 69.

SEQ ID NO: 71 is a nucleotide sequence of a canine influenza virus (Jacksonville/2005) encoding an NP protein that can be used according to the present invention.

SEQ ID NO: 72 is the amino acid sequence encoded by SEQ ID NO: 71.

SEQ ID NO: 73 is a nucleotide sequence of a canine influenza virus (Jacksonville/2005) encoding an NA protein that can be used according to the present invention.

SEQ ID NO: 74 is the amino acid sequence encoded by SEQ ID NO: 73.

SEQ ID NO: 75 is a nucleotide sequence of a canine influenza virus (Jacksonville/2005) encoding an MA protein that can be used according to the present invention.

SEQ ID NO: 76 is the amino acid sequence encoded by SEQ ID NO: 75.

SEQ ID NO: 77 is a nucleotide sequence of a canine influenza virus (Jacksonville/2005) encoding an HA protein that can be used according to the present invention.

SEQ ID NO: 78 is the amino acid sequence encoded by SEQ ID NO: 77.

SEQ ID NO: 79 is an oligonucleotide that can be used according to the present invention.

SEQ ID NO: 80 is an oligonucleotide that can be used according to the present invention.

SEQ ID NO: 81 is an oligonucleotide that can be used according to the present invention.

SEQ ID NO: 82 is an oligonucleotide that can be used according to the present invention.

SEQ ID NO: 83 is an oligonucleotide that can be used according to the present invention.

SEQ ID NO: 84 is an oligonucleotide that can be used according to the present invention.

SEQ ID NO: 85 is an oligonucleotide that can be used according to the present invention.

SEQ ID NO: 86 is an oligonucleotide that can be used according to the present invention.

SEQ ID NO: 87 is an oligonucleotide that can be used according to the present invention.

SEQ ID NO: 88 is an oligonucleotide that can be used according to the present invention.

DETAILED DISCLOSURE OF THE INVENTION

The subject invention concerns isolated influenza virus that is capable of infecting canids and causing respiratory disease. In one embodiment, an influenza virus of the invention comprises a polynucleotide which encodes a protein having an amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a specific embodiment, the polynucleotide comprises the nucleotide sequence shown in any of SEQ ID Nos: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, or a fragment or variant thereof. Influenza virus of the present invention can have an HA subtype of H1, H2, H3, H4, H5, H6, H7, H8, and H9, H10, H11, H12, H13, H14, H15, or H16 or an NA subtype of N1, N2, N3, N4, N5, N6, N7, N8, OR N9. In a specific embodiment, an influenza virus of the present invention is a subtype H3. Virus can be isolated from infected dogs and cultured in cells or eggs according to methods described herein. In an exemplified embodiment, the influenza virus is an influenza A virus.

The subject invention also concerns polynucleotides that comprise all or part of a gene or genes or a genomic segment of an influenza virus of the present invention. In one embodiment, a polynucleotide of the invention comprises an influenza hemagglutinin (HA) gene, neuraminidase (NA) gene, nucleoprotein (NP) gene, matrix protein (MA or M) gene, polymerase basic (PB) protein gene, polymerase acidic (PA) protein gene, non-structural (NS) protein gene, or a functional fragment or variant of any of these genes. In a specific embodiment, a polynucleotide of the invention comprises the hemagglutinin (HA) gene, or a functional fragment or variant thereof. In a further embodiment, the HA gene encodes a hemagglutinin protein having one or more of the following: a serine at position 83; a leucine at position 222; a threonine at position 328; and/or a threonine at position 483, versus the amino acid sequence of equine H3 consensus sequence. In one embodiment, the HA gene encodes a polypeptide having an amino acid sequence shown in SEQ ID NOs: 16, 32, 62, or 78, or a functional and/or immunogenic fragment or variant thereof. In a specific embodiment, the HA gene comprises a nucleotide sequence shown in SEQ ID NOs: 15, 31, 61, or 77.

In one embodiment, a polynucleotide of the invention encodes a polypeptide having the amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a specific embodiment, the polynucleotide encoding the amino acid sequence shown in SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, comprises the nucleotide sequence shown in SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, respectively, or a sequence encoding a functional and/or immunogenic fragment or variant of any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78. Thus, the subject invention concerns polynucleotide sequences comprising the nucleotide sequence shown in any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, or a fragment or variant, including a degenerate variant, of any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77. In a further specific embodiment, a polynucleotide of the invention can comprise: Nucleotides 1-2271 of SEQ ID NO: 3; Nucleotides 1-2148 of SEQ ID NO: 5; Nucleotides 1-657 of SEQ ID NO: 7; Nucleotides 1-1494 of SEQ ID NO: 9; Nucleotides 1-1410 of SEQ ID NO: 11; Nucleotides 1-756 of SEQ ID NO: 13; Nucleotides 1-1695 of SEQ ID NO: 15; Nucleotides 1-2271 of SEQ ID NO: 19; Nucleotides 1-2148 of SEQ ID NO: 21; Nucleotides 1-657 of SEQ ID NO: 23; Nucleotides 1-1494 of SEQ ID NO: 25; Nucleotides 1-756 of SEQ ID NO: 29; Nucleotides 1-1695 of SEQ ID NO: 31; Nucleotides 1-2277 of SEQ ID NO: 47; Nucleotides 1-2271 of SEQ ID NO: 49; Nucleotides 1-2148 of SEQ ID NO: 51; Nucleotides 1-690 of SEQ ID NO: 53; Nucleotides 1-1494 of SEQ ID NO: 55; Nucleotides 1-1410 of SEQ ID NO: 57; Nucleotides 1-756 of SEQ ID NO: 59; Nucleotides 1-1695 of SEQ ID NO: 61; Nucleotides 1-2277 of SEQ ID NO: 63; Nucleotides 1-2271 of SEQ ID NO: 65; Nucleotides 1-2148 of SEQ ID NO: 67; Nucleotides 1-690 of SEQ ID NO: 69; Nucleotides 1-1494 of SEQ ID NO: 71; Nucleotides 1-1410 of SEQ ID NO: 73; Nucleotides 1-756 of SEQ ID NO: 75; and Nucleotides 1-1695 of SEQ ID NO: 77. Nucleotide and amino acid sequences of viral polynucleotide and polypeptide sequences contemplated within the scope of the present invention have also been deposited with GenBank at accession Nos. DQ124147 through DQ124161 and DQ124190, the disclosure of which is incorporated herein by reference.

The subject invention also concerns polypeptides encoded by polynucleotides of an influenza virus of the present invention. The subject invention also concerns functional and/or immunogenic fragments and variants of the subject polypeptides. Polypeptides contemplated include HA protein, NA protein, NS protein, nucleoprotein, polymerase basic protein, polymerase acidic protein, and matrix protein of an influenza virus of the invention. In an exemplified embodiment, a polypeptide of the invention has an amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof.

The subject invention also concerns polynucleotide expression constructs comprising a polynucleotide sequence of the present invention. In one embodiment, an expression construct of the invention comprises a polynucleotide sequence encoding a polypeptide comprising an amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a specific embodiment, the polynucleotide encoding the amino acid sequence shown in SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78 comprises the nucleotide sequence shown in SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, respectively, or a sequence encoding a functional and/or immunogenic fragment or variant of any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78. Thus, the subject invention concerns expression constructs comprising a polynucleotide sequence comprising the nucleotide sequence shown in any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, or a fragment or variant, including a degenerate variant, of any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77. In a preferred embodiment, an expression construct of the present invention provides for overexpression of an operably linked polynucleotide of the invention.

Expression constructs of the invention generally include regulatory elements that are functional in the intended host cell in which the expression construct is to be expressed. Thus, a person of ordinary skill in the art can select regulatory elements for use in, for example, human host cells, mammalian host cells, insect host cells, yeast host cells, bacterial host cells, and plant host cells. In one embodiment, the regulatory elements are ones that are functional in canine cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct. Preferably, the promoter associated with an expression construct of the invention provides for overexpression of an operably linked polynucleotide of the invention.

Promoters for use with an expression construct of the invention in eukaryotic cells can be of viral or cellular origin. Viral promoters include, but are not limited to, cytomegalovirus (CMV) gene promoters, SV40 early or late promoters, or Rous sarcoma virus (RSV) gene promoters. Promoters of cellular origin include, but are not limited to, desmin gene promoter and actin gene promoter Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739 and An, 1997)) or a CaMV 19S promoter can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625, 136), maize CDPK gene promoter, and RUBISCO SSU promoter (U.S. Pat. No. 5,034,322) can also be used. Root-specific promoters, such as any of the promoter sequences described in U.S. Pat. No. 6,455,760 or U.S. Pat. No. 6,696, 623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention. Tissue-specific promoters, for example fruit-specific promoters, such as the E8 promoter of tomato (accession number: AF515784; Good et al. (1994)) can also be used. Seed-specific promoters such as the promoter from a β-phaseolin gene (for example, of kidney bean) or a glycinin gene (for example, of soybean), and others, can also be used.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent.

DNA sequences which direct polyadenylation of mRNA transcribed from the expression construct can also be included in the expression construct, and include, but are not limited to, an octopine synthase or nopaline synthase signal.

Expression constructs can also include one or more dominant selectable marker genes, including, for example, genes encoding antibiotic resistance and/or herbicide-resistance for selecting transformed cells. Antibiotic-resistance genes can provide for resistance to one or more of the following antibiotics: hygromycin, kanamycin, bleomycin, G418, streptomycin, paromomycin, neomycin, and spectinomycin. Kanamycin resistance can be provided by neomycin phosphotransferase (NPT II). Herbicide-resistance genes can provide for resistance to phosphinothricin acetyltransferase or glyphosate. Other markers used for cell transformation screening include, but are not limited to, genes encoding β-glucuronidase (GUS), β-galactosidase, luciferase, nopaline synthase, chloramphenicol acetyltransferase (CAT), green fluorescence protein (GFP), or enhanced GFP (Yang et al., 1996).

The subject invention also concerns polynucleotide vectors comprising a polynucleotide sequence of the invention that encodes a polypeptide of the invention. Unique restriction enzyme sites can be included at the 5' and 3' ends of an expression construct or polynucleotide of the invention to allow for insertion into a polynucleotide vector. As used herein, the term "vector" refers to any genetic element, including, for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, pGEM series, and pBLUESCRIPT vectors (Stratagene, La Jolla, Calif. and Promega, Madison, Wis.).

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting influenza virus nucleic acid sequences. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety, and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100, or 101 or more nucleotides in length are contemplated within the scope of the invention. In one embodiment, probes and primers are any of 9, 10, 11, 12, 13, 14, 15, 16, 17, 18, 19, 20, 21, 22, 23, 24, 25, 26, 27, 28, 29, or 30 nucleotides in length. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. Exemplified probes and primers of the invention include those having the nucleotide sequence shown in any of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46, or a functional fragment or variant of any of the SEQ ID NOs: 35-46.

As used herein, the terms "nucleic acid," "polynucleotide," and "oligonucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. Polynucleotide sequences include the DNA strand sequence that can be transcribed into RNA and the RNA strand that can be translated into protein. The complementary sequence of any nucleic acid, polynucleotide, or oligonucleotide of the present invention is also contemplated within the scope of the invention. Polynucleotide sequences also include both full-length sequences as well as shorter sequences derived from the full-length sequences. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode a polypeptide of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, polypeptides of the subject invention. These degenerate variant and alternative polynucleotide sequences are within the scope of the subject invention. As used herein, references to "essentially the same" sequence refers to sequences which encode amino acid substitutions, deletions, additions, or insertions which do not materially alter the functional and/or immunogenic activity of the polypeptide encoded by the polynucleotides of the present invention.

The subject invention also concerns variants of the polynucleotides of the present invention that encode polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Substitution of amino acids other than those specifically exemplified or naturally present in a polypeptide of the invention are also contemplated within the scope of the present invention. For example, non-natural amino acids can be substituted for the amino acids of a polypeptide, so long as the polypeptide having the substituted amino acids retains substantially the same functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a polypeptide of the present invention are also encompassed within the scope of the invention.

Amino acids can be generally categorized in the following classes: non-polar, uncharged polar, basic, and acidic. Conservative substitutions whereby a polypeptide of the present invention having an amino acid of one class is replaced with another amino acid of the same class fall within the scope of the subject invention so long as the polypeptide having the substitution still retains substantially the same functional activity as the polypeptide that does not have the substitution. Polynucleotides encoding a polypeptide having one or more amino acid substitutions in the sequence are contemplated within the scope of the present invention. Table 11 below provides a listing of examples of amino acids belonging to each class. Single letter amino acid abbreviations are defined in Table 12.

Fragments and variants of polypeptides of influenza virus of the present invention can be generated using standard methods known in the art and tested for the presence of function or immunogenicity using standard techniques known in the art. For example, for testing fragments and/or variants of a neuraminidase polypeptide of the invention, enzymatic activity can be assayed. Thus, an ordinarily skilled artisan can readily prepare and test fragments and variants of a polypeptide of the invention and determine whether the fragment or variant retains activity relative to full-length or a non-variant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

Tm=81.5 C+16.6 Log[Na+]+0.41(% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

The subject invention also concerns viral proteins and peptides encoded by the genes of an influenza virus of the present invention. In one embodiment, the viral protein is a mature HA protein. In a specific embodiment, the mature HA protein comprises one or more of the following: a serine at position 82; a leucine at position 221; a threonine at position 327; and/or a threonine at position 482. In an exemplified embodiment, the mature HA protein has an amino acid sequence shown in SEQ ID NO: 33 or SEQ ID NO: 34, or a functional and/or immunogenic fragment or variant of SEQ ID NO: 33 or SEQ ID NO: 34. In another embodiment, the viral protein is an NA protein, NS protein, PB protein, PA protein, or MA protein. Viral proteins and peptides of the invention can be used to generate antibodies that bind specifically to the protein or peptide. Viral proteins and peptides of the present invention can also be used as immunogens and in vaccine compositions.

The subject invention also concerns compositions and methods for inducing an immune response against an influenza virus that is capable of infecting a susceptible host animal and causing respiratory disease. The invention can be used to induce an immune response against an influenza virus of any subtype in a susceptible host animal. For example, the influenza virus can be an HA subtype of H1, H2, H3, H4, H5, H6, H7, H8, H9, H10, H11, H12, H13, H14, H15, or H16, and an NA subtype of N1, N2, N3, N4, N5, N6, N7, N8, or N9. In one embodiment, the HA subtype is H3 or H5. In a further embodiment, the NA subtype is N7 or N8. In a specific embodiment, an immune response is induced against an influenza virus of subtype H3N8. In one embodiment, the host animal is a canid. Canines include wild, zoo, and domestic canines, such as wolves, coyotes, and foxes. Canines also include dogs, particularly domestic dogs, such as, for example, pure-bred and/or mongrel companion dogs, show dogs, working dogs, herding dogs, hunting dogs, guard dogs, police dogs, racing dogs, and/or laboratory dogs. In a specific embodiment, the host animal is a domesticated dog, such as a greyhound. In one embodiment, an animal is administered an effective amount of an immunogenic composition of the present invention sufficient to induce an immune response against an influenza virus of the invention. The immune response can be a humoral and/or cellular immune response. In a specific embodiment, the immune response is a protective immune response that is capable of preventing or minimizing viral infection in the immunized host animal for some period of time subsequent to the immunization. Thus, the subject invention also concerns vaccine compositions and methods that can provide a vaccinated animal with a protective immune response to a virus of the present invention.

As described herein, the vaccine or immunogenic compositions of the subject invention may comprise cell-free whole virus, including attenuated or inactivated virus, or portions of the virus, including subvirion particles (including "split vaccine" wherein a virion is treated to remove some or all viral lipids), viral proteins (including individual proteins and macromolecular complexes of multiple proteins), polypeptides, and peptides, as well as virus-infected cell lines, or a combination of any of these. Vaccine or immunogenic compositions comprising virus-infected cell lines may comprise multiple cell lines, each infected with a different viral strain.

In one embodiment of the invention, a canine may be immunized with one or more inactivated (i.e., killed) and/or live attenuated influenza virus vaccines or vaccines comprising one or a multiplicity of influenza virus antigens from one or more virus isolates. In one embodiment, the influenza virus is a canine influenza virus. In another embodiment, the influenza virus is an equine influenza virus that encodes or expresses a polypeptide that has at least about 90%, or at least about 95%, or at least about 96%, or 97%, or 98%, or 99% or more amino acid sequence identity with a canine influenza virus polypeptide. In one embodiment, an influenza antigen used in a vaccine of the present invention has at least about 96% sequence identity with an HA antigen and/or NA antigen of a canine influenza virus.

An example of an inactivated vaccine is EQUICINE II™, which has been marketed by Intervet Inc. (Millsboro, Del., USA) as a liquid vaccine. EQUICINE II™ contains inactivated A/Pennsylvania/63 influenza virus ("A/Pa/63") and A/equine/Kentucky/93 influenza virus ("A/KY/93") with carbopol (i.e., HAVLOGEN® (Intervet Inc.)). More specifically, a dose of EQUICINE II™ contains: inactivated A/Pa/63 at $10^{6.0}$ $EID_{50}$, inactivated A/KY/93 at $10^{6.7}$ $EID_{50}$, 0.25% by volume carbopol, and sufficient PBS to create a total volume of 1 ml.

Another example of an inactivated vaccine is equine flu virus A/equine/Ohio/03 ("Ohio 03"). In some embodiments, such a vaccine contains CARBIGEN™, which is an emulsified polymer-based adjuvant commercially available from MVP Laboratories, Inc. (Ralston, Nebr.). In such vaccines, a dosage unit typically comprises at least about 250 HA units of the virus, from about 250 to about 12,500 HA units of the virus, or from about 1000 to about 6200 HA units of the virus. The recommended concentration of CARBIGEN™ is from about 5 to about 30% (by mass).

An example of a live attenuated vaccine is modified live equine/Kentucky/91 ("A/KY/91") influenza in the form of a freeze-dried vaccine that may be reconstituted with water. In some embodiments, this reconstitution is conducted using vaccine-grade water sufficient to bring the vaccine dosage to a total volume of 1 ml. Aspects of such vaccines are discussed in, for example, U.S. Pat. Nos. 6,436,408; 6,398,774; and 6,177,082, which are incorporated by reference in their entirety into this patent. When reconstituted, a dose of such a vaccine may, for example, contain A/KY/91 at 107.2 $TCID_{50}$ per ml, 0.015 grams N-Z AMINE AS™ per ml, 0.0025 grams gelatin per ml, and 0.04 grams D lactose per ml. N-Z AMINE AS™ is a refined source of amino acids and peptides produced by enzymatic hydrolysis of casein. N-Z AMINE AS™ is marketed by Kerry Bio-Science (Norwich, N.Y., USA).

In a preferred embodiment, the vaccine comprises an H3 influenza antigen having at least about 93% homology with Florida/43/2004 in HA coding sequences, such as, for example, the equine/New Market/79 strain. Preferred homology is at least about 96%, such as, for example, the equine/Alaska/1/91 and equine/Santiago/85 strains. In the examples that follow, the equine/Kentucky/91, equine-2/Kentucky/93, equine-1/Pennsylvania/63, and equine Ohio/03 influenza antigens were incorporated into vaccines. Preferred vaccines also include vaccines comprising equine/Wisconsin/03, equine/Kentucky/02, equine/Kentucky/93, and equine/New Market 2/93. In the examples that follow, H3N8 viruses were used. It is believed, however, that other H3 influenza viruses can be used in accordance with this invention.

Live attenuated vaccines can be prepared by conventional means. Such means generally include, for example, modifying pathogenic strains by in vitro passaging, cold adaptation, modifying the pathogenicity of the organism by genetic manipulation, preparation of chimeras, insertion of antigens into viral vectors, selecting non-virulent wild type strains, etc.

In some embodiments, the live attenuated virus strain is derived by serial passage of the wild-type virus through cell culture, laboratory animals, non-host animals, or eggs. The accumulation of genetic mutation during such passage(s) typically leads to progressive loss of virulence of the organism to the original host.

In some embodiments, the live attenuated virus strain is prepared by co-infection of permissible cells with an attenuated mutant virus and pathogenic virus. The desired resultant recombinant virus has the safety of the attenuated virus with genes coding for protective antigens from the pathogenic virus.

In some embodiments, the live attenuated virus strain is prepared by cold adaptation. A cold-adapted virus has an advantage of replicating only at the temperature found in upper respiratory tract. A method of generation of a cold-adapted equine influenza virus has been described in U.S. Pat. No. 6,177,082. A desired resulting cold-adapted virus confers one or more of the following phenotypes: cold adaptation, temperature sensitivity, dominant interference, and/or attenuation.

In some embodiments, the live attenuated virus strain is prepared by molecular means, such as point mutation, deletion, or insertion to convert a pathogenic virus to a non-pathogenic or less-pathogenic virus compared to the original virus, while preserving the protective properties of the original virus.

In some embodiments, the live attenuated virus is prepared by cloning the candidate of genes of protective antigens into a genome of a non-pathogenic or less-pathogenic virus or other organism.

Inactivated (i.e., "killed") virus vaccines may be prepared by inactivating the virus using conventional methods. Typically, such vaccines include excipients that may enhance an immune response, as well as other excipients that are conventionally used in vaccines. For example, in the examples that follow, EQUICINE II™ comprises HAVLOGEN®. Inactivation of the virus can be accomplished by treating the virus with inactivation chemicals (e.g., formalin, beta propiolactone ("BPL"), bromoethylamine ("BEA"), and binary ethylenimine ("BEI")) or by non-chemical methods (e.g., heat, freeze/thaw, or sonication) to disable the replication capacity of the virus.

In the examples that follow, equine/Ohio/03 was used as a challenge virus. It is known to have about 99% homology with Florida/43/04 isolates, and has been shown to induce symptoms of infection and seroconversion in dogs. Example 18 illustrates the efficacy of equine influenza vaccine in dogs, showing hemagglutination inhibition (or "HI" or "HAI") titers in dogs vaccinated with inactivated Ohio 03 antigen in a vaccine composition comprising CARBIGEN™ adjuvant. Table 29 shows titers pre-vaccination, post-vaccination, and post-second vaccination, as well as post-challenge. The results indicate HI titers at each stage post-vaccination for the vaccinated dogs, with little or no increase for controls. Table 30 illustrates the clinical signs, virus isolation, and histopathology results from the same study. Although challenged animals did not show clinical signs, virus shedding, or positive histopathology, the positive HI titers (Table 29) indicate significant antibody titers in immunized animals.

It should be noted that other H3 influenza virus antigen vaccines are encompassed by this invention as well. Those described in this specification and the following examples are provided to illustrate the invention and its preferred embodiments, and not to limit the scope of the invention claimed.

It should further be noted that influenza antigens other than H3 influenza virus antigens may be used in accordance with this invention. Such antigens include, for example, those from equine/PA/63, which is an equine A1 subtype (H7N7). It is contemplated that one or more of such antigens may be used with or without one or more H3 influenza antigens.

In general, the vaccine is administered in a therapeutically effective amount. A "therapeutically effective amount" is an amount sufficient to induce a protective response in the canine patient against the target virus. Typically, a dosage is "therapeutically effective" if it prevents, reduces the risk of, delays the onset of, reduces the spread of, ameliorates, suppresses, or eradicates the influenza or one or more (typically two or more) of its symptoms. Typical influenza symptoms include, for example, fever (for dogs, typically $\geq 103.0°$ F.; $\geq 39.4°$ C.), cough, sneezing, histopathological lesions, ocular discharge, nasal discharge, vomiting, diarrhea, depression, weight loss, gagging, hemoptysis, and/or audible rales. Other often more severe symptoms may include, for example, hemorrhage in the lungs, mediastanum, or pleural cavity; tracheitis; bronchitis; bronchiolitis; supportive bronchopneumonia; and/or infiltration of the epithelial lining and airway lumens of the lungs with neutrophils and/or macrophages.

The vaccine may be administered as part of a combination therapy, i.e., a therapy that includes, in addition to the vaccine itself, administering one or more additional active agents, adjuvants, therapies, etc. In that instance, it should be recognized the amount of vaccine that constitutes a "therapeutically effective" amount may be less than the amount of vaccine that would constitute a "therapeutically effective" amount if the vaccine were to be administered alone. Other therapies may include those known in the art, such as, for example, anti-viral medications, analgesics, fever-reducing medications, expectorants, anti-inflammation medications, antihistamines, antibiotics to treat bacterial infection that results from the influenza virus infection, rest, and/or administration of fluids. In some embodiments, the vaccine of this invention is administered in combination with a *bordetella* vaccine, adenovirus vaccine, and/or parainfluenza virus vaccine.

In some embodiments, for example, a typical dose for a live attenuated vaccine is at least about $10^3$ pfu/canine, and more typically from about $10^3$ to about $10^9$ pfu/canine. In this patent, "pfu" means "plaque forming units". In some embodiments, a typical dose for a live attenuated vaccine is at least about $10^3$ TCID$_{50}$/canine, and more typically from about $10^3$ to about $10^9$ TCID$_{50}$/canine. In some embodiments, a typical dose for a live attenuated vaccine is at least about $10^3$ EID$_{50}$/canine, and more typically from about $10^3$ to about $10^9$ EID$_{50}$/canine. In some embodiments, a typical dose for a killed vaccine is at least about 40 HA units, typically from about 40 to about 10,000 HA units, and more typically from about 500 to about 6200 HA units. In some embodiments, the dose is from about 6100 to about 6200 HA units.

In some preferred embodiments, the vaccine comprises a live attenuated vaccine at a concentration which is at least about $10^{0.5}$ pfu/canine greater than the immunogenicity level. In some preferred embodiments, the vaccine comprises a live attenuated vaccine at a concentration which is at least about $10^{0.5}$ TCID$_{50}$/canine greater than the immunogenicity level. In some preferred embodiments, the vaccine comprises a live attenuated vaccine at a concentration which is at least about $10^{0.5}$ EID$_{50}$/canine greater than the immunogenicity level.

The immunogenicity level may be determined experimentally by challenge dose titration study techniques generally known in the art. Such techniques typically include vaccinating a number of canines with the vaccine at different dosages, and then challenging the canines with the virulent virus to determine the minimum protective dose.

Factors affecting the preferred dosage regimen may include, for example, the type (e.g., species and breed), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art using conventional means. It should further be noted that live attenuated viruses are generally self-propagating; thus, the specific amount of such a virus administered is not necessarily critical.

It is contemplated that the vaccine may be administered to the canine patient a single time; or, alternatively, two or more times over days, weeks, months, or years. In some embodiments, the vaccine is administered at least two times. In some such embodiments, for example, the vaccine is administered twice, with the second dose (e.g., the booster) being administered at least about 2 weeks after the first. In some embodiments, the vaccine is administered twice, with the second dose being administered no greater than 8 weeks after the first. In some embodiments, the second dose is administered at from about 2 weeks to about 4 years after the first dose, from about 2 to about 8 weeks after the first dose, or from about 3 to about 4 weeks after the first dose. In some embodiments, the second dose is administered about 4 weeks after the first dose. In the above embodiments, the first and subsequent dosages may vary, such as, for example, in amount and/or form. Often, however, the dosages are the same as to amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount.

In some embodiments, the vaccine is administered before the canine recipient is infected with influenza. In such embodiments, the vaccine may, for example, be administered to prevent, reduce the risk of, or delay the onset of influenza or one or more (typically two or more) influenza symptoms.

In some embodiments, the vaccine is administered after the canine recipient is infected with influenza. In such embodiments, the vaccine may, for example, ameliorate, suppress, or eradicate the influenza or one or more (typically two or more) influenza symptoms.

The preferred composition of the vaccine depends on, for example, whether the vaccine is an inactivated vaccine, live attenuated vaccine, or both. It also depends on the method of administration of the vaccine. It is contemplated that the vaccine will comprise one or more conventional pharmaceutically acceptable carriers, adjuvants, other immune-response enhancers, and/or vehicles (collectively referred to as "excipients"). Such excipients are generally selected to be compatible with the active ingredient(s) in the vaccine. Use of excipients is generally known to those skilled in the art.

The term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient canine.

The vaccines may be administered by conventional means, including, for example, mucosal administration, (such as intranasal, oral, intratracheal, and ocular), and parenteral administration. Mucosal administration is often particularly advantageous for live attenuated vaccines. Parenteral administration is often particularly advantageous for inactivated vaccines.

Mucosal vaccines may be, for example, liquid dosage forms, such as pharmaceutically acceptable emulsions, solutions, suspensions, syrups, and elixirs. Excipients suitable for such vaccines include, for example, inert diluents commonly used in the art, such as, water, saline, dextrose, glycerol, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. Excipients also can comprise various wetting, emulsifying, suspending, flavoring (e.g., sweetening), and/or perfuming agents.

Oral mucosal vaccines also may, for example, be tableted or encapsulated for convenient administration. Such capsules or tablets can contain a controlled-release formulation. In the case of capsules, tablets, and pills, the dosage forms also can comprise buffering agents, such as sodium citrate, or magnesium or calcium carbonate or bicarbonate. Tablets and pills additionally can be prepared with enteric coatings.

It is contemplated that the vaccine may be administered via the canine patient's drinking water and/or food. It is further contemplated that the vaccine may be administered in the form of a treat or toy.

"Parenteral administration" includes subcutaneous injections, submucosal injections, intravenous injections, intramuscular injections, intrasternal injections, transcutaneous injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The vaccine may include one or more excipients that enhance a canine patient's immune response (which may include an antibody response, cellular response, or both), thereby increasing the effectiveness of the vaccine. Use of such excipients (or "adjuvants") may be particularly beneficial when using an inactivated vaccine. The adjuvant(s) may be a substance that has a direct (e.g., cytokine or Bacillé Calmette-Guerin ("BCG")) or indirect effect (liposomes) on cells of the canine patient's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A, ISCOM). As noted above, adjuvants also include, for example, CARBIGEN™ and carbopol. It should be recognized that this invention encompasses both vaccines that comprise an adjuvant(s), as well as vaccines that do not comprise any adjuvant.

It is contemplated that the vaccine may be freeze-dried (or otherwise reduced in liquid volume) for storage, and then reconstituted in a liquid before or at the time of administration. Such reconstitution may be achieved using, for example, vaccine-grade water.

The present invention further comprises kits that are suitable for use in performing the methods described above. The kit comprises a dosage form comprising a vaccine described above. The kit also comprises at least one additional component, and, typically, instructions for using the vaccine with the additional component(s). The additional component(s) may, for example, be one or more additional ingredients (such as, for example, one or more of the excipients discussed above, food, and/or a treat) that can be mixed with the vaccine before or during administration. The additional component(s) may alternatively (or additionally) comprise one or more apparatuses for administering the vaccine to the canine patient. Such an apparatus may be, for example, a syringe, inhaler, nebulizer, pipette, forceps, or any medically acceptable delivery vehicle. In some embodiments, the apparatus is suitable for subcutaneous administration of the vaccine. In some embodiments, the apparatus is suitable for intranasal administration of the vaccine.

Other excipients and modes of administration known in the pharmaceutical or biologics arts also may be used.

The vaccine or immunogenic compositions of the subject invention also encompass recombinant viral vector-based constructs that may comprise, for example, genes encoding HA protein, NA protein, nucleoprotein, polymerase basic protein, polymerase acidic protein, and/or matrix protein of an influenza virus of the present invention. Any suitable viral vector that can be used to prepare a recombinant vector/virus construct is contemplated for use with the subject invention. For example, viral vectors derived from adenovirus, avipox, herpesvirus, vaccinia, canarypox, entomopox, swinepox, West Nile virus and others known in the art can be used with the compositions and methods of the present invention. Recombinant polynucleotide vectors that encode and express components can be constructed using standard genetic engineering techniques known in the art. In addition, the various vaccine compositions described herein can be used separately and in combination with each other. For example, primary immunizations of an animal may use recombinant vector-based constructs, having single or multiple strain components, followed by secondary boosts with vaccine compositions comprising inactivated virus or inactivated virus-infected cell lines. Other immunization protocols with the vaccine compositions of the invention are apparent to persons skilled in the art and are contemplated within the scope of the present invention.

The subject invention also concerns reassortant virus comprising at least one gene or genomic segment of an influenza virus of the present invention and the remainder of viral genes or genomic segments from a different influenza virus of the invention or from an influenza virus other than a virus of the present invention. Reassortant virus can be produced by genetic reassortant of nucleic acid of a donor influenza virus of the present invention with nucleic acid of a recipient influenza virus and then selecting for reassortant virus that comprises the nucleic acid of the donor virus. Methods to produce and isolate reassortant virus are well known in the art (Fields et al., 1996). In one embodiment, a reassortant virus of the invention comprises genes or genomic segments of a human, avian, swine, or equine influenza virus. A reassortant virus of the present invention can include any combination of nucleic acid from donor and recipient influenza virus so long as the reassortant virus comprises at least one gene or genomic segment from a donor influenza virus of the present invention. In one embodiment, a recipient influenza virus can be an equine influenza virus.

Natural, recombinant or synthetic polypeptides of viral proteins, and peptide fragments thereof, can also be used as vaccine compositions according to the subject methods. In one embodiment, a vaccine composition comprises a polynucleotide or a polypeptide of a canine influenza virus. In one embodiment, a vaccine composition comprises a polynucleotide encoding a polypeptide having the amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a specific embodiment, the polynucleotide encoding the amino acid sequence shown in SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, comprises the nucleotide sequence shown in SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, respectively, or a sequence encoding a functional and/or immunogenic fragment or variant of any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78. In a further specific embodiment, a polynucleotide of the invention can comprise: Nucleotides 1-2271 of SEQ ID NO: 3; Nucleotides 1-2148 of SEQ ID NO: 5; Nucleotides 1-657 of SEQ ID NO: 7; Nucleotides 1-1494 of SEQ ID NO: 9; Nucleotides 1-1410 of SEQ ID NO: 11; Nucleotides 1-756 of SEQ ID NO: 13; Nucleotides 1-1695 of SEQ ID NO: 15; Nucleotides 1-2271 of SEQ ID NO: 19; Nucleotides 1-2148 of SEQ ID NO: 21; Nucleotides 1-657 of SEQ ID NO: 23; Nucleotides 1-1494 of SEQ ID NO: 25; Nucleotides 1-756 of SEQ ID NO: 29; Nucleotides 1-1695 of SEQ ID NO: 31; Nucleotides 1-2277 of SEQ ID NO: 47; Nucleotides 1-2271 of SEQ ID NO: 49; Nucleotides 1-2148 of SEQ ID NO: 51; Nucleotides 1-690 of SEQ ID NO: 53; Nucleotides 1-1494 of SEQ ID NO: 55; Nucleotides 1-1410 of SEQ ID NO: 57; Nucleotides 1-756 of SEQ ID NO: 59; Nucleotides 1-1695 of SEQ ID NO: 61; Nucleotides 1-2277 of SEQ ID NO: 63; Nucleotides 1-2271 of SEQ ID NO: 65; Nucleotides 1-2148 of SEQ ID NO: 67; Nucleotides 1-690 of SEQ ID NO: 69; Nucleotides 1-1494 of SEQ ID NO: 71; Nucleotides 1-1410 of SEQ ID NO: 73; Nucleotides 1-756 of SEQ ID NO: 75; and Nucleotides 1-1695 of SEQ ID NO: 77. In another embodiment, a vaccine composition comprises a polypeptide having the amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a further embodiment, a vaccine composition comprises a polynucleotide or a polypeptide of an equine influenza virus wherein the polynucleotide or polypeptide has at least about 90%, or at least about 95%, or at least about 96%, or 97%, or 98%, or 99% or more sequence identity with a canine influenza polynucleotide or polypeptide. In one embodiment, viral polypeptides derived from multiple strains can be combined in a vaccine composition and are used to vaccinate a host animal. For example, polypeptides based on the viral HA protein from at least two different strains of influenza virus of the invention can be combined in the vaccine. The polypeptides may be homologous to one strain or may comprise "hybrid" or "chimeric" polypeptides whose amino acid sequence is derived from joining or linking polypeptides from at least two distinct strains. Procedures for preparing viral polypeptides are well known in the art. For example, viral polypeptides and peptides can be synthesized using solid-phase synthesis methods (Merrifield, 1963). Viral polypeptides and peptides can also be produced using recombinant DNA techniques wherein a polynucleotide molecule encoding an viral protein or peptide is expressed in a host cell, such as bacteria, yeast, or mammalian cell lines, and the expressed protein purified using standard techniques of the art.

Vaccine compositions of the present invention also include naked nucleic acid compositions. In one embodiment, a nucleic acid may comprise a nucleotide sequence encoding an HA and/or an NA protein of an influenza virus of the present invention. Methods for nucleic acid vaccination are known in the art and are described, for example, in U.S. Pat. Nos. 6,063,385 and 6,472,375. The nucleic acid can be in the form of a plasmid or a gene expression cassette. In one embodiment, the nucleic acid is provided encapsulated in a liposome which is administered to an animal.

Vaccine compositions and immunogens, such as polypeptides and nucleic acids, that can be used in accordance with the present invention can be provided with a pharmaceutically-acceptable carrier or diluent. Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin, Easton Pa., Mack Publishing Company, 19$^{th}$ ed., 1995, describes formulations which can be used in connection with the subject invention. In general, the compositions of the subject invention will be formulated such that an effective amount of an immunogen is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of an immunogen of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the immunogen or immunogens based on the weight of the total composition including carrier or diluent.

The vaccine and immunogenic compositions of the subject invention can be prepared by procedures well known in the art. For example, the vaccine or immunogens are typically prepared as injectables, e.g., liquid solutions or suspensions. The vaccine or immunogens are administered in a manner that is compatible with dosage formulation, and in such amount as will be therapeutically effective and immunogenic in the recipient. The optimal dosages and administration patterns for a particular vaccine or immunogens formulation can be readily determined by a person skilled in the art.

Peptides and/or polypeptides of the present invention can also be provided in the form of a multiple antigenic peptide (MAP) construct. The preparation of MAP constructs has been described in Tam (1988). MAP constructs utilize a core matrix of lysine residues onto which multiple copies of an immunogen are synthesized (Posnett et al., 1988). Multiple MAP constructs, each containing the same or different immunogens, can be prepared and administered in a vaccine composition in accordance with methods of the present invention. In one embodiment, a MAP construct is provided with and/or administered with one or more adjuvants. Influenza polypeptides of the invention can also be produced and administered as macromolecular protein structures comprising one or more polypeptides. Published U.S. Patent Application US2005/0009008 describes methods for producing virus-like particles as a vaccine for influenza virus.

According to the methods of the subject invention, the vaccine and immunogenic compositions described herein are administered to susceptible hosts, typically canids, and more typically domesticated dogs, in an effective amount and manner to induce protective immunity against subsequent challenge or infection of the host by virus. In one embodiment, the host animal is a canid. Canines include wild, zoo, and domestic canines, such as wolves, coyotes, and foxes. Canines also include dogs, particularly domestic dogs, such as, for example, pure-bred and/or mongrel companion dogs, show dogs, working dogs, herding dogs, hunting dogs, guard dogs, police dogs, racing dogs, and/or laboratory dogs. In a specific embodiment, the host animal is a domesticated dog, such as a greyhound. The vaccines or immunogens are typically administered parenterally, by injection, for example, either subcutaneously, intraperitoneally, or intramuscularly. Other suitable modes of administration include oral or nasal administration. Usually, the vaccines or immunogens are administered to an animal at least two times, with an interval of one or more weeks between each administration. However, other regimens for the initial and booster administrations of the vaccine or immunogens are contemplated, and may depend on the judgment of the practitioner and the particular host animal being treated.

Virus and virus-infected cells in a vaccine formulation may be inactivated or attenuated using methods known in the art. For example, whole virus and infected cells can be inactivated or attenuated by exposure to paraformaldehyde, formalin, beta propiolactone (BPL), bromoethylamine (BEA), binary ethylenimine (BEI), phenol, UV light, elevated temperature, freeze thawing, sonication (including ultrasonication), and the like. The amount of cell-free whole virus in a vaccine dose can be in the range from about 0.1 mg to about 5 mg, and more usually being from about 0.2 mg to about 2 mg. The dosage for vaccine formulations comprising virus-infected cell lines will usually contain from about $10^6$ to about $10^8$ cells per dose, and more usually from about $5\times10^6$ to about $7.5\times10^7$ cells per dose. The amount of protein or peptide immunogen in a dose for an animal can vary from about 0.1 μg to 10000 μg, or about 1 μg to 5000 μg, or about 10 μg to 1000 μg, or about 25 μg to 750 μg, or about 50 μg to 500 μg, or 100 μg to 250 μg, depending upon the size, age, etc., of the animal receiving the dose.

An immunogenic or vaccine composition of the invention, such as virus or virus-infected cells or viral proteins or peptides, can be combined with an adjuvant, typically just prior to administration. Adjuvants contemplated for use in the vaccine formulations include threonyl muramyl dipeptide (MDP) (Byars et al., 1987), saponin, *Cornebacterium parvum*, Freund's complete and Freund's incomplete adjuvants, aluminum, or a mixture of any of these. A variety of other adjuvants suitable for use with the methods and vaccines of the subject invention, such as alum, are well known in the art and are contemplated for use with the subject invention.

The subject invention also concerns antibodies that bind specifically to a protein or a peptide of the present invention. Antibodies of the subject invention include monoclonal and polyclonal antibody compositions. Preferably, the antibodies of the subject invention are monoclonal antibodies. Whole antibodies and antigen binding fragments thereof are contemplated in the present invention. Thus, for example, suitable antigen binding fragments include $Fab_2$, Fab and Fv antibody fragments. Antibodies of the invention can be labeled with a detectable moiety, such as a fluorescent molecule (e.g., fluorescein or an enzyme).

The subject invention also concerns methods and compositions for detection and identification of an influenza virus of the invention and for diagnosis of infection of an animal with an influenza virus of the present invention. The methods of the invention include detection of the presence of canine influenza, in a biological sample from an animal. The detection of canine influenza in a sample, is useful to diagnose canine influenza in an animal. In turn, this information can provide the ability to determine the prognosis of an animal based on distinguishing levels of canine influenza present over time, and can assist in selection of therapeutic agents and treatments for the animal, and assist in monitoring therapy. The method also provides the ability to establish the absence of canine influenza in an animal tested.

The ability to detect canine influenza in an animal permits assessment of outbreaks of canine influenza in different geographical locations. This information also permits early detection so that infected animals can be isolated, to limit the spread of disease, and allows early intervention for treatment options. In addition, having this information available can provide direction to medical personnel for preparing to treat large numbers of ill animals, including assembling medical supplies, and, if available, vaccines.

In one embodiment, a method of the present invention involves the collection of a biological sample from a test animal, such as a canine. The biological sample may be any biological material, including, cells, tissue, hair, whole blood, serum, plasma, nipple aspirate, lung lavage, cerebrospinal fluid, saliva, sweat and tears.

The animal test sample may come from an animal suspected of having canine influenza virus, whether or not the animal exhibits symptoms of the disease. Control samples can also be provided or collected from animals known to be free of canine influenza. Additional controls may be provided, e.g., to reduce false positive and false negative results, and verify that the reagents in the assay are actively detecting canine influenza A virus.

In addition to detecting the presence or absence of canine influenza in a biological sample, the methods of detection used in the invention can detect mutations in canine influenza virus, such as changes in nucleic acid sequence, that may result from the environment, drug treatment, genetic manipulations or mutations, injury, change in diet, aging, or any other characteristic(s) of an animal. Mutations may also cause canine influenza A to become resistant to a drug that was formerly effective, or to enable the virus to infect and propagate in a different species of animal, or human. For example, avian influenza A virus has been shown to infect other animals and humans.

In one embodiment for detecting an influenza virus in an animal, diagnosis is facilitated by the collection of high-quality specimens, their rapid transport to a testing facility, and appropriate storage, before laboratory testing. Virus is best detected in specimens containing infected cells and secretions. In one embodiment, specimens for the direct detection of viral antigens and/or for nucleic acids and/or virus isolation in cell cultures are taken during the first 3 days after onset of clinical symptoms. A number of types of specimens are suitable to diagnose virus infections of the upper respiratory tract, including, but not limited to, nasal swab, nasopharyngeal swab, nasopharyngeal aspirate, nasal wash and throat swabs. In addition to swabs, samples of tissue or serum may be taken, and invasive procedures can also be performed.

In one embodiment, respiratory specimens are collected and transported in 1-5 ml of virus transport media. A number of media that are satisfactory for the recovery of a wide variety of viruses are commercially available. Clinical specimens are added to transport medium. Nasal or nasopharyngeal swabs can also be transported in the virus transport medium. One example of a transport medium is 10 gm of veal infusion broth and 2 gm of bovine albumin fraction V, added to sterile distilled water to 400 m. Antibiotics such as 0.8 ml gentamicin sulfate solution (50 mg/ml) and 3.2 ml amphotericin B (250 µg/ml) can also be added. The medium is preferably sterilized by filtration. Nasal washes, such as sterile saline (0.85% NaCl), can also be used to collect specimens of respiratory viruses.

In one embodiment, sera is collected in an amount of from 1-5 ml of whole blood from an acute-phase animal, soon after the onset of clinical symptoms, and preferably not later than 7 days. A convalescent-phase serum specimen can also be collected, for example at about 14 days after onset of symptoms. Serum specimens can be useful for detecting antibodies against respiratory viruses in a neutralization test.

In some instances, samples may be collected from individual animals over a period of time (e.g., once a day, once a week, once a month, biannually or annually). Obtaining numerous samples from an individual animal, over a period of time, can be used to verify results from earlier detections, and/or to identify response or resistance to a specific treatment, e.g., a selected therapeutic drug.

The methods of the present invention can be used to detect the presence of one or more pathological agents in a test sample from an animal, and the level of each pathological agent. Any method for detecting the pathological agent can be used, including, but not limited to, antibody assays including enzyme-linked immunosorbent assays (ELISAs), indirect fluorescent antibody (IFA) tests, hemagglutinating, and inhibition of hemagglutination (HI) assays, and Western Blot. Known cell-culture methods can also be used. Positive cultures can be further identified using immunofluorescence of cell cultures or HI assay of the cell culture medium (supernatant).

In addition, methods for detecting nucleic acid (DNA or RNA) or protein can be used. Such methods include, but are not limited to, polymerase chain reaction (PCR), and reverse transcriptase (RT) PCR tests and real time tests, and quantitative nuclease protection assays. There are commercially available test kits available to perform these assays. For example, QIAGEN (Valencia, Calif.) sells a one step RT-PCR kit, and viral RNA extraction kit.

In one embodiment, the method utilizes an antibody specific for a virus or viral protein of the invention. In a specific embodiment, an antibody specific for an HA protein of a virus of the invention is utilized. In another embodiment, an antibody specific for an NP protein of a virus of the invention is used. A suitable sample, such as from the nasal or nasopharyngeal region, is obtained from an animal and virus or viral protein is isolated therefrom. The viral components are then screened for binding of an antibody specific to a protein, such as HA or NP, of a virus of the invention. In another embodiment, a serum sample (or other antibody containing sample) is obtained from an animal and the serum screened for the presence of antibody that binds to a protein of a virus of the invention. For example, an ELISA assay can be performed where the plate walls have HA and/or NP protein, or a peptide fragment thereof, bound to the wall. The plate wall is then contacted with serum or antibody from a test animal. The presence of antibody in the animal that binds specifically to the HA and/or NP protein is indicative that the test animal is infected or has been infected with an influenza virus of the present invention.

In one embodiment, the presence of a pathological agent is detected by determining the presence or absence of antibodies against the agent, in a biological sample. It can take some time (e.g. months) after an animal is infected before antibodies can be detected in a blood test. Once formed, antibodies usually persist for many years, even after successful treatment of the disease. Finding antibodies to canine influenza A may not indicate whether the infection was recent, or sometime in the past.

Antibody testing can also be done on fluid(s). Antibody assays include enzyme-linked immunosorbent assays (ELISAs), indirect fluorescent antibody (IFA) assays, and Western Blot. Preferably, antibody testing is done using multiple assays, for example ELISA or IFA followed by Western blot. Antibody assays can be done in a two-step process, using either an ELISA or IFA assay, followed by a Western blot assay. ELISA is considered a more reliable and accurate assay than IFA, but IFA may be used if ELISA is not available. The Western blot test (which is a more specific test) can also be done in all animals, particularly those that have tested positive or borderline positive (equivocal) in an ELISA or IFA assay.

Other antibody-based tests that can be used for detection of influenza virus include hemagglutination inhibition assays. Hemagglutination activity can be detected in a biological sample from an animal, using chicken or turkey red blood cells as described (Burleson et al., 1992) and Kendal et al., 1982). In one embodiment, an influenza or an HA protein or peptide of the invention is contacted with a test sample containing serum or antibody. Red blood cells (RBC) from an animal, such as a bird, are then added. If antibody to HA is present, then the RBC will not agglutinate. If antibody to HA is not present, the RBC will agglutinate in the presence of HA. Variations and modifications to standard hemagglutination inhibition assays are known in the art and contemplated within the scope of the present invention.

Infection of an animal can also be determined by isolation of the virus from a sample, such as a nasal or nasopharyngeal swab. Viral isolation can be performed using standard methods, including cell culture and egg inoculation.

In a further embodiment, a nucleic acid-based assay can be used for detection of a virus of the present invention. In one embodiment, a nucleic acid sample is obtained from an animal and the nucleic acid subjected to PCR using primers that will generate an amplification product if the nucleic acid contains a sequence specific to an influenza virus of the present invention. In a specific embodiment, RT-PCR is used in an assay for the subject virus. In an exemplified embodiment, real-time RT-PCR is used to assay for an influenza virus of the invention. PCR, RT-PCR and real-time PCR methods are known in the art and have been described in U.S. Pat. Nos. 4,683,202; 4,683,195; 4,800,159; 4,965,188; 5,994,056; 6,814,934; and in Saiki et al. (1985); Sambrook et al. (1989); Lee et al. (1993); and Livak et al. (1995). In one embodiment, the PCR assay uses oligonucleotides specific for an influenza matrix (MA) gene and/or HA gene. The amplification product can also be sequenced to determine if the product has a sequence of an influenza virus of the present invention. Other nucleic acid-based assays can be used for detection and diagnosis of viral infection by a virus of the invention and such assays are contemplated within the scope of the present invention. In one embodiment, a sample containing a nucleic acid is subjected to a PCR-based amplification using forward and reverse primers where the primers are specific for a viral polynucleotide or gene sequence. If the nucleic acid in the sample is RNA, then RT-PCR can be performed. For real-time PCR, a detectable probe is utilized with the primers.

Primer sets specific for the hemagglutinin (HA) gene of many of the circulating influenza viruses are known, and are continually being developed. The influenza virus genome is single-stranded RNA, and a DNA copy (cDNA) must be made using a reverse transcriptase (RT) polymerase. The amplification of the RNA genome, for example using RT-PCR, requires a pair of oligonucleotide primers, typically designed on the basis of the known HA sequence of influenza A subtypes and of neuraminadase (NM)-1. The primers can be selected such that they will specifically amplify RNA of only one virus subtype. DNAs generated by using subtype-specific primers can be further analyzed by molecular genetic techniques such as sequencing. The test is preferably run with a positive control, or products are confirmed by sequencing and comparison with known sequences. The absence of the target PCR products (i.e, a "negative" result) may not rule out the presence of the virus. Results can then be made available within a few hours from either clinical swabs or infected cell cultures. PCR and RT-PCR tests for influenza A virus are described by Fouchier et al., 2000 and Maertzdorf et al., 2004.

The subject invention also concerns methods for screening for compounds or drugs that have antiviral activity against a virus of the present invention. In one embodiment, cells infected with a virus of the invention are contacted with a test compound or drug. The amount of virus or viral activity following contact is then determined. Those compounds or drugs that exhibit antiviral activity can be selected for further evaluation.

The subject invention also concerns isolated cells infected with an influenza virus of the present invention. In one embodiment, the cell is a canine cell, such as canine kidney epithelial cells.

The subject invention also concerns cells transformed with a polynucleotide of the present invention encoding a polypeptide of the invention. Preferably, the polynucleotide sequence is provided in an expression construct of the invention. More preferably, the expression construct provides for overexpression in the cell of an operably linked polynucleotide of the invention. In one embodiment, the cell is transformed with a polynucleotide sequence comprising a sequence encoding the amino acid sequence shown in any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional fragment or variant thereof. In a specific embodiment, the cell is transformed with a polynucleotide encoding the amino acid sequence shown in SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78 comprises the nucleotide sequence shown in SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, respectively, or a sequence encoding a functional fragment or variant of any of SEQ ID NOs: 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78. Thus, the subject invention concerns cells transformed with a polynucleotide sequence comprising the nucleotide sequence shown in any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, or a fragment or variant, including a degenerate variant, of any of SEQ ID NOs: 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77.

The transformed cell can be a eukaryotic cell, for example, a plant cell, including protoplasts, or the transformed cell can be a prokaryotic cell, for example, a bacterial cell such as *E. coli* or *B. subtilis*. Animal cells include human cells, mammalian cells, partially canine cells, avian cells, and insect cells. Plant cells include, but are not limited to, dicotyledonous, monocotyledonous, and conifer cells.

The subject invention also concerns plants, including transgenic plants that express and produce a viral protein or polypeptide of the present invention. Plants, plant tissues, and plant cells transformed with or bred to contain a polynucleotide of the invention are contemplated by the present invention. Preferably, the polynucleotide of the invention is overexpressed in the plant, plant tissue, or plant cell. Plants can be used to produce influenza vaccine compositions of the present invention and the vaccines can be administered through consumption of the plant (see, for example, U.S. Pat. Nos. 5,484,719 and 6,136,320).

The subject invention also concerns kits for detecting a virus or diagnosing an infection by a virus of the present invention. In one embodiment, a kit comprises an antibody of the invention that specifically binds to an influenza virus of the present invention, or an antigenic portion thereof. In another embodiment, a kit comprises one or more polypeptides or peptides of the present invention. In a specific embodiment, the polypeptides have an amino acid sequence shown in any of SEQ ID NOs. 2, 4, 6, 8, 10, 12, 14, 16, 18, 20, 22, 24, 26, 28, 30, 32, 33, 34, 48, 50, 52, 54, 56, 58, 60, 62, 64, 66, 68, 70, 72, 74, 76, or 78, or a functional and/or immunogenic fragment or variant thereof. In a further embodiment, a kit comprises one or more polynucleotides or oligonucleotides of the present invention. In a specific embodiment, the polynucleotides have a nucleotide sequence shown in any of SEQ ID NOs. 1, 3, 5, 7, 9, 11, 13, 15, 17, 19, 21, 23, 25, 27, 29, 31, 47, 49, 51, 53, 55, 57, 59, 61, 63, 65, 67, 69, 71, 73, 75, or 77, or a fragment or variant thereof. A kit may optionally comprise one or more control antibody, control polypeptide or peptide, and/or control polynucleotide or oligonucleotide. The antibody, polypeptides, peptides, polynucleotides, and/or oligonucleotides of the kit can be provided in a suitable container or package.

The subject application also concerns the use of mongrel dogs as a model for infection and pathogenesis of influenza virus. In one embodiment, a mongrel dog is inoculated with an influenza virus, such as a canine influenza virus of the present invention. Optionally, the dog can be administered therapeutic agents subsequent to inoculation. The dog can also have been administered a composition for generating an immune response against an influenza virus prior to inoculation with virus. Tissue, blood, serum, and other biological samples can be obtained before and/or after inoculation and examined for the presence of virus and pathogenesis of tissue using methods known in the art including, but not limited to, PCR, RT-PCR, nucleic acid sequencing, and immunohistochemistry.

Canine influenza virus strains (designated as "A/canine/Florida/43/2004" (ATCC Accession No. PTA-7914)and "A/canine/Florida/242/2003") (ATCC Accession No. PTA-7915)were deposited with American Type Culture Collection (ATCC), P.O. Box 1549, Manassas, Va. 20108, on Oct. 9, 2006. Canine influenza virus strains (designated as "canine/Jax/05" (ATCC Accession No. PTA-7941)and "canine/Miami/05"(ATCC Accession No. PTA-7940), were deposited with American Type Culture Collection (ATCC), P.O. Box 1549, Manassas, Va. 20108, on Oct. 17, 2006. The subject virus strains have been deposited under conditions that assure that access to the cultures will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject virus deposits will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Table 57 illustrates the similarities among the amino acid sequences encoded by the hemagglutinin (or "HA"), neuraminidase (or "NA"), and nucleoprotein (NP) genes of the canine influenza virus identified as A/canine/Florida/43/2004 (Ca/Fla/43/04) with H3N8 equine isolates, as well as the canine/Florida/242/2003 isolate.

Any element of any embodiment disclosed herein can be combined with any other element or embodiment disclosed herein and such combinations are specifically contemplated within the scope of the present invention.

All patents, patent applications, provisional applications, and publications referred to or cited herein are incorporated by reference in their entirety, including all figures and tables, to the extent they are not inconsistent with the explicit teachings of this specification.

MATERIALS AND METHODS FOR EXAMPLES 1-6

Blood and Nasal Swab Collection from Greyhounds

Acute and convalescent blood samples were collected by jugular venipuncture from clinically diseased or normal greyhounds in racing kennels experiencing outbreaks of respiratory disease. Convalescent samples were collected 4 to 12 weeks after the acute sample. Serum was harvested and stored at −80° C. Nasal swabs were collected and placed in Amies transport medium with charcoal (Becton Dickinson Biosciences) pending submission for bacterial isolation.

Postmortem Examination of Greyhounds.

Complete postmortem examinations were performed by the Anatomic Pathology Service at the University of Florida College of Veterinary Medicine (UF CVM) on 5 of the 8 greyhounds that died in the January 2004 outbreak at a Florida track. Postmortem examination of another dog was performed at a private veterinary clinic with submission of tissues to the UF CVM for histopathologic diagnosis. Tissues were fixed in 10% neutral buffered formalin, embedded in paraffin, and 5-μm sections were either stained with hematoxylin and eosin for histopathologic diagnosis or processed for immunohistochemistry as described below. Unfixed tissues were submitted for bacterial culture and also stored at −80° C.

Serological Tests for Canine Viral Respiratory Pathogens.

Paired acute and convalescent serum samples were submitted to the Animal Health Diagnostic Laboratory (AHDL) at the Cornell University College of Veterinary Medicine for serum neutralization assays against canine distemper virus, adenovirus type 2, and parainfluenza virus. Antibody titers were expressed as the last dilution of serum that inhibited viral infection of cell cultures. Seroconversion, defined as a ≧4-fold increase in antibody titer between the acute and convalescent sample, indicated viral infection. No seroconversions to these viral pathogens were detected.

Microbial Tests for Canine Bacterial Respiratory Pathogens.

Paired nasal swabs and postmortem tissues were submitted to the Diagnostic Clinical Microbiology/Parasitology/Serology Service at the UF CVM for bacterial isolation and identification. The samples were cultured on nonselective media as well as media selective for *Bordetella* species (Regan-Lowe; Remel) and *Mycoplasma* species (Remel). All cultures were held for 21 days before reporting no growth. Nasal swabs from some of the greyhounds were also submitted to the Department of Diagnostic Medicine/Pathobiology at the Kansas State University College of Veterinary Medicine for bacterial culture. Of 70 clinically diseased dogs tested, *Bordetella bronchiseptica* was isolated from the nasal cavity of 1 dog, while *Mycoplasma* spp. were recovered from the nasal cavity of 33 dogs. *Pasteurella multocida* was commonly recovered from the nasal cavity of dogs with purulent nasal discharges. Two of the dogs that died in the January 2004 outbreak had scant growth of *Escherichia coli* in the lungs postmortem, one dog had scant growth of *E. coli* and *Streptococcus canis*, and another had scant growth of *Pseudomonas aeruginosa* and a yeast. Neither *Bordetella bronchiseptica* nor *Mycoplasma* was isolated from the trachea or lungs of dogs that died.

Virus Isolation from Postmortem Tissues.

Frozen tissues were thawed and homogenized in 10 volumes of minimum essential medium (MEM) supplemented with 0.5% bovine serum albumin (BSA) and antibiotics. Solid debris was removed by centrifugation and supernatants were inoculated onto cultured cells or into 10-day old embryonated chicken eggs. Tissue homogenates from greyhounds that died were inoculated into diverse cell cultures that supported the replication of a broad range of viral pathogens. The cell cultures included Vero (African green monkey kidney epithelial cells, ATCC No. CCL-81), A-72 (canine tumor fibroblasts, CRL-1542), HRT-18 (human rectal epithelial cells, CRL-11663), MDCK (canine kidney epithelial cells, CCL-34), primary canine kidney epithelial cells (AHDL, Cornell University), primary canine lung epithelial cells (AHDL), and primary bovine testicular cells (AHDL). MDCK and HRT cells were cultured in MEM supplemented with 2.5 ug/mL TPCK-treated trypsin (Sigma); the remaining cell lines were cultured in MEM supplemented with 10% fetal calf serum and antibiotics. Cells were grown in 25 cm$^2$ flasks at 37° C. in a humidified atmosphere containing 5% $CO_2$. A control culture was inoculated with the supplemented MEM. The cultures were observed daily for morphologic changes and harvested at 5 days post inoculation. The harvested fluids and cells were clarified by centrifugation and inoculated onto fresh cells as described for the initial inoculation; two blind passages were performed. Hemagglutination activity in the clarified supernatants was determined using chicken or turkey red blood cells as described (Burleson et al., 1992; Kendal et al., 1982). For virus isolation in chicken embryos, 0.1 mL of tissue homogenate was inoculated into the allantoic sac and incubated for 48 hours at 35° C. After two blind passages, the hemagglutination activity in the allantoic fluids was determined as described (Burleson et al., 1992; Kendal et al., 1982).

RT-PCR, Nucleotide Sequencing and Phylogenetic Analyses.

Total RNA was extracted from tissue culture supernatant or allantoic fluid using the RNeasy kit (Qiagen, Valencia, Calif.) according to manufacturer's instructions. The total RNA (10 ng) was reverse transcribed to cDNA using a one-step RT-PCR Kit (Qiagen, Valencia, Calif.) according to manufacturer's instructions. PCR amplification of the coding region of the 8 influenza viral genes in the cDNA was performed as previously described (Klimov et al., 1992a), using universal gene-specific primer sets. The resulting DNA amplicons were used as templates for automated sequencing on an Applied Biosystems 3100 automated DNA sequencer using cycle sequencing dye terminator chemistry (ABI). Nucleotide sequences were analyzed using the GCG Package©, Version 10.0 (Accelyrs) (Womble, 2000). The Phylogeny Inference Package© Version 3.5 was used to estimate phylogenies and calculate bootstrap values from the nucleotide sequences (Felsenstein, 1989). Phylogenetic trees were compared to those generated by neighbor-joining analysis with the Tamura-Nei gamma model implemented in the MEGA© program (Kumar et al., 2004) and confirmed by the PAUP© 4.0 Beta program (Sinauer Associates).

Experimental Inoculation of Dogs.

Four 6-month old specific pathogen-free beagles [(2 males and 2 females (Liberty Research)] were used. Physical examination and baseline blood tests including complete blood cell count/differential, serum chemistry panel, and urinalysis determined that the animals were healthy. They were housed together in a BSL 2-enhanced facility accredited by the Association for Assessment and Accreditation of Laboratory Animal Care. Baseline rectal temperatures were recorded twice daily for 7 days. The dogs were anesthetized by intravenous injection of propofol (Diprivan®, Zeneca Pharmaceuticals, 0.4 mg/kg body weight to effect) for intubation with endotracheal tubes. Each dog was inoculated with a total dose of $10^{6.6}$ median tissue culture infectious doses ($TCID_{50}$) of A/Canine/Florida/43/2004 (Canine/FL/04) (H3N8) virus with half the dose administered into the distal trachea through the endotracheal tube and the other half administered into the deep nasal passage through a catheter. Physical examinations and rectal temperature recordings were performed twice daily for 14 days post inoculation (p.i.). Blood samples (4 mL) were collected by jugular venipuncture on days 0, 3, 5, 7, 10, and 14 p.i. Nasal and oropharyngeal specimens were collected with polyester swabs (Fisher Scientific) from each dog on days 0 to 5, 7, 10, and 14 p.i. The swabs were placed in viral transport medium (Remel) and stored at −80° C. Two dogs (1 male and 1 female) were euthanatized by intravenous inoculation of Beuthanasia-D® solution (1 mL/5 kg body weight; Schering-Plough Animal Health Corp) on day 5 p.i. and the remaining 2 dogs on day 14 for postmortem examination. Tissues for histological analysis were processed as described. Tissues for virus culture were stored at −80° C. This study was approved by the University of Florida Institutional Animal Care and Use Committee.

Virus Shedding from Experimentally Inoculated Dogs.

Serial dilutions of lung homogenates and swab extracts, prepared by clarification of the swab transport media by centrifugation, were set up in MEM supplemented with 0.5% BSA and antibiotics. Plaque assays were performed as described (Burleson et al., 1992) using monolayers of MDCK cells in 6-well tissue culture plates. Inoculated cell monolayers were overlaid with supplemented MEM containing 0.8% agarose and 1.5 ug/mL of TPCK-trypsin. Cells were cultured for 72 hours at 37° C. in a humidified atmosphere containing 5% $CO_2$ prior to fixation and staining with crystal violet. Virus concentration was expressed as plaque forming units (PFU) per gram of tissue or per swab.

Immunohistochemistry.

Deparaffinized and rehydrated 5-μm lung tissue sections from the greyhounds and beagles were mounted on Bond-Rite™ slides (Richard-Allan Scientific, Kalamazoo, Mich.) and subsequently treated with proteinase K (DakoCytomation, Carpenteria, Calif.) followed by peroxidase blocking reagent (Dako® EnVision™ Peroxidase Kit, Dako Corp.). The sections were incubated with 1:500 dilutions of monoclonal antibodies to canine distemper virus (VMRD, Inc.), canine adenovirus type 2 (VMRD, Inc.), canine parainfluenza virus (VMRD, Inc.), or influenza A H3 (Chemicon International, Inc.) for 2 hours at room temperature. Controls included incubation of the same sections with mouse IgG (1 mg/mL, Serotec, Inc.), and incubation of the monoclonal antibodies with normal canine lung sections. Following treatment with the primary antibodies, the sections were incubated with secondary immunoperoxidase and peroxidase substrate reagents (Dako® EnVision™ Peroxidase Kit, Dako Corp.) according to the manufacturer's instructions. The sections were counterstained with hematoxylin, treated with Clarifier #2 and Bluing Reagent (Richard-Allan Scientific, Kalamazoo, Mich.), dehydrated, and coverslips applied with Permount (ProSciTech).

Hemagglutination Inhibition (HI) Assay.

Serum samples were incubated with receptor destroying enzyme (RDE, Denka) (1 part serum: 3 parts RDE) for 16 hours at 37° C. prior to heat inactivation for 60 minutes at 56° C. Influenza A/Canine/FL/04 (H3N8) virus was grown in MDCK cells for 36-48 hr at 37° C. Virus culture supernatants were harvested, clarified by centrifugation, and stored at −80° C. The HI assay was performed as described previously (Kendal et al., 1982). Briefly, 4 hemagglutinating units of virus in 25 μl were added to an equal volume of serially diluted serum in microtiter wells and incubated at room temperature for 30 minutes. An equal volume of 0.5% v/v turkey erythrocytes was added and the hemagglutination titers were estimated visually after 30 minutes. The endpoint HI titer was defined as the last dilution of serum that completely inhibited hemagglutination. Seroconversion was defined as ≧4-fold increase in HI titer between paired acute and convalescent samples. Seropositivity of a single sample was defined as a HI antibody titer ≧1:32.

Microneutralization (MN) Assay.

Neutralizing serum antibody responses to A/Canine/FL/04 (H3N8) were detected by a MN assay as described previously (Rowe et al., 1999) except that canine sera were RDE-treated as described above prior to the assay. The endpoint titer was defined as the highest dilution of serum that gave 50% neutralization of 100 $TCID_{50}$ of virus. Seroconversion was defined as ≧4-fold increase in MN titer between paired acute and convalescent samples. Seropositivity of a single sample was defined as a MN titer ≧1:80.

Following are examples which illustrate procedures for practicing the invention. These examples should not be construed as limiting. All percentages are by weight and all solvent mixture proportions are by volume unless otherwise noted.

Example 1

In January 2004, an outbreak of respiratory disease occurred in 22 racing greyhounds housed in 2 kennels at a Florida track and the local farm that supplied dogs to these kennels. There were approximately 60 dogs in each kennel building and 300 dogs at the farm. The outbreak occurred over a 6-day period after which no new cases were identified. Fourteen of the 22 dogs had fevers of 39.5 to 41.5° C., a soft, gagging cough for 10 to 14 days, and eventual recovery. Of the remaining 8 dogs, 6 apparently healthy dogs died unexpectedly with hemorrhage from the mouth and nose. Two other dogs were euthanatized within 24 hours of onset of hemorrhage from the mouth and nose due to rapid deterioration. Both of these dogs had fevers of 41° C. Four of the 8 deaths occurred in the kennel buildings and 4 occurred at the farm. Fifty percent of the deaths occurred on day 3 of the outbreak. The 22 dogs ranged in age from 17 months to 4 years, but 73% were 17 to 33 months old.

Figure 3A:
FIG. 3 shows the characteristic histological changes in the bronchi of greyhounds that died from hemorrhagic pneumonia associated with influenza virus infection. The tissues are stained with H&E. Upper panel: Normal bronchus with ciliated epithelial cells, mucous cells, and basal cells. Lower panel: Bronchus from a greyhound with spontaneous influenza. There is necrosis and erosion of the bronchial ciliated epithelial cells. Scale bar, 100 µm.
Figure 3B:
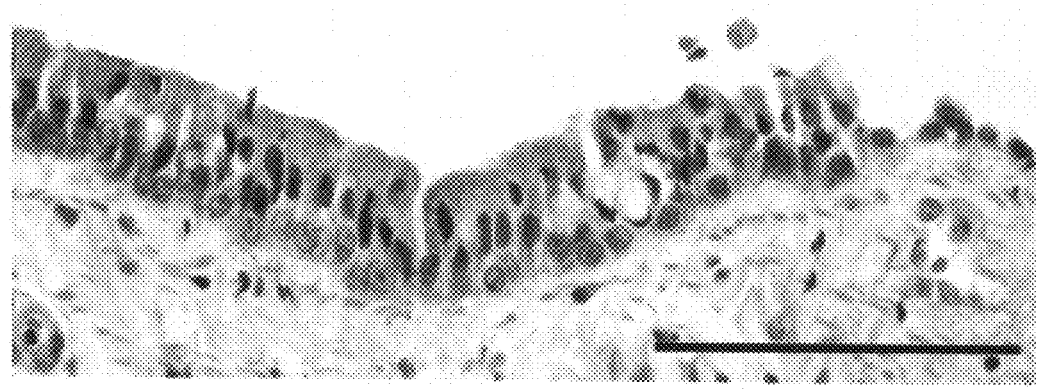

Two clinical syndromes were evident: a milder illness characterized by initial fever and then cough for 10-14 days (14 dogs) with subsequent recovery, or a peracute death associated with hemorrhage in the respiratory tract (8 dogs for a mortality rate of 36%). Postmortem examinations were performed on 6 of the 8 fatal cases. All dogs had extensive hemorrhage in the lungs, mediastinum, and pleural cavity. Histological examination of the respiratory tract revealed that in addition to pulmonary hemorrhage, all dogs had tracheitis, bronchitis, bronchiolitis, and suppurative bronchopneumonia (FIG. 3). The epithelial lining and airway lumens in these tissues were infiltrated by neutrophils and macrophages. Lung homogenates prepared from these dogs were inoculated into a variety of monkey, human, bovine, and canine cell lines for virus culture. The lung homogenate from one dog caused cytopathic effects in Madin-Darby canine kidney epithelial cells (MDCK) cultured in the presence of trypsin, and the cell culture supernatant agglutinated chicken red blood cells. Preliminary evidence of an influenza type A virus was provided by a commercial ELISA for detection of the nucleoprotein of influenza A and B viruses, and by PCR analysis using primers specific for the matrix gene of influenza A viruses. In addition, the hemagglutinating activity was inhibited by reference antisera to the equine influenza A H3 subtype, but not by antisera specific for human influenza A subtypes H1-H11 and H13 (Table 3). To characterize the molecular properties of the virus, we determined the nucleotide sequences of the 8 RNA segments of the viral genome. Sequence comparisons with known influenza virus genes and phylogenetic analyses indicated that the 8 genes of the canine isolate were most similar to those from contemporary equine influenza A (H3N8) viruses, with which they shared 296-97% sequence identity (FIG. 1A, Table 4). In contrast, representative genes from avian, swine, and human influenza A isolates had ≦94% identity with the canine isolate (Table 4). These data identified the canine isolate A/Canine/Florida/43/2004 (Canine/FL/04) as an influenza A H3N8 virus closely related to contemporary lineages of equine influenza viruses. Since all genes of the canine isolate were of equine influenza virus origin, we concluded that the entire genome of an equine influenza virus had been transmitted to the dog.

Example 2

Figures 2A, 2B:
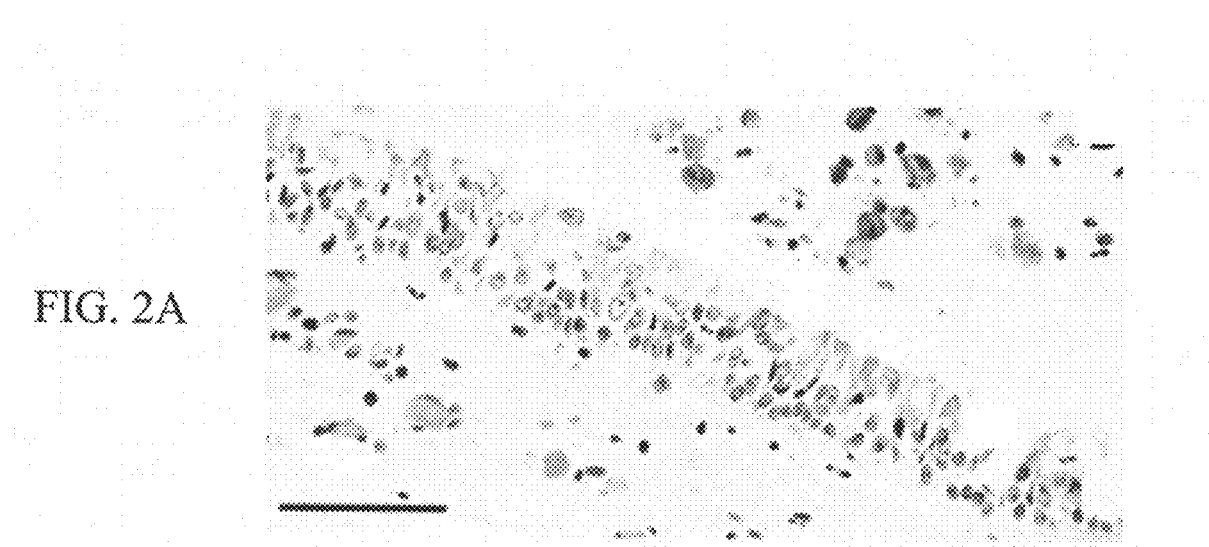
FIGS. 2A-2B show immunohistochemical detection of influenza H3 antigen in the lungs. Lung tissue sections were probed with a mouse monoclonal antibody to H3 hemagglutinin and binding was detected by immunoperoxidase reaction (brown precipitate).

To investigate the role of the Canine/FL/04 virus in the clinical and pathological observations in the greyhounds, we performed immunohistochemical staining (IHC) on lung tissues using a monoclonal antibody to influenza A H3. Viral H3 antigen was consistently detected in the cytoplasm of bronchial and bronchiolar epithelial cells, bronchial gland epithelial cells, and macrophages in airway lumens and alveolar spaces (FIG. 2A). These data support a diagnosis of pulmonary infection with influenza virus of the H3 subtype in multiple dogs.

Example 3

To determine involvement of a Canine/FL/04-like virus in the etiology of the respiratory disease outbreak, we analyzed paired acute and convalescent sera from 11 sick dogs and 16 asymptomatic contacts by hemagglutination inhibition (HI) and microneutralization (MN). Seroconversion, defined as a ≧4-fold rise in antibody titer to Canine/FL/04 from the acute to convalescent phase, occurred in 8 of 11 (73%) sick dogs in both assays (Table 1). Seroconversion occurred in 6 of 16 (38%) asymptomatic contacts in the HI assay, while 8 of 16 (50%) seroconverted in the MN assay (Table 1). The seroconversion data demonstrated infection of the dogs with a Canine/FL/04-like virus which coincided temporally with the onset of respiratory disease in most animals.

Single serum samples were collected 3 months after the outbreak from an additional 46 asymptomatic dogs housed with the sick dogs. Of these, 43 (93%) were seropositive in both assays. For the total population of 73 dogs tested, 93% were seropositive in both assays, including 82% (9/11) of the sick dogs and 95% (59/62) of the healthy contacts. The high seroprevalence in dogs with no history of respiratory disease indicates that most infections with canine influenza virus are subclinical and suggest efficient spread of the virus among dogs. It is not known if subclinical infections contribute to the spread of the virus.

Example 4

To better understand the capacity of the Canine/FL/04 virus to infect dogs, four 6-month old purpose-bred beagles were each inoculated with $10^{6.6}$ median tissue culture infectious doses ($TCID_{50}$) by the intratracheal and intranasal routes. All dogs developed a fever (rectal temperature ≧39° C.) for the first 2 days postinoculation (p.i.), but none exhibited respiratory symptoms such as cough or nasal discharge over a 14 day observation period. Virus shedding was examined by quantification of virus in nasal and oropharyngeal swabs. Only 2 of the 4 dogs shed detectable amounts of virus. One dog shed virus on days 1 and 2 p.i. (1.0-2.5 $\log_{10}$ PFU per swab), whereas the other dog shed virus for 4 consecutive days after inoculation (1.4-4.5 $\log_{10}$ PFU per swab). Postmortem examination of 2 dogs on day 5 p.i. revealed necrotizing and hyperplastic tracheitis, bronchitis, and bronchiolitis similar to that found in the spontaneous disease in greyhounds, but there was no pulmonary hemorrhage or bronchopneumonia. Viral H3 antigen was detected in the cytoplasm of epithelial cells of bronchi, bronchioles, and bronchial glands by IHC (FIG. 2B). Infectious virus was recovered from the lung tissue of one of the dogs. Postmortem examination of the remaining 2 dogs on day 14 p.i. showed minimal histological changes in respiratory tissues, no viral H3 antigen by IHC, and no recovery of virus from lung homogenates. Seroconversion in these latter 2 dogs was detected in MN assays by day 7 p.i., with a further 2- to 3-fold increase in antibody titers by day 14. These results established the susceptibility of dogs to infection with Canine/FL/04, as evidenced by the febrile response, presence of viral antigen and infectious virus in the lung parenchyma, histopathological findings typical for influenza, and seroconversion. The failure to reproduce severe disease and death in the experimentally inoculated beagles is not surprising since a large proportion of the naturally infected greyhounds were asymptomatic.

Example 5

To investigate whether a Canine/FL/04-like influenza virus had circulated among greyhound populations in Florida prior to the January 2004 outbreak, archival sera from 65 racing greyhounds were tested for the presence of antibodies to Canine/FL/04 using the HI and MN assays. There were no detectable antibodies in 33 dogs sampled from 1996 to 1999. Of 32 dogs sampled between 2000 and 2003, 9 were seropositive in both assays—1 in 2000, 2 in 2002, and 6 in 2003 (Table 5). The seropositive dogs were located at Florida tracks involved in outbreaks of respiratory disease of unknown etiology from 1999 to 2003, suggesting that a Canine/FL/04-like virus may have been the causative agent of those outbreaks. To investigate this possibility further, we examined archival tissues from greyhounds that died from hemorrhagic bronchopneumonia in March 2003. Lung homogenates inoculated into MDCK cells and chicken embryos from one dog yielded H3N8 influenza virus, termed A/Canine/Florida/242/2003 (Canine/FL/03). Sequence analysis of the complete genome of Canine/FL/03 revealed >99% identity to Canine/FL/04 (Table 4), indicating that Canine/FL/04-like viruses had infected greyhounds prior to 2004.

Example 6

From June to August 2004, respiratory disease outbreaks occurred in thousands of racing greyhounds at 14 tracks in Florida, Texas, Alabama, Arkansas, West Virginia, and Kansas.

Officials at some of these tracks estimated that at least 80% of their dog population had clinical disease. Most of the dogs had clinical signs of fever (≧39° C.) and cough similar to the dogs in the January 2004 outbreak, but many dogs also had a mucopurulent nasal discharge. Multiple deaths were reported but an accurate mortality rate could not be determined.

We collected paired acute and convalescent sera from 94 dogs located at 4 Florida tracks: 56% of these dogs had ≧4-fold rises in antibody titers to Canine/FL/04, and 100% were seropositive (Table 6). Convalescent sera from 29 dogs in West Virginia and Kansas also had antibodies to Canine/FL/04. We isolated influenza A (H3N8) virus from the lungs of a greyhound that died of hemorrhagic bronchopneumonia at a track in Texas. Sequence analysis of the entire genome of this isolate, named A/Canine/Texas/1/2004 (Canine/TX/04), revealed ≧99% identity to Canine/FL/04 (Table 4). The isolation of three closely related influenza viruses from fatal canine cases over a 13-month period and from different geographic locations, together with the substantial serological evidence of widespread infection among racing greyhounds, suggested sustained circulation of a Canine/FL/04-like virus in the dog population.

Figure 1B:
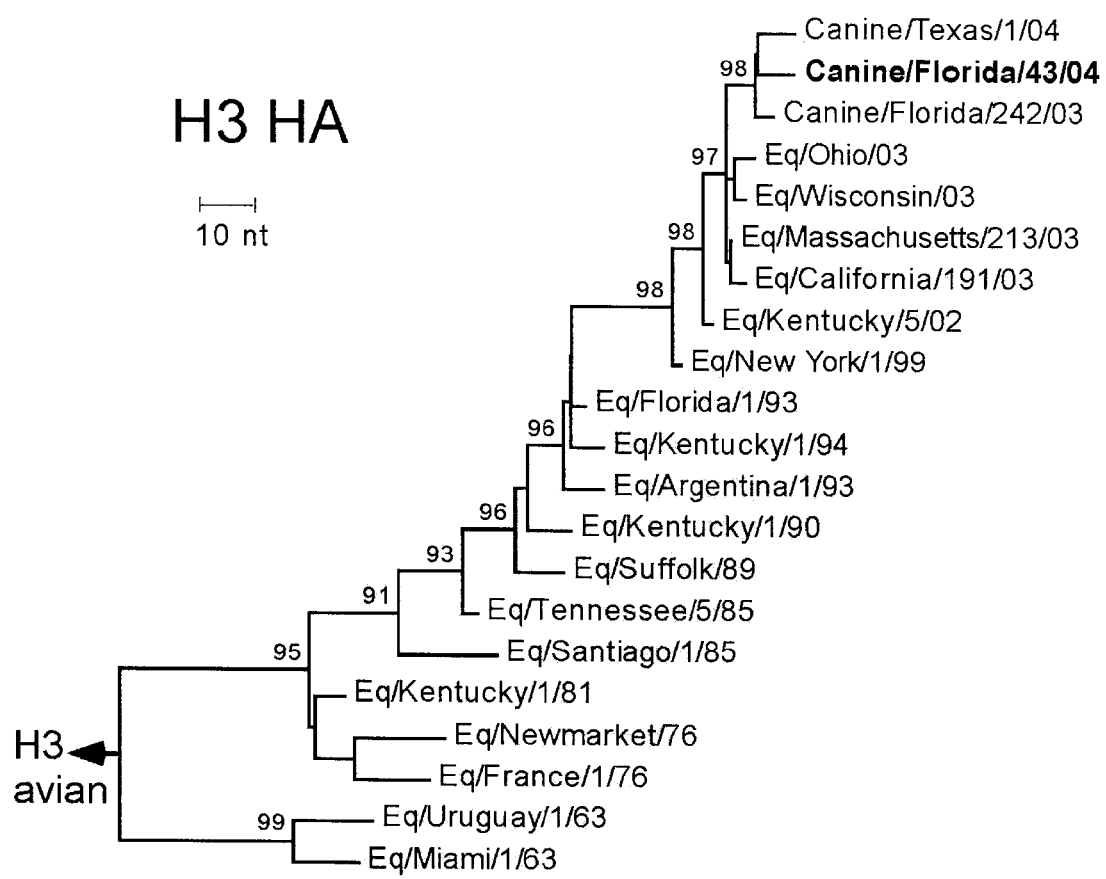

Phylogenetic analysis of the HA genes of Canine/FL/03, Canine/FL/04, and Canine/TX/04 showed that they constitute a monophyletic group with robust bootstrap support that was clearly distinct from contemporary H3 genes of equine viruses isolated in 2002 and 2003 (FIG. 1B). Phylogentic analysis and pairwise nucleotide sequence comparisons of the other 7 genomic segments supported the segregation of the canine genes as a distinct sub-lineage most closely related to the equine virus lineage (data not shown, and Table 4). The clustering of the canine influenza genes as a monophyletic group separate from equine influenza is also supported by the presence of 4 signature amino acid changes in the HA (Table 2). Together with the serological results from 2003 and 2004, these data are consistent with a single virus transmission event from horses to dogs with subsequent horizontal spread of the virus in the greyhound population. However, repeated introductions of this unique lineage of influenza virus from an unidentified reservoir species can not be formally excluded, unlikely as it may be.

The viral HA is a critical determinant of host species specificity of influenza virus (Suzuki et al., 2000). To identify residues within HA that may be associated with adaptation to the canine host, we compared the deduced amino acid sequence of canine HAs to those of contemporary equine viruses. Four amino acid changes differentiate the equine and canine mature HA consensus amino acid sequences: N83S, W222L, I328T, and N483T (see Table 2). The canine viruses have an amino acid deletion when compared to the consensus equine sequences. Therefore, amino acid position 7 in the HA equine sequence is position 6 in the HA canine sequence, amino acid position 29 in the HA equine sequence is position 28 in the HA canine sequence, amino acid position 83 in the HA equine sequence is position 82 in the HA canine sequence, etc. Thus, the four substituted amino acids are at position 82, 221, 327, and 482 of the amino acid sequence shown in SEQ ID NO: 33 and SEQ ID NO: 34. The substitution of serine for asparagine at consensus sequence position 83 is a change of unknown functional significance since various polar residues are found in H3 molecules from other species. The strictly conserved isoleucine at consensus sequence position 328 near the cleavage site of the H3 HA has been replaced by threonine. The pivotal role of HA cleavage by host proteases in pathogenesis suggests that this change merits further study. The substitution of leucine for tryptophan at consensus sequence position 222 is quite remarkable because it represents a non-conservative change adjacent to the sialic acid binding pocket which could modulate receptor function (Weis et al., 1988). Interestingly, leucine at position 222 is not unique to canine H3 HA since it is typically found in the H4, H8, H9, and H12 HA subtypes (Nobusawa et al., 1991; Kovacova et al., 2002). The leucine substitution may be more compatible with virus specificity for mammalian hosts since infections of swine with subtype H4 (Karasin et al., 2000) and humans and swine with subtype H9 (Peiris et al., 1999) viruses have been reported. The substitution of asparagine with threonine at consensus sequence position 483 resulted in the loss of a glycosylation site in the HA2 subunit that is conserved in all HA subtypes (Wagner et al., 2002). Although the importance of these amino acid changes in the HA for adaptation of an equine virus to dogs remains to be determined, similar amino acid changes have been observed previously in association with interspecies transfer (Vines et al., 1998; Matrosovich et al., 2000). Amino acid differences between other influenza viral proteins of the invention and equine consensus sequence are shown in Tables 19 to 25.

The source of the equine influenza virus that initially infected racing greyhounds remains speculative. Kennels at greyhound racetracks are not located near horses or horse racetracks, suggesting that contact between greyhounds and shedding horses is not a sufficient explanation for the multiple outbreaks in different states in 2004. A potential source of exposure to the equine virus is the feeding of horsemeat to greyhounds, whose diet is supplemented with raw meat supplied by packing houses that render carcasses, including horses which could carry influenza. Precedents for this mode of infection include reports of interspecies transmission of H5N1 avian influenza virus to pigs and zoo felids fed infected chicken carcasses (Webster, 1998; Keawcharoen et al., 2004; Kuiken et al., 2004). Although this is a plausible route for the initial introduction of equine influenza into dogs, it does not explain the recent multiple influenza outbreaks in thousands of dogs in different states. Our experimental inoculation study demonstrated the presence of virus in the nasal passages and oropharynx of dogs, albeit at modest titers. Nevertheless, these results indicate that shedding is possible, and that dog-to-dog transmission of virus by large droplet aerosols, fomites, or direct mucosal contact could play a role in the epizootiology of the disease.

The interspecies transfer of a whole mammalian influenza virus to an unrelated mammal species is a rare event. Previous studies have provided limited serological or virological evidence, but not both, of transient infection of dogs with human influenza A (H3N2) viruses (Nikitin et al., 1972, Kilbourne, et al., 1975; Chang et al., 1976; Houser et al., 1980). However, there was no evidence of sustained circulation in the canine host. Although direct transfer of swine influenza viruses from pigs to people is well-documented (Dacso et al., 1984; Kimura et al., 1998; Patriarca et al., 1984; Top et al., 1977), there is no evidence for adaptation of the swine viruses in human hosts. In this report, we provide virological, serological, and molecular evidence for interspecies transmission of an entire equine influenza A (H3N8) virus to another mammalian species, the dog. Unique amino acid substitutions in the canine virus HA, coupled with serological confirmation of infection of dogs in multiple states in the U.S., suggest adaptation of the virus to the canine host. Since dogs are a primary companion animal for humans, these findings have implications for public health; dogs may provide a new source for transmission of novel influenza A viruses to humans.

TABLE 1

Antibody response to A/Canine/Florida/43/2004 (H3N8).

| Response | Sick Dogs (11)[a] | | Healthy Contacts (16)[b] | |
|---|---|---|---|---|
| | HI[c] | SN[d] | HI | SN |
| Seroconversion (%)[e] | 73 | 73 | 38 | 50 |
| Seropositive (%)[f] | 82 | 82 | 100 | 100 |
| Geometric mean titer[g] | 329 | 424 | 268 | 431 |

[a]Number of dogs with clinical signs of disease.
[b]Number of asymptomatic dogs housed in contact with clinically diseased dogs.
[c]Hemagglutination-inhibition (HI) assay using A/Canine/Florida/43/2004 virus.
[d]Microneutralization (MN) assay using A/Canine/Florida/43/2004 virus.
[e]Percentage of dogs with at least a 4-fold increase in antibody titer in paired acute and convalescent sera.
[f]Percentage of dogs with a positive antibody titer (HI titer ≧32: MN titer ≧80) in the convalescent sera.
[g]Geometric mean antibody titer for the convalescent sera.

TABLE 2

Amino acid differences between the canine and equine H3 hemagglutinins.

| Equine H3 consensus | Can/FL/03 | Can/FL/04 | Can/TX/04 | Potential functional significance |
|---|---|---|---|---|
| G7* | D | —† | — | D also found in duck and human H3 HA |
| I29 | — | M | M | I is conserved in H3 HAs from all species |
| N83 | S | S | S | Various polar amino acids present at this position in H3 HAs of other species |
| S92 | — | N | — | N is present in some duck H3 HAs |
| L118 | — | — | V | L is conserved in all H3 HAs |
| W222 | L | L | L | W is conserved in most H3 HAs of all species; located near the receptor binding site |
| A272 | V | A | V | V is present in some recent equine isolates |
| I328 | T | T | T | T is strictly conserved in all avian, swine or humans H3 HAs |
| N483 | T | T | T | N occurs in all H3 and other HA subtypes. Replacement results in loss of a glycosylation site. |
| K541 | — | R | — | Basic amino acid conservative change |

*Amino acid residue (single letter code) and position in the mature H3 HA. The amino acid code is: A = alanine, D = aspartic acid, G = glycine, I = isoleucine, K = lysine, L = leucine, M = methionine, N = asparagine, R = arginine, S = serine, T = threonine, V = valine, W = tryptophan.
†Denotes no change from the consensus equine H3 HAs.

TABLE 3

Hemagglutination inhibition of a virus isolate by reference antisera to different HA subtypes.

| Reference Antisera | HA Specificity | HI titer[a] |
|---|---|---|
| Puerto Rico/8/34 | H1 | 5 |
| Swine/Iowa15/30 | H1 | 5 |
| Singapore/01/57 | H2 | 5 |
| Shanghai/11/87 | H3[b] | 5 |
| Equine/Miami/1/63 | H3 | 160 |
| Duck/Czechoslovakia/56 | H4 | 5 |
| Tern/South Africa/61 | H5 | 5 |
| Turkey/Massachussetts/65 | H6 | 5 |
| Fowl Plague/Dutch/27 | H7 | 5 |
| Fowl Plague/Rostock/34 | H7 | 5 |
| Equine/Prague/1/56 | H7 | 5 |
| Turkey/Ontario/6118/68 | H8 | 5 |
| Quail/Hong Kong/G1/97 | H9[b] | 5 |
| Chicken/Hong Kong/G9/97 | H9[b] | 5 |
| Chicken/Germany/49 | H10 | 5 |
| Duck/England/56 | H11 | 5 |
| Gull/Maryland/704/77 | H13 | 5 |
| Normal sheep serum | — | 5 |
| Normal ferret serum | — | 5 |

[a]Hemagglutination inhibition titer to virus isolate from dog # 43.
[b]Polyclonal antisera were produced in ferrets, whereas all other antisera were produced in sheep or goats.

TABLE 4

Sequence homology of A/Canine/Florida/43/2004 (H3N8) genes to equine, avian, swine, and human strains of influenza A.

| Gene | Equine | Avian | Swine | Human |
|---|---|---|---|---|
| PB2 DQ124147 | 96.9 (98.7)[a] Eq/Kentucky/2/8 M73526 | 88.6 (96.8) Mall/Alberta/98/85 AY633315 | 87.9 (96.8) Sw/Ontario/ 01911-1/99 AF285892 | 86.2 (96.4) PR/8/34 (HK/213/03) AF389115 (AY576381) |
| PB1 DQ124148 | 97.1 (98.8) Eq/Tennessee/5/86 M25929 | 83.9 (97.1) Ck/BritishColumbia/04 (Gull/Md/704/77) AY61675 (M25933) | 83.9 (97.1) Sw/Korea/S109/04 (Sw/Saskatch/ 18789/02) AY790287 (AY619955) | 83.9 (97.1) WSN/33 (Sing/1/57) J02178 (M25924) |
| PA DQ124149 | 96.3 (97.5) M26082 Eq/Tennessee/5/86 | 87.0 (94.3) Ck/Chile/4591/02 (Ostrich/SA/08103/95) AY303660(AF508662) | 84.3 (94.6) Sw/Hong Kong/ 126/02 M26081 | 83.8 (93.4) Taiwan/2/70 (Viet Nam/ 1203/04) AY210199 (AY818132) |
| HA (H3) | 97.4 (97.1) | 80.7 (89.0) | 80.0 (87.7) | 81.8 (87.9) |

TABLE 4-continued

Sequence homology of A/Canine/Florida/43/2004 (H3N8) genes to equine, avian, swine, and human strains of influenza A.

| Gene | Equine | Avian | Swine | Human |
|---|---|---|---|---|
| DQ124190 | Eq/FL/1/93 L39916 | Dk/Norway/1/03 AJ841293 | Sw/Ontario/42729a/01 AY619977 | HK/1/68 AF348176 |
| NP DQ124150 | 96.6 (97.9) Eq/Tennesee/5/86 M30758 | 87.9 (95.1) Ck/Chile/176822/02 AY303658 | 85.4 (93.5) Sw/Ontario/42729a/01 (Sw/Fujian/1/2003) AY619974 (AY747611) | 84.7 (93.0) HK/1073/99 (Hong Kong/ 538/97) AF255742 (AF255751) |
| NA (N8) DQ124151 | 96.8 (97.0) Eq/Tennesee/5/86 L06583 | 84.0 (85.2) Dk/NJ/2000 L06583 | na[b] | na[b] |
| M DQ124152 | 97.9 (95.7) Eq/Tennesee/5/86 (Eq/Kentucky/92) M63529 (AF001683) | 94.1 (94.0) Tky/Mn/833/80 AF001683 | 93.7 (93.5) Sw/Saskatchewan/ 18789/02 M63527 | 91.2 (95.4) WSN/33 (Hong Kong/ 1073/99) J02177 (AJ278646) |
| NS DQ124153 | 97.5 (95.7) Eq/Tn/5/86 (Eq/Kentucky/92) M80973 (AF001671) | 92.0 (90.4) Mal/NY/6750/78 M80945 | 91.1 (89.1) Sw/China/8/78 (Sw/Korea/s452/04) M80968 (AY790309) | 91.4 (90.0) Brevig Mission/1/18 AF333238 |

[a]Percent nucleotide and amino acid (in parentheses) sequence identity of A/Canine/Florida/43/2004 (H3N8) genes to the most homologous gene of influenza virus virus isolates from the species, followed by their Genbank sequence database accession numbers.
[b]Not applicable: N8 neuraminidase was never reported in human or swine viruses.

TABLE 5

Antibody titers to A/canine/Florida/43/2004 (H3N8) in greyhound serum collected from 1996 to 2003.

| | Year[a] | | | | | |
|---|---|---|---|---|---|---|
| | 1996 | 1997 | 1998 | 2000 | 2002 | 2003 |
| No. of dogs tested | 8 | 6 | 19 | 4 | 6 | 22 |
| No. of seropositive dogs | 0 | 0 | 0 | 1 | 2 | 6 |
| Antibody titers[b] | | | | 512 | 232, 524 | 280-2242 |

[a]The year of serum sample collection from racing greyhounds in Florida.
[b]Microneutralization assay antibody titers for seropositive dogs, including the range for the six 2003 seropositive dogs.

TABLE 6

Antibody response to A/canine/Florida/43/2004 (H3N8) in racing greyhounds at 4 Florida tracks in June 2004.

| Response | Track A | Track B | Track C | Track D |
|---|---|---|---|---|
| Number of dogs tested[a] | 37 | 10 | 22 | 25 |
| Seroconversion (%)[b] | 46 | 90 | 100 | 64 |
| Seropositive (%)[c] | 100 | 100 | 100 | 100 |
| Geometric mean titer[d] | 401 | 512 | 290 | 446 |

[a]Number of clinically diseased dogs tested by HI using A/canine/Florida/43/2004 (H3N8).
[b]Percentage of dogs with ≧4-fold increase in antibody titer between acute and convalescent sera.
[c]Percentage of dogs with a positive antibody titer (HI titer > 16) in the convalescent sera.
[d]Geometric mean antibody titer for the convalescent sera.

MATERIALS AND METHODS FOR EXAMPLES 7-11

Canine Tissues

Postmortem examinations were performed by the Anatomic Pathology Service at the University of Florida College of Veterinary Medicine on 6 mixed breed dogs that died in April/May 2005 during an influenza outbreak in a shelter facility in northeast Florida, and on a pet Yorkshire Terrier dog that died in May 2005 during an influenza outbreak in a veterinary clinic in southeast Florida. Tissues were fixed in 10% neutral buffered formalin, embedded in paraffin, and 5-µm sections were stained with hematoxylin and eosin for histopathologic diagnosis. Unfixed tissues were stored at −80° C. pending virological analyses.

RNA Extraction from Canine Tissue Samples

Frozen lung tissues from each of the 7 dogs were thawed and homogenized in minimum essential medium (MEM) supplemented with 0.5% bovine serum albumin (BSA) and antibiotics (gentamycin and ciprofloxacin) using a disposable tissue grinder (Kendall, Lifeline Medical Inc., Danbury, Conn.). Total RNA was extracted using a commercial kit (RNeasy® Mini Kit, QIAGEN Inc., Valencia, Calif.) according to manufacturer's instructions and eluted in a final volume of 60 µL of buffer. Total RNA was also extracted from lung tissue collected from dogs without respiratory disease.

Real-time RT-PCR

A single-step quantitative real-time RT-PCR was performed on total RNA extracted from the canine tissue samples using the QuantiTect® Probe RT-PCR Kit containing ROX as a passive reference dye (QIAGEN Inc., Valencia, Calif.). Briefly, 2 primer-probe sets were used for detection of influenza A sequences in each sample (Table 7). One primer-probe set was selective for canine hemagglutinin (H3) gene sequences. The other primer-probe set targeted a highly conserved region of the matrix (M) gene of type A influenza virus. For each real-time RT-PCR reaction, 5 µL of extracted total RNA were added to a reaction mixture containing 12.5 µL of 2× QuantiTech® Probe RT-PCR Master Mix, 0.25 µL of QuantiTech® RT Mix, forward and reverse primers (0.4 µM final concentration for each), probe (0.1 µM final concentration) and RNase-free water in a final volume of 25 µL. The TaqMan® Ribosomal RNA Control Reagents (Applied Biosystems, Foster City, Calif.) were used according to manufacturer's instructions for detection of 18S rRNA as an endogenous internal control for the presence of RNA extracted from the canine tissue samples.

Quantitative one-step real-time RT-PCR was performed on the reaction mixtures in a Mx3000P® QPCR System (Stratagene, La Jolla, Calif.). Cycling conditions included a reverse transcription step at 50° C. for 30 minutes, an initial denaturation step at 95° C. for 15 minutes to activate the HotStarTaq® DNA polymerase, and amplification for 40 cycles. Each amplification cycle included denaturation at 94° C. for 15 seconds followed by annealing/extension at 60° C. for 1 minute. The FAM (emission wavelength 518 nm) and VIC (emission wavelength 554 nm) fluorescent signals were recorded at the end of each cycle. The threshold cycle (Ct) was determined by setting the threshold fluorescence (dR) at 1000 in each individual experiment. The Mx3000P® version 2.0 software program (Stratagene, La Jolla, Calif.) was used for data acquisition and analysis. Samples were considered positive for influenza A virus when the threshold cycle (Ct) for the H3 or M gene was 3 units smaller than the Ct for lung tissues from dogs without respiratory disease. The positive control consisted of amplification of RNA extracted from A/canine/FL/242/03 (H3N8) virus.

Virus Isolation in MDCK Cells

Frozen lung tissues from each of the 7 dogs were thawed and homogenized in 10 volumes of Dulbecco's Modified Eagle Medium (DMEM) supplemented with 0.5% (BSA) and antibiotics (gentamycin and ciprofloxacin). Solid debris was removed by centrifugation and supernatants were inoculated onto Madin-Darby canine kidney (MDCK) cells cultured in DMEM supplemented with 1 µg/mL TPCK-treated trypsin (Sigma-Aldrich Corp., St. Louis, Mo.) and antibiotics (gentamycin and ciprofloxacin). Cells were grown in 25 cm$^2$ flasks at 37° C. in a humidified atmosphere containing 5% $CO_2$. The cultures were observed daily for morphologic changes and harvested at 5 days post inoculation. The harvested cultures were clarified by centrifugation and the supernatants inoculated onto fresh MDCK cells as described for the initial inoculation; two additional passages were performed for samples that did not show evidence of influenza virus by hemagglutination or RT-PCR. Hemagglutination activity in the clarified supernatants was determined using 0.5% turkey red blood cells as previously described (Burleson, F. et al., 1992; Kendal, P. et al., 1982). RT-PCR was performed as described below.

Virus Isolation in Embryonated Chicken Eggs

Homogenates were prepared from frozen lung tissues as described above for inoculation of MDCK cells. The homogenates (0.2 mL) were inoculated into the allantoic sac of 10-day old embryonated chicken eggs. After 48 hours of incubation at 35° C., the eggs were chilled at 4° C. overnight before harvesting the allantoic fluid. Hemagglutination activity in the clarified supernatants was determined using 0.5% turkey red blood cells as previously described (Burleson, F. et al., 1992; Kendal, P. et al., 1982). RT-PCR was performed as described below. Two additional passages in embryonated eggs were performed for samples that did not show evidence of influenza virus after the initial inoculation.

RT-PCR, Nucleotide Sequencing, and Phylogenetic Analyses

Viral RNA was extracted from MDCK supernatant or allantoic fluid using the QIAamp® Viral RNA Mini Kit (QIAGEN Inc., Valencia, Calif.) according to manufacturer's instructions. The viral RNA was reverse transcribed to cDNA using the QIAGEN® OneStep RT-PCR Kit (QIAGEN Inc., Valencia, Calif.) according to manufacturer's instructions. PCR amplification of the coding region of the 8 influenza viral genes in the cDNA was performed as previously described (Klimov, A. et al., 1992b), using universal gene-specific primer sets (primer sequences available on request). The resulting DNA amplicons were used as templates for automated sequencing in the ABI PRISM® 3100 automated DNA sequencer using cycle sequencing dye terminator chemistry (Applied Biosystems, Foster City, Calif.). Nucleotide sequences were analyzed using the Lasergene 6 Package® (DNASTAR, Inc., Madison, Wis.). The PHYLIP Version 3.5© software program was used to estimate phylogenies and calculate bootstrap values from the nucleotide sequences (Felsenstein, J., 1989). Phylogenetic trees were compared to those generated by neighbor-joining analysis with the Tamura-Nei model implemented in the MEGA© program (Kumar, S. et al., 2004) and confirmed by the PAUP© 4.0 Beta program (Sinauer Associates, Inc., Sunderland, Mass.).

Hemagglutination Inhibition (HI) Assay

Serum samples were incubated with receptor destroying enzyme (RDE, DENKA SEIKEN Co., Ltd., Tokyo, Japan) (1 part serum: 3 parts RDE) for 16 hours at 37° C. prior to heat inactivation for 30 minutes at 56° C. Influenza A/Canine/Jacksonville/05 (H3N8) virus was grown in MDCK cells for 72 hrs at 37° C. in 5% $CO_2$. Virus culture supernatants were harvested, clarified by centrifugation, and stored at −80° C. All other viruses used in the HI assay were grown in 10-day old embryonated chicken eggs from which allantoic fluid was collected and stored at −80° C. The HI assay was performed as described previously (Kendal, P. et al., 1982). Briefly, 4 hemagglutinating units of virus in 25 µl were added to an equal volume of serially diluted serum in 96-well plastic plates and incubated at room temperature for 30 minutes. An equal volume of 0.5% turkey erythrocytes was added and the hemagglutination titers were estimated visually after 30 minutes. The endpoint HI titer was defined as the last dilution of serum that completely inhibited hemagglutination.

Example 7

Clinical Cases

In April and May 2005, a previously described (Crawford, P. C. et al., 2005) respiratory disease outbreak occurred in dogs housed in a shelter facility in northeast Florida. The outbreak involved at least 58 dogs ranging in age from 3 months to 9 years, and included purebred dogs as well as mixed breeds. The most common clinical signs were purulent nasal discharge and a cough for 7 to 21 days. Of the 43 dogs that had clinical disease for ≧7 days, 41 had HI antibody titers to canine/FL/04 (H3N8) ranging from 32 to >1024. At least 10 dogs progressed to pneumonia, of which 6 were euthanized. These 6 mixed breed dogs included 3 males and 3 females ranging in age from 4 months to 3 years. The duration of clinical signs ranged from 2 to 10 days at the time of euthanasia. On postmortem examination, these dogs had pulmonary congestion and edema. Histological examination of the respiratory tract revealed rhinitis, tracheitis, bronchitis, bronchiolitis, and suppurative bronchopneumonia. There was epithelial cell necrosis and erosion in the trachea, bronchi, bronchioles, and bronchial glands. The respiratory tissues were infiltrated by neutrophils and macrophages.

In May 2005, a respiratory disease outbreak occurred in 40 pet dogs at a veterinary clinic in southeast Florida. The most common clinical signs were purulent nasal discharge and a cough for 10 to 30 days. Of the 40 dogs, 17 were seropositive for canine/FL/04 (H3N8) with HI antibody tiers ranging from 32 to >1024. Seroconversion occurred in 10 dogs for which paired acute and convalescent sera were available. Three dogs progressed to pneumonia. One of these dogs, a 9-year old male Yorkshire Terrier, died 3 days after onset of clinical signs. This dog had tracheobronchitis, pulmonary edema and congestion, and severe bronchopneumonia. Similar to the 6 shelter dogs, there was epithelial cell necrosis and erosion of the airways and neutrophilic infiltrates in the tissues.

Example 8

Real-time RT-PCR and Viral Isolation

Lung tissues from the 7 dogs were analyzed by quantitative real-time RT-PCR assays that detect the M gene of influenza type A and the H3 gene of canine H3N8 influenza A virus. The lungs from all 7 dogs were positive for both the influenza A M gene and the canine influenza H3 gene (Table 8). After 3 passages in MDCK cells, influenza A subtype H3N8 virus was isolated from the lungs of a shelter dog that died after 3 days of pneumonia. This virus was named A/canine/Jacksonville/05 (H3N8) (canine/Jax/05). After 2 passages in embryonated chicken eggs, influenza A subtype H3N8 virus was recovered from the lungs of the pet dog that also died after 3 days of pneumonia. This virus was named A/canine/Miami//05 (H3N8) (canine/Miami/05).

Example 9

Genetic Analyses of the Canine Influenza A H3N8 Isolates

Figure 4A:
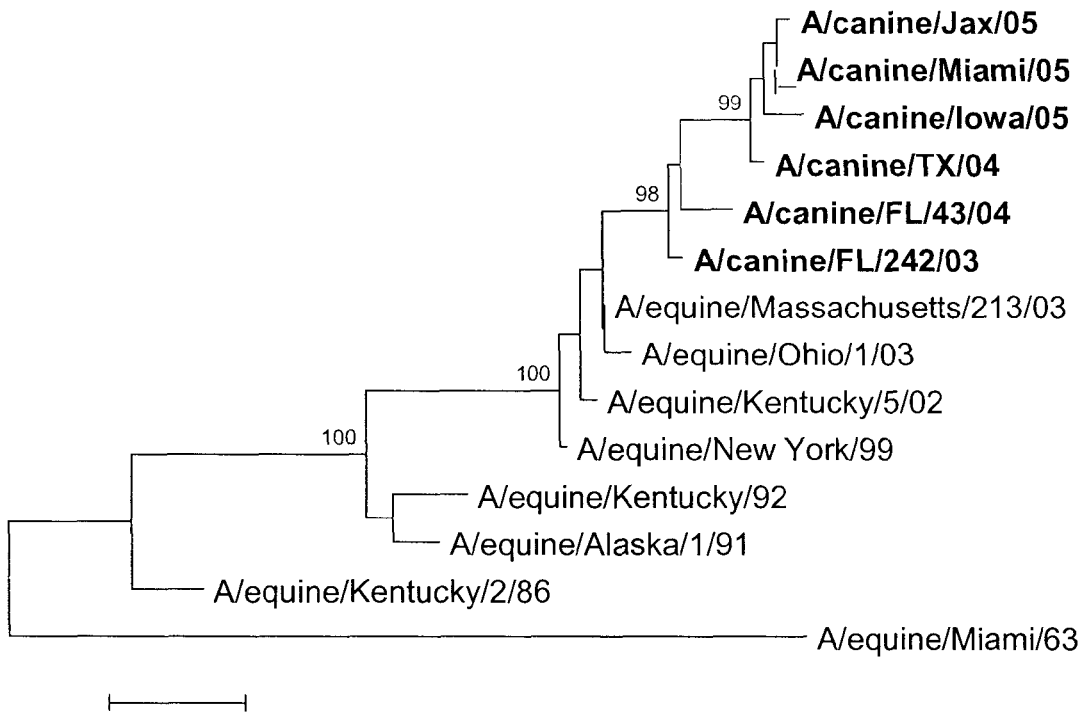
FIGS. 4A-4B shows phylogenetic relationships among the H3 hemagglutinin genes.
Figure 4B:
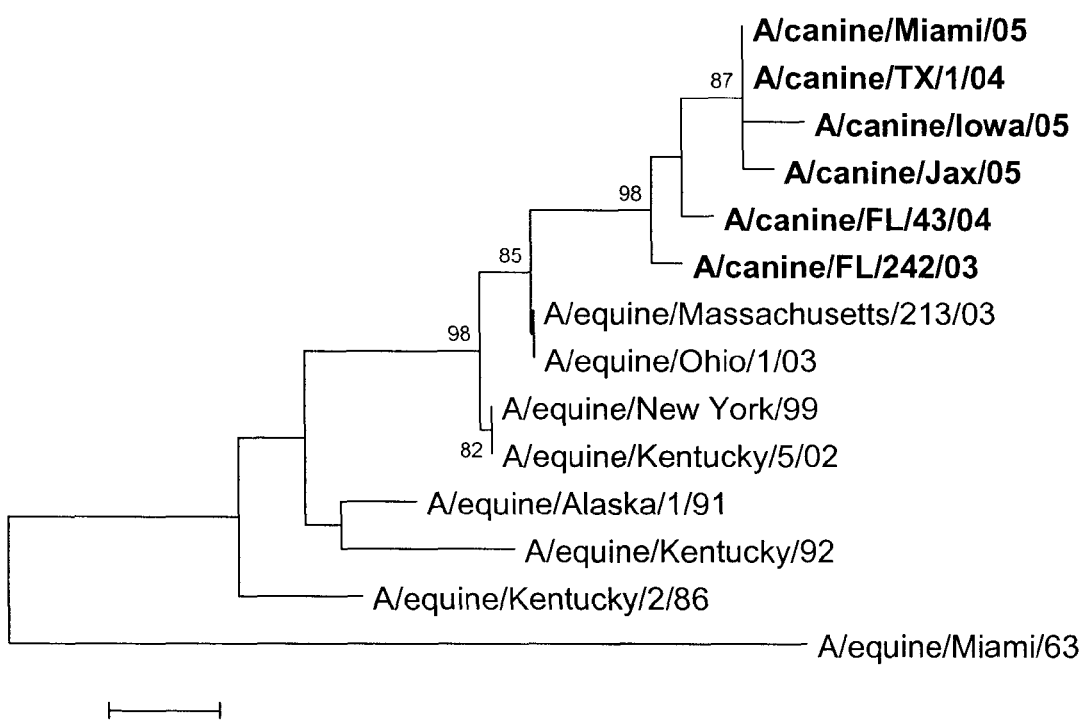

Sequence analyses of canine/Jax/05 and canine/Miami/05 revealed that their hemagglutinin (HA) genes were 98% identical to the canine/FL/04, canine/TX/04, and canine/Iowa/05 isolates recovered from the lungs of racing greyhounds that died of pneumonia during influenza outbreaks at tracks in 2004 and 2005 (Crawford, P. C. et al., 2005; Yoon K-Y. et al., 2005). In addition, the HA genes of canine/Jax/05 and canine/Miami/05 were 98% identical to contemporary equine influenza viruses isolated after the year 2000. Phylogenetic comparisons of the HA genes showed that the canine/Jax/05 and canine/Miami/05 viruses were clustered with the canine/FL/04, canine/TX/04, and canine/Iowa/05 greyhound isolates and contemporary equine isolates, forming a distinct group from the older equine viruses isolated in the early 1990's (FIG. 4). Furthermore, the canine/Jax/05, canine/Miami/05, and canine/Iowa/05 isolates were more closely related to canine/Tx/04 than to either canine/FL/04 or canine/FL/03. The 2005 isolates formed a subgroup that appears to branch off from the earlier 2003 and 2004 canine viruses with differences at approximately 10 parsimony-informative sites. These differences support the hypothesis that canine influenza virus is being transmitted horizontally from dog-to-dog as opposed to being reintroduced periodically from an outside source. The accumulation of mutations from 2003 to 2005 illustrates the ongoing process of adaptation that the virus must undergo after being transmitted to a new host, as is expected to have happened for the canine influenza viruses.

Example 10

Amino Acid Analyses of the Canine Influenza A H3N8 Isolates

There were conserved amino acid substitutions in all 6 canine isolates that differentiated them from contemporary equine influenza viruses (Table 9). These conserved substitutions were I15M, N83S, W222L, I328T, and N483T. Phylogenetic comparisons of the mature HA protein showed that the canine/Jax/05, canine/Miami/05, and canine/Iowa/05 viruses formed a subgroup with the canine/TX/04 isolate (FIG. 4). There were 3 amino acid changes (L118V, K261N, and G479E) that differentiated this subgroup from the other canine viruses (Table 9). There were 2 amino acid changes (F79L and G218E) that differentiated the 2005 isolates from their canine/TX/04 root. Furthermore, the 2005 isolates from non-greyhound dogs, canine/Jax/05 and canine/Miami/05, differed from the canine/Iowa/05 greyhound isolate by one amino acid change, R492K. Finally, canine/Jax/05 differed from canine/Miami/05 at a single amino acid, S107P. In all other H3N8 equine and canine viruses, S is conserved at position 107 except for A/Equine/Jilin/1/89 which has a T (Guo Y. et al., 1992).

Example 11

Antigenic Analyses of the Canine Influenza A H3N8 Isolates

Hemagglutination inhibition (HI) tests were performed using an antigen panel of older and contemporary equine influenza viruses and the canine influenza viruses, and serum collected in 2005 from horses and dogs that had been infected with influenza virus (Table 10). Serum from ferrets immunized against canine/FL/04 was also included in the analyses. The HI antibody titers in equine serum were 8 to 16-fold higher when tested with contemporary equine viruses compared to older isolates, but decreased by at least 4-fold when tested with the canine viruses. The canine serum was nonreactive with the older equine viruses, but the antibody titers increased 4-fold when tested with contemporary equine isolates and canine isolates. This was also observed for the serum from ferrets immunized against canine influenza virus. These seroreactivity patterns demonstrated the antigenic similarity between the canine influenza viruses and contemporary equine influenza viruses and were consistent with the phylogenetic analyses. The antibody titers in equine, canine, and ferret sera to the canine/Miami/05 isolate were similar to those for the 2003 and 2004 canine isolates. However, the titers were 2 to 4-fold lower for the canine/Jax/05 isolate. This suggests that canine/Jax/05 is antigenically distinct from the other canine isolates, which may in part be related to the single amino acid change at position 107 in the mature HA.

TABLE 7

Primers and probes for quantitative real-time RT-PCR analysis for the matrix gene of influenza A virus and the H3 gene of canine influenza A (H3N8).

| Primer | Target | Sequence | Application |
| --- | --- | --- | --- |
| Ca-H3-F387 | H3 (nt 387-406) | 5'-tatgcatcgctccgatccat-3' (SEQ ID NO: 79) | Forward primer for H3 |
| Ca-H3-R487 | H3 (nt 487-467) | 5'-gctccacttcttccgttttga-3' (SEQ ID NO: 80) | Reverse primer for H3 |

TABLE 7-continued

Primers and probes for quantitative real-time RT-PCR analysis for the matrix gene of influenza A virus and the H3 gene of canine influenza A (H3N8).

| Primer | Target | Sequence | Application |
|---|---|---|---|
| Ca-H3-P430 | H3 (nt 430-459) | FAM-aattcacagcagagggattcacatggacag-BHQ1 (SEQ ID NO: 81) | TaqMan ® probe |
| FluA-M-F151 | M (nt 151-174) | 5'-catgga<u>r</u>tggctaaagacaagacc-3' <sup>a</sup> (SEQ ID NO: 82) | Forward primer for M |
| FluA-M-R276 | M (nt 276-253) | 5'-agggcattttggacaaa<u>k</u>cgtcta-3' (SEQ ID NO: 83) | Reverse primer for M |
| FluA-M-P218 | M (nt 218-235) | FAM-acgcTcaccgTgcccAgt-BHQ1 <sup>b</sup> (SEQ ID NO: 84) | TaqMan ® probe |

[a] Underlined letter r represents nucleotide a or g and underlined letter k represents nucleotide g or t.
[b] Uppercase letters represent locked nucleic acid residues.

TABLE 8

Quantitative real-time RT-PCR and viral isolation performed on lung tissues from dogs that died from pneumonia during respiratory disease outbreaks in a shelter and veterinary clinic in Florida.

| Dog ID | Location | Duration of clinical disease | Real-time RT-PCR M (Ct) | HA (Ct) | Virus Isolation |
|---|---|---|---|---|---|
| | A/canine/FL/242/03 positive control | | 28.15 | 27.36 | |
| 1079 | Shelter (NE FL) | 2 days | 29.81 | 28.84 | none |
| 1078 | Shelter (NE FL) | 3 days | 30.37 | 29.71 | MDCK 3rd passage |
| 318 | Shelter (NE FL) | 9 days | 33.89 | 32.97 | none |
| 320 | Shelter (NE FL) | 10 days | 39.44 | 37.09 | none |
| 319 | Shelter (NE FL) | 6 days | 33.87 | 32.23 | none |
| 1080 | Shelter (NE FL) | 6 days | 38.87 | 38.23 | none |
| 374 | Veterinary clinic (SE FL) | 3 days | 24.05 | 22.65 | Egg 2nd passage |

TABLE 9

Amino acid comparison of the mature HA for canine influenza viruses and contemporary equine influenza viruses.

| | Amino Acid | | | | | | | | | | | | | | | | |
|---|---|---|---|---|---|---|---|---|---|---|---|---|---|---|---|---|---|
| | 7 | 15 | 54 | 78 | 79 | 83 | 92 | 107 | 118 | 159 | 218 | 222 | 261 | 328 | 479 | 483 | 492 | 541 |
| A/equine/KY/5/02 | G | I | N | V | F | N | S | S | L | N | G | W | K | I | G | N | R | K |
| A/equine/MA/213/03 | . | . | . | A | . | . | . | . | . | S | . | . | . | . | . | . | . | . |
| A/equine/OH/1/03 | D | . | K | A | . | . | . | . | . | S | . | . | . | . | . | . | . | . |
| A/canine/FL/242/03 | . | M | K | A | . | S | . | . | . | S | . | L | . | T | . | T | . | . |
| A/canine/FL/43/04 | . | M | K | A | . | S | N | . | . | S | . | L | . | T | . | T | . | R |
| A/canine/TX/1/04 | . | M | K | A | . | S | . | . | V | S | . | L | N | T | E | T | . | . |
| A/canine/Iowa/05 | . | M | K | A | L | S | . | . | V | S | E | L | N | T | E | T | . | . |
| A/canine/Miami/05 | . | M | K | A | L | S | . | . | V | S | E | L | N | T | E | T | K | . |
| A/canine/Jacksonville/05 | . | M | K | A | L | S | . | P | V | S | E | L | N | T | E | T | K | . |

TABLE 10

Antibody titers in equine, canine, and ferret serum to older and contemporary equine influenza viruses and canine influenza viruses.

| | Serum antibody titers[a] | | |
|---|---|---|---|
| Antigens | Equine | Canine | Ferret[b] |
| equine/Miami/63 | 40 | <10 | 16 |
| equine/Ky/86 | 40 | 40 | 32 |
| equine/KY/92 | 40 | <10 | 32 |
| equine/NY/99 | 320 | 40 | 128 |
| equine/KY/05/02 | 320 | 160 | 256 |
| equine/MA/213/03 | 640 | 160 | 512 |
| equine/OH/01/03 | 640 | 160 | 512 |
| canine/FL/03 | 160 | 160 | 512 |
| canine/FL/04 | 160 | 80 | 512 |
| canine/Tx/04 | 160 | 160 | 512 |
| canine/Miami/05 | 160 | 80 | 256 |
| canine/Jax/05 | 40 | 40 | 128 |

[a] Antibody titers were determined in a hemagglutination inhibition assay performed with serial dilutions of equine, canine, or ferret serum and the viruses listed in the antigen column.
[b] Serum from ferrets immunized with canine/FL/04 virus.

MATERIALS AND EXAMPLES METHODS FOR EXAMPLES 12-15

Canine Influenza Virus Inoculum

The virus inoculum was prepared by inoculation of Madin-Darby canine kidney (MDCK) epithelial cells with a stock of A/canine/FL/43/04 (H3N8) representing passage 3 of the original isolate previously described (Crawford et al., 2005). The inoculated MDCK cells in Dulbecco's Minimal Essential Media (DMEM) supplemented with 1 μg/mL TPCK-treated trypsin (Sigma-Aldrich Corp., St. Louis, Mo.) and antibiotics (gentamycin and ciprofloxacin) were grown in 250 cm² flasks at 37° C. in a humidified atmosphere containing 5% $CO_2$. The cultures were observed daily for morphologic changes and harvested at 5 days post inoculation. The harvested cultures were clarified by centrifugation and the supernatants were stored at −80° C. pending inoculation of dogs. An aliquot of supernatant was used for determination of virus titer by the Reed and Muench method. The titer was $10^7$ median tissue culture infectious doses ($TCID_{50}$) of A/canine/Florida/43/2004 (canine/FL/04) per mL.

Experimental Inoculation.

Eight 4-month old colony bred mongrel dogs (Marshall BioResources, North Rose, N.Y.) (4 males and 4 females) were used for the experimental inoculation study approved by the University of Florida Institutional Animal Care and Use Committee. The dogs' body weights ranged from 13 to 17 kg. The dogs were healthy based on physical examinations, baseline blood tests, and recording of body temperatures for 2 weeks prior to inoculation. All dogs were free from prior exposure to canine influenza virus based on serology tests performed on paired serum samples collected at the time of arrival into the facility and 2 weeks later. The dogs were anesthetized by intravenous injection of propofol (Diprivan®, Zeneca Pharmaceuticals, 0.4 mg/kg body weight to effect) for intubation with endotracheal tubes. Six dogs (3 males and 3 females) were each inoculated with 107 $TCID_{50}$ of canine/FL/04 virus in 5 mL of sterile saline administered into the distal trachea through a small diameter rubber catheter inserted into the endotracheal tube. Two dogs (1 male and 1 female) were sham-inoculated with an equal volume of sterile saline. The sham-inoculated control dogs were housed in a different room from the virus-inoculated dogs and cared for by different personnel. Physical examinations and rectal temperature recordings were performed twice daily for 6 days post inoculation (p.i.).

Pharyngeal and Rectal Swab Collection.

To monitor for virus shedding, oropharyngeal specimens were collected twice daily from each dog on days 0 to 6 p.i. using polyester swabs (Fisher Scientific International Inc., Pittsburgh, Pa.). The swabs were placed in 1 mL of sterile phosphate-buffered saline (PBS) containing 0.5% bovine serum albumin (BSA). Rectal swabs were collected from each dog daily from days 0 to 6. Swab extracts were prepared by clarification of the swab transport media by centrifugation. An aliquot of swab extract was tested immediately for influenza A virus nucleoprotein using the Directigen™ commercial immunoassay kit (BD, Franklin Lakes, N.J.) according to the manufacturer's instructions. The remaining extract was stored at −80° C. pending other virological assays.

Postmortem Examinations.

On day 1 p.i., one sham-inoculated dog and one virus-inoculated dog were euthanatized by intravenous inoculation of Beuthanasia-D® solution (1 mL/5 kg body weight; Schering-Plough Animal Health Corp). One virus-inoculated dog was similarly euthanatized each day from days 2 to 5 p.i. On day 6 p.i., the remaining sham-inoculated and virus-inoculated dog were euthanatized. Complete postmortem examinations were performed by one of the investigators (WLC). Tissues were fixed in 10% neutral buffered formalin, embedded in paraffin, and 5-μm sections were either stained with hematoxylin and eosin for histopathologic diagnosis or processed for immunohistochemistry as described below. Unfixed lung tissues were submitted to the Diagnostic Clinical Microbiology/Parasitology/Serology Service at the University of Florida College of Veterinary Medicine for bacterial isolation and identification. The samples were cultured on nonselective media as well as media selective for *Bordetella* species (Regan-Lowe; Remel, Lenexa, Kans.) and *Mycoplasma* species (Remel). All cultures were held for 21 days before reporting no growth. Unfixed tissues were also stored at −80° C. pending virological analyses.

Immunohistochemistry.

Deparaffinized and rehydrated 5-μm trachea and lung tissue sections were mounted on Bond-Rite™ slides (Richard-Allan Scientific, Kalamazoo, Mich.) and subsequently treated with proteinase K (DAKOCytomation Inc., Carpenteria, Calif.) followed by peroxidase blocking reagent (DAKO® EnVision™ Peroxidase Kit, DAKO Corp., Carpenteria, Calif.). The sections were incubated with a 1:500 dilution of monoclonal antibody to influenza A H3 (Chemicon International, Inc., Ternecula, Calif.) for 2 hours at room temperature. Controls included incubation of the same sections with mouse IgG (1 mg/mL, Serotec, Inc. Raleigh, N.C.), and incubation of the monoclonal antibody with normal canine lung sections. Following treatment with the primary antibody, the sections were incubated with secondary immunoperoxidase and peroxidase substrate reagents (Dako® EnVision™ Peroxidase Kit, Dako Corp.) according to the manufacturer's instructions. The sections were counterstained with hematoxylin, treated with Clarifier #2 and Bluing Reagent (Richard-Allan Scientific, Kalamazoo, Mich.), dehydrated, and coverslips applied with Permount (ProSciTech, Queensland, Australia).

RNA Extraction from Swabs and Tissues.

Lung and tracheal tissues from each dog were thawed and homogenized in minimum essential medium (MEM) supplemented with 0.5% bovine serum albumin (BSA) and antibiotics (gentamycin and ciprofloxacin) using a disposable tissue grinder (Kendall, Lifeline Medical Inc., Danbury, Conn.). Total RNA was extracted from the tissue homogenates as well as orpharyngeal and rectal swab extracts using a commercial kit (RNeasy® Mini Kit, QIAGEN Inc., Valencia, Calif.) according to manufacturer's instructions and eluted in a final volume of 60 μL of buffer.

Real-Time RT-PCR.

A single-step quantitative real-time RT-PCR was performed on the total RNA using the QuantiTect® Probe RT-PCR Kit containing ROX as a passive reference dye (QIAGEN Inc., Valencia, Calif.) and a primer-probe set that targeted a highly conserved region of the matrix (M) gene of type A influenza virus (Payungpom S. et al., 2006a; Payungpom S. et al., 2006b). For each real-time RT-PCR reaction, 5 μL of extracted total RNA were added to a reaction mixture containing 12.5 μL of 2× QuantiTech® Probe RT-PCR Master Mix, 0.25 μL of QuantiTech® RT Mix, forward and reverse primers (0.4 μM final concentration for each), probe (0.1 μM final concentration) and RNase-free water in a final volume of 25 μL. The TaqMan® GAPDH Control Reagents (Applied Biosystems, Foster City, Calif.) were used according to manufacturer's instructions for detection of GAPDH as an endogenous internal control for the presence of RNA extracted from the swab and tissue samples and as a normalization control.

Quantitative one-step real-time RT-PCR was performed on the reaction mixtures in a Mx3000P® QPCR System (Stratagene, La Jolla, Calif.). Cycling conditions included a reverse transcription step at 50° C. for 30 minutes, an initial denaturation step at 95° C. for 15 minutes to activate the HotStarTaq® DNA polymerase, and amplification for 40 cycles. Each amplification cycle included denaturation at 94° C. for 15 seconds followed by annealing/extension at 60° C. for 1 minute. The FAM (emission wavelength 518 nm) and VIC (emission wavelength 554 nm) fluorescent signals were recorded at the end of each cycle. The threshold cycle (Ct) was determined by setting the threshold fluorescence (dR) at 1000 in each individual experiment. The Mx3000P® version 2.0 software program (Stratagene, La Jolla, Calif.) was used for data acquisition and analysis. The positive control consisted of amplification of RNA extracted from A/canine/FL/242/03 (H3N8) virus. The results were normalized by dividing the M Ct value by the corresponding GAPDH Ct value for each sample.

Virus Re-isolation from Tissues.

Frozen lung and trachea tissues from virus-inoculated dogs were thawed and homogenized in 10 volumes of DMEM supplemented with 0.5% BSA and antibiotics. Solid debris was removed by centrifugation and supernatants were inoculated onto MDCK cells cultured in DMEM supplemented with 1 µg/mL TPCK-treated trypsin (Sigma-Aldrich Corp., St. Louis, Mo.) and antibiotics as described above. Cells were grown in 25 cm$^2$ flasks at 37° C. in a humidified atmosphere containing 5% $CO_2$. The cultures were observed daily for morphologic changes and harvested at 5 days post inoculation. The harvested cultures were clarified by centrifugation and the supernatants inoculated onto fresh MDCK cells as described for the initial inoculation; two additional passages were performed for samples that did not show evidence of influenza virus by hemagglutination or RT-PCR. Hemagglutination activity in the clarified supernatants was determined using 0.5% turkey red blood cells as previously described (Crawford et al., 2005). RT-PCR was performed as described below.

RT-PCR, Nucleotide Sequencing, and Phylogenetic Analyses.

Viral RNA was extracted from MDCK supernatant using the QIAamp® Viral RNA Mini Kit (QIAGEN Inc., Valencia, Calif.) according to manufacturer's instructions. The viral RNA was reverse transcribed to cDNA using the QIAGEN® OneStep RT-PCR Kit (QIAGEN Inc., Valencia, Calif.) according to manufacturer's instructions. PCR amplification of the coding region of the 8 influenza viral genes in the cDNA was performed as previously described (Crawford et al., 2005), using universal gene-specific primer sets (primer sequences available on request). The resulting DNA amplicons were used as templates for automated sequencing in the ABI PRISM® 3100 automated DNA sequencer using cycle sequencing dye terminator chemistry (Applied Biosystems, Foster City, Calif.). Nucleotide sequences were analyzed using the Lasergene 6 Package® (DNASTAR, Inc., Madison, Wis.). The nucleotide sequences for viruses recovered from infected dogs were compared to the sequences of the virus in the inoculum to determine if any changes had occurred during replication in the respiratory tract.

Example 12

Clinical Disease

All 6 virus-inoculated dogs developed a transient fever (rectal temperature ≧39° C.) for the first 2 days p.i., but none exhibited respiratory signs such as cough or nasal discharge over the 6-day observation period. The sham-inoculated dogs remained clinically healthy.

Example 13

Virus Shedding

Influenza A nucleoprotein was detected in the oropharyngeal swab collected from one of the virus-inoculated dogs at 24 hours p.i. The oropharyngeal swabs collected from one dog at 72, 84, and 120 hours p.i., and another dog at 108, 120, and 132 hours p.i., were positive for virus by quantitative real-time RT-PCR (Table 11). The absolute number of influenza M gene copies per µL of swab extract increased with time from 3 to 6 days p.i. No virus was detected in the rectal swabs.

Example 14

Postmortem Examinations

Figure 5:
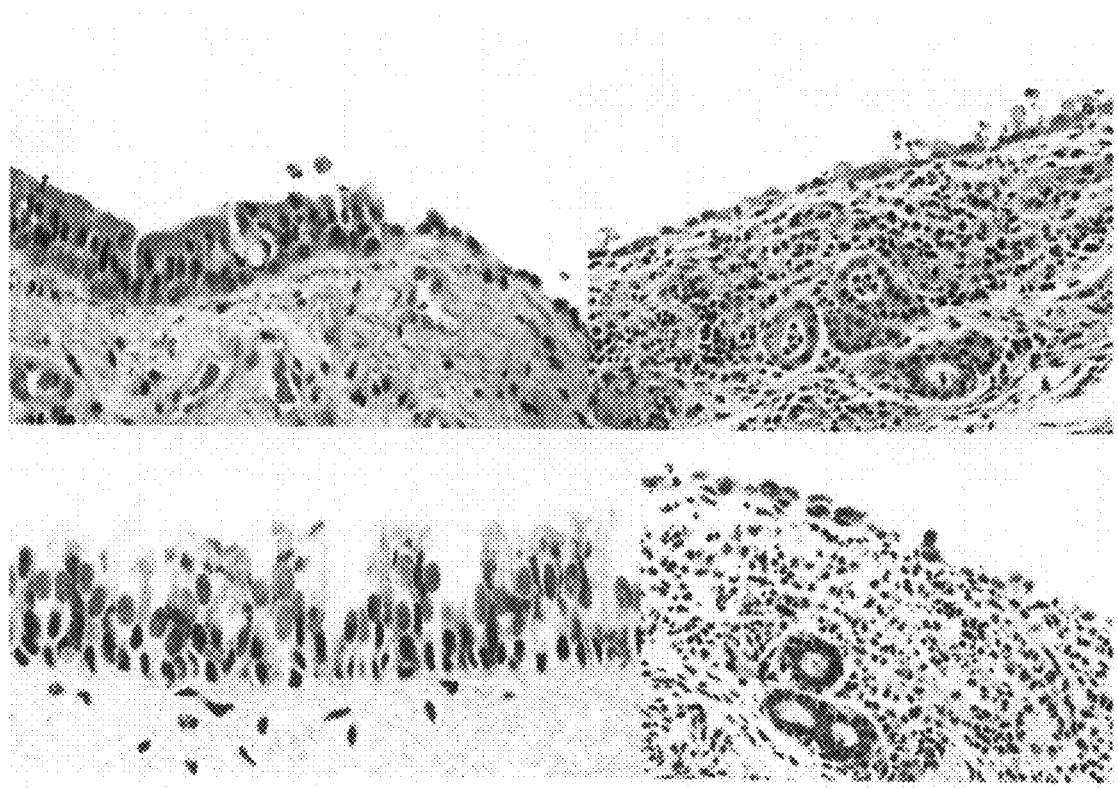
FIG. 5 shows Influenza virus H3 protein in epithelial cells of bronchi and bronchial glands in lungs of dogs that died of pneumonia associated with influenza virus infection. Upper panels: Erosion of ciliated bronchial epithelial cells in bronchi. Tissues were stained with H&E. Lower panels: Influenza virus H3 protein in the cytoplasm of bronchial (left) and bronchial gland (right) epithelial cells. Tissues were stained with a monoclonal antibody to influenza H3 detected by immunoperoxidase reaction (brown precipitate) and counterstained with hematoxylin.

In contrast to the previous experimental infection using specific pathogen-free Beagles (Crawford et al., 2005), the virus-inoculated mongrel dogs had pneumonia as evidenced by gross and histological analyses of the lungs from days 1 to 6 p.i. In addition to pneumonia, the dogs had rhinitis, tracheitis, bronchitis, and bronchiolitis similar to that described in naturally infected dogs (Crawford et al., 2005). There was epithelial necrosis and erosion of the lining of the airways and bronchial glands with neutrophil and macrophage infiltration of the submucosal tissues (FIG. 5, upper panels). Immunohistochemistry detected viral H3 antigen in the epithelial cells of bronchi, bronchioles, and bronchial glands (FIG. 5, lower panels). No bacterial superinfection was present. The respiratory tissues from the 2 sham-inoculated dogs were normal.

Example 15

Virus Replication in Trachea and Lungs

The trachea and lungs were positive for virus by quantitative real-time RT-PCR in all dogs from 1 to 6 days p.i. (Table 12). The absolute number of influenza M gene copies per µL of trachea homogenate increased from 1 to 5 days p.i., then decreased on day 6. The absolute number of M gene copies per µL of lung homogenate decreased from 1 to 6 days p.i. In general, the trachea contained ≧one $\log_{10}$ more virus than the lung on each of the 6 days p.i.

TABLE 11

Detection of virus shedding in the oropharynx of mongrel dogs inoculated with canine influenza virus by quantitative real-time RT-PCR.

| Dog ID | Time p.i. (hours)[a] | M/GAPDH ratio[b] | Matrix gene (copies/uL)[c] |
|---|---|---|---|
| 860 | 72 | 1.20 | 1.57E+02 |
|  | 84 | 1.30 | 8.25E+02 |
|  | 120 | 1.23 | 1.47E+03 |
| 894 | 108 | 1.17 | 1.17E+02 |
|  | 120 | 1.41 | 1.37E+02 |
|  | 132 | 1.27 | 3.74E+02 |

[a]Time that oropharyngeal swabs were collected from the dogs following inoculation with A/canine/FL/43/04 (H3N8) virus.
[b]Normalization ratios were calculated by dividing the M (Ct) by the GAPDH (Ct) for each swab extract.
[c]The absolute number of matrix gene copies per uL of swab extract.

TABLE 12

Detection of virus replication in the trachea and lung of mongrel dogs inoculated with canine influenza virus by quantitative real-time RT-PCR.

| Dog ID | Time p.i. (hours)[a] | M/GAPDH ratio[b] | | Matrix gene (copies/uL)[c] | |
|---|---|---|---|---|---|
|  |  | Lung | Trachea | Lung | Trachea |
| 797 | 24 | 1.20 | 1.43 | 8.22E+05 | 3.11E+04 |
| 801 | 48 | 1.33 | 0.99 | 1.15E+05 | 6.52E+06 |
| 789 | 72 | 1.44 | 1.12 | 2.39E+04 | 1.56E+05 |
| 819 | 96 | 1.40 | 1.27 | 3.19E+04 | 1.43E+05 |

TABLE 12-continued

Detection of virus replication in the trachea and lung of mongrel dogs inoculated with canine influenza virus by quantitative real-time RT-PCR.

| Dog ID | Time p.i. (hours)[a] | M/GAPDH ratio[b] | | Matrix gene (copies/uL)[c] | |
|---|---|---|---|---|---|
| | | Lung | Trachea | Lung | Trachea |
| 860 | 120 | 1.59 | 1.04 | 3.48E+03 | 1.17E+06 |
| 894 | 144 | 1.70 | 1.15 | 4.78E+02 | 1.50E+03 |

[a]Time that tissues were collected from the dogs following inoculation with A/canine/FL/43/04 (H3N8) virus.
[b]Normalization ratios were calculated by dividing the M (Ct) by the GAPDH (Ct) for each tissue homogenate.
[c]The absolute number of matrix gene copies per uL of tissue homogenate.

MATERIALS AND EXAMPLES METHODS FOR EXAMPLE 16

Virus Strains

Canine influenza virus strains as well as those of avian, equine and human origin (listed in Table 15) were propagated in embryonated eggs or MDCK cells and their infectivity was titrated by endpoint dilution in chicken embryos, or plaque assay. Rapid virus quantification was performed by hemagglutination assay using turkey red blood cell erythrocytes.

Diagnostic Specimens

A Total of 60 canine's lung tissues collected from suspect cases of viral respiratory disease during the year of 2005 were tested for the presence of canine influenza virus.

RNA Extraction from Canine Tissue Samples

Blocks of lung tissue weighing between 20 and 30 mg were homogenized in a disposable tissue grinder (Kendal). Total RNA was extracted using a commercial kit (RNeasy Mini Kit, Qiagen, Valencia, Calif.) and eluted in a final volume of 60 μL, following the manufacturer's recommendations.

Primers and Probes Design

Multiple sequence alignments of the H3 and M genes from various subtypes and from diverse species were performed using the CLUSTAL X program (Version 1.8). Matrix (M) primers and probe were selected from the conserved regions of over the known sequences corresponding to different subtypes of influenza A virus, whereas the H3 hemagglutinin gene-specific primers and probe set were selected to specifically match equine and canine influenza A virus genes and mismatch the homologous avian and human genes (Table 13). Primer design software (OLIGOS Version 9.1) and the web based analysis tools provided by EXIQON (http://lna-tools.com) was used for Tm calculation and prediction of secondary structure as well as self hybridization. A conserved region of an 18S rRNA gene was used as endogenous internal control for the presence of RNA extracted from canine tissue sample. The Pre-Developed TaqMan® Assay Reagents for Eukaryotic 18S rRNA (VIC/TAMRA) (Applied Biosystems) was used for the real-time detection of 18S rRNA in tissue samples.

Real-time RT-PCR Condition

A single-step real-time RT-PCR was performed by using the Quantitect Probe RT-PCR Kit containing ROX as a passive reference dye (Qiagen, Valencia, Calif.). In each real-time RT-PCR reaction, 5 μL of RNA sample were used as a template to combine with a reaction mixture containing 10 μL of 2× QuantiTech Probe RT-PCR Master Mix, 0.2 μL of QuantiTech RT Mix, primers (0.4 μM final conc. for H3 gene or 0.6 μM final conc. for M gene), probe (0.1 μM final conc. for H3 gene or 0.2 μM final conc. for M gene) and RNase-free water in a final volume of 20 μL. One-step real-time RT-PCR was performed in the Mx3005P Real-Time QPCR System (Stratagene). Cycling conditions included a reverse transcription step at 50° C. for 30 minutes. After an initial denaturation step at 95° C. for 15 minutes in order to activate the HotStarTaq DNA polymerase, amplification was performed during 40 cycles including denaturation (94° C. for 15 seconds) and annealing/extension (60° C. for 30 seconds). The FAM (emission wavelength 516 nm for H3 and M detection) and VIC (emission wavelength 555 nm for 18S rRNA detection) fluorescent signals were obtained once per cycle at the end of the extension step. Data acquisition and analysis of the real-time PCR assay were performed using the Mx3005P software version 2.02 (Stratagene).

Specificity of H3 Primers/Probe Set for Canine Influenza (H3N8) and Universality of M Primers/Probe Set for Type A Influenza Virus In order to test the specificity of each primers/probe set, RNA extracted from several known subtypes of influenza A viruses were used as a template in the real-time RT-PCR assay (Table 15).

RNA Standard for Determination of the Real-Timer RT-PCR Performance

The genes of canine influenza A virus (A/canine/Florida/242/2003(H3N8)) were used to generate the PCR amplicons for H3 (nt 1-487) and M (nt 1-276) by using primers linked with T7 promoter (Table 13). Then the purified PCR amplicons of H3 and M genes were used as templates for in vitro transcription by using Riboprobe in vitro Transcription System-T7 (Promega) following the manufacturer's recommendations. The concentration of the transcribed RNAs was calculated by measuring absorbance at 260 nm. The RNAs were then serially diluted 10-fold, ranging from $10^8$ to 10 copies/μL to perform sensitivity tests. Moreover, a standard curve was generated by plotting the log of initial RNA template concentrations (copies/μL) against the threshold cycle (Ct) obtained from each dilution in order to determine the overall performance of real-time RT-PCR.

Comparative Sensitivity Tests Between Real-Time RT-PCR and Directigen Flu A Test Kit Stock viruses of two viral strains including A/Wyoming/3/2003 (H3N2) at $10^{6.67}$ $EID_{50}$/mL (HA=64) and A/canine/Florida/242/2003(H3N8) at $10^{7.17}$ $EID_{50}$/mL (HA=16) were used for the detection threshold assay. Logarithmic dilution of specimens in phosphate-buffered saline (PBS) (125 μL) were used in a rapid influenza A antigen detection kit, Directigen Flu A, (Becton, Dickinson and Company) following the manufacturer's instructions. Each Directigen Flu A test device has an H1N1 influenza antigen spot in the center of the membrane which develops as a purple dot and indicates the integrity of the test, which is based on a monoclonal antibody to the nucleoprotein (NP). The development of a purple triangle surrounding the dot is indicative of the presence of influenza NP in the tested specimen. The intensity of the purple signal from the triangle was scored as + (outline of triangle), ++ (lightly colored triangle), +++ (dark-purple triangle) and ++++ (very dark-purple triangle). Viral RNA was extracted 125 μL aliquots of each virus dilution by using QIAamp Viral RNA Mini Kit (Qiagen, Valencia, Calif.) and eluting in a final volume of 50 μL. A volume of 5 uL of the extracted viral RNAs were tested by real-time RT-PCR for comparative sensitivity test with Directigen Flu A kit.

Example 16

The real-time RT-PCR assay for canine influenza relies on information from three molecular probes which target 18S rRNA from host cell was well as M and H3 from the influenza A virus genome (Table 14). Amplification of the host gene is a reporter of specimen quality and integrity. Clinical, necropsy or laboratory samples containing canine influenza (H3N8) virus are expected to yield amplification signal with the three probes. Specimens yielding amplification signal with M and 18S rRNA probes but negative for H3 would be indicative of an influenza virus subtype H3 from human, swine or avian origin or from non-H3 subtypes. These rare cases could be resolved by RT-PCR using HA universal primers to generate amplicon cDNA that can be analyzed by sequencing. Properly collected and handled specimens lacking influenza A virus yield 18S rRNA amplification signal only. Situations in which only the 18S rRNA probe and the H3 probes yield amplification signal are indicative of faulty technique, unless proven otherwise; either a false negative with M probes or false positive for H3 need to be demonstrated. Finally, specimens failing to yield amplification signals with the three probes are indicative of defective sample collection, degradation, faulty RNA extraction or the presence of inhibitors the polymerases used in PCR.

In order to test the specificity of the H3 primers/probe set for canine influenza A virus (H3N8) and the universality of M primers/probe set for type A influenza, several subtypes of influenza A viruses were tested by real-time RT-PCR. The results show that H3 primers/probe set yielded a positive amplification signal only with canine influenza (H3N8). No significant false positive or non-specific amplification signals were observed in other subtypes or human H3 strains. The M primers/probe set yielded positive amplification signal with all of the strains tested (Table 15). These results indicated that H3 primers/probe specifically detects canine influenza A virus (H3N8) whereas M primers/probe detect multiple subtypes of type A influenza viruses.

Figures 6A, 6B:
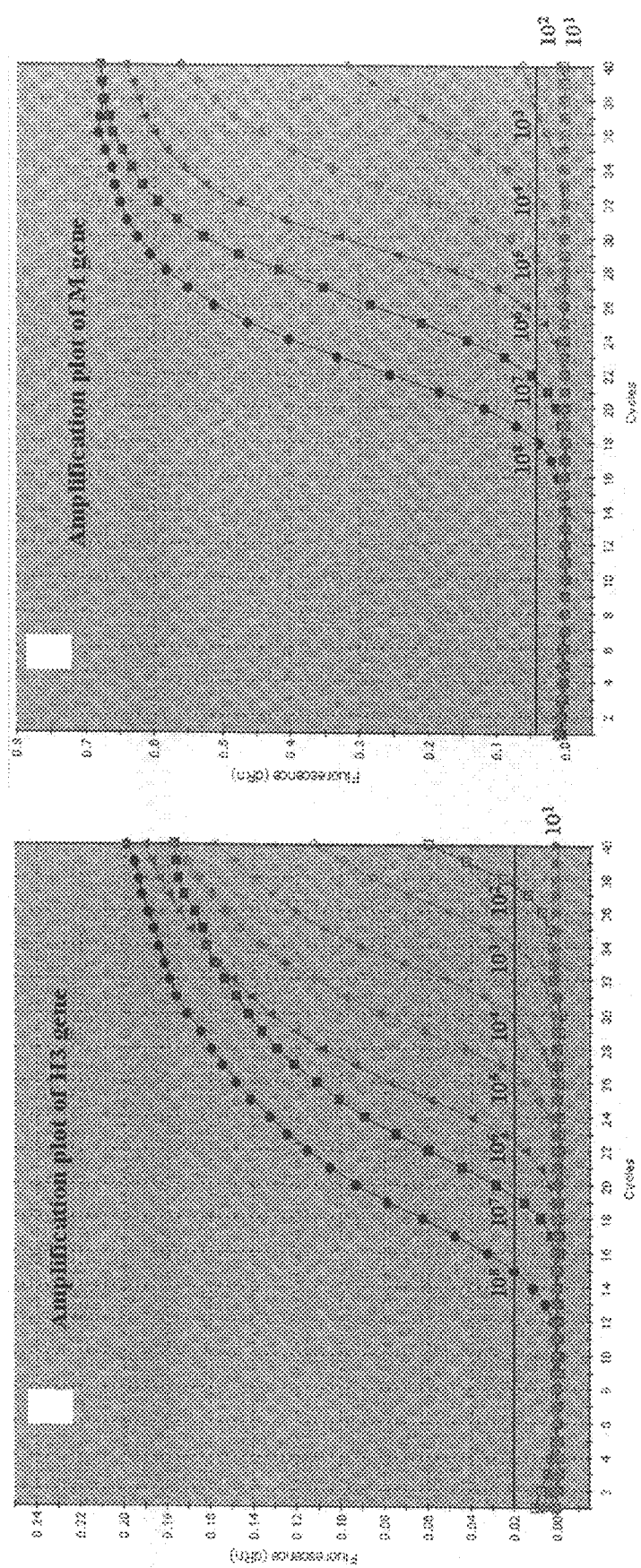
FIGS. 6A-6D show amplification plots of H3 and Matrix genes (FIG. 6A and FIG. 6B) obtained from the amplification of 10-fold serially diluted in vitro transcribed RNA standards. Standard curves of H3 and Matrix genes (FIG. 6C and FIG. 6D) constructed by plotting the log of starting RNA concentrations against the threshold cycle (Ct) obtained from each dilution.
Figures 6C, 6D:
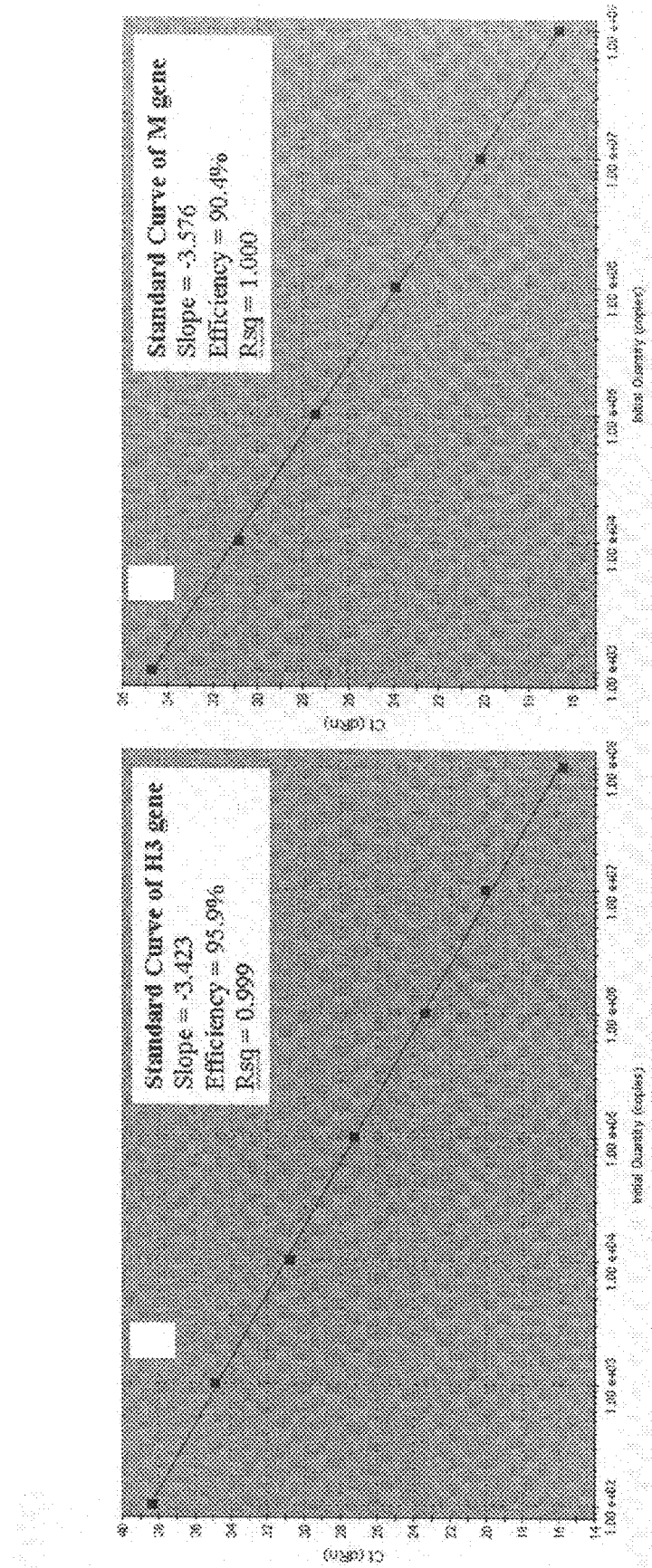

The performance of real-time RT-PCR assays was evaluated by endpoint dilution of M and H3 in vitro transcribed RNAs. As expected, the threshold cycle (Ct) increased in direct correlation with the dilution of the RNA standards. The fluorescent signals can be detected at RNA standard dilutions of M and H3 as low as $10^3$ and $10^2$ copies/µL, respectively (FIGS. 6A and 6B). The standard curves of M and H3 genes were constructed by plotting the log of starting RNA concentrations against the threshold cycle (Ct) obtained from each dilution (FIGS. 6C and 6D). The slope of the standard curve is used to determine the PCR reaction efficiency, which is theoretically exponential; 100% amplification efficiency would imply doubling of amplicon concentration each cycle. The standard curves with a slope between approximately –3.1 and –3.6 are typically acceptable for most applications requiring accurate quantification (90-110% reaction efficiency). An Rsq value is the fit of all data to the standard curve plot. If all the data lie perfectly on the line, the Rsq will be 1.00. As the data fall further from the line, the Rsq decreases. An Rsq value $\geq 0.985$ is acceptable for most assays. The M standard curve revealed a slope of –3.576 (efficiency=90.4%) and Rsq=1.00 whereas H3 standard curve yielded a slope of –3.423 (efficiency=95.9%) and Rsq=0.999. These values indicate satisfactory amplification efficiency and overall performance of the real-time RT-PCR assays. We attribute the lower efficiency and sensitivity of M primers/probe set as compared to H3 primers/probe set to the N-fold degeneracy of M primer sequences required to ensure broad coverage of M gene sequences variability across viruses of multiple subtypes, hosts and lineages.

Figure 7:
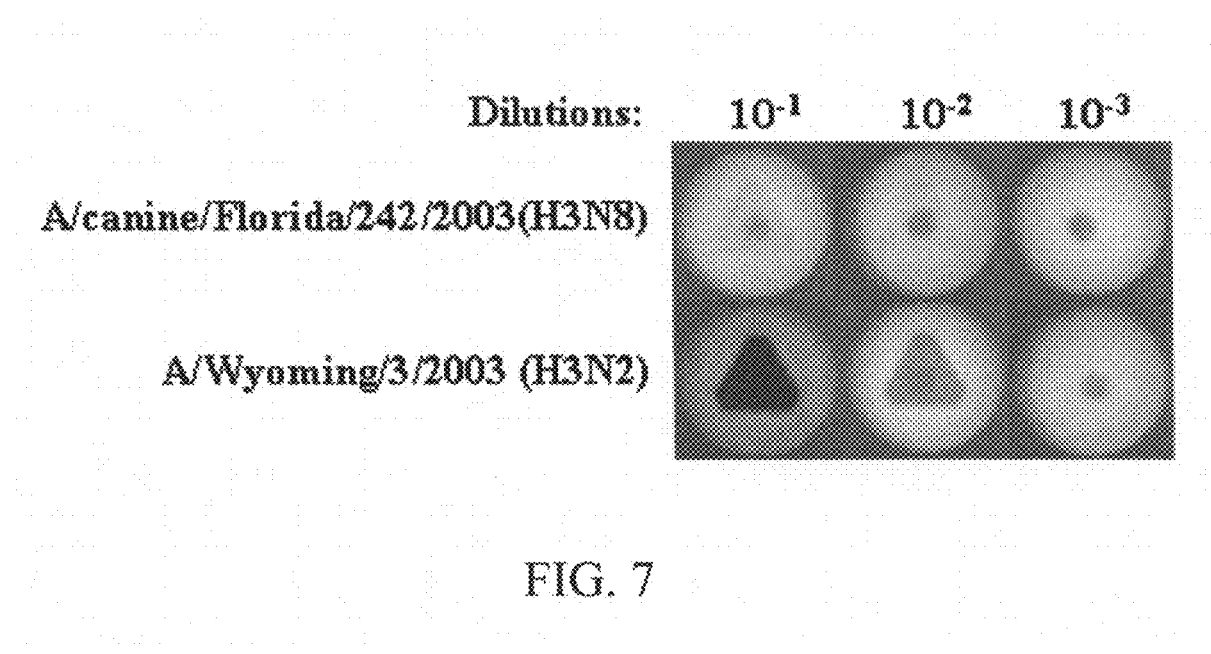
FIG. 7 shows sensitivity of Directigen Flu A was tested with 10-fold serially diluted virus stocks including A/Wyoming/3/2003 and A/canine/FL/242/2003. The purple triangle indicates positive result.

The sensitivity of real-time RT-PCR assay was also compared with the commercial rapid antigen detection assay (Directigen Flu A). Logarithmic dilutions of A/Wyoming/3/2003 (H3N2) and A/canine/Florida/242/2003(H3N8) were analyzed with Directigen Flu A and by real-time RT-PCR. The results of Directigen Flu A showed that the sensitivities against both viral strains are approximately 100-fold dilution from the stock viruses used in these experiments (FIG. 7). The signals (purple color) generated by the canine virus (A/canine/Florida/242/2003: $10^{6.x}$ PFU/ml) samples were much weaker than those found in human virus (A/Wyoming/3/2003: $10^{7.x}$ PFU/ml), in agreement with the lower virus concentration in these samples. Alternatively, lower signal for canine influenza could be attributed to the molecular specificity of monoclonal antibodies against the NP; i.e. poor conservation of the amino acids within the NP epitope of canine influenza A viruses.

Real-time RT-PCR of the M gene yielded Ct values above threshold with virus 10 and 30 PFU equivalents per reaction of A/canine/Florida/242/2003 and A/Wyoming/3/2003, respectively (Table 16). The differences between the sensitivity value of 2 viral strains because the differences in the original viral titers. The H3 gene detection comparison between canine and human influenza viruses was not performed because the H3 primers/probe in our realtime RT-PCR assay amplifies exclusively canine influenza A virus. RT-PCR was $10^5$ times more sensitive than the rapid antigen detection kit.

To evaluate the performance of the RT-PCR test in necropsy specimens from dogs with acute respiratory disease, sixty canine lung tissue samples submitted during the year of 2005 were tested for the presence of canine influenza A virus by real-time RT-PCR. A total of 12 out of 60 samples (20%) were positive with both M and H3 genes whereas the remaining 48 samples yielded negative result for both M and H3 gene. Virus isolation attempts were conducted by egg and MDCK cell inoculation, to evaluate the specificity of the realtime assay; 2 out 12 samples that were positive for canine influenza by RT-PCR yielded canine influenza virus (data not shown, manuscript in preparation). Although all of the tissues were collected from dogs with a history of severe respiratory disease, most of the samples yielded no canine influenza virus by either realtime PCR or conventional isolation, suggesting a high incidence of other respiratory pathogens such as *Bordetella bronchiseptica*, canine distemper or parainfluenza virus. The single step real-time RT-PCR assay herein provides a rapid, sensitive and cost-effective approach for canine influenza A virus (H3N8) detection. Rapid laboratory diagnosis of canine influenza A virus (H3N8) infections in the early stage of the disease can yield information relevant to clinical patient and facility management.

TABLE 13

Primers and probes used for real-time
RT-PCR detection and in vitro transcription

| Oligo name | Type | Target | Sequence * | Application |
|---|---|---|---|---|
| Ca-H3-F387 | Forward primer | H3 (nt 387-406) | 5'-tatgcatcgctccgatccat-3' (SEQ ID NO: 79) | Real-time PCR |

TABLE 13-continued

Primers and probes used for real-time
RT-PCR detection and in vitro transcription

| Oligo name | Type | Target | Sequence * | Application |
|---|---|---|---|---|
| Ca-H3-R487 | Reverse primer | H3 (nt 487-467) | 5'-gctccacttcttccgttttga-3' (SEQ ID NO: 80) | |
| Ca-H3-P430 | TaqMan probe | H3 (nt 430-459) | FAM-aattcacagcagagggattcacatggacag-BHQ1 (SEQ ID NO: 81) | |
| FluA-M-F151 | Forward primer | M (nt 151-174) | 5'-catggartggctaaagacaagacc-3' (SEQ ID NO: 82) | Real-time PCR |
| FluA-M-R276 | Reverse primer | M (nt 276-253) | 5'-agggcattttggacaaakcgtcta-3' (SEQ ID NO: 83) | |
| FluA-M-P218 | LNA TaqMan probe | M (nt 218-235) | FAM-acgcTcaccgTgcccAgt-BHQ1 (SEQ ID NO: 84) | |
| H3-F1 | Forward primer | H3 (nt 1-14) | 5'-tattcgtctcagggagcaaaagcagggg-3' (SEQ ID NO: 85) | In vitro transcription |
| T7/H3-R490 | Reverse primer | T7/H3 (nt 487-467) | 5'-tgtaatacgactcactatagggctccacttcttccgttttga-3' (SEQ ID NO: 86) | |
| M-F1 | Forward primer | M (nt 1-15) | 5'-gatcgctcttcagggagcaaaagcaggtag-3' (SEQ ID NO: 87) | In vitro transcription |
| T7/M-R276 | Reverse primer | M (nt 276-253) | 5'-tgtaatacgactcactatagggcattttggacaaagcgtc-3' (SEQ ID NO: 88) | |

* Note:
Uppercases = LNA (Locked Nucleic Acid) residues, r = a or g, k = g or t, underline = T7 promoter sequence

TABLE 14

Interpretation of the real-time RT-PCR assay

| | Results | | |
|---|---|---|---|
| Interpretation | M | H3 | 18S rRNA |
| Positive for canine influenza A virus (H3N8) | + | + | + |
| Positive for influenza A virus (unknown subtype) | + | − | + |
| Negative for influenza A virus | − | − | + |
| Error in RNA extraction or presence of PCR inhibitor | − | − | − |

TABLE 15

Specificity test of canine H3 primers/probe set and universality test of M primers/probe set with several subtypes of influenza A viruses

| | | | Real-time RT-PCR detection | |
|---|---|---|---|---|
| Subtypes | Strain Name | Host | H3 gene (Ct) | M gene (Ct) |
| H1 | A/Ohio/1983 | Human | No Ct | 15.40 |
| | A/WSN/1933 | Human | No Ct | 20.09 |
| H3 | A/Wyoming/3/2003 | Human | No Ct | 28.85 |
| | A/Victoria/3/1975 | Human | No Ct | 16.62 |
| | A/canine/FL/242/2003 | Canine | 28.43 | 29.25 |
| H4 | Turkey/MN/1066/1980 | Avian | No Ct | 17.49 |
| | Clinical sample* | Avian | No Ct | 20.87 |
| H5 | AChicken/Thailand/CUK2/2004 | Avian | No Ct | 20.13 |
| | A/Pheasant/NJ/1335/1998 | Avian | No Ct | 16.64 |
| H6 | Clinical sample* | Avian | No Ct | 19.52 |
| H10 | Clinical sample* | Avian | No Ct | 25.64 |
| | Clinical sample* | Avian | No Ct | 19.59 |
| H11 | Clinical sample* | Avian | No Ct | 15.72 |
| | Clinical sample* | Avian | No Ct | 24.55 |

*Note that subtypes of clinical samples were confirmed by nucleotide sequencing.

TABLE 16

Comparative sensitivity tests for influenza A virus detection between real-time RT-PCR and Directigen Flu A

| | Directigen Flu A | | Real-time RT-PCR of M (Ct) | |
|---|---|---|---|---|
| Virus dilutions | A/canine/242/03 | A/Wyoming/3/03 | A/canine/242/03 | A/Wyoming/3/2003 |
| $10^{-1}$ | ++ | ++++ | 22.42 | 19.48 |
| $10^{-2}$ | + | +++ | 25.85 | 22.66 |
| $10^{-3}$ | − | − | 29.27 | 25.76 |
| $10^{-4}$ | Not done | Not done | 32.66 | 28.66 |
| $10^{-5}$ | Not done | Not done | 35.48 | 33.14 |
| $10^{-6}$ | Not done | Not done | 37.51 | 35.06 |
| $10^{-7}$ | Not done | Not done | 39.09 | 36.44 |
| $10^{-8}$ | Not done | Not done | No Ct | 38.93 |

TABLE 17

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

TABLE 18

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |

TABLE 18-continued

| Letter Symbol | Amino Acid |
|---|---|
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

TABLE 19

Amino acid differences between PB2 proteins of H3N8 equine and canine influenza viruses

| Position | Equine Consensus* | Canine/FL/03 | Canine/FL/04 |
|---|---|---|---|
| 5 | K | K | E |
| 12 | S | L | L |
| 37 | G | G | E |
| 175 | R | R | I |
| 374 | L | I | I |
| 375 | R | R | K |
| 447 | Q | Q | H |

TABLE 20

Amino acid differences between PB1 proteins of H3N8 equine and canine influenza viruses

| Position | Equine Consensus* | Canine/FL/03 | Canine/FL/04 |
|---|---|---|---|
| 114 | V | I | I |
| 154 | D | G | G |
| 221 | A | T | T |
| 317 | M | I | I |
| 459 | I | I | V |
| 682 | I | I | V |

TABLE 21

Amino acid differences between PA proteins of H3N8 equine and canine influenza viruses

| Position | Equine Consensus* | Canine/FL/03 | Canine/FL/04 |
|---|---|---|---|
| 27 | D | N | N |
| 62 | I | V | V |
| 213 | R | K | K |
| 337 | A | T | T |
| 343 | A | E | E |
| 345 | L | I | I |
| 353 | K | R | R |
| 400 | T | T | A |
| 450 | V | I | I |
| 460 | M | M | I |
| 673 | R | R | K |
| 675 | N | D | D |

*Based on available genes of viruses isolated between 1963 and 1998.

TABLE 22

Amino acid differences between NP proteins of H3N8 equine and canine influenza viruses

| Position | Equine Consensus* | Canine/FL/03 | Canine/FL/04 |
|---|---|---|---|
| 16 | G | D | D |
| 157 | A | T | T |
| 214 | R | R | K |
| 285 | V | V | I |
| 286 | A | T | T |
| 359 | A | T | T |
| 375 | D | D | N |
| 384 | R | K | K |
| 452 | R | K | K |

TABLE 23

Amino acid differences between NA proteins of H3N8 equine and canine influenza viruses

| Position | Equine Consensus* | Canine/FL/03 | Canine/FL/04 |
|---|---|---|---|
| 9 | A/T | T | A |
| 12 | S | F | F |
| 20 | L | I | I |
| 40 | G | R | R |
| 42 | G | D | D |
| 46 | N | K | K |
| 52 | E | E | K |
| 61 | R | K | K |
| 69 | N | S | S |
| 72 | E | K | K |
| 201 | V | I | I |
| 261 | I | V | V |
| 301 | I | I | V |
| 396 | N | D | D |
| 397 | L | P | P |

TABLE 24

Amino acid differences between M1 proteins of H3N8 equine and canine influenza viruses

| Position | Equine Consensus* | Canine/FL/03 | Canine/FL/04 |
|---|---|---|---|
| M1 161 | S | S | A |
| M1 208 | K/Q | R | R |

*Based on available genes of viruses isolated between 1963 and 1998.

TABLE 25

Amino acid differences between NS1 proteins of H3N8 equine and canine influenza viruses

| Position | Equine Consensus* | Canine/FL/03 | Canine/FL/04 |
|---|---|---|---|
| 44 | K | R | R |
| 59 | R | H | H |
| 71 | E | K | K |
| 86 | A | T | T |
| 88 | R | R | L |
| 140 | R | G | G |
| 216 | P | S | S |

*Based on available genes of viruses isolated between 1963 and 1998.

Example 17

Canine Influenza Challenge Model Development

The canine influenza (canine flu) virus, which was isolated from flu outbreaks in Florida, was observed to be a H3N8 type influenza virus, and closely related to equine flu virus strain, A/equine/Ohio/03 (Crawford et al., SCIENCE Vol. 309, September 2005, incorporated by reference in its entirety into this patent). The potential of using the equine flu virus strain A/equine/Ohio/03 to induce influenza-like disease in dogs was investigated in this study.

Procedure:

Ten 13-week-old beagles of mixed sex were obtained from a commercial supplier, and housed in individual cages in a BSL-2 facility. The dogs were randomly assigned to two groups of 5 dogs each. As shown in Table 26, one group was subjected to a intratracheal challenge, and the other group was subjected to an oronasal challenge. The dogs were challenged at 14 weeks-of-age.

The dogs were observed for flu related clinical signs for 14 days post-challenge. Serum samples were collected from each dog on day zero (before challenge), and days 7 and 14 post-challenge for determining the HI titer using a H3N8 equine influenza virus with a standard protocol (SAM 124, CVB, USDA, Ames, Iowa). All dogs were humanely euthanized and lung tissues were collected in 10% buffered formalin for histopathological evaluation.

Results:

The results of this experiment are summarized in Table 27. Influenza related clinical signs were observed in a few dogs after challenge. These signs included fever (>103° F.; >39.4° C.) and cough. Two of 5 dogs (i.e., 40%) had fevers (>103° F.; >39.4° C.) in Group 1, compared to 1 of 5 (i.e., 20%) dogs in Group 2. One dog from the oronasal challenge group had sneezing, and another had cough following the challenge. An HI titer range from 10 to 80, with a geometric mean titer (GMT) of 20, was observed for Group 1. A titer range of 40 to 160, with a GMT of 86, was observed for Group 2. One dog from each group had histopathological lesions compatible with or pathognomic for influenza.

TABLE 27

Canine flu challenge - clinical signs, virus isolation, histopathology results and serology results

| Dog* ID | Challenge method* | Clinical signs | Virus isolation | | | Microscopic lesion (histopathology) | Serology (HI titer) | | |
| | | | Nasal/oral swab | Tracheal scraping | Lung tissues | | Pre-challenge | 7-days post challenge | 14-days post challenge |
|---|---|---|---|---|---|---|---|---|---|
| AAH | Intratracheal | none | negative | negative | negative | negative | 10 | 10 | 20 |
| ADB | Intratracheal | none | negative | negative | negative | negative | 10 | 80 | 20 |
| ADC | Intratracheal | Fever* | negative | negative | negative | negative | 10 | 20 | 20 |
| AEB | Intratracheal | Fever | negative | negative | negative | positive | 10 | 40 | 20 |
| AEE | Intratracheal | none | negative | negative | negative | inconclusive | 10 | 20 | 10 |
| AAE | Oronasal | none | negative | negative | negative | negative | 10 | 80 | 80 |
| AAG | Oronasal | none | negative | negative | negative | negative | 10 | 40 | 80 |
| ABY | Oronasal | Occasional sneeze, occasional cough | negative | negative | negative | positive | 10 | 80 | 160 |
| ADY | Oronasal | Fever, occasional sneeze | negative | negative | negative | negative | 10 | 80 | 80 |
| ADZ | Oronasal | none | negative | negative | negative | negative | 10 | 80 | 160 |

*The animals were challenged with an Equine flu isolate Ohio 03.
** Rectal temperature ≧103° F.; ≧39.4° C.

TABLE 26

Experimental Design

| Group | Number of Dogs | Challenge Route |
|---|---|---|
| 1 | 5 | Intratracheal |
| 2 | 5 | Oronasal |

A cell culture grown equine flu virus A/equine/Ohio/03 was used as the challenge virus. For intratracheal challenge, the challenge virus was administered via a delivery tube, which consisted of a cuffed tracheal tube (Size 4.0/4.5, Sheridan, USA) and feeding tube (size 5Fr, 1.7 mm, /16 inches in length, Kendall, USA) in 0.5 to 1.0 ml volume. For oronasal challenge, the challenge virus ($10^7$ to $10^8$ TCID50 per dog) was administered as a mist using a nebulizer (DeVilbiss ULTRA-NEB99 ultrasonic nebulizer, Sunrise Medical, USA) in a 2 to 3 ml volume.

Example 18

Efficacy of an Equine Influenza Virus Vaccine for Dogs

The canine influenza (canine flu) virus isolated from flu outbreaks in Florida was observed to be a H3N8 type influenza virus, and was closely related to equine flu virus, A/equine/Ohio/03 based on the sequence similarity. The following study was conducted to determine the efficacy of an experimental inactivated equine influenza virus vaccine.

Procedure:

Nine 7-week-old beagles of mixed sex were obtained from a commercial supplier, and housed in individual cages in a BSL-2 facility. These dogs were randomly assigned to two groups, as summarized in Table 28:

TABLE 28

Experimental Design

| Group | Number of Dogs | Treatment |
|---|---|---|
| 1 | 5 | Vaccine |
| 2 | 4 | Control |

The first group consisted of 5 dogs, which were vaccinated with an inactivated, CARBIGEN™ (MVP Laboratories, Inc., Omaha, Nebr.) adjuvanted, equine flu virus A/equine/Ohio/03 vaccine at 8 and 12 weeks-of age via subcutaneous (SQ) route. The A/equine/Ohio/03 was inactivated by binary ethylenimine ("BEI") using a standard method. Each dose of the vaccine contained 5% by mass CARBIGEN™, 4096 HA units of the inactivated virus, sufficient PBS to bring the total volume of the dose to 1 ml, and sufficient NaOH to adjust the pH to between 7.2 and 7.4. Serum samples were collected from all dogs on the day of first and second vaccination and day 7 and 14, post-first and -second vaccination, and at pre-challenge for determining the HI titer using a H3N8 equine influenza virus a standard protocol (SAM 124, CVB, USDA, Ames, Iowa). At 3 weeks post-second vaccination, the 5 vaccinated dogs and the second group (i.e., the control group) consisting of 4 age-matched dogs were challenged oronasally with a cell-culture-grown equine influenza virus A/equine/Ohio/03 ($10^{7.0}$ to $10^{8.0}$ TCID50 per dog) in a 1-2 ml volume per dose. The challenge virus was administered to the dogs as a mist using a nebulizer (DeVilbiss Ultra-Neb99 ultrasonic nebulizer, Sunrise Medical, USA). The dogs were observed for flu-related clinical signs for 14 days post-challenge. Five dogs (3 vaccinates and 2 controls) 7 days post-challenge and 4 dogs (2 controls and 2 vaccinates) 14 days post-challenge were humanely euthanized for collection of lung tissues in 10% buffered formalin for histopathological evaluation.

Results:

The results of this experiment are summarized in Tables 29 and 30. All vaccinated dogs seroconverted following the vaccination. An HI titer range from 40 to 640, with the GMT of 129, was observed during the post-vaccination period with equine influenza virus A/equine/Ohio/03, and a HI titer of 160 to 320, with a geometric mean titer of 211, was observed with canine flu isolate, A/canine/Florida/242/03. Two of 6 vaccinates had a fever of >103° F. (>39.4° C.) for one day and no other clinical signs were observed in any of the dogs following challenge.

Conclusion:

All the vaccinated dogs responded to the inactivated, CARBIGEN™ adjuvanted equine influenza vaccine. The HI titer results with a canine influenza virus isolate suggest that the inactivated equine influenza vaccine did induce a detectable level of cross reactive antibody to canine influenza virus. Even though the challenge virus used in this did not induce any noticeable clinical disease in beagle dogs, based on the HI titer with a canine influenza virus isolate, it was concluded that inactivated equine vaccine could be used in dogs to induce cross reactive antibodies, which could potentially protect dogs against "canine flu" disease caused by H3N8 type canine influenza viruses.

TABLE 29

Serology - Pre- and post-vaccination and post-challenge HI titers

| | | | HI titers | | | | | | |
|---|---|---|---|---|---|---|---|---|---|
| | | | Post-1$^{st}$ vaccination | | Post-2$^{nd}$ vaccination | | | Post-challenge* | |
| Dog* | Group | Pre-vaccination | 7-d | 14-d | 7-d | 14-d | 21-d | 7-d | 14-d |
| AKT | Vaccinate** | <10 | 40 | 80 | 640 | 640 | 640 | 320 | 320 |
| ALH | Vaccinate** | <10 | 40 | 80 | 320 | 160 | 160 | 80 | *** |
| ALU | Vaccinate** | <10 | 40 | 80 | 320 | 160 | 160 | 80 | 80 |
| ANJ | Vaccinate** | <10 | 40 | 80 | 320 | 160 | 80 | 320 | *** |
| ANU | Vaccinate** | <10 | 40 | 80 | 320 | 160 | 80 | 160 | *** |
| AJW | Control | <10 | <10 | <10 | <10 | <10 | <10 | 10 | *** |
| AKR | Control | <10 | <10 | <10 | <10 | <10 | <10 | 10 | *** |
| ALZ | Control | <10 | <10 | <10 | <10 | <10 | <10 | 20 | 20 |
| ARC | Control | <10 | <10 | <10 | <10 | <10 | <10 | 10 | 10 |

*The animals were challenged with an equine flu isolate Ohio 03
**CARBIGEN ™ adjuvanted inactivated equine flu virus Ohio 03 vaccine was used for vaccination
*** Euthanized 7-days post-challenge

TABLE 30

Canine flu challenge* - clinical signs, virus isolation, histopathology results

| | | | Virus isolation | | | |
|---|---|---|---|---|---|---|
| Dog ID | Treatment group | Clinical signs | Nasal swab | Tracheal scraping | Lung tissues | Microscopic lesion (histopathology) |
| AKT | Vaccinate** | none | negative | negative | negative | negative |
| ALH | Vaccinate** | none | negative | negative | negative | negative |
| ALU | Vaccinate** | none | negative | negative | negative | negative |
| ANJ | Vaccinate** | none | negative | negative | negative | negative |
| ANU | Vaccinate** | none | negative | negative | negative | negative |
| AJW | Control | none | negative | negative | negative | negative |
| AKR | Control | none | negative | negative | negative | negative |

TABLE 30-continued

Canine flu challenge* - clinical signs, virus isolation, histopathology results

| Dog ID | Treatment group | Clinical signs | Virus isolation | | Lung tissues | Microscopic lesion (histopathology) |
| | | | Nasal swab | Tracheal scraping | | |
|---|---|---|---|---|---|---|
| ALZ | Control | none | negative | negative | negative | negative |
| ARC | Control | none | negative | negative | negative | negative |

*The animals were challenged with an Equine flu isolate Ohio 03
**CARBIGEN ™ adjuvanted inactivated equine flu virus Ohio 03 vaccine was used for vaccination Example 19

Efficacy of an Equine Influenza Virus Vaccine for Dogs

The canine influenza virus isolated from flu outbreaks in Florida was characterized is closely related to a number of H3N8 type equine influenza virus isolates. By DNA and amino acid sequence similarity analysis it was demonstrated that the canine influenza virus is very similar to an equine influenza virus, A/equine/Ohio/03. The following study was conducted in dogs to determine the efficacy of commercially available equine influenza vaccines in dogs.

Procedure:

Approximately 16 month old, 20 mongrels and 20 beagles of mixed sex were used in the study. The dogs were randomly assigned to 6 groups (Table 31) of 6-7 dogs each. Dogs in groups 1 and 4 were vaccinated with a commercially available inactivated, adjuvanted equine influenza vaccine (EQUICINE ™, Intervet Inc., Millsboro, Del.) at 16 and 17 months of age via subcutaneous (SQ) route. The dogs in groups 2 and 5 were vaccinated with a modified live equine/Kentucky/91 influenza vaccine in a 1 ml volume via intranasal route (single nostril). Blood samples were collected on the day of vaccination, day 7 and 14 post first vaccination (groups 1, 2, 4, and 5) and post second vaccination (groups 1 and 4) for determining the HI titer using an H3N8 equine influenza virus and a canine influenza virus using per a standard protocol (SAM 124, CVB, USDA, Ames, Iowa).

Vaccinates (at 72 days post final vaccination) and the controls were challenged oronasally with a cell-culture grown equine influenza virus strain A/equine/Ohio/03 ($10^{7.0}$ to $10^{8.0}$ TCID50 per dog) in a 1-2 ml volume. The challenge virus was administered to the dogs as mist using a nebulizer (DeVilbiss ULTRA-NEB 99 ultrasonic nebulizer, Sunrise Medical, USA). The dogs were observed for influenza-related clinical signs for 12 days post-challenge. The nasal and oropharyngeal swabs were collected in Earl's MEM medium with antibiotics (neomycin and polymyxin B) daily from day −1 to day 12 post challenge for virus isolation. The presence of virus in the swabs indicates that the animal is excreting the virus in nasal/oral secretions. All dogs were humanely euthanized on day 12 post-challenge and lung tissues were collected in 10% buffered formalin for histopathological evaluation.

TABLE 31

Experimental design

| Group | Number of dogs | Breed | Treatment | Number of doses | Route of vaccination |
|---|---|---|---|---|---|
| 1 | 7 | Beagle | EQUICINE II ™** | 2 | Subcutaneous |
| 2 | 7 | Beagle | A/KY/91*** | 1 | Intranasal |
| 3 | 6 | Beagle | Control | N/A* | N/A* |
| 4 | 7 | Mongrel | EQUICINE II ™ | 2 | Subcutaneous |
| 5 | 7 | Mongrel | A/KY/91 | 1 | Intranasal |
| 6 | 6 | Mongrel | Control | N/A* | N/A* |

*Not applicable
**EQUICINE II ™ is marketed by Intervet Inc. as a liquid vaccine. EQUICINE II ™ contains inactivated A/Pennsylvania/63 influenza (or "A/Pa/63") virus and A/equine/Kentucky/93 influenza (or "A/KY/93") virus with carbopol (i.e., HAVLOGEN ® (Intervet Inc.)). More specifically, a dose of EQUICINE II ™ contains: inactivated A/Pa/63 at $10^{6.0}$ EID$_{50}$, inactivated A/KY/93 at $10^{6.7}$ EID$_{50}$, 0.25% by volume carbopol, and sufficient PBS to create a total volume of 1 ml.
***A/KY/91 is a freeze-dried vaccine that was reconstituted with water. Such reconstitution was conducted using vaccine-grade water sufficient to bring the vaccine dosage to a total volume of 1 ml. The vaccine contained equine/Kentucky/91 influenza (or "A/KY/91") virus, and is discussed in, for example, U.S. Pat. Nos. 6,436,408; 6,398,774; and 6,177,082, which are incorporated by reference in their entirety into this patent. When reconstituted, a dose of the vaccine contained A/KY/91 at $10^{7.2}$ TCID$_{50}$ per ml, 0.015 grams N-Z AMINE AS ™ per ml, 0.0025 grams gelatin per ml, and 0.04 grams D lactose per ml. N-Z AMINE AS ™ is a refined source of amino acids and peptides produced by enzymatic hydrolysis of casein. N-Z AMINE AS ™ is marketed by Kerry Bio-Science (Norwich, NY, USA).

Results:

All vaccinated dogs seroconverted following the vaccination and the HI titers ranged from 10 to 80 for EQUICINE II™ vaccine group dogs compared to 10 to 40 for the A/KY/91 vaccine group dogs using an equine influenza virus (H3N8 type).

The samples collected at 2 weeks post vaccination (post second vaccination for EQUICINE II™ vaccine) were analyzed for HI titer determination with a canine influenza as well as with an equine influenza virus (H3N8 type). The HI results are shown in Table 32. The clinical signs include fever (>103° F.; >39.4° C.), occasional cough, and mild nasal discharge observed following the challenge.

TABLE 32

Serology - HI titers at 2 weeks post vaccination

| | | | | HI titer with | | | |
| | | | | Equine influenza virus | | Canine influenza virus | |
| Group | Number of dogs | Breed | Treatment | Range | GMT | Range | GMT |
|---|---|---|---|---|---|---|---|
| 1 | 7 | Beagle | Equicine II ™ | 10-80 | 36 | 10-80 | 33 |
| 2 | 7 | Beagle | A/KY/91 | 10-20 | 12 | 20-160 | 54 |
| 3 | 6 | Beagle | Control | N/A* | N/A* | N/A* | N/A* |
| 4 | 7 | Mongrel | Equicine II ™ | 40-80 | 54 | 40-80 | 50 |

TABLE 32-continued

Serology - HI titers at 2 weeks post vaccination

| | | | | HI titer with | | | |
|---|---|---|---|---|---|---|---|
| | Number of | | | Equine influenza virus | | Canine influenza virus | |
| Group | dogs | Breed | Treatment | Range | GMT | Range | GMT |
| 5 | 7 | Mongrel | A/KY/91 | 10-40 | 24 | 40-80 | 49 |
| 6 | 6 | Mongrel | Control | N/A* | N/A* | N/A* | N/A* |

*Not applicable

Among beagles, 2 of 6 dogs in the EQUICINE II™ vaccine group (Group 1), 1 of 7 dogs in the A/KY/91 vaccine group (Group 2) and 2 of 6 dogs in the control group (Group 3) had fever. One of 6 dogs in Group 3 (control) was positive for virus in the cell culture supernatant of nasal swab material by hemagglutination assay with 0.25% chicken red blood cells (CRBC). One of 6 dogs in the control group (Group 3) and 1 of 7 dogs in the A/KY/91 vaccine group (Group 2) had mild nasal discharge during the post challenge observation period. There was no statistical significant difference (P>0.05) between control and vaccine groups for beagle dogs.

Among mongrels, 5 of 7 dogs in the EQUICINE II™ vaccine group (Group 4), 1 of 7 dogs in the A/KY/91 vaccine group (Group 5) and 5 of 6 dogs in the control group (Group 6) had fever. One dog from each of Group 4 and 6 had a mild nasal discharge, and one dog from Group 5 had an occasional cough. Two of 7 dogs in the EQUICINE II™ vaccine group (Group 4) and 3 of 6 dogs in the control group (Group 6) were positive for influenza virus in the nasal swab by HA assay. None of the dogs from the A/KY/91 group (Group 5) were positive for influenza virus in the nasal swab materials.

Conclusion:

By serology, it was demonstrated that vaccination of dogs with commercially available equine influenza vaccines stimulated a moderate level influenza antibody response. There may be some breed difference in development of influenza-related clinical signs in dogs following a challenge with H3N8 type influenza virus. The live attenuated equine influenza vaccine (A/KY/91) provided a significant (P<0.05) protection from clinical disease development in rectal temperature in mongrels. Also, the live attenuated viral vaccine prevented the shedding of influenza virus in the nasal secretions.

Example 20

Canine Influenza Challenge Model Development

In view of reports that inducing disease in canines for purposes of study had not proven successful, the potential for using a canine influenza virus, H3N8, to develop a canine influenza challenge model in dogs was investigated in the following study.

Procedure:

Ten mongrels of mixed sex were obtained from a commercial supplier, and housed in cages in a BSL-2 facility. The dogs were randomly assigned to two groups of 5 dogs each. As shown in Table 33, one group was subjected to an intratracheal/intranasal challenge, and the other group was subjected.

TABLE 33

Experimental design

| Group | Number of dogs | Challenge route |
|---|---|---|
| 1 | 5 | Intratracheal/intranasal |
| 2 | 5 | Oronasal |

The dogs were challenged at approximately 12 weeks-of-age. Embryonated-chicken-egg grown canine influenza virus (A/canine/Florida/242/03) virus was used as challenge virus. Each dog received a total of approximately $10^{7.2}$ TCID50 of virus in either 2 ml (for oronasal route) or 4 ml (intratracheal/intranasal route) volume.

For intratracheal/intranasal challenge, 3 ml of the challenge virus was administered into the trachea first, followed by 5 ml of PBS using a delivery tube, which consisted of a cuffed tracheal tube (Size 4.5/5.0, Sheridan, USA) and feeding tube (size 5Fr, 1.7 mm; 16 inches (41 cm) in length, Kendall, USA), and a 1 ml challenge virus, followed by 3 ml of atmospheric air was administered into nostrils using a syringe.

For oronasal challenge, the challenge virus was administered as a mist using a nebulizer (NEBULAIR™, DVM Pharmaceuticals, Inc., Miami, Fla.) in approximately 2 ml volume. The dogs were observed for flu-related clinical signs for 14 days post-challenge. The dogs were euthanized at day 14 post challenge, and tissue (lung and trachea) samples were collected in 10% buffered formalin for histopathological examination.

Results:

All dogs in groups 1 and 2 developed canine influenza clinical signs within 24 to 48 hours. Each dog had 2 or more of the following clinical signs: fever (>103.0° F.; >39.4° C.), cough, serous or mucopurulent ocular discharge, serous or mucopurulent nasal discharge, vomiting, diarrhea, depression, weight loss, gagging, hemoptysis, and audible rales. Lung tissues from 5 of 5 dogs from group 1 and 4 of 5 dogs from group 2 had histopathological lesions which included one or more of the following: diffuse suppurative bronchopneumonia, bronchitis/bronchiolitis with plugs of neutrophilic exudate in the lumina and marked mononuclear cell aggregation in mucosa and peribronchiolar tissue, mixed exudate within alveoli with large numbers of foamy macrophages, lymphocellular and plasma cellular as well as granulocytic cell infiltration, and thickening of alveolar septa with proliferation of type II pneumocytes compatible with or pathognomic to an influenza virus infection. The trachea tissue samples were normal.

Conclusion:

An H3N8 canine influenza isolate such as the one used in this study may be used for inducing canine influenza disease in dogs using one of the methods described in this study or a similar method.

Example 21

Canine Influenza Challenge Model Development

The potential for using a canine influenza virus, H3N8, to develop a canine influenza challenge model in dogs was further investigated in the following study.

Procedure:

Fifteen 17- to 18-week-old mongrels and five 15-week-old beagles were obtained from commercial suppliers, and were housed in cages in a BSL-2 facility. The mongrels were randomly assigned to 3 groups (Groups 1 to 3) of 5 dogs each. All beagles were assigned to one group (Group 4) as shown in Table 34:

TABLE 34

Experimental design

| Group | Breed | Number of dogs | Challenge virus dose |
|---|---|---|---|
| 1 | Mongrels | 5 | $10^{6.8}$ TCID$_{50}$ |
| 2 | Mongrels | 5 | $10^{5.8}$ TCID$_{50}$ |
| 3 | Mongrels | 5 | $10^{4.8}$ TCID$_{50}$ |
| 4 | Beagles | 5 | $10^{6.8}$ TCID$_{50}$ |

The dogs were challenged oronasally with a virulent canine influenza virus, A/Canine/Florida/242/2003 (isolated from lung of a greyhound dog with canine influenza disease (provided by Dr. Cynda Crawford at the University of Florida)). The challenge virus was administered as a mist using a nebulizer (NEBULAIR™) in approximately 2 ml volume. The dogs were observed for flu-related clinical signs for 14 days post-challenge.

Results:

Eighty percent (4 of 5) of the dogs in Group 1 and 4, 100% of the dogs in Group 2 and 3, developed canine influenza clinical signs within 48 hours. Each dog had one or more of the following clinical signs: fever (>103.0° F.; >39.4° C.), cough, serous or mucopurulent ocular discharge, serous or mucopurulent nasal discharge, vomiting, diarrhea, depression, weight loss, gagging, and rales. The clinical signs observed in beagles were generally milder and short-course compared to mongrels.

Conclusion:

An H3N8 canine influenza isolate such as the one used in this study may be used for inducing canine-influenza-like or kennel-cough-like disease in dogs using method described in this study or a similar method with a challenge dose range from 104.8 to 106.8 TCID50. There were some differences in clinical signs observed in mongrels and beagles. In general, beagles tend to have milder flu-related clinical signs compared to mongrels.

Example 22

Canine Influenza Vaccine Efficacy Study

The following study was conducted to assess the efficacy of an H3N8 equine influenza vaccine in dogs against canine influenza virus.

Procedure:

Seventeen 14-week-old mongrels and ten 8-week-old beagles were obtained from commercial suppliers. The dogs were randomly assigned to 5 groups as shown in Table 35, and housed in a research facility.

TABLE 35

Experimental design

| Group | Age | Number of dogs | Treatment | Number of doses | Age at Vaccination (weeks) |
|---|---|---|---|---|---|
| 1 | 14 weeks | 7 | Vaccinate | 2 | 14 & 18 |
| 2 | 14 weeks | 5 | Vaccinate | 1 | 18 |
| 3 | 14 weeks | 5 | Control | — | — |
| 4 | 8 weeks | 5 | Vaccinate | 2 | 8 & 12 |
| 5 | 8 weeks | 5 | Control | — | — |

The vaccine used in this study was a HAVLOGEN®-adjuvanted, inactivated equine influenza virus (A/equine/KY/02) vaccine. To prepare this vaccine, the virus was inactivated by binary ethylenimine (BEI) using a standard method. Each vaccine dose contained HAVLOGEN® (10% v/v), 6144 HA units of the inactivated virus, 0.1% (v/v) of 10% thimerosal, 0.1% (v/v) of phenol red, sufficient NaOH to adjust the pH to from 6.8 to 7.2, and sufficient PBS to bring the total dose volume to 1 ml.

The dogs in Groups 1 and 4 were vaccinated with 2 doses of the vaccine. The second dose (i.e., the booster) was administered 4 weeks after the first. The dogs in Group 2 were vaccinated with 1 dose at 18 weeks-of-age. Blood samples were collected to assess HI titer using a standard protocol (e.g., SAM 124, CVB, USDA, Ames, Iowa) with an H3N8 canine influenza isolate on days zero (before vaccination), 7, and 14 post first and second vaccinations. Approximately 5 days before challenge, the dogs were moved to a BSL-2 facility and housed in individual cages.

All vaccinates and age-matched control dogs were challenged oronasally with a virulent canine influenza virus ($10^{7.7}$ TCID50 of A/Canine/Florida/242/2003 per dog) at 2 weeks post second vaccination of Groups 1 and 4 and first vaccination of Group 2. The challenge virus was administered as a mist using a nebulizer (NEBULAIR™) at 2 ml per dog. The dogs were observed for influenza-related clinical signs for 17 days post-challenge. Nasal and oropharygeal swabs were collected in tubes containing 2 ml of virus transport medium for virus isolation from day −1 (i.e., one day before challenge) to day 17 days post-challenge. All dogs were euthanized at day 17 post-challenge and lung and tracheal samples were collected in 10% buffered formalin for histopathology. Blood samples were collected on days 7 and 14 post challenge for HI titer determination. The clinical sign score assignments used for the post challenge observation are shown in Table 36.

Results:

All dogs in 2-dose vaccination groups (Group 1 and 4) developed HI antibody titer responses to the canine influenza virus isolate (Table 37). Following the challenge, approximately a 4-fold increase in titer on day 14 post challenge in all groups indirectly indicated that all dogs were exposed to the challenge virus. All dogs exhibited one or more of the following signs of canine influenza: fever (>103.0° F.; >39.4° C.), cough, serous or mucopurulent ocular discharge, serous or mucopurulent nasal discharge, vomiting, diarrhea, depression, weight loss, and dyspnea. Vaccinates had less severe clinical signs, compared to age-matched controls (Table 38). There was a significant reduction in clinical signs due to the 2-dose vaccination in both 8-week-old (P=0.040) and 14-week-old (P=0.003) dogs (Groups 4 and 1 respectively). In this experiment, one-dose vaccination did not provide a significant (P=0.294) reduction in clinical signs (Group 2)

Virus isolation results are shown in Table 39. Among 14-week-old dogs, canine influenza virus was isolated from swab samples collected from 2 of 7 dogs (29%) from the 2-dose vaccine group (Group 1), 3 of 5 dogs (60%) from the 1-dose vaccine group (Group 2), and 5 of 5 dogs (100%) from the control group (Group 3). Among 8-week-old dogs, the virus was isolated from 1 of 5 dogs (20%) from the 2-dose vaccine group (Group 4), and 4 of 5 dogs (80%) from the control group (Group 5). There was a significant reduction (P=0.003) in the number of dogs positive for canine influenza virus in swab samples due to 2-dose vaccination (Groups 1 and 4) compared to unvaccinated controls (Groups 3 and 5). Although there was a reduction in the number of dogs (60% vs. 100%) positive for canine influenza virus in swab samples between 1-dose vaccine group (Group 2) and the control group (Group 3), the difference was not statistically significant (P=0.222).

Histopathological evaluation of lung and tracheal tissue samples for lesions was conducted to identify lesions compatible with or pathognomic to canine influenza disease. This includes, for example, determination of whether one or more of the following exist: areas with suppurative bronchopneumonia; peribronchitis/peribronchiolitis with mononuclear cell aggregation (lymphocytes, plasma cells); presence of plugs of granulocytic cellular debris in the lumina; hyperplasia of respiratory epithelium; mixed exudate in the alveoli with large amount of granulocytic cells and cell debris; aggregates of (foamy) macrophages, plasma cells, and lymphocytes; and thickening of alveolar septa with proliferation of type II pneumocytes.

Table 40 provides a summary of the extent of lesions in this experiment for the dogs. Among 14-week-old dogs, the lung lesions were less extensive and less severe in 5 of 7 dogs in the 2-dose vaccination group (Group 2), and 4 of 5 dogs in the 1-dose vaccination group (Group 1). All controls dogs (Group 3) had severe and extensive lesions suggestive of no protection. There was no difference in tracheal lesions due to 1- or 2-dose vaccination among 14-week-old dogs. Among 8-week-old dogs, there was no difference in lung lesions between 2-dose vaccinates and control dogs. None of the dogs had any tracheal lesions.

Conclusion:

The results from this study demonstrate that: (1) inactivated H3N8 equine influenza virus can induce canine influenza virus cross reactive HI antibody responses in vaccinated dogs, (2) use of an H3N8 equine influenza virus vaccine can reduce the severity of canine influenza virus disease in dogs, and (3) use of an H3N8 equine influenza virus vaccine can reduce virus excretion in nasal and/or oral secretions.

TABLE 36

Clinical signs and scoring system

| Clinical signs | Score per day |
|---|---|
| Temp | |
| <103.0° F. (<39.4° C.) | 0 |
| 103.0-103.9° F. (39.4- | 2 |
| 104.0-104.9° F. (40.0-40.5° C.) | 3 |
| >105.0° F. (>40.6° C.) | 4 |

TABLE 36-continued

Clinical signs and scoring system

| Clinical signs | Score per day |
|---|---|
| Coughing | |
| No coughing | 0 |
| Occasional | 2 |
| Paroxysmal | 4 |
| Sneezing | |
| No sneezing | 0 |
| Occasional | 1 |
| Paroxysmal | 2 |
| Nasal discharge | |
| No discharge | 0 |
| Serous-slight | 1 |
| Serous-copious | 1 |
| Mucopurulent-slight | 2 |
| Mucopurulent-copious | 3 |
| Ocular discharge | |
| No discharge | 0 |
| Serous-slight | 1 |
| Serous-copious | 1 |
| Mucopurulent-slight | 2 |
| Mucopurulent-copious | 3 |
| Hemoptysis | |
| No | 0 |
| Yes | 5 |
| Depression | |
| No | 0 |
| Yes | 1 |
| Anorexia | |
| No | 0 |
| Yes | 1 |
| Respiratory signs | |
| None | 0 |
| Rales | 3 |
| Dyspnea | 4 |
| Gasping | 5 |
| Mucous expectorate | |
| No | 0 |
| Yes | 2 |
| Vomiting | |
| No | 0 |
| Yes | 1 |
| Fecal abnormalities | |
| No | 0 |
| Yes | 1 |

TABLE 37

Serology - Hemagglutination inhibition titers

| Group No | Dog ID | Age (week) | Treatment | Number of doses | HI titer: Days post first vaccination of Groups 1 and 4: 0* | 7 | 14 | 28** | 35 | 42*** | Days post challenge: 7 | 14 |
|---|---|---|---|---|---|---|---|---|---|---|---|---|
| 1 | 921 | 14 | Vaccinate | 2 | <10 | <10 | 10 | 20 | 40 | 20 | 160 | 320 |
| 1 | 926 | 14 | Vaccinate | 2 | <10 | <10 | <10 | 40 | 40 | 80 | 80 | >640 |
| 1 | 931 | 14 | Vaccinate | 2 | <10 | <10 | <10 | 10 | 20 | 20 | 80 | >640 |
| 1 | 955 | 14 | Vaccinate | 2 | <10 | <10 | <10 | 10 | 40 | 40 | 160 | 320 |
| 1 | 011 | 14 | Vaccinate | 2 | <10 | <10 | <10 | 10 | 20 | 40 | 160 | 320 |
| 1 | 013 | 14 | Vaccinate | 2 | <10 | <10 | <10 | 20 | 40 | 40 | 160 | 320 |
| 1 | 019 | 14 | Vaccinate | 2 | <10 | <10 | <10 | 10 | 20 | 40 | 80 | >640 |
| 2 | 922 | 14 | Vaccinate | 1 | <10 | <10 | <10 | <10 | <10 | <10 | >640 | >640 |
| 2 | 953 | 14 | Vaccinate | 1 | <10 | <10 | <10 | <10 | <10 | <10 | 320 | >640 |

TABLE 37-continued Serology - Hemagglutination inhibition titers

| Group No | Dog ID | Age (week) | Treatment | Number of doses | HI titer — Days post first vaccination of Groups 1 and 4 | | | | | | HI titer — Days post challenge | |
|---|---|---|---|---|---|---|---|---|---|---|---|---|
| | | | | | 0* | 7 | 14 | 28** | 35 | 42*** | 7 | 14 |
| 2 | 015 | 14 | Vaccinate | 1 | <10 | <10 | <10 | <10 | <10 | <10 | 320 | >640 |
| 2 | 016 | 14 | Vaccinate | 1 | <10 | <10 | <10 | <10 | <10 | <10 | 160 | 320 |
| 2 | 017 | 14 | Vaccinate | 1 | <10 | <10 | <10 | <10 | <10 | <10 | 320 | >640 |
| 3 | 923 | 14 | Control | N/A | <10 | <10 | <10 | <10 | <10 | <10 | 40 | 160 |
| 3 | 012 | 14 | Control | N/A | <10 | <10 | <10 | <10 | <10 | <10 | 40 | 320 |
| 3 | 014 | 14 | Control | N/A | <10 | <10 | <10 | <10 | <10 | <10 | 40 | 160 |
| 3 | 018 | 14 | Control | N/A | <10 | <10 | <10 | <10 | <10 | <10 | 40 | 160 |
| 3 | 01A | 14 | Control | N/A | <10 | <10 | <10 | <10 | <10 | <10 | 40 | 160 |
| 4 | 406 | 8 | Vaccinate | 2 | <10 | <10 | 10 | 40 | 80 | 80 | 160 | >640 |
| 4 | 407 | 8 | Vaccinate | 2 | <10 | 20 | 20 | 40 | 40 | 40 | 320 | >640 |
| 4 | 504 | 8 | Vaccinate | 2 | <10 | <10 | 10 | 20 | 20 | 80 | 160 | >640 |
| 4 | 704 | 8 | Vaccinate | 2 | <10 | <10 | 10 | 40 | 80 | 160 | 160 | >640 |
| 4 | 705 | 8 | Vaccinate | 2 | <10 | <10 | <10 | 40 | 80 | 160 | 160 | >640 |
| 5 | 404 | 8 | Control | N/A | <10 | <10 | <10 | <10 | <10 | <10 | 80 | 160 |
| 5 | 405 | 8 | Control | N/A | <10 | <10 | <10 | <10 | <10 | <10 | 80 | 80 |
| 5 | 610 | 8 | Control | N/A | <10 | <10 | <10 | <10 | <10 | <10 | 20 | 40 |
| 5 | 702 | 8 | Control | N/A | <10 | <10 | <10 | <10 | <10 | <10 | 80 | 160 |
| 5 | 703 | 8 | Control | N/A | <10 | <10 | <10 | <10 | <10 | <10 | 40 | 160 |

*First vaccination - Groups 1 and 4
**Second vaccination - Groups 1 and 4; First vaccination - Group 2
***Day of challenge

TABLE 38

Analysis of total canine influenza disease clinical scores

| Group | Treatment | Number of doses of vaccine | Age at first vaccination of Groups 1 and 4 | Average total Score per dog | P-value* |
|---|---|---|---|---|---|
| 1 | Vaccinate | 2 | 14 weeks | 8.7 | 0.003 (Group 1 vs. 3) |
| 2 | Vaccinate | 1 | 14 weeks (these dogs were vaccinated once, when they were 18 weeks old) | 21.8 | 0.294 (Group 2 vs. 3) |
| 3 | Control | — | 14 weeks (these dogs were not vaccinated) | 25.4 | — |
| 4 | Vaccinate | 2 | 8 weeks | 2.0 | 0.040 (Group 4 vs. 5) |
| 5 | Control | — | 8 weeks (these dogs were not vaccinated) | 5.4 | — |

*Analyzed using a NPAR1WAY procedure of SAS ® Version 8.2 (the vaccine groups were compared using the Wilcoxon rank sum test)

TABLE 39

Virus shedding

| Group No | Dog ID | Age (week) | Treatment | Number of vaccine doses | Days post-challenge | | | | | | | | | | | | | | | | |
|---|---|---|---|---|---|---|---|---|---|---|---|---|---|---|---|---|---|---|---|---|---|
| | | | | | -1 | 0 | 1 | 2 | 3 | 4 | 5 | 6 | 7 | 8 | 9 | 10 | 11 | 12 | 13 | 14 | 15 | 16 | 17 |
| 1 | 921 | 14 | Vaccinate | 2 | N | N | N | N | N | N | N | N | N | N | N | N | N | N | N | N | N | N | N |
| 1 | 926 | 14 | Vaccinate | 2 | N | N | N | N | N | N | N | N | N | N | N | N | N | N | N | N | N | N | N |
| 1 | 931 | 14 | Vaccinate | 2 | N | N | N | N | N | N | N | N | N | N | N | N | N | N | N | N | N | N | N |
| 1 | 955 | 14 | Vaccinate | 2 | N | N | N | N | N | N | N | N | N | N | N | N | N | N | N | N | N | N | N |
| 1 | 011 | 14 | Vaccinate | 2 | N | N | P | N | N | P | N | N | N | N | N | N | N | N | N | N | N | N | N |
| 1 | 013 | 14 | Vaccinate | 2 | N | N | N | N | N | P | N | N | N | N | N | N | N | N | N | N | N | N | N |
| 1 | 019 | 14 | Vaccinate | 2 | N | N | N | N | N | N | N | N | N | N | N | N | N | N | N | N | N | N | N |
| 2 | 922 | 14 | Vaccinate | 1 | N | N | N | N | N | N | N | N | N | N | N | N | N | N | N | N | N | N | N |
| 2 | 953 | 14 | Vaccinate | 1 | N | N | N | N | N | N | N | N | N | N | N | N | N | N | N | N | N | N | N |
| 2 | 015 | 14 | Vaccinate | 1 | N | N | N | P | N | P | P | N | N | N | N | N | N | N | N | N | N | N | N |
| 2 | 016 | 14 | Vaccinate | 1 | N | N | N | P | N | P | P | N | N | N | N | N | N | N | N | N | N | N | N |
| 2 | 017 | 14 | Vaccinate | 1 | N | N | N | N | P | P | N | N | N | N | N | N | N | N | N | N | N | N | N |
| 3 | 923 | 14 | Control | N/A | N | N | N | N | N | P | N | N | N | N | N | N | N | N | N | N | N | N | N |
| 3 | 012 | 14 | Control | N/A | N | N | N | P | N | P | N | N | N | N | N | N | N | N | N | N | N | N | N |

TABLE 39-continued

Virus shedding

| Group No | Dog ID | Age (week) | Treatment | Number of vaccine doses | -1 | 0 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|---|---|---|
| | | | | | | | | | | | Days post-challenge | | | | | | | | | | | | |
| 3 | 014 | 14 | Control | N/A | N | N | P | N | N | P | P | N | N | N | N | N | N | N | N | N | N | N | N |
| 3 | 018 | 14 | Control | N/A | N | N | N | P | P | P | N | N | N | N | N | N | N | N | N | N | N | N | N |
| 3 | 01A | 14 | Control | N/A | N | N | N | P | P | P | P | N | N | N | N | N | N | N | N | N | N | N | N |
| 4 | 406 | 8 | Vaccinate | 2 | N | N | N | N | N | N | N | N | N | N | N | N | N | N | N | N | N | N | N |
| 4 | 407 | 8 | Vaccinate | 2 | N | N | N | N | N | N | N | N | N | N | N | N | N | N | N | N | N | N | N |
| 4 | 504 | 8 | Vaccinate | 2 | N | N | N | P | N | N | N | N | N | N | N | N | N | N | N | N | N | N | N |
| 4 | 704 | 8 | Vaccinate | 2 | N | N | N | N | N | N | N | N | N | N | N | N | N | N | N | N | N | N | N |
| 4 | 705 | 8 | Vaccinate | 2 | N | N | N | N | N | N | N | N | N | N | N | N | N | N | N | N | N | N | N |
| 5 | 404 | 8 | Control | N/A | N | N | P | P | N | P | N | N | N | N | N | N | N | N | N | N | N | N | N |
| 5 | 405 | 8 | Control | N/A | N | N | P | N | N | N | P | N | N | N | N | N | N | N | N | N | N | N | N |
| 5 | 610 | 8 | Control | N/A | N | N | N | N | N | N | N | N | N | N | N | N | N | N | N | N | N | N | N |
| 5 | 702 | 8 | Control | N/A | N | N | N | P | N | N | N | N | N | N | N | N | N | N | N | N | N | N | N |
| 5 | 703 | 8 | Control | N/A | N | N | N | N | N | N | P | N | N | N | N | N | N | N | N | N | N | N | N |

TABLE 40

Histopathological evaluation of tissue samples

| Group No | Dog ID | Age (week) | Treatment | Number of doses | Microscopic lesion (Histopathology) Lungs | Trachea |
|---|---|---|---|---|---|---|
| 1 | 921 | 14 | Vaccinate | 2 | +/− | − |
| 1 | 926 | 14 | Vaccinate | 2 | − | +/− |
| 1 | 931 | 14 | Vaccinate | 2 | − | − |
| 1 | 955 | 14 | Vaccinate | 2 | +/− | − |
| 1 | 011 | 14 | Vaccinate | 2 | +/− | − |
| 1 | 013 | 14 | Vaccinate | 2 | +/− | +/− |
| 1 | 019 | 14 | Vaccinate | 2 | +/− | +/− |
| 2 | 922 | 14 | Vaccinate | 1 | +/− | − |
| 2 | 953 | 14 | Vaccinate | 1 | +/− | +/− |
| 2 | 015 | 14 | Vaccinate | 1 | +/− | + |
| 2 | 016 | 14 | Vaccinate | 1 | − | − |
| 2 | 017 | 14 | Vaccinate | 1 | +/− | +/− |
| 3 | 923 | 14 | Control | N/A | + | +/− |
| 3 | 012 | 14 | Control | N/A | + | − |
| 3 | 014 | 14 | Control | N/A | + | − |
| 3 | 018 | 14 | Control | N/A | + | − |
| 3 | 01A | 14 | Control | N/A | + | +/− |
| 4 | 406 | 8 | Vaccinate | 2 | +/− | − |
| 4 | 407 | 8 | Vaccinate | 2 | − | − |
| 4 | 504 | 8 | Vaccinate | 2 | +/− | − |
| 4 | 704 | 8 | Vaccinate | 2 | − | − |
| 4 | 705 | 8 | Vaccinate | 2 | − | − |
| 5 | 404 | 8 | Control | N/A | − | − |
| 5 | 405 | 8 | Control | N/A | − | − |
| 5 | 610 | 8 | Control | N/A | +/− | − |
| 5 | 702 | 8 | Control | N/A | +/− | − |
| 5 | 703 | 8 | Control | N/A | − | − |

"+" Severe lesion consistent or pathognomic to an influenza infection
"+/−" Mild lesion (inconclusive)
"−" Normal Example 23

Canine Influenza Vaccine Efficacy Study

The following study was conducted to determine the efficacy of a multivalent H3N8 equine influenza vaccine against canine influenza virus in dogs.

Procedure:

Seventeen 15-week-old beagles were obtained from a commercial supplier. The dogs were randomly assigned to 3 groups as shown in Table 41, and housed in a research facility.

TABLE 41

Experimental design

| Group | Number of dogs | Treatment | Number of doses | Age at Vaccination (weeks) |
|---|---|---|---|---|
| 1 | 7 | Vaccinate | 2 | 15 & 19 |
| 2 | 5 | Vaccinate | 1 | 19 |
| 3 | 5 | Control | — | — |

The vaccine used in this study was a HAVLOGEN® adjuvanted, inactivated equine influenza (A/equine/KY/02, A/equine/KY/93, and A/equine/NM/2/93) vaccine. To prepare this vaccine, the viruses were inactivated by binary ethylenimine (BEI) using a standard method. Each vaccine dose contained HAVLOGEN® (10% v/v), 2048 HA units of each of the inactivated virus, 0.1% (v/v) of 10% thimerosal, 0.1% (v/v) of phenol red, sufficient NaOH to adjust the pH to 6.8 to 7.2, and sufficient PBS to bring the total dose volume to 1 ml.

The dogs in Group 1 were vaccinated with 2 doses of the vaccine. The second (i.e., booster) dose was administered 4 weeks after the first dose. The dogs in Group 2 were vaccinated with 1 dose of vaccine at 19 weeks-of-age. Blood samples were collected to assess HI titer using a standard protocol with an H3N8 canine influenza isolate on days zero (before vaccination), 7, and 14 post first and second vaccinations. Seven days before challenge, the dogs were moved to a BSL-2 facility and housed in individual cages.

All vaccinates and age-matched control dogs were challenged oronasally with a virulent canine influenza virus ($10^{7.3}$ TCID50 of A/Canine/Florida/242/2003 per dog) at 2 weeks post second vaccination of Group 1 and first vaccination of Group 2. The challenge virus was administered as a mist using a nebulizer (NEBULAIR™) at 2 ml per dog. The dogs were observed for influenza-related clinical signs for 14 days post challenge. All dogs were euthanized at day 14 post-challenge, and lung and trachea samples were collected in 10% buffered formalin for histopathology. Blood samples were collected on days 7 and 14 post challenge for HI titer determination. The clinical sign score assignments used for the post challenge observation are shown in Table 42.

Results:

All vaccinated dogs developed HI antibody titer responses to the canine influenza virus isolate (Table 43). Following the challenge, approximately a 4 fold increase in HI titer on day 14 post challenge compared to the pre-challenge HI titer in all groups indirectly indicate that all dogs were exposed to the challenge virus. All dogs exhibited signs canine influenza disease with each dog demonstrating one or more of the following clinical signs: fever (>103.0° F.; >39.4° C.), cough, serous or mucopurulent ocular discharge, serous or mucopurulent nasal discharge, vomiting, diarrhea, depression, weight loss, and dyspnea. Vaccinates had less severe clinical signs, compared to age-matched controls (Table 44). There was a significant (P=0.028) reduction in clinical signs due to the 2-dose vaccination in dogs (Group 1). One dose vaccination did not provide a significant (P=0.068) reduction in clinical signs (Group 2).

As in Example 22, histopathological evaluation of lung and tracheal tissue samples for lesions was conducted to identify lesions compatible with or pathognomic to canine influenza disease. Table 45 provides a summary of the extent of lesions in this experiment for the dogs. Among 15-week-old dogs, vaccination of dogs with either 1 dose or 2 doses prevented the lung lesions in all dogs. Four of 5 control dogs (80%) had severe suppurative bronchopneumonia consistent with an influenza disease. One of 7 dogs from the 2-dose vaccine group (Group 1) and 1 of 5 dogs from the control group (Group 3) had mild trachea lesions suggestive of tracheitis which could be attributed to influenza disease.

Conclusion:

The results from this study demonstrate that 1) inactivated H3N8 equine influenza virus can induce canine influenza virus cross reactive HI antibody responses in vaccinated dogs, and 2) Use of a H3N8 equine influenza virus vaccine can reduce the severity of canine influenza virus disease in dogs.

TABLE 42

Clinical signs and scoring system

| Clinical signs | Score per day |
|---|---|
| Temp | |
| <103.0° F. (<39.4° C.) | 0 |
| 103.0-103.9° F. (39.4- | 2 |
| 104.0-104.9° F. (40.0- | 3 |
| >105.0° F. (>40.6° C.) | 4 |
| Coughing | |
| No coughing | 0 |
| Occasional | 2 |
| Paroxysmal | 4 |

TABLE 42-continued

Clinical signs and scoring system

| Clinical signs | Score per day |
|---|---|
| Sneezing | |
| No sneezing | 0 |
| Occasional | 1 |
| Paroxysmal | 2 |
| Nasal discharge | |
| No discharge | 0 |
| Serous-slight | 1 |
| Serous-copious | 1 |
| Mucopurulent-slight | 2 |
| Mucopurulent-copious | 3 |
| Ocular discharge | |
| No discharge | 0 |
| Serous-slight | 1 |
| Serous-copious | 1 |
| Mucopurulent-slight | 2 |
| Mucopurulent-copious | 3 |
| Hemoptysis | |
| No | 0 |
| Yes | 5 |
| Depression | |
| No | 0 |
| Yes | 1 |
| Anorexia | |
| No | 0 |
| Yes | 1 |
| Respiratory signs | |
| None | 0 |
| Rales | 3 |
| Dyspnea | 4 |
| Gasping | 5 |
| Mucous expectorate | |
| No | 0 |
| Yes | 2 |
| Vomiting | |
| No | 0 |
| Yes | 1 |
| Fecal abnormalities | |
| No | 0 |
| Yes | 1 |

TABLE 43

Serology - Hemagglutination inhibition titers

| Group | | | Number of | HI titer | | | | | | | |
|---|---|---|---|---|---|---|---|---|---|---|---|
| | | | | Days post first vaccination of Group 1 | | | | | | Days post challenge | |
| No | Dog ID | Treatment | doses | 0* | 7 | 14 | 28** | 35 | 42*** | 7 | 14 |
| 1 | ALK | Vaccinate | 2 | <10 | <10 | 20 | 20 | 80 | 40 | 160 | 320 |
| 1 | AMF | Vaccinate | 2 | <10 | <10 | 10 | 20 | 20 | 40 | 160 | 320 |
| 1 | AKY | Vaccinate | 2 | <10 | 20 | 20 | 20 | 40 | 40 | 160 | 80 |
| 1 | ALC | Vaccinate | 2 | <10 | 10 | 10 | 10 | 40 | 40 | 160 | 160 |
| 1 | ALL | Vaccinate | 2 | <10 | <10 | 10 | 10 | 40 | 20 | 160 | 320 |
| 1 | ALM | Vaccinate | 2 | <10 | <10 | 10 | 20 | 40 | 40 | 80 | 160 |
| 1 | AMU | Vaccinate | 2 | <10 | 20 | 40 | 40 | 40 | 40 | 40 | 160 |
| 2 | ALA | Vaccinate | 1 | <10 | <10 | <10 | <10 | <10 | 10 | 320 | 160 |
| 2 | AMA | Vaccinate | 1 | <10 | <10 | <10 | <10 | <10 | 20 | >640 | 80 |
| 2 | APD | Vaccinate | 1 | <10 | <10 | <10 | <10 | <10 | 10 | >640 | 320 |
| 2 | APG | Vaccinate | 1 | <10 | <10 | <10 | <10 | <10 | 10 | 320 | 80 |
| 2 | APT | Vaccinate | 1 | <10 | <10 | <10 | <10 | <10 | 10 | 320 | 320 |

TABLE 43-continued

Serology - Hemagglutination inhibition titers

| Group | | | Number of | HI titer | | | | | | Days post challenge | |
|---|---|---|---|---|---|---|---|---|---|---|---|
| | | | | Days post first vaccination of Group 1 | | | | | | | |
| No | Dog ID | Treatment | doses | 0* | 7 | 14 | 28** | 35 | 42*** | 7 | 14 |
| 3 | ALT | Control | N/A | <10 | <10 | <10 | <10 | <10 | <10 | 40 | 160 |
| 3 | AMS | Control | N/A | <10 | <10 | <10 | <10 | <10 | <10 | 80 | 160 |
| 3 | AKX | Control | N/A | <10 | <10 | <10 | <10 | <10 | <10 | 20 | 80 |
| 3 | ALX | Control | N/A | <10 | <10 | <10 | <10 | <10 | <10 | 80 | 80 |
| 3 | AMI | Control | N/A | <10 | <10 | <10 | <10 | <10 | <10 | 40 | 80 |

*First vaccination - Group 1
**Second vaccination - Group 1; First vaccination - Group 2
***Day of challenge

TABLE 44

Analysis of total canine influenza disease clinical scores

| Group | Treatment | Number of doses | Age at first vaccination of Group 1 | Average total Score per dog | P-value* |
|---|---|---|---|---|---|
| 1 | Vaccinate | 2 | 15 weeks | 6.3 | 0.028 (Group 1 vs. 3) |
| 2 | Vaccinate | 1 | 15 weeks (these dogs were vaccinated once, when they were 19 weeks old) | 14.2 | 0.068 (Group 2 vs. 3) |
| 3 | Control | — | 15 weeks (these dogs were not vaccinated) | 24.4 | — |

*Analyzed using a NPAR1WAY procedure of SAS ® Version 8.2 (the vaccine groups were compared using the Wilcoxon rank sum test)

TABLE 45

Histopathological evaluation of tissue samples

| Group | | | Number of | Microscopic lesion (Histopathology) | |
|---|---|---|---|---|---|
| No | Dog ID | Treatment | doses | Lung | Trachea |
| 1 | ALK | Vaccinate | 2 | − | +/− |
| 1 | AMF | Vaccinate | 2 | − | − |
| 1 | AKY | Vaccinate | 2 | − | − |
| 1 | ALC | Vaccinate | 2 | − | − |
| 1 | ALL | Vaccinate | 2 | − | − |
| 1 | ALM | Vaccinate | 2 | − | − |
| 1 | AMU | Vaccinate | 2 | − | − |
| 2 | ALA | Vaccinate | 1 | − | − |
| 2 | AMA | Vaccinate | 1 | − | − |
| 2 | APD | Vaccinate | 1 | − | − |
| 2 | APG | Vaccinate | 1 | − | − |
| 2 | APT | Vaccinate | 1 | − | − |
| 3 | ALT | Control | N/A | +/− | − |
| 3 | AMS | Control | N/A | + | − |
| 3 | AKX | Control | N/A | + | − |
| 3 | ALX | Control | N/A | + | +/− |
| 3 | AMI | Control | N/A | − | − |

"+" Severe lesion consistent or pathognomic to an influenza infection
"+/−" Mild lesions (inconclusive)
"−" Normal Example 24

Canine Influenza Vaccine Efficacy Study

The following study was conducted to determine: (1) the efficacy of monovalent versus multivalent H3N8 equine influenza vaccines against canine influenza virus in dogs, and (2) the effect of route of administration on vaccine efficacy.
Procedure:

Thirty 10-week old mongrels were obtained from a commercial supplier. The dogs were randomly assigned to 6 groups as shown in Table 46, and housed in a research facility.

TABLE 46

Experimental design

| Group | Number of dogs | Treatment | Route of vaccination | Number of doses | Age at Vaccination (weeks) |
|---|---|---|---|---|---|
| 1 | 5 | VAX-1 | IN | 2 | 10 & 14 |
| 2 | 5 | VAX-2 | SQ | 2 | 10 & 14 |
| 3 | 5 | VAX-2 | IN | 2 | 10 & 14 |
| 4 | 5 | VAX-3 | SQ | 2 | 10 & 14 |
| 5 | 5 | VAX-3 | N | 2 | 10 & 14 |
| 6 | 5 | Control | — | — | — |

Three types of vaccines (VAX-1, VAX-2, and VAX-3) were used. The VAX-1 was a HAVLOGEN®-adjuvanted, inactivated equine influenza virus (A/equine/KY/02) monovalent vaccine, and each dose contained HAVLOGEN® (10% v/v), 6144 HA units of the inactivated virus, 0.1% (v/v) of 10% thimerosal, 0.1% (v/v) of phenol red, sufficient NaOH to adjust the pH to 6.8 to 7.2, and sufficient PBS to bring the total dose volume to 1 ml. The VAX-2 was a HAVLOGEN®-adjuvanted, inactivated equine influenza virus (A/equine/KY/02) monovalent vaccine, and each dose of vaccine contained HAVLOGEN® (10% v/v), 4096 HA units of the inactivated virus, 0.1% (v/v) of 10% thimerosal, 0.1% (v/v) of phenol red, sufficient NaOH to adjust the pH to 6.8 to 7.2, and sufficient PBS to bring the total dose volume to 1 ml. The VAX-3 was a HAVLOGEN®-adjuvanted, inactivated equine influenza (A/equine/KY/02, A/equine/KY/93, and A/equine/NM/2/93) multivalent vaccine, and contained HAVLOGEN® (10% v/v), 2048 HA units of inactivated virus per strain, 0.1% (v/v) of 10% thimerosal, 0.1% (v/v) of phenol red, sufficient NaOH to adjust the pH to 6.8 to 7.2, and sufficient PBS to bring the total dose volume to 1 ml. All influenza viruses used for the vaccine formulation were inactivated by binary ethylenimine (BEI) using a standard method.

The vaccines and routes of administration for each group are described in Table 46. All dogs in the vaccinated groups were vaccinated either via the intranasal (IN) or the subcutaneous (SQ) route, and each dog received 2 doses. The second (i.e., booster) dose was administered 4 weeks after the first dose. Blood samples were collected to assess HI titer using a standard protocol with an H3N8 canine influenza isolate on days zero (before vaccination), 7, and 14 post first and second vaccinations. Seven days before challenge, the dogs were moved to a BSL-2 facility and housed in individual cages.

All vaccinates and age-matched control dogs were challenged oronasally with a virulent canine influenza virus ($10^{7.4}$ TCID50 of A/Canine/Florida/242/2003 per dog) at 2 weeks post second vaccination. The challenge virus was administered as a mist using a nebulizer (NEBULAIR™) in a 2 ml volume per day. The dogs were observed for influenza-related clinical signs for 14 days post-challenge. Blood samples were collected on days 7 and 14 post challenge for HI titer determination. All dogs were euthanized at day 14 post-challenge, and lung and trachea samples were collected in 10% buffered formalin for histopathology. The clinical sign score assignments used for the post challenge observation are shown in Table 47.

Results:

All dogs vaccinated via the SQ route developed HI antibody titer responses to the canine influenza virus isolate, regardless of the vaccine type (Table 48). None of the dogs from the IN vaccination groups (i.e., Groups 1, 3, and 5) developed HI antibody titer responses to the canine influenza virus isolate, regardless of the vaccine type, during the post vaccination period. There was, however, a 4-fold increase in titer by day 14 post challenge in all dogs indirectly, indicating that all dogs were exposed to the challenge virus (Table 47).

All dogs exhibited one or more of the following clinical signs of canine influenza: fever (>103.0° F.; >39.4° C.), cough, serous or mucopurulent ocular discharge, serous or mucopurulent nasal discharge, vomiting, diarrhea, depression, weight loss, and dyspnea. Vaccinates had less severe clinical signs, compared to age-matched controls (Table 49). There was a significant reduction in clinical signs in dogs vaccinated with VAX-3 via the SQ route (Group 4). In this experiment, IN administration of either VAX-1, VAX-2, or VAX-3 did not provide a significant reduction in clinical signs of canine influenza virus.

As in Examples 22 and 23, histopathological evaluation of lung and tracheal tissue samples for lesions was conducted to identify lesions compatible with or pathognomic to canine influenza disease. Table 50 provides a summary of the extent of lesions in this experiment for the dogs. Five of 5 control dogs (Group 6) had lung lesions consistence with an influenza infection. Two of 5 dogs vaccinated with VAX-2 via the SC route (Group 2) and 3 of 5 dogs vaccinated with VAX-3 via the SC route (Group 4) were free of any influenza-related lung lesions. All the dogs that received the vaccine via the intranasal route, irrespective of the vaccine type, had severe lung lesions consistent with an influenza infection. The trachea lesions observed in this study were very mild.

Conclusion:

The results from this study demonstrate that: (1) inactivated H3N8 equine influenza virus can induce canine influenza virus cross reactive HI antibody responses in dogs vaccinated via the SQ route, (2) intranasal administration of either monovalent (VAX-1 and VAX-2) or multivalent vaccine (VAX-3) was not efficacious in dogs, and (3) subcutaneous administration of multivalent vaccine (VAX-3) provided a significant (P=0.016) reduction in severity of canine influenza virus disease in dogs.

TABLE 47

Clinical signs and scoring system

| Clinical signs | Score per day |
|---|---|
| Temp | |
| <103.0° F. (<39.4° C.) | 0 |
| 103.0-103.9° F. (39.4- | 2 |
| 104.0-104.9° F. (40.0- | 3 |
| >105.0° F. (>40.6° C.) | 4 |
| Coughing | |
| No coughing | 0 |
| Occasional | 2 |
| Paroxysmal | 4 |
| Sneezing | |
| No sneezing | 0 |
| Occasional | 1 |
| Paroxysmal | 2 |
| Nasal discharge | |
| No discharge | 0 |
| Serous-slight | 1 |
| Serous-copious | 1 |
| Mucopurulent-slight | 2 |
| Mucopurulent-copious | 3 |
| Ocular discharge | |
| No discharge | 0 |
| Serous-slight | 1 |
| Serous-copious | 1 |
| Mucopurulent-slight | 2 |
| Mucopurulent-copious | 3 |
| Hemoptysis | |
| No | 0 |
| Yes | 5 |
| Depression | |
| No | 0 |
| Yes | 1 |
| Anorexia | |
| No | 0 |
| Yes | 1 |
| Respiratory signs | |
| None | 0 |
| Rales | 3 |
| Dyspnea | 4 |
| Gasping | 5 |
| Mucous expectorate | |
| No | 0 |
| Yes | 2 |
| Vomiting | |
| No | 0 |
| Yes | 1 |
| Fecal abnormalities | |
| No | 0 |
| Yes | 1 |

TABLE 48

Serology - Hemagglutination inhibition titers

| Group No | Dog ID | Treatment | Route of vaccination | Number of doses | HI titer Days post vaccination 0* | 7 | 14 | 28** | 35 | 42*** | Days post challenge 7 | 14 |
|---|---|---|---|---|---|---|---|---|---|---|---|---|
| 1 | 248 | Vaccinate | IN | 2 | <10 | <10 | <10 | <10 | <10 | <10 | 80 | 40 |
| 1 | 501 | Vaccinate | IN | 2 | <10 | 10 | <10 | <10 | <10 | <10 | 160 | 160 |
| 1 | 502 | Vaccinate | IN | 2 | <10 | <10 | <10 | <10 | <10 | <10 | 80 | 160 |
| 1 | 469 | Vaccinate | IN | 2 | <10 | <10 | <10 | <10 | <10 | <10 | 80 | 160 |
| 1 | 46A | Vaccinate | IN | 2 | <10 | <10 | <10 | <10 | <10 | <10 | 80 | 80 |
| 2 | 232 | Vaccinate | SQ | 2 | <10 | <10 | <10 | 20 | 20 | 40 | 320 | 640 |
| 2 | 511 | Vaccinate | SQ | 2 | <10 | 10 | 10 | 20 | 20 | 20 | 160 | 640 |
| 2 | 514 | Vaccinate | SQ | 2 | <10 | <10 | 40 | 40 | 80 | 40 | 160 | 320 |
| 2 | 461 | Vaccinate | SQ | 2 | <10 | 10 | 10 | 20 | 20 | 20 | >640 | >640 |
| 2 | 463 | Vaccinate | SQ | 2 | <10 | 10 | 40 | 80 | 80 | 40 | 80 | 320 |
| 3 | 246 | Vaccinate | IN | 2 | <10 | 10 | <10 | <10 | <10 | <10 | 40 | 40 |
| 3 | 505 | Vaccinate | IN | 2 | <10 | <10 | <10 | <10 | <10 | <10 | 80 | 80 |
| 3 | 506 | Vaccinate | IN | 2 | <10 | <10 | <10 | <10 | <10 | <10 | 80 | 160 |
| 3 | 464 | Vaccinate | IN | 2 | <10 | <10 | <10 | <10 | <10 | <10 | 80 | 80 |
| 3 | 465 | Vaccinate | IN | 2 | <10 | <10 | <10 | <10 | <10 | <10 | 80 | 160 |
| 4 | 23B | Vaccinate | SQ | 2 | <10 | 10 | 10 | 40 | 40 | 20 | 160 | 160 |
| 4 | 247 | Vaccinate | SQ | 2 | <10 | <10 | <10 | 20 | 20 | 20 | 160 | 320 |
| 4 | 508 | Vaccinate | SQ | 2 | <10 | 10 | 40 | 40 | 80 | 80 | 320 | 320 |
| 4 | 512 | Vaccinate | SQ | 2 | <10 | <10 | 20 | 20 | 80 | 80 | 320 | 160 |
| 4 | 516 | Vaccinate | SQ | 2 | <10 | 10 | 10 | 20 | 80 | 80 | 160 | >640 |
| 5 | 503 | Vaccinate | IN | 2 | <10 | 10 | <10 | <10 | <10 | <10 | 80 | 160 |
| 5 | 513 | Vaccinate | IN | 2 | <10 | <10 | <10 | <10 | <10 | <10 | 80 | 80 |
| 5 | 462 | Vaccinate | IN | 2 | <10 | <10 | <10 | <10 | <10 | <10 | 80 | 320 |
| 5 | 466 | Vaccinate | IN | 2 | <10 | <10 | <10 | <10 | <10 | <10 | 80 | 80 |
| 5 | 46B | Vaccinate | IN | 2 | <10 | <10 | <10 | <10 | <10 | <10 | 80 | 160 |
| 6 | 236 | Control | — | 2 | <10 | <10 | <10 | <10 | <10 | <10 | 80 | 160 |
| 6 | 504 | Control | — | 2 | <10 | <10 | <10 | <10 | <10 | <10 | 160 | 160 |
| 6 | 507 | Control | — | 2 | <10 | <10 | <10 | <10 | <10 | <10 | 80 | 160 |
| 6 | 515 | Control | — | 2 | <10 | <10 | <10 | <10 | <10 | <10 | 80 | 160 |
| 6 | 468 | Control | — | 2 | <10 | <10 | <10 | <10 | <10 | <10 | 80 | 160 |

*First vaccination
**Second vaccination
***Day of challenge

TABLE 49

Analysis of total canine influenza disease clinical scores

| Group | Treatment | Route of vaccination | Average total Score per dog | P-value* |
|---|---|---|---|---|
| 1 | VAX-1 | IN | 35.2 | 0.500 (Group 1 vs. 6) |
| 2 | VAX-2 | SQ | 31.0 | 0.345 (Group 2 vs. 6) |
| 3 | VAX-2 | IN | 39.4 | 0.631 (Group 3 vs. 6) |
| 4 | VAX-3 | SQ | 13.0 | 0.016 (Group 4 vs. 6) |
| 5 | VAX-3 | IN | 42.6 | 0.790 (Group 4 vs. 6) |
| 6 | Control | — | 36.8 | — |

*Analyzed using a NPAR1WAY procedure of SAS ® Version 8.2 (the vaccine groups were compared using the Wilcoxon rank sum test)

TABLE 50

Histopathological evaluation of tissue samples

| Group No | Dog ID | Treatment | Route of vaccination | Number of doses | Microscopic lesion (Histopathology) Lung | Trachea |
|---|---|---|---|---|---|---|
| 1 | 248 | Vaccinate | IN | 2 | + | − |
| 1 | 501 | Vaccinate | IN | 2 | + | − |
| 1 | 502 | Vaccinate | IN | 2 | + | − |
| 1 | 469 | Vaccinate | IN | 2 | + | + |
| 1 | 46A | Vaccinate | IN | 2 | + | + |
| 2 | 232 | Vaccinate | SQ | 2 | + | − |
| 2 | 511 | Vaccinate | SQ | 2 | + | − |
| 2 | 514 | Vaccinate | SQ | 2 | − | − |
| 2 | 461 | Vaccinate | SQ | 2 | + | − |
| 2 | 463 | Vaccinate | SQ | 2 | − | − |
| 3 | 246 | Vaccinate | IN | 2 | + | − |
| 3 | 505 | Vaccinate | IN | 2 | + | − |
| 3 | 506 | Vaccinate | IN | 2 | + | + |
| 3 | 464 | Vaccinate | IN | 2 | + | − |
| 3 | 465 | Vaccinate | IN | 2 | + | + |
| 4 | 23B | Vaccinate | SQ | 2 | − | − |
| 4 | 247 | Vaccinate | SQ | 2 | +/− | − |
| 4 | 508 | Vaccinate | SQ | 2 | − | − |
| 4 | 512 | Vaccinate | SQ | 2 | − | +/− |
| 4 | 516 | Vaccinate | SQ | 2 | + | + |
| 5 | 503 | Vaccinate | IN | 2 | + | +/− |
| 5 | 513 | Vaccinate | IN | 2 | + | + |
| 5 | 462 | Vaccinate | IN | 2 | + | +/− |
| 5 | 466 | Vaccinate | IN | 2 | + | + |
| 5 | 46B | Vaccinate | IN | 2 | + | − |
| 6 | 236 | Control | — | 2 | + | − |

TABLE 50-continued

Histopathological evaluation of tissue samples

| Group No | Dog ID | Treatment | Route of vaccination | Number of doses | Microscopic lesion (Histopathology) Lung | Trachea |
|---|---|---|---|---|---|---|
| 6 | 504 | Control | — | 2 | + | + |
| 6 | 507 | Control | — | 2 | + | + |
| 6 | 515 | Control | — | 2 | + | +/− |
| 6 | 468 | Control | — | 2 | + | + |

"+" Severe lesion consistent or pathognomic to an influenza infection
"+/−" Mild lesion (inconclusive)
"−" Normal Example 25

Canine Influenza Vaccine Efficacy Study

Canine influenza disease is caused by an H3N8 influenza virus (CIV). CIV is very closely related to equine H3N8 viruses (Crawford et al., 2005) and infects all exposed dogs. Approximately 80% of exposed dogs develop clinical signs. In the following study the efficacy of an inactivated H3N8 equine influenza virus vaccine and a canine influenza virus vaccine were determined.

Procedure:

Thirty-five beagles and five mongrels were used in this study. Beagles were randomly assigned to three groups (Table 51). All mongrels were assigned to control group (Group 3). All dogs were fed with a standard growth diet and water was available as libitum.

TABLE 51

Experimental design

| Group | Treatment | Vaccination route | Number of dogs | Age at vaccination (weeks) | Challenge |
|---|---|---|---|---|---|
| 1 | VAX-1 | IM | 15 | 8 & 12 | Yes |
| 2 | VAX-2 | SC | 5 | 8 & 12 | Yes |
| 3 | Control | N/A | 20 | N/A | Yes |

The dogs in Groups 1 and 2 were vaccinated with either VAX-1 or VAX-2 (Table 51). VAX-1 was a HAVLOGEN® adjuvanted, inactivated equine influenza virus (A/equine/KY/02) vaccine. For vaccine preparation, the vaccine virus was inactivated by binary ethylenimine (BEI) using a standard method. Each dose of vaccine contained HAVLOGEN® (10% v/v), 6144 HA units of the inactivated virus, 0.1% (v/v) of 10% thimerosal, 0.1% (v/v) of phenol red and sufficient PBS to bring the total dose volume to 1 ml and sufficient NaOH to adjust the pH to 6.8 to 7.2.

VAX-2 was an inactivated, CARBIGEN™ adjuvanted, canine influenza antigen vaccine (A/canine/Fl/43/2004). The A/canine/Fl/43/2004 was inactivated by binary ethylenimine ("BEI") using a standard method. Each dose of the vaccine contained 5% by mass CARBIGEN™, approximately 1280 HA units of the inactivated virus, sufficient PBS to bring the total volume of the dose to 1 ml, and sufficient NaOH to adjust the pH to between 7.2 and 7.4. Serum samples were collected from all dogs on the day of first and second vaccination, days 7 and 14 post first and second vaccinations, and at pre-challenge to determine the HI titers using an H3N8 equine influenza virus standard protocol (SAM 124, CVB, USDA, Ames, IA). Seven days before challenge, the dogs were moved to a ABSL-2 facility and housed in individual cages.

All vaccinates and age-matched control dogs were challenged oronasally with virulent canine influenza virus ($10^{7.2}$ TCID50 of A/Canine/Florida/242/2003 per dog) at 2 weeks post second vaccination. The challenge virus was administered as a mist (2 ml/dog) using a nebulizer (NEBULAIR™). The dogs were observed for influenza-related clinical signs for 14 days post-challenge. Nasal and oropharyngeal swabs were collected daily in tubes containing 2 ml of virus transport medium for virus isolation from day −1 (i.e., one day before challenge) through day 14 post-challenge. Blood samples were collected on days 7 and 14 post challenge for HI titer determination. The clinical sign score assignments used for post challenge observation are shown in Table 52.

Results:

All vaccinated dogs (Groups 1 and 2) developed HI antibody titer responses to the canine influenza virus isolate (Table 53). All dogs exhibited one or more of the following signs of canine influenza: fever (>103.0° F.; >39.4° C.), cough, serous or mucopurulent ocular discharge, serous or mucopurulent nasal discharge, vomiting, diarrhea, depression, and anorexia. Vaccinates had less severe clinical signs, compared to age-matched controls (Table 54). There was a significant ($P<0.001$) reduction in clinical signs in dogs vaccinated with either VAX-1 (Group 1) or VAX-2 (Group 2).

Virus isolation results are shown in Tables 55 and 56. Following a virulent canine influenza virus challenge, the canine influenza virus was isolated from 5 of 15 (33%) dogs from Group 1 (VAX-1), 0 of 5 (0%) dogs from Group 2 (VAX-2) and 17 of 20 (85%) controls (Group 3). Both inactivated equine influenza vaccine (VAX-1) and canine influenza virus (VAX-2) vaccinates demonstrated a significant ($P=0.004$) reduction in virus shedding in nasal or oral secretions or both (Table 55) compared to controls.

Conclusion:

The results from this study demonstrate that: (1) inactivated H3N8 equine influenza virus and canine influenza virus vaccines can induce canine influenza virus reactive HI antibody responses in vaccinated dogs, (2) use of an H3N8 equine influenza virus or canine influenza virus vaccine can reduce the severity of canine influenza virus disease in dogs, and (3) use of an H3N8 equine influenza virus or canine influenza virus vaccine can reduce virus excretion in nasal and/or oral secretions.

TABLE 52

Clinical signs and scoring system

| Clinical signs | Score per day |
|---|---|
| Temp | |
| <103.0° F. (<39.4° C.) | 0 |
| 103.0-103.9° F. (39.4- | 2 |
| 104.0-104.9° F. (40.0-40.5° C.) | 3 |
| >105.0° F. (>40.6° C.) | 4 |
| Coughing | |
| No coughing | 0 |
| Occasional | 2 |
| Paroxysmal | 4 |
| Sneezing | |
| No sneezing | 0 |
| Occasional | 1 |
| Paroxysmal | 2 |

TABLE 52-continued

Clinical signs and scoring system

| Clinical signs | Score per day |
|---|---|
| Nasal discharge | |
| No discharge | 0 |
| Serous-slight | 1 |
| Serous-copious | 1 |
| Mucopurulent-slight | 2 |
| Mucopurulent-copious | 3 |
| Ocular discharge | |
| No discharge | 0 |
| Serous-slight | 1 |
| Serous-copious | 1 |
| Mucopurulent-slight | 2 |
| Mucopurulent-copious | 3 |
| Hemoptysis | |
| No | 0 |
| Yes | 5 |
| Depression | |
| No | 0 |
| Yes | 1 |
| Anorexia | |
| No | 0 |
| Yes | 1 |
| Respiratory signs | |
| None | 0 |
| Rales | 3 |
| Dyspnea | 4 |
| Gasping | 5 |
| Mucous expectorate | |
| No | 0 |
| Yes | 2 |
| Vomiting | |
| No | 0 |
| Yes | 1 |
| Fecal abnormalities | |
| No | 0 |
| Yes | 1 |

TABLE 53

Serology - Hemagglutination inhibition titers

| Group No | Dog ID | Treatment | Vaccination route | Days post vaccination | | | | Days post challenge | | | |
|---|---|---|---|---|---|---|---|---|---|---|---|
| | | | | 0* | 7 | 14 | 28** | 35 | 42*** | 7 | 14 |
| 1 | AYS | Vaccinate | IM | <10 | <10 | <10 | 20 | 40 | 40 | 80 | ≧640 |
| 1 | AZV | Vaccinate | IM | <10 | <10 | <10 | 20 | 40 | 40 | 160 | ≧640 |
| 1 | BAD | Vaccinate | IM | <10 | <10 | <10 | 40 | 40 | 80 | 80 | 320 |
| 1 | BAE | Vaccinate | IM | <10 | <10 | 10 | 20 | 20 | 20 | 40 | 320 |
| 1 | BAH | Vaccinate | IM | <10 | <10 | 10 | 10 | 40 | 40 | 160 | ≧640 |
| 1 | BAJ | Vaccinate | IM | <10 | <10 | 10 | 20 | 80 | 80 | 40 | 320 |
| 1 | BAN | Vaccinate | IM | <10 | 10 | 10 | 20 | 40 | 40 | 40 | 320 |
| 1 | BBN | Vaccinate | IM | <10 | 10 | 10 | 20 | 80 | 80 | 40 | 320 |
| 1 | BBT | Vaccinate | IM | <10 | <10 | <10 | 20 | 40 | 40 | 40 | 160 |
| 1 | BBY | Vaccinate | IM | <10 | <10 | <10 | 20 | 80 | 80 | 160 | ≧640 |
| 1 | BCS | Vaccinate | IM | <10 | 10 | 40 | 40 | 160 | 160 | 160 | 160 |
| 1 | BCZ | Vaccinate | IM | <10 | 10 | 10 | 20 | 80 | 40 | 160 | 160 |
| 1 | BDP | Vaccinate | IM | <10 | <10 | <10 | 20 | 40 | 40 | 80 | ≧640 |
| 1 | BEE | Vaccinate | IM | <10 | 10 | 20 | 40 | 80 | 80 | 160 | 320 |
| 1 | BEY | Vaccinate | IM | <10 | <10 | 10 | 10 | 40 | 40 | 160 | 160 |
| 2 | AZH | Vaccinate | SC | <10 | <10 | 10 | 20 | 80 | 80 | 160 | 160 |
| 2 | AZT | Vaccinate | SC | <10 | <10 | 10 | 10 | 40 | 80 | 320 | ≧640 |
| 2 | BBC | Vaccinate | SC | <10 | <10 | 20 | 40 | 160 | 160 | 80 | 160 |
| 2 | BCM | Vaccinate | SC | <10 | <10 | 10 | 20 | 80 | 40 | 80 | 160 |
| 2 | BEB | Vaccinate | SC | <10 | <10 | <10 | 10 | 20 | 40 | 80 | 160 |
| 3 | AYT | Control | N/A | <10 | <10 | <10 | <10 | <10 | <10 | 40 | 320 |
| 3 | AZJ | Control | N/A | <10 | <10 | <10 | <10 | <10 | <10 | 20 | 160 |
| 3 | AZL | Control | N/A | <10 | <10 | <10 | <10 | <10 | <10 | 40 | 160 |
| 3 | AZN | Control | N/A | <10 | <10 | <10 | <10 | <10 | <10 | 160 | 160 |
| 3 | BAB | Control | N/A | <10 | <10 | <10 | <10 | <10 | <10 | 40 | 320 |
| 3 | BBD | Control | N/A | <10 | <10 | <10 | <10 | <10 | <10 | 320 | ≧640 |
| 3 | BBU | Control | N/A | <10 | <10 | <10 | <10 | <10 | <10 | 160 | 160 |
| 3 | BBZ | Control | N/A | <10 | <10 | <10 | <10 | <10 | <10 | 20 | 160 |
| 3 | BCC | Control | N/A | <10 | <10 | <10 | <10 | <10 | <10 | 40 | 320 |
| 3 | BCD | Control | N/A | <10 | <10 | <10 | <10 | <10 | <10 | 80 | ≧640 |
| 3 | BCG | Control | N/A | <10 | <10 | <10 | <10 | <10 | <10 | 40 | ≧640 |
| 3 | BCI | Control | N/A | <10 | <10 | <10 | <10 | <10 | <10 | 20 | 320 |
| 3 | BCL | Control | N/A | <10 | <10 | <10 | <10 | <10 | <10 | 80 | ≧640 |
| 3 | BCV | Control | N/A | <10 | <10 | <10 | <10 | <10 | <10 | 40 | 320 |
| 3 | BDU | Control | N/A | <10 | <10 | <10 | <10 | <10 | <10 | 80 | ≧640 |
| 3 | MFI | Control | N/A | NT | NT | NT | NT | <10 | <10 | 80 | 320 |
| 3 | MFJ | Control | N/A | NT | NT | NT | NT | <10 | <10 | 40 | 320 |
| 3 | MFK | Control | N/A | NT | NT | NT | NT | <10 | <10 | 80 | 320 |

TABLE 53-continued

Serology - Hemagglutination inhibition titers

| Group No | Dog ID | Treatment | Vaccination route | HI titer Days post vaccination 0* | 7 | 14 | 28** | Days post challenge 35 | 42*** | 7 | 14 |
|---|---|---|---|---|---|---|---|---|---|---|---|
| 3 | MFR | Control | N/A | NT | NT | NT | NT | <10 | <10 | 80 | 320 |
| 3 | MFS | Control | N/A | NT | NT | NT | NT | <10 | <10 | 160 | ≧640 |

*First vaccination
**Second vaccination
***Day of challenge

TABLE 54

Analysis of total canine influenza disease clinical scores

| Group | Treatment | Average total Score per dog | P-value* |
|---|---|---|---|
| 1 | VAX-1 | 9.1 | <0.001 (Group 1 vs. 3) |
| 2 | VAX-2 | 5.4 | <0.001 (Group 2 vs. 3) |
| 3 | Control | 24.1 | — |

*Analyzed using a NPARIWAY procedure of SAS ® Version 9.1 (the vaccine groups were compared using the GLM procedure)

TABLE 55

Post-challenge virus shedding

| Group | Treatment | Percent dogs excreted the virus | P-value* |
|---|---|---|---|
| 1 | VAX-1 | 33% (5/15) | 0.004 (Group 1 vs. 3) |
| 2 | VAX-2 | 0% (0/5) | 0.004 (Group 2 vs. 3) |
| 3 | Control | 85% (17/20) | — |

*Analyzed using a FREQ procedure of SAS ® (Version 9.1) and P-value associated with Fisher's exact test

TABLE 56

Serology - Hemagglutination inhibition titers

| Group No | Dog ID | Treatment | Vaccination route | Days post-challenge −1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|
| 1 | AYS | Vaccinate | IM | N | N | N | N | N | N | N | N | N | N | N | N | N | N | N | N |
| 1 | AZV | Vaccinate | IM | N | N | N | P | N | N | N | N | N | N | N | N | N | N | N | N |
| 1 | BAD | Vaccinate | IM | N | N | N | N | N | N | N | N | N | N | N | N | N | N | N | N |
| 1 | BAE | Vaccinate | IM | N | N | N | P | P | N | N | N | N | N | N | N | N | N | N | N |
| 1 | BAH | Vaccinate | IM | N | N | N | N | N | N | N | N | N | N | N | N | N | N | N | N |
| 1 | BAJ | Vaccinate | IM | N | N | N | P | N | N | N | N | N | N | N | N | N | N | N | N |
| 1 | BAN | Vaccinate | IM | N | N | N | N | N | N | N | N | N | N | N | N | N | N | N | N |
| 1 | BBN | Vaccinate | IM | N | N | N | N | N | N | N | N | N | N | N | N | N | N | N | N |
| 1 | BBT | Vaccinate | IM | N | N | N | N | N | N | N | N | N | N | N | N | N | N | N | N |
| 1 | BBY | Vaccinate | IM | N | N | N | N | N | N | N | N | N | N | N | N | N | N | N | N |
| 1 | BCS | Vaccinate | IM | N | N | N | N | N | N | N | N | N | N | N | N | N | N | N | N |
| 1 | BCZ | Vaccinate | IM | N | N | N | N | N | N | N | N | N | N | N | N | N | N | N | N |
| 1 | BDP | Vaccinate | IM | N | N | N | P | N | N | N | N | N | N | N | N | N | N | N | N |
| 1 | BEE | Vaccinate | IM | N | N | N | N | N | N | N | N | N | N | N | N | N | N | N | N |
| 1 | BEY | Vaccinate | IM | N | N | N | P | N | N | N | N | N | N | N | N | N | N | N | N |
| 2 | AZH | Vaccinate | SC | N | N | N | N | N | N | N | N | N | N | N | N | N | N | N | N |
| 2 | AZT | Vaccinate | SC | N | N | N | N | N | N | N | N | N | N | N | N | N | N | N | N |
| 2 | BBC | Vaccinate | SC | N | N | N | N | N | N | N | N | N | N | N | N | N | N | N | N |
| 2 | BCM | Vaccinate | SC | N | N | N | N | N | N | N | N | N | N | N | N | N | N | N | N |
| 2 | BEB | Vaccinate | SC | N | N | N | N | N | N | N | N | N | N | N | N | N | N | N | N |
| 3 | AYT | Control | N/A | N | N | N | N | N | N | N | N | N | N | N | N | N | N | N | N |
| 3 | AZJ | Control | N/A | N | N | N | N | N | P | P | N | N | N | N | N | N | N | N | N |
| 3 | AZL | Control | N/A | N | N | N | N | N | N | P | N | N | N | N | N | N | N | N | N |
| 3 | AZN | Control | N/A | N | N | N | P | N | N | N | N | N | N | N | N | N | N | N | N |
| 3 | BAB | Control | N/A | N | N | N | P | N | N | N | N | N | N | N | N | N | N | N | N |
| 3 | BBD | Control | N/A | N | N | N | N | N | N | N | N | N | N | N | N | N | N | N | N |
| 3 | BBU | Control | N/A | N | N | N | N | N | N | P | N | N | N | N | N | N | N | N | N |
| 3 | BBZ | Control | N/A | N | N | N | P | N | N | P | N | N | N | N | N | N | N | N | N |
| 3 | BCC | Control | N/A | N | N | N | P | N | P | N | N | N | N | N | N | N | N | N | N |
| 3 | BCD | Control | N/A | N | N | N | N | N | N | P | P | N | N | N | N | N | N | N | N |
| 3 | BCG | Control | N/A | N | N | N | P | N | P | N | N | N | N | N | N | N | N | N | N |
| 3 | BCI | Control | N/A | N | N | N | N | P | P | N | N | N | N | N | N | N | N | N | N |
| 3 | BCL | Control | N/A | N | N | N | N | P | P | P | N | N | N | N | N | N | N | N | N |
| 3 | BCV | Control | N/A | N | N | N | N | N | P | P | N | N | N | N | N | N | N | N | N |
| 3 | BDU | Control | N/A | N | N | N | P | N | P | N | N | N | N | N | N | N | N | N | N |
| 3 | MFI | Control | N/A | N | N | N | P | P | P | P | N | N | N | N | N | N | N | N | N |
| 3 | MFJ | Control | N/A | N | N | N | P | N | N | N | N | N | N | N | N | N | N | N | N |
| 3 | MFK | Control | N/A | N | N | N | P | N | N | N | N | N | N | N | N | N | N | N | N |

TABLE 56-continued

Serology - Hemagglutination inhibition titers

| Group | | | Vaccination | Days post-challenge | | | | | | | | | | | | | | |
|---|---|---|---|---|---|---|---|---|---|---|---|---|---|---|---|---|---|---|
| No | Dog ID | Treatment | route | −1 | 0 | 1 | 2 | 3 | 4 | 5 | 6 | 7 | 8 | 9 | 10 | 11 | 12 | 13 | 14 |
| 3 | MFR | Control | N/A | N | N | N | N | N | N | N | N | N | N | N | N | N | N | N | N |
| 3 | MFS | Control | N/A | N | N | N | P | P | P | N | N | N | N | N | N | N | N | N |

N - No virus isolated from oral or nasal swabs
P - Virus isolated from nasal or oral or nasal and oral swabs.

TABLE 57

Hemagglutinin, neuraminidase and nucleoprotein gene amino acid sequence similarities among influenza viruses

| Gene (Canine/Florida/43/2004) | Amino acid sequence similarity | Gene of influenza virus used for comparison |
|---|---|---|
| Hemagglutinin | 88 | equine/Algiers/72 |
| HA | 90 | equine/Sao paulo/6/69 |
| HA | 91 | equine/Miami/1/63 |
| HA | 93 | equine/Newmarket/79 |
| HA | 94 | equine/Kentucky/1/81 |
| HA | 95 | Equi-2/Ludhiana/87 |
| HA | 96 | Equine/Alaska/1/91 |
| HA | 97 | equine/Tennessee/5/86 |
| HA | 98 | equine/Kentucky/5/02 |
| HA | 99 | equine/Ohio/1/2003 |
| HA | 99 | canine/Florida/242/2003 |
| Neuraminidase | 88 | Eq/Algiers/72 |
| NA | 90 | equine/Sao Paulo/6/69 |
| NA | 91 | equine/Miami/1/63 |
| NA | 93 | equine/Newmarket/79 |
| NA | 94 | equine/Kentucky/1/81 |
| NA | 95 | Equi-2/Ludhiana/87 |
| NA | 96 | equine/Santiago/85 |
| NA | 97 | equine/Tennessee/5/86 |
| NA | 98 | equine/Kentucky/5/2002 |
| NA | 99 | equine/Ohio/1/2003 |
| NA | 99 | canine/Florida/242/2003 |
| Nucleoprotein ("NP") | 94 | equi/Miami/1/63 |
| NP | 97 | equine/Kentucky/1/81 |
| NP | 99 | equine/Kentucky/5/02 |
| NP | 99 | equine/Ohio/1/2003 |
| NP | 99 | canine/Florida/242/2003 |

The words "comprise," "comprises," and "comprising" in this patent (including the claims) are to be interpreted inclusively rather than exclusively. This interpretation is intended to be the same as the interpretation that these words are given under United States patent law.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 5,106,739
U.S. Pat. No. 5,034,322
U.S. Pat. No. 6,455,760
U.S. Pat. No. 6,696,623
U.S. Pat. No. 4,683,202
U.S. Pat. No. 4,683,195
U.S. Pat. No. 4,800,159
U.S. Pat. No. 4,965,188
U.S. Pat. No. 5,994,056
U.S. Pat. No. 6,814,934
U.S. Pat. No. 6,436,408
U.S. Pat. No. 6,398,774
U.S. Pat. No. 6,177,082
Published U.S. Application No. 20040078841
Published U.S. Application No. 20040067506
Published U.S. Application No. 20040019934
Published U.S. Application No. 20030177536
Published U.S. Application No. 20030084486
Published U.S. Application No. 20040123349
Greyhound Daily News, Jan. 28, 1999. National Greyhound Association (NGA), Abilene, Kans. http://www.NGAgreyhounds.com.
Personal communication, Dr. William Duggar, veterinarian at Palm Beach Kennel Club, West Palm Beach, Fla.
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
An, G. (1987) "Binary Ti vectors for plant transformation and promoter analysis" *Methods Enzymol.* 153:292-305.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Burleson, F. et al. (1992) *Virology: A Laboratory Manual* (Academic Press).
Byars, N. E., A. C. Allison (1987) "Adjuvant formulation for use in vaccines to elicit both cell-mediated and humoral immunity" *Vaccine* 5:223-228.
Crawford, P. C. et al. (2005) "Transmission of equine influenza virus to dogs" *Science* 310:482-485.
Chang, C. P. et al. (1976) "Influenza virus isolations from dogs during a human epidemic in Taiwan" *Int J Zoonoses* 3:61-64.
Dacso, C. C. et al. (1984) "Sporadic occurrence of zoonotic swine influenza virus infections" *J Clin Microbiol* 20:833-835.
de Boer, H. A., Comstock, L. J., Vasser, M. (1983) "The tac promoter: a functional hybrid derived from the trp and lac promoters" *Proc. Natl. Acad. Sci. USA* 80(1):21-25.
Felsenstein, J. (1989) *Cladistics* 5:164.
Fields et al. (1946) *Fields Virology*, 3$^{rd}$ ed., Lippincott-Raven publishers.
Ford, R. B., Vaden, S. L. (1998) "Canine infectious tracheobronchitis" In *Infectious Diseases of the Dog and Cat, 2$^{nd}$ edition*, C. E. Greene, editor, W.B. Saunders Co., Philadelphia, Pa., pp. 33-38.

Fouchier et al., (2000) *Journal of Clinical Microbiology* 38 (11):4096-4101.

Good, X. et al. (1994) "Reduced ethylene synthesis by transgenic tomatoes expressing S-adenosylmethionine hydrolase" *Plant Molec. Biol.* 26:781-790.

Guan, Y. et al. (2004) "H5N1 influenza: a protean pandemic threat" *Proc Natl Acad Sci U S A* 101:8156-8161.

Guo, Y. et al. (1992) "Characterization of a new avian-like influenza A virus from horses in China" *Virology* 188:245-255.

Houser, R. E. et al. (1980) "Evidence of prior infection with influenza A/Texas/77 (H3N2) virus in dogs with clinical parainfluenza" *Can J Comp Med* 44:396-402.

Karasin, A. I. et al. (2000) "Isolation and characterization of H4N6 avian influenza viruses from pigs with pneumonia in Canada" *J Virol* 74:9322-9327.

Karlin S, and Altschul, S. F. (1990) "Methods for Assessing the Statistical Significance of Molecular Sequence Features by Using General Scoring Schemes" *Proc. Natl. Acad. Sci. USA* 87:2264-2268.

Karlin S, and Altschul, S. F. (1993) "Applications and Statistics for Multiple High-Scoring Segments in Molecular Sequences" *Proc. Natl. Acad. Sci. USA* 90:5873-5877.

Kawaoka, Y. et al., (1989) "Avian-to-human transmission of the PB1 gene of influenza A viruses in the 1957 and 1968 pandemics" *J Virol* 63:4603-4608.

Keawcharoen, J. et al. (2004) "Avian influenza H5N1 in tigers and leopards" *Emerg Infect D is* 10:2189-2191.

Kendal, A. P. et al. (1982) In *Concepts and Procedures for Laboratory-based Influenza Surveillance*. A. P. Kendal, M. S. Pereira, J. J. Skehel, Eds. (U.S. Department of Health and Human Services, Centers for Disease Control and Prevention and Pan-American Health Organization, Atlanta, Ga., United States) pp. B17-B35.

Kilbourne, E. D. et al. (1975) "Demonstration of antibodies to both hemagglutinin and neuraminidase antigens of H3N2 influenza A virus in domestic dogs" *Intervirology* 6:315-318.

Kimura, K. et al. (1998) "Fatal case of swine influenza virus in an immunocompetent host" *Mayo Clin Proc* 73:243-245.

Klimov, A. I. et al. (1992a) "Sequence changes in the live attenuated, cold-adapted variants of influenza A/Leningrad/134/57 (H2N2) virus" *Virology* 186:795-797.

Klimov A. et al. (1992b) "Subtype H7 influenza viruses: comparative antigenic and molecular analysis of the HA-, M-, and NS-genes" *Arch Virol.* 122:143-161.

Kovacova, A. et al. (2002) "Sequence similarities and evolutionary relationships of influenza virus A hemagglutinins" *Virus Genes* 24:57-63.

Kuiken, T. et al. (2004) "Avian H5N1 influenza in cats" *Science* 306:241.

Kumar, S. et al. (2004) "MEGA3: Integrated software for Molecular Evolutionary Genetics Analysis and sequence alignment" *Brief Bioinform* 5:150-163.

Lee, L. G. et al. (1993) "Allelic discrimination by nick-translation PCR with fluorogenic probes" *Nucleic Acids Res.* 21(16):3761-3766.

Lewin, B. (1985) *Genes II*, John Wiley & Sons, Inc., p. 96.

Lipatov, A. S. et al. (2004) "Influenza: emergence and control" *J Virol* 78:8951-8959.

Livak, K. J. et al. (1995) "Oligonucleotides with fluorescent dyes at opposite ends provide a quenched probe system useful for detecting PCR product and nucleic acid hybridization" *PCR Methods Appl.* 4(6):357-362.

Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.

Matrosovich, M. et al. (2000) "Early alterations of the receptor-binding properties of H1, H2, and H3 avian influenza virus hemagglutinins after their introduction into mammals" *J Virol* 74:8502-8512.

Maertzdorf et al., (2004) *Clin Microbiol.* 42(3):981-986.

Merrifield, R. B. (1963) "Solid Phase Peptide Synthesis. I. The Synthesis of a Tetrapeptide" *J. Amer. Chem. Soc.* 85:2149-2154.

Nikitin, A. et al. (1972) "Epidemiological studies of A-Hong Kong-68 virus infection in dogs" *Bull World Health Organ* 47:471-479.

Nobusawa, E. et al. (1991) "Comparison of complete amino acid sequences and receptor-binding properties among 13 serotypes of hemagglutinins of influenza A viruses" *Virology* 182:475-485.

Patriarca, P. A. et al. (1984) "Lack of significant person-to-person spread of swine influenza-like virus following fatal infection in an immunocompromised child" *Am J Epidemiol* 119:152-158.

Payungpom S. et al. (2006a) "Detection of canine influenza A virus (H3N8) RNA by real-time RT-PCR" (in preparation for *Journal of Clinical Microbiology*).

Payungporn S, et al. (2006b) "Isolation and characterization of influenza A subtype H3N8 viruses from dogs with respiratory disease in a shelter and veterinary clinic in Florida" (in preparation for *Emerging Infectious Diseases*).

Peiris, M. et al. (1999) "Human infection with influenza H9N2" *Lancet* 354:916-917.

Peiris, J. S. et al. (2004) "Re-emergence of fatal human influenza A subtype H5N1 disease" *Lancet* 363:617-619.

Posnett, D. N. et al. (1988) "A Novel Method for Producing Anti-peptide Antibodies" *J. Biol. Chem.* 263(4):1719-1725.

Putnam, Bob (Feb. 10, 1999) "Two illnesses seen in death of dogs" *St. Petersburg Times*.

Reid, A. H. et al. (2004) "Evidence of an absence: the genetic origins of the 1918 pandemic influenza virus" *Nat Rev Microbiol* 2:909-914.

Rowe, T. et al. (1999) "Detection of antibody to avian influenza A (H5N1) virus in human serum by using a combination of serologic assays" *J Clin Microbiol* 37: 937-943.

Saiki, R. (1985) "Enzymatic amplification of beta-globin genomic sequences and restriction site analysis for diagnosis of sickle cell anemia" *Science* 230:1350-1354.

Sambrook, J. et al. (1989) "Plasmid Vectors" In: *Molecular Cloning: A Laboratory Manual*, 2d Edition, pp. 1.82-1.104. Cold Spring Harbor Laboratory Press, Cold Spring Harbor, N.Y.

Subbarao, K. et al. (1998) "Characterization of an avian influenza A (H5N1) virus isolated from a child with a fatal respiratory illness" *Science* 279:393-396.

Suzuki, Y. et al. (2000) "Sialic acid species as a determinant of the host range of influenza A viruses" *J Virol* 74:11825-11831.

Tam, J. P. (1988) "Synthetic Peptide Vaccine Design: Synthesis and Properties of a High-Density Multiple Antigenic Peptide System" *PNAS USA* 85(15):5409-5413.

Top, Jr., F. H. et al. (1977) "Swine influenza A at Fort Dix, N.J. (January-February 1976). IV. Summary and speculation" *J Infect Dis* 136 Suppl:S376-S380.

Vines, A. et al. (1998) "The role of influenza A virus hemagglutinin residues 226 and 228 in receptor specificity and host range restriction" *J Virol* 72:7626-7631.

Wagner, R. et al. (2002) "N-Glycans attached to the stem domain of haemagglutinin efficiently regulate influenza A virus replication" *J Gen Virol* 83:601-609.

Webby, R. et al. (2004) "Molecular constraints to interspecies transmission of viral pathogens" *Nat Med* 10:S77-S81.

Webster, R. G. (1998) "Influenza: an emerging disease" *Emerg Infect Dis.* 4:436-441.

Webster, R. G. et al. (1992) "Evolution and ecology of influenza A viruses" *Microbiol Rev.* 56:152-179.

Weis, W. et al. (1988) "Structure of the influenza virus haemagglutinin complexed with its receptor, sialic acid" *Nature* 333:426-431.

Womble, D. D. (2000) "GCG: The Wisconsin Package of sequence analysis programs" *Methods Mol Biol* 132:3-22.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Yang, T. T. et al. (1996) "Optimized Codon Usage and Chromophore Mutations Provide Enhanced Sensitivity with the Green Fluorescent Protein" *Nucleic Acid Research* 24(22): 4592-4593.

Yoon K-Y. et al. (2005) "Influenza virus infection in racing greyhounds" *Emerg Infect Dis.* 11:1974-1975.

---

We claim:

1. An isolated canine influenza virus wherein said influenza virus comprises a polynucleotide which encodes a polypeptide comprising the amino acid sequence of SEQ ID NO:33, or a polynucleotide encodes a polypeptide having 99% or greater sequence identity with the amino acid sequence of SEQ ID NO:33.

2. The canine influenza virus according to claim 1, wherein said influenza virus is inactivated or attenuated.

3. The canine influenza virus according to claim 1, wherein said influenza virus is provided in a pharmaceutically acceptable carrier or diluent.

4. An isolated cell comprising a canine influenza virus of claim 1.

5. The cell according to claim 4, wherein said cell is a canid animal cell.

6. A vaccine comprising a canine influenza virus of claim 2.

7. The canine influenza vaccine according to claim 6, wherein said influenza virus is inactivated.

8. The canine influenza vaccine according to claim 6, wherein said influenza virus is attenuated.

9. A composition comprising a canine influenza virus wherein said influenza virus comprises a polynucleotide which encodes a polypeptide comprising the amino acid sequence of SEQ ID NO:33, or a polynucleotide encodes a polypeptide having 99% or greater sequence identity with the amino acid sequence of SEQ ID NO:33.

10. The composition according to claim 9, wherein said composition further comprises cell-free whole virus, or a portion thereof; a viral polynucleotide; a viral protein; a viral polypeptide or peptide; a virus infected cell; a recombinant viral vector based construct; a reassortant virus; or naked nucleic acid of said virus.

11. The canine influenza virus according to claim 9, wherein said influenza virus is inactivated or attenuated.

12. The composition according to claim 11, wherein said composition is formulated in a pharmaceutically acceptable carrier or diluent.

13. A method for inducing an immune response in an animal against an influenza virus capable of infecting a canid animal, said method comprising administering to said animal an effective amount of a composition according to claim 12.

14. The method according to claim 13, wherein said influenza virus is the viral isolate designated as A/canine/Florida/43/2004.

15. The method according to claim 13, wherein said immune response is a protective immune response that inhibits infection of said animal by an influenza virus.

16. The method according to claim 13, wherein said influenza virus has a H3 serotype.

17. The method according to claim 13, wherein said influenza virus has the serotype H3N8.

18. The method according to claim 13, wherein said composition further comprises an adjuvant.

19. The method according to claim 13, wherein said animal is a canid.

20. The method according to claim 19, wherein said canid animal is a domesticated dog.

21. The method according to claim 13, wherein said composition is administered parenterally.

22. The method according to claim 21, wherein said composition is administered subcutaneously, intraperitoneally, or intramuscularly.

23. The method according to claim 13, wherein said composition is administered nasally or orally.

24. The method according to claim 13, wherein said composition comprises a polynucleotide encoding a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

25. The method according to claim 13, wherein said composition comprises a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

26. The method according to claim 25, wherein said composition is provided in a pharmaceutically acceptable carrier or diluent.

27. A reassortant virus comprising a polynucleotide which encodes a polypeptide comprising the amino acid sequence of SEQ ID NO:33, or said polynucleotide encodes a polypeptide having 99% or greater sequence identity with the amino acid sequence of SEQ ID NO:33.

28. The reassortant virus according to claim 27, wherein said reassortant virus is formulated in a pharmaceutically acceptable carrier or diluent.

29. An isolated virus that comprises one or more polynucleotides wherein said one or more polynucleotides encode a canine influenza virus polypeptide comprising the amino acid sequence of SEQ ID NO:33, or said polynucleotide encodes a polypeptide having 99% or greater sequence identity with the amino acid sequence of SEQ ID NO:33.

30. The virus according to claim 29, wherein said virus is provided in a pharmaceutically acceptable carrier or diluent.

31. An isolated canine influenza virus, wherein said influenza virus comprises a polynucleotide encoding a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

32. An isolated canine influenza virus, wherein said influenza virus comprises a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

33. A composition comprising a canine influenza virus, wherein said canine influenza virus comprises a polynucleotide encoding a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence, wherein said canine influenza virus is capable of inducing an immune response against an influenza virus that is capable of infecting a canid animal.

34. A composition comprising a canine influenza virus, wherein said canine influenza virus comprises a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence, wherein said canine influenza virus is capable of inducing an immune response against an influenza virus that is capable of infecting a canid animal.

35. A reassortant virus comprising a polynucleotide encoding a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

36. A reassortant virus comprising a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

37. An isolated virus comprising a polynucleotide encoding a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

38. An isolated virus comprising a hemagglutinin (HA) comprising the amino acid sequence of SEQ ID NO:33, or an amino acid sequence having greater than 95% amino acid sequence identity to SEQ ID NO:33, wherein said HA protein comprises a serine at position 82, a leucine at position 221, a threonine at position 327, and a threonine at position 482 of the amino acid sequence.

39. The canine influenza virus according to claim 31, wherein said polynucleotide encodes a hemagglutinin (HA) that comprises the amino acid sequence of SEQ ID NO:16, or an amino acid sequence having greater than 95% amino acid sequence identity to SEQ ID NO:16.

40. The canine influenza virus according to claim 32, wherein said hemagglutinin (HA) comprises the amino acid sequence of SEQ ID NO:16, or an amino acid sequence having greater than 95% amino acid sequence identity to SEQ ID NO:16.

41. The reassortant virus according to claim 35, wherein said reassortant virus comprises a polynucleotide encoding a hemagglutinin (HA) comprising the amino acid sequence of SEQ ID NO:16, or an amino acid sequence having greater than 95% amino acid sequence identity to SEQ ID NO:16.

42. The reassortant virus according to claim 36, wherein said reassortant virus comprises a hemagglutinin (HA) comprising the amino acid sequence of SEQ ID NO:16, or an amino acid sequence having greater than 95% amino acid sequence identity to SEQ ID NO:16.

43. The virus according to claim 37, wherein said virus comprises a polynucleotide encoding a hemagglutinin (HA) comprising the amino acid sequence of SEQ ID NO:16, or an amino acid sequence having greater than 95% amino acid sequence identity to SEQ ID NO:16.

44. The virus according to claim 38, wherein said virus comprises a hemagglutinin (HA) comprising the amino acid sequence of SEQ ID NO:16, or an amino acid sequence having greater than 95% amino acid sequence identity to SEQ ID NO:16.

45. The canine influenza virus according to claim 31, wherein said influenza virus is inactivated.

46. The canine influenza virus according to claim 31, wherein said influenza virus is provided in a pharmaceutically acceptable carrier or diluent.

47. The canine influenza virus according to claim 32, wherein said influenza virus is inactivated.

48. The canine influenza virus according to claim 32, wherein said influenza virus is provided in a pharmaceutically acceptable carrier or diluent.

49. The reassortant virus according to claim 35, wherein said virus is inactivated.

50. The reassortant virus according to claim 35, wherein said virus is provided in a pharmaceutically acceptable carrier or diluent.

51. The reassortant virus according to claim 36, wherein said virus is inactivated.

52. The reassortant virus according to claim 36, wherein said virus is provided in a pharmaceutically acceptable carrier or diluent.

53. The virus according to claim 37, wherein said virus is inactivated.

54. The virus according to claim 37, wherein said virus is provided in a pharmaceutically acceptable carrier or diluent.

55. The virus according to claim 38, wherein said virus is inactivated.

56. The virus according to claim 38, wherein said virus is provided in a pharmaceutically acceptable carrier or diluent.

57. The canine influenza virus according to claim 39, wherein said influenza virus is inactivated.

58. The canine influenza virus according to claim 39, wherein said influenza virus is provided in a pharmaceutically acceptable carrier or diluent.

59. The canine influenza virus according to claim 40, wherein said influenza virus is inactivated.

60. The canine influenza virus according to claim 40, wherein said influenza virus is provided in a pharmaceutically acceptable carrier or diluent.

61. The reassortant virus according to claim 41, wherein said virus is inactivated.

62. The reassortant virus according to claim 41, wherein said virus is provided in a pharmaceutically acceptable carrier or diluent.

63. The reassortant virus according to claim 42, wherein said virus is inactivated.

64. The reassortant virus according to claim 42, wherein said virus is provided in a pharmaceutically acceptable carrier or diluent.

65. The virus according to claim 43, wherein said virus is inactivated.

66. The virus according to claim 43, wherein said virus is provided in a pharmaceutically acceptable carrier or diluent.

67. The virus according to claim 44, wherein said virus is inactivated.

68. The virus according to claim 44, wherein said virus is provided in a pharmaceutically acceptable carrier or diluent.

69. The canine influenza virus according to claim 31, wherein said influenza virus is attenuated.

70. The canine influenza virus according to claim 32, wherein said influenza virus is attenuated.

71. The reassortant virus according to claim 35, wherein said virus is attenuated.

72. The reassortant virus according to claim 36, wherein said virus is attenuated.

73. The virus according to claim 37, wherein said virus is attenuated.

74. The virus according to claim 38, wherein said virus is attenuated.

75. The canine influenza virus according to claim 39, wherein said influenza virus is attenuated.

76. The canine influenza virus according to claim 40, wherein said influenza virus is attenuated.

77. The reassortant virus according to claim 41, wherein said virus is attenuated.

78. The reassortant virus according to claim 42, wherein said virus is attenuated.

79. The virus according to claim 43, wherein said virus is attenuated.

80. The virus according to claim 44, wherein said virus is attenuated.

81. A vaccine comprising a canine influenza virus of claims 45 and 69.

82. A vaccine comprising a canine influenza virus of claims 47 and 70.

83. The canine influenza vaccine according to claim 81, wherein said polynucleotide encodes a hemagglutinin (HA) that comprises the amino acid sequence of SEQ ID NO:16, or an amino acid sequence having greater than 95% amino acid sequence identity to SEQ ID NO:16.

84. The canine influenza vaccine according to claim 82, wherein said hemagglutinin (H-A) comprises the amino acid sequence of SEQ ID NO:16, or an amino acid sequence having greater than 95% amino acid sequence identity to SEQ ID NO:16.

85. The canine influenza vaccine according to claim 81, wherein said influenza virus is inactivated.

86. The canine influenza vaccine according to claim 81, wherein said influenza virus is attenuated.

87. The canine influenza vaccine according to claim 82, wherein said influenza virus is inactivated.

88. The canine influenza vaccine according to claim 82, wherein said influenza virus is attenuated.

89. The canine influenza vaccine according to claim 83, wherein said influenza virus is inactivated.

90. The canine influenza vaccine according to claim 83, wherein said influenza virus is attenuated.

91. The canine influenza vaccine according to claim 84, wherein said influenza virus is inactivated.

92. The canine influenza vaccine according to claim 84, wherein said influenza virus is attenuated.

93. A canine influenza virus wherein said influenza virus is the viral isolate designated as A/canine/Florida/43/2004 (ATCC Accession No. PTA-7914).

94. A canine influenza virus wherein said influenza virus is the viral isolate designated as A/canine/Florida/242/2003 (ATCC Accession No. PTA-7915).

95. A canine influenza virus wherein said influenza virus is the viral isolate designated as canine/Jax/05 (ATCC Accession No. PTA-7941).

96. A canine influenza virus wherein said influenza virus is the viral isolate designated as canine/Miami/05 (ATCC Accession No. PTA-7940).

* * * * *

UNITED STATES PATENT AND TRADEMARK OFFICE
CERTIFICATE OF CORRECTION

PATENT NO. : 7,959,929 B2
APPLICATION NO. : 11/584818
DATED : June 14, 2011
INVENTOR(S) : Patti Cynthia Crawford et al.

Page 1 of 1

It is certified that error appears in the above-identified patent and that said Letters Patent is hereby corrected as shown below:

Column 316
Line 25, "45 and 69" should read --45 or 69--.
Line 27, "47 and 70" should read --47 or 70--.

Signed and Sealed this
Twelfth Day of July, 2011

David J. Kappos
*Director of the United States Patent and Trademark Office*

UNITED STATES PATENT AND TRADEMARK OFFICE
CERTIFICATE OF CORRECTION

Page 1 of 4

PATENT NO. : 7,959,929 B2
APPLICATION NO. : 11/584818
DATED : June 14, 2011
INVENTOR(S) : Patti Cynthia Crawford et al.

It is certified that error appears in the above-identified patent and that said Letters Patent is hereby corrected as shown below:

Column 8,
Line 35, "N8, OR N9." should read --N8, or N9.--.

Column 16,
Line 53, "at 107.2 TCID$_{50}$" should read --at $10^{7.2}$ TCID$_{50}$--.

Column 23,
Line 14, "an viral" should read --a viral--.

Column 30,
Line 6, "242/2003")" should read --242/2003"--.
Lines 8-9, "on Oct. 9, 2006" should read --on October 10, 2006--.

Column 34,
Line 60, "296-97%" should read --$\geq$96-97%--.

Column 45,
Lines 22-23, "A/canine/Miami//05 (H3N8)" should read --A/canine/Miami/05 (H3N8)--.

Columns 47-48,
Table 9,

"
| 15 | 54 | 78 | 79 | 83 | 92 | 107 | 118 | 159 | 218 | 222 | 261 | 328 | 479 | 483 | 492 | 541 |
|----|----|----|----|----|----|-----|-----|-----|-----|-----|-----|-----|-----|-----|-----|-----|
| I  | N  | V  | F  | N  | S  | S   | L   | N   | G   | W   | K   | I   | G   | N   | R   | K   |
| .  | .  | A  | .  | .  | .  | .   | .   | S   | .   | .   | .   | .   | .   | .   | .   | .   |
| .  | K  | A  | .  | .  | .  | .   | .   | S   | .   | .   | .   | .   | .   | .   | .   | .   |
| M  | K  | A  | .  | S  | .  | .   | .   | S   | .   | L   | .   | T   | .   | T   | .   | .   |
| M  | K  | A  | .  | S  | N  | .   | .   | S   | .   | L   | .   | T   | .   | T   | .   | R   |
| M  | K  | A  | .  | S  | .  | .   | V   | S   | .   | L   | N   | T   | E   | T   | .   | .   |
| M  | K  | A  | L  | S  | .  | .   | V   | S   | E   | L   | N   | T   | E   | T   | .   | .   |
| M  | K  | A  | L  | S  | .  | .   | V   | S   | E   | L   | N   | T   | E   | T   | K   | .   |
| M  | K  | A  | L  | S  | .  | P   | V   | S   | E   | L   | N   | T   | E   | T   | K   | .   |
"

Signed and Sealed this
Tenth Day of January, 2012

David J. Kappos
*Director of the United States Patent and Trademark Office* should read

| 15 | 54 | 78 | 79 | 83 | 92 | 107 | 118 | 159 | 218 | 222 | 261 | 328 | 479 | 483 | 492 | 541 |
|----|----|----|----|----|----|-----|-----|-----|-----|-----|-----|-----|-----|-----|-----|-----|
| I  | N  | V  | F  | N  | S  | S   | L   | N   | G   | W   | K   | I   | G   | N   | R   | K   |
| .  | .  | A  | .  | .  | .  | .   | .   | S   | .   | .   | .   | .   | .   | .   | .   | .   |
| .  | K  | A  | .  | .  | .  | .   | .   | S   | .   | .   | .   | .   | .   | .   | .   | .   |
| M  | K  | A  | .  | S  | .  | .   | .   | S   | .   | L   | .   | T   | .   | T   | .   | .   |
| M  | K  | A  | .  | S  | N  | .   | .   | S   | .   | L   | .   | T   | .   | T   | .   | R   |
| M  | K  | A  | .  | S  | .  | .   | V   | S   | .   | L   | N   | T   | E   | T   | .   | .   |
| M  | K  | A  | L  | S  | .  | .   | V   | S   | E   | L   | N   | T   | E   | T   | .   | .   |
| M  | K  | A  | L  | S  | .  | .   | V   | S   | E   | L   | N   | T   | E   | T   | K   | .   |
| M  | K  | A  | L  | S  | .  | P   | V   | S   | E   | L   | N   | T   | E   | T   | K   | .   |

--.

Column 50,
Line 33, "orpharyngeal" should read --oropharyngeal--.
Lines 43-44, "Payungpom... Payungpom" should read --Payungporn... Payungporn--.

Column 55,
Line 1, "was well as" should read --as well as--.

Column 56,
Line 32, "realtime" should read --real-time--.
Line 45, "realtime" should read --real-time--.
Line 50, "realtime" should read --real-time--.

Column 69,
Table 35, Lines 60-61, "Numberof doses" should read --Number of doses--.

Columns 73-76,
Table 39,

"[table image]" should read -- [table image] --.

Column 80,
Table 46, Route of vaccination corresponding to Group 5, "N" should read --IN--.

Columns 90-92,
Table 56,

"[table image]" should read -- [table image] --.

CERTIFICATE OF CORRECTION (continued)
U.S. Pat. No. 7,959,929 B2

Column 94,
Line 23, "Payungpom" should read --Payungporn--.

Column 316,
Line 33, "hemagglutinin (H-A)" should read --hemagglutinin (HA)--.